US009907849B2

(12) United States Patent
Petit et al.

(10) Patent No.: US 9,907,849 B2
(45) Date of Patent: Mar. 6, 2018

(54) COMBINATION OF A PD-1 ANTAGONIST AND A LISTERIA-BASED VACCINE FOR TREATING PROSTATE CANCER

(71) Applicants: Advaxis, Inc., Princeton, NJ (US); Merck Sharp and Dohme Corp., Rahway, NJ (US)

(72) Inventors: Robert Petit, Newtown, PA (US); David J. Mauro, Washington Crossing, PA (US); Rodolfo F. Perini, North Wales, PA (US)

(73) Assignees: Advaxis, Inc., Princeton, NJ (US); Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 14/802,607

(22) Filed: Jul. 17, 2015

(65) Prior Publication Data

US 2016/0022814 A1    Jan. 28, 2016

Related U.S. Application Data

(60) Provisional application No. 62/039,011, filed on Aug. 19, 2014, provisional application No. 62/026,221, filed on Jul. 18, 2014.

(51) Int. Cl.
| | | |
|---|---|---|
| G01N 33/53 | (2006.01) | |
| A61K 39/395 | (2006.01) | |
| A61K 39/00 | (2006.01) | |

(52) U.S. Cl.
CPC .... *A61K 39/39558* (2013.01); *A61K 39/0011* (2013.01); *A61K 2039/522* (2013.01); *A61K 2039/523* (2013.01); *A61K 2039/572* (2013.01)

(58) Field of Classification Search
None
See application file for complete search history.

(56) References Cited

U.S. PATENT DOCUMENTS

| | | | |
|---|---|---|---|
| 4,816,567 A | 3/1989 | Cabilly et al. | |
| 6,500,432 B1 | 12/2002 | Dalemans et al. | |
| 6,855,320 B2 | 2/2005 | Paterson | |
| 7,488,802 B2 | 2/2009 | Collins et al. | |
| 7,521,051 B2 | 4/2009 | Collins et al. | |
| 7,563,869 B2 | 7/2009 | Honjo et al. | |
| 7,595,048 B2 | 9/2009 | Honjo et al. | |
| 7,635,479 B2 | 12/2009 | Paterson et al. | |
| 7,655,238 B2 | 2/2010 | Paterson et al. | |
| 7,998,479 B2 | 8/2011 | Honjo et al. | |
| 8,008,449 B2 | 8/2011 | Korman et al. | |
| 8,168,179 B2 | 5/2012 | Honjo et al. | |
| 8,168,767 B2 | 5/2012 | Nichols et al. | |
| 8,246,955 B2 | 8/2012 | Honjo et al. | |
| 8,354,509 B2 | 1/2013 | Carven et al. | |
| 8,383,796 B2 | 2/2013 | Korman et al. | |
| 8,728,474 B2 | 5/2014 | Honjo et al. | |
| 8,771,702 B2 | 7/2014 | Paterson et al. | |
| 8,951,518 B2 | 2/2015 | Honjo et al. | |
| 9,067,999 B1 | 6/2015 | Honjo et al. | |
| 9,073,944 B2 | 7/2015 | Honjo et al. | |
| 9,393,301 B2 | 7/2016 | Honjo et al. | |
| 9,402,899 B2 | 8/2016 | Honjo et al. | |
| 9,439,962 B2 | 9/2016 | Honjo et al. | |
| 2002/0165172 A1 | 11/2002 | Sallberg et al. | |
| 2006/0110383 A1 | 5/2006 | Honjo et al. | |
| 2007/0253976 A1 | 11/2007 | Paterson et al. | |
| 2008/0025979 A1 | 1/2008 | Honjo et al. | |
| 2009/0263865 A1 | 10/2009 | Honjo et al. | |
| 2009/0297518 A1 | 12/2009 | Honjo et al. | |
| 2011/0081341 A1 | 4/2011 | Honjo et al. | |
| 2011/0129499 A1 | 6/2011 | Maciag et al. | |
| 2011/0271358 A1 | 11/2011 | Freeman et al. | |
| 2011/0280878 A1 | 11/2011 | Honjo et al. | |
| 2013/0164294 A1 | 6/2013 | Honjo et al. | |
| 2014/0186387 A1 | 7/2014 | Lauer et al. | |
| 2014/0314714 A1 | 10/2014 | Honjo et al. | |
| 2015/0093380 A1 | 4/2015 | Honjo et al. | |
| 2015/0118234 A1 | 4/2015 | Honjo et al. | |
| 2015/0197572 A1 | 7/2015 | Honjo et al. | |
| 2016/0158355 A1 | 6/2016 | Honjo et al. | |
| 2016/0158356 A1 | 6/2016 | Honjo et al. | |
| 2017/0051060 A1 | 2/2017 | Honjo et al. | |

FOREIGN PATENT DOCUMENTS

| | | |
|---|---|---|
| WO | 9639154 | 12/1996 |
| WO | 9703211 | 1/1997 |
| WO | 2004004771 A1 | 1/2004 |
| WO | 2004056875 A1 | 7/2004 |
| WO | 2004072286 A1 | 8/2004 |
| WO | 2008156712 A1 | 12/2008 |
| WO | 2010027827 A2 | 3/2010 |

(Continued)

OTHER PUBLICATIONS

Hannan et al (Cancer Immunol. 2012. 61(12): 2227-38).*
Chen, B.J., et al., "PD-L1 Expression Is Characteristic of a Subset of Aggressive B-cell Lymphomas and Virus-Associated Malignancies," Clinical Cancer Research, 19(13), pp. 3462-3473 (2013).
WHO Drug Information, vol. 27, No. 2, pp. 161-162 (2013).
WHO Drug Information, vol. 27, No. 1, pp. 68-69 (2013).
Wallecha, A., et al., "Construction and Characterization of an Attenuated Listeria monocytogenes Strain for Clinical Use in Cancer Immunotherapy," Clinical and Vaccine Immunology, 16(1), pp. 96-103 (2009).
Sharpe, A.H., et al., "The function of programmed cell death 1 and its ligands in regulating autoimmunity and infection," Nature Immunology, 8(3), pp. 239-245 (2007).
Dong H., et al., "Tumor-associated B7-H1 promotes T-cell apoptosis: A potential mechanism of immune evasion," Nature Medicine, 8(8), pp. 793-800 (2002).

(Continued)

*Primary Examiner* — Jennifer Graser
(74) *Attorney, Agent, or Firm* — Fitzpatrick, Cella, Harper & Scinto

(57) ABSTRACT

The present disclosure describes combination therapies comprising an antagonist of Programmed Death 1 receptor (PD-1) and a *Listeria* based strain that expresses prostate-tissue specific antigen (PSA), and the use of the combination therapies for the treatment of prostate cancer.

15 Claims, 15 Drawing Sheets

(56) References Cited

FOREIGN PATENT DOCUMENTS

| WO | 2010077634 A1 | 7/2010 |
| WO | 2011066342 A2 | 6/2011 |
| WO | 2012/135408 * | 10/2012 |
| WO | 2012135408 A1 | 10/2012 |
| WO | 2013019906 A1 | 2/2013 |
| WO | 2014100079 A1 | 6/2014 |

OTHER PUBLICATIONS

Yang, W., et al., "PD-L1: PD-1 Interaction Contributes to the Functional Suppression of T-Cell Responses to Human Uveal Melanoma Cells in Vitro," Investigative Ophthalmology & Visual Science, 49(6), pp. 2518-2525 (2008).

Ghebeh, H., et al., "The B7-H1 (PD-L1) T Lymphocyte-Inhibitory Molecule is Expressed in Breast Cancer Patients with Infiltrating Ductal Carcinoma: Correlation with Important High-Risk Prognostic Factors," Neoplasia, 8(3), pp. 190-198 (2006).

Hamanishi J., et al., "Programmed cell death 1 ligand 1 and tumor-infiltrating CD8+ T lymphocytes are prognostic factors of human ovarian cancer," Proceeding of the National Academy of Sciences, 104(9), pp. 3360-3365 (2007).

Thompson R.H., et al., "Significance of B7-H1 Overexpression in Kidney Cancer," Clinical Genitourinary Cancer, 5, pp. 206-211 (2006).

Nomi, T., et al., "Clinical Significance and Therapeutic Potential of the Programmed Death-1 Ligand/Programmed Death-1 Pathway in Human Pancreatic Cancer," Clinical Cancer Research, 13(7), pp. 2151-2157 (2007).

Ohigashi, Y., et al., "Clinical Significance of Programmed Death-1 Ligand-1 and Programmed Death-1 Ligand-2 Expression in Human Esophageal Cancer," Clinical Cancer Research, 11(8), pp. 2947-2953 (2005).

Inman, B.A., et al., "PD-L1 (B7-H1) Expression by Urothelial Carcinoma of the Bladder and BCG-Induced Granulomata: Associations With Localized Stage Progression," Cancer, 109(8), pp. 1499-1505 (2007).

Shimauchi, T., et al., "Augmented expression of programmed death-1 in both neoplastic and non-neoplastic CD4+ T-cells in adult T-cell leukemia/lymphoma," Int. J. Cancer, 121, pp. 2585-2590 (2007).

Gao, Q., et al., "Overexpression of PD-L1 Significantly Associates with Tumor Aggressiveness and Postoperative Recurrence in Human Hepatocellular Carcinoma," Clinical Cancer Research, 15(3), pp. 971-979 (2009).

Nakanishi, J., et al., "Overexpression of B7-H1 (PD-L1) significantly associates with tumor grade and postoperative prognosis in human urothelial cancers," Cancer Immunol. Immunother., 56, pp. 1173-1182 (2007).

Hino, R., et al., "Tumor Cell Expression of Programmed Cell Death-1 Ligand 1 is a Prognostic Factor for Malignant Melanoma," Cancer, pp. 1757-1768 (2010).

Ghebeh, H., et al., "FOXP3+ Tregs and B7-H1+/PD-1+T lymphocytes co-infiltrate the tumor tissues of high-risk breast cancer patients: Implication for immunotherapy," BMC Cancer, 8(57) (2008).

Ahmadzadeh, M., et al., "Tumor antigen-specific CD8 T cells infiltrating the tumor express high levels of PD-1 and are functionally impaired," Blood, 114(8), pp. 1537-1544 (2009).

Thompson, R.H., et al., "PD-1 Is Expressed by Tumor Infiltrating Immune Cells and Is Associated with Poor Outcome for Patients with Renal Cell Carcinoma," Clinical Cancer Research, 13(6), pp. 1757-1761 (2007).

\* cited by examiner hPD-1.08A light chain CDR1 (SEQ ID NO:1)

Arg Ala Ser Lys Ser Val Ser Thr Ser Gly Phe Ser Tyr Leu His hPD-1.08A light chain CDR2 (SEQ ID NO:2)

Leu Ala Ser Asn Leu Glu Ser hPD-1-08A light chain CDR3 (SEQ ID NO:3)

Gln His Ser Trp Glu Leu Pro Leu Thr hPD-1.08A heavy chain CDR1 (SEQ ID NO:4)

Ser Tyr Tyr Leu Tyr hPD-1.08A heavy chain CDR2 (SEQ ID NO:5)

Gly Val Asn Pro Ser Asn Gly Gly Thr Asn Phe Ser Glu Lys Phe Lys Ser hPD-1.08A heavy chain CDR3 (SEQ ID NO:6)

Arg Asp Ser Asn Tyr Asp Gly Gly Phe Asp Tyr

Figure 1 hPD-1.09A light chain CDR1 (SEQ ID NO:7)

Arg Ala Ser Lys Gly Val Ser Thr Ser Gly Tyr Ser Tyr Leu His hPD-1.09A light chain CDR2 (SEQ ID NO:8)

Leu Ala Ser Tyr Leu Glu Ser hPD-1.09A light chain CDR3 (SEQ ID NO:9)

Gln His Ser Arg Asp Leu Pro Leu Thr hPD-1.09A heavy chain CDR1 (SEQ ID NO:10)

Asn Tyr Tyr Met Tyr hPD-1.09A heavy chain CDR2 (SEQ ID NO:11)

Gly Ile Asn Pro Ser Asn Gly Gly Thr Asn Phe Asn Glu Lys Phe Lys Asn hPD-1.09A heavy chain CDR3 (SEQ ID NO:12)

Arg Asp Tyr Arg Phe Asp Met Gly Phe Asp Tyr

Figure 2

109A-H heavy chain variable region (SEQ ID NO:13)

Gln Val Gln Leu Val Gln Ser Gly Val Glu Val Lys Lys Pro Gly Ala Ser Val Lys
Val Ser Cys Lys Ala Ser Gly Tyr Thr Phe Thr Asn Tyr Tyr Met Tyr Trp Val Arg
Gln Ala Pro Gly Gln Gly Leu Glu Trp Met Gly Gly Ile Asn Pro Ser Asn Gly Gly
Thr Asn Phe Asn Glu Lys Phe Lys Asn Arg Val Thr Leu Thr Thr Asp Ser Ser Thr
Thr Thr Ala Tyr Met Glu Leu Lys Ser Leu Gln Phe Asp Asp Thr Ala Val Tyr Tyr
Cys Ala Arg Arg Asp Tyr Arg Phe Asp Met Gly Phe Asp Tyr Trp Gly Gln Gly Thr
Thr Val Thr Val Ser Ser

409A-H heavy chain full length (SEQ ID NO:14)

Gln Val Gln Leu Val Gln Ser Gly Val Glu Val Lys Lys Pro Gly Ala Ser Val Lys
Val Ser Cys Lys Ala Ser Gly Tyr Thr Phe Thr Asn Tyr Tyr Met Tyr Trp Val Arg
Gln Ala Pro Gly Gln Gly Leu Glu Trp Met Gly Gly Ile Asn Pro Ser Asn Gly Gly
Thr Asn Phe Asn Glu Lys Phe Lys Asn Arg Val Thr Leu Thr Thr Asp Ser Ser Thr
Thr Thr Ala Tyr Met Glu Leu Lys Ser Leu Gln Phe Asp Asp Thr Ala Val Tyr Tyr
Cys Ala Arg Arg Asp Tyr Arg Phe Asp Met Gly Phe Asp Tyr Trp Gly Gln Gly Thr
Thr Val Thr Val Ser Ser Ala Ser Thr Lys Gly Pro Ser Val Phe Pro Leu Ala Pro
Cys Ser Arg Ser Thr Ser Glu Ser Thr Ala Ala Leu Gly Cys Leu Val Lys Asp Tyr
Phe Pro Glu Pro Val Thr Val Ser Trp Asn Ser Gly Ala Leu Thr Ser Gly Val His
Thr Phe Pro Ala Val Leu Gln Ser Ser Gly Leu Tyr Ser Leu Ser Ser Val Val Thr
Val Pro Ser Ser Ser Leu Gly Thr Lys Thr Tyr Thr Cys Asn Val Asp His Lys Pro
Ser Asn Thr Lys Val Asp Lys Arg Val Glu Ser Lys Tyr Gly Pro Pro Cys Pro Pro
Cys Pro Ala Pro Glu Phe Leu Gly Gly Pro Ser Val Phe Leu Phe Pro Pro Lys Pro
Lys Asp Thr Leu Met Ile Ser Arg Thr Pro Glu Val Thr Cys Val Val Val Asp Val
Ser Gln Glu Asp Pro Glu Val Gln Phe Asn Trp Tyr Val Asp Gly Val Glu Val His
Asn Ala Lys Thr Lys Pro Arg Glu Glu Gln Phe Asn Ser Thr Tyr Arg Val Val Ser
Val Leu Thr Val Leu His Gln Asp Trp Leu Asn Gly Lys Glu Tyr Lys Cys Lys Val
Ser Asn Lys Gly Leu Pro Ser Ser Ile Glu Lys Thr Ile Ser Lys Ala Lys Gly Gln
Pro Arg Glu Pro Gln Val Tyr Thr Leu Pro Pro Ser Gln Glu Glu Met Thr Lys Asn
Gln Val Ser Leu Thr Cys Leu Val Lys Gly Phe Tyr Pro Ser Asp Ile Ala Val Glu
Trp Glu Ser Asn Gly Gln Pro Glu Asn Asn Tyr Lys Thr Thr Pro Pro Val Leu Asp
Ser Asp Gly Ser Phe Phe Leu Tyr Ser Arg Leu Thr Val Asp Lys Ser Arg Trp Gln
Glu Gly Asn Val Phe Ser Cys Ser Val Met His Glu Ala Leu His Asn His Tyr Thr
Gln Lys Ser Leu Ser Leu Ser Leu Gly Lys

Figure 3

K09A-L-11 light chain variable region (SEQ ID NO:15)

Glu Ile Val Leu Thr Gln Ser Pro Ala Thr Leu Ser Leu Ser Pro Gly Glu Arg Ala
Thr Leu Ser Cys Arg Ala Ser Lys Gly Val Ser Thr Ser Gly Tyr Ser Tyr Leu His
Trp Tyr Gln Gln Lys Pro Gly Gln Ala Pro Arg Leu Leu Ile Tyr Leu Ala Ser Tyr
Leu Glu Ser Gly Val Pro Ala Arg Phe Ser Gly Ser Gly Ser Gly Thr Asp Phe Thr
Leu Thr Ile Ser Ser Leu Glu Pro Glu Asp Phe Ala Val Tyr Tyr Cys Gln His Ser
Arg Asp Leu Pro Leu Thr Phe Gly Gly Gly Thr Lys Val Glu Ile Lys

K09A-L-16 light chain variable region (SEQ ID NO:16)

Glu Ile Val Leu Thr Gln Ser Pro Leu Ser Leu Pro Val Thr Pro Gly Glu Pro Ala
Ser Ile Ser Cys Arg Ala Ser Lys Gly Val Ser Thr Ser Gly Tyr Ser Tyr Leu His
Trp Tyr Leu Gln Lys Pro Gly Gln Ser Pro Gln Leu Leu Ile Tyr Leu Ala Ser Tyr
Leu Glu Ser Gly Val Pro Asp Arg Phe Ser Gly Ser Gly Ser Gly Thr Asp Phe Thr
Leu Lys Ile Ser Arg Val Glu Ala Glu Asp Val Gly Val Tyr Tyr Cys Gln His Ser
Arg Asp Leu Pro Leu Thr Phe Gly Gln Gly Thr Lys Leu Glu Ile Lys

K09A-L-17 light chain variable region (SEQ ID NO:17)

Asp Ile Val Met Thr Gln Thr Pro Leu Ser Leu Pro Val Thr Pro Gly Glu Pro Ala
Ser Ile Ser Cys Arg Ala Ser Lys Gly Val Ser Thr Ser Gly Tyr Ser Tyr Leu His
Trp Tyr Leu Gln Lys Pro Gly Gln Ser Pro Gln Leu Leu Ile Tyr Leu Ala Ser Tyr
Leu Glu Ser Gly Val Pro Asp Arg Phe Ser Gly Ser Gly Ser Gly Thr Ala Phe Thr
Leu Lys Ile Ser Arg Val Glu Ala Glu Asp Val Gly Leu Tyr Tyr Cys Gln His Ser
Arg Asp Leu Pro Leu Thr Phe Gly Gln Gly Thr Lys Leu Glu Ile Lys

Figure 4

K09A-L-11 light chain full length (SEQ ID NO:18)

Glu Ile Val Leu Thr Gln Ser Pro Ala Thr Leu Ser Leu Ser Pro Gly Glu Arg Ala
Thr Leu Ser Cys Arg Ala Ser Lys Gly Val Ser Thr Ser Gly Tyr Ser Tyr Leu His
Trp Tyr Gln Gln Lys Pro Gly Gln Ala Pro Arg Leu Leu Ile Tyr Leu Ala Ser Tyr
Leu Glu Ser Gly Val Pro Ala Arg Phe Ser Gly Ser Gly Ser Gly Thr Asp Phe Thr
Leu Thr Ile Ser Ser Leu Glu Pro Glu Asp Phe Ala Val Tyr Tyr Cys Gln His Ser
Arg Asp Leu Pro Leu Thr Phe Gly Gly Gly Thr Lys Val Glu Ile Lys Arg Thr Val
Ala Ala Pro Ser Val Phe Ile Phe Pro Pro Ser Asp Glu Gln Leu Lys Ser Gly Thr
Ala Ser Val Val Cys Leu Leu Asn Asn Phe Tyr Pro Arg Glu Ala Lys Val Gln Trp
Lys Val Asp Asn Ala Leu Gln Ser Gly Asn Ser Gln Glu Ser Val Thr Glu Gln Asp
Ser Lys Asp Ser Thr Tyr Ser Leu Ser Ser Thr Leu Thr Leu Ser Lys Ala Asp Tyr
Glu Lys His Lys Val Tyr Ala Cys Glu Val Thr His Gln Gly Leu Ser Ser Pro Val
Thr Lys Ser Phe Asn Arg Gly Glu Cys

K09A-L-16 light chain full length (SEQ ID NO:19)

Glu Ile Val Leu Thr Gln Ser Pro Leu Ser Leu Pro Val Thr Pro Gly Glu Pro Ala
Ser Ile Ser Cys Arg Ala Ser Lys Gly Val Ser Thr Ser Gly Tyr Ser Tyr Leu His
Trp Tyr Leu Gln Lys Pro Gly Gln Ser Pro Gln Leu Leu Ile Tyr Leu Ala Ser Tyr
Leu Glu Ser Gly Val Pro Asp Arg Phe Ser Gly Ser Gly Ser Gly Thr Asp Phe Thr
Leu Lys Ile Ser Arg Val Glu Ala Glu Asp Val Gly Val Tyr Tyr Cys Gln His Ser
Arg Asp Leu Pro Leu Thr Phe Gly Gln Gly Thr Lys Leu Glu Ile Lys Arg Thr Val
Ala Ala Pro Ser Val Phe Ile Phe Pro Pro Ser Asp Glu Gln Leu Lys Ser Gly Thr
Ala Ser Val Val Cys Leu Leu Asn Asn Phe Tyr Pro Arg Glu Ala Lys Val Gln Trp
Lys Val Asp Asn Ala Leu Gln Ser Gly Asn Ser Gln Glu Ser Val Thr Glu Gln Asp
Ser Lys Asp Ser Thr Tyr Ser Leu Ser Ser Thr Leu Thr Leu Ser Lys Ala Asp Tyr
Glu Lys His Lys Val Tyr Ala Cys Glu Val Thr His Gln Gly Leu Ser Ser Pro Val
Thr Lys Ser Phe Asn Arg Gly Glu Cys

Figure 5A

K09A-L-17 light chain full length (SEQ ID NO:20)

```
Asp Ile Val Met Thr Gln Thr Pro Leu Ser Leu Pro Val Thr Pro Gly Glu Pro Ala
Ser Ile Ser Cys Arg Ala Ser Lys Gly Val Ser Thr Ser Gly Tyr Ser Tyr Leu His
Trp Tyr Leu Gln Lys Pro Gly Gln Ser Pro Gln Leu Leu Ile Tyr Leu Ala Ser Tyr
Leu Glu Ser Gly Val Pro Asp Arg Phe Ser Gly Ser Gly Ser Gly Thr Ala Phe Thr
Leu Lys Ile Ser Arg Val Glu Ala Glu Asp Val Gly Leu Tyr Tyr Cys Gln His Ser
Arg Asp Leu Pro Leu Thr Phe Gly Gln Gly Thr Lys Leu Glu Ile Lys Arg Thr Val
Ala Ala Pro Ser Val Phe Ile Phe Pro Pro Ser Asp Glu Gln Leu Lys Ser Gly Thr
Ala Ser Val Val Cys Leu Leu Asn Asn Phe Tyr Pro Arg Glu Ala Lys Val Gln Trp
Lys Val Asp Asn Ala Leu Gln Ser Gly Asn Ser Gln Glu Ser Val Thr Glu Gln Asp
Ser Lys Asp Ser Thr Tyr Ser Leu Ser Ser Thr Leu Thr Leu Ser Lys Ala Asp Tyr
Glu Lys His Lys Val Tyr Ala Cys Glu Val Thr His Gln Gly Leu Ser Ser Pro Val
Thr Lys Ser Phe Asn Arg Gly Glu Cys
```

Heavy chain (SEQ ID NO:21)

| | | | | | |
|---|---|---|---|---|---|
| QVQLVQSGVE | VKKPGASVKV | SCKASGYTFT | NYYMYWVRQA | PGQGLEWMGG | 50 |
| INPSNGGTNF | NEKFKNRVTL | TTDSSTTTAY | MELKSLQFDD | TAVYYCARRD | 100 |
| YRFDMGFDYW | GQGTTVTVSS | ASTKGPSVFP | LAPCSRSTSE | STAALGCLVK | 150 |
| DYFPEPVTVS | WNSGALTSGV | HTFPAVLQSS | GLYSLSSVVT | VPSSSLGTKT | 200 |
| YTCNVDHKPS | NTKVDKRVES | KYGPPCPPCP | APEFLGGPSV | FLFPPKPKDT | 250 |
| LMISRTPEVT | CVVVDVSQED | PEVQFNWYVD | GVEVHNAKTK | PREEQFNSTY | 300 |
| RVVSVLTVLH | QDWLNGKEYK | CKVSNKGLPS | SIEKTISKAK | GQPREPQVYT | 350 |
| LPPSQEEMTK | NQVSLTCLVK | GFYPSDIAVE | WESNGQPENN | YKTTPPVLDS | 400 |
| DGSFFLYSRL | TVDKSRWQEG | NVFSCSVMHE | ALHNHYTQKS | LSLSLGK | 447 |

Light chain (SEQ ID NO:22)

| | | | | | |
|---|---|---|---|---|---|
| EIVLTQSPAT | LSLSPGERAT | LSCRASKGVS | TSGYSYLHWY | QQKPGQAPRL | 50 |
| LIYLASYLES | GVPARFSGSG | SGTDFTLTIS | SLEPEDFAVY | YCQHSRDLPL | 100 |
| TFGGGTKVEI | KRTVAAPSVF | IFPPSDEQLK | SGTASVVCLL | NNFYPREAKV | 150 |
| QWKVDNALQS | GNSQESVTEQ | DSKDSTYSLS | STLTLSKADY | EKHKVYACEV | 200 |
| THQGLSSPVT | KSFNRGEC | | | | 219 |

Figure 6

Nivolumab

Heavy chain (SEQ ID NO:23)

| | | | | | |
|---|---|---|---|---|---|
|QVQLVESGGG|VVQPGRSLRL|DCKASGITFS|NSGMHWVRQA|PGKGLEWVAV|50|
|IWYDGSKRYY|ADSVKGRFTI|SRDNSKNTLF|LQMNSLRAED|TAVYYCATND|100|
|DYWGQGTLVT|VSSASTKGPS|VFPLAPCSRS|TSESTAALGC|LVKDYFPEPV|150|
|TVSWNSGALT|SGVHTFPAVL|QSSGLYSLSS|VVTVPSSSLG|TKTYTCNVDH|200|
|KPSNTKVDKR|VESKYGPPCP|PCPAPEFLGG|PSVFLFPPKP|KDTLMISRTP|250|
|EVTCVVVDVS|QEDPEVQFNW|YVDGVEVHNA|KTKPREEQFN|STYRVVSVLT|300|
|VLHQDWLNGK|EYKCKVSNKG|LPSSIEKTIS|KAKGQPREPQ|VYTLPPSQEE|350|
|MTKNQVSLTC|LVKGFYPSDI|AVEWESNGQP|ENNYKTTPPV|LDSDGSFFLY|400|
|SRLTVDKSRW|QEGNVFSCSV|MHEALHNHYT|QKSLSLSLGK| |440|

Light chain (SEQ ID NO:24)

| | | | | | |
|---|---|---|---|---|---|
|EIVLTQSPAT|LSLSPGERAT|LSCRASQSVS|SYLAWYQQKP|GQAPRLLIYD|50|
|ASNRATGIPA|RFSGSGSGTD|FTLTISSLEP|EDFAVYYCQQ|SSNWPRTFGQ|100|
|GTKVEIKRTV|AAPSVFIFPP|SDEQLKSGTA|SVVCLLNNFY|PREAKVQWKV|150|
|DNALQSGNSQ|ESVTEQDSKD|STYSLSSTLT|LSKADYEKHK|VYACEVTHQG|200|
|LSSPVTKSFN|RGEC| | | |214|

Figure 7

Figure 9C cggagtgtatactggcttactatgttggcactgatgagggtgtcagtgaagtgcttcatgtggcaggagaaaaaaggctgcaccggtgc
gtcagcagaatatgtgatacaggatatattccgcttcctcgctcactgactcgctacgctcggtcgttcgactgcggcgagcggaaatg
gcttacgaacggggcggagatttcctggaagatgccaggaagatacttaacagggaagtgagagggccgcggcaaagccgtttttc
cataggctccgccccccctgacaagcatcacgaaatctgacgctcaaatcagtggtggcgaaacccgacaggactataaagataccag
gcgtttccccctggcggctccctcgtgcgctctcctgttcctgcctttcggtttaccggtgtcattccgctgttatggccgcgtttgtctcatt
ccacgcctgacactcagttccgggtaggcagttcgctccaagctggactgtatgcacgaaccccccgttcagtccgaccgctgcgcct
tatccggtaactatcgtcttgagtccaacccggaaagacatgcaaaagcaccactggcagcagccactggtaattgatttagaggagtt
agtcttgaagtcatgcgccggttaaggctaaactgaaggacaagttttggtgactgcgctcctccaagccagttacctcggttcaaaga
gttggtagctcagagaaccttcgaaaaaccgccctgcaaggcggttttttcgttttcagagcaagagattacgcgcagaccaaaacgat
ctcaagaagatcatcttattaatcagataaaatatttctagccctcctttgattagtatattcctatcttaaagttacttttatgtggaggcattaa
catttgttaatgacgtcaaaaggatagcaagactagaataaagctataaagcaagcatataatattgcgtttcatctttagaagcgaatttc
gccaatattataattatcaaaagagaggggtggcaaacggtatttggcattattaggttaaaaaatgtagaaggagagtgaaacccatga
aaaaaataatgctagtttttattacacttatattagttagtctaccaattgcgcaacaaactgaagcaaaggatgcatctgcattcaataaag
aaaattcaatttcatccatggcaccaccagcatctccgcctgcaagtcctaagacgccaatcgaaaagaaacacgcggatgaaatcga
taagtatatacaaggattggattacaataaaaacaatgtattagtataccacggagatgcagtgacaaatgtgccgccaagaaaaggtta
caaagatggaaatgaatatattgttgtggagaaaaagaagaaatccatcaatcaaaataatgcagacattcaagttgtgaatgcaatttcg
agcctaacctatccaggtgctctcgtaaaagcgaattcggaattagtagaaaatcaaccagatgttctccctgtaaaacgtgattcattaa
cactcagcattgatttgccaggtatgactaatcaagacaataaaatagttgtaaaaaatgccactaaatcaaacgttaacaacgcagtaa
atacattagtggaaagatggaatgaaaaatatgctcaagcttatccaaatgtaagtgcaaaaattgattatgatgacgaaatggcttacag
tgaatcacaattaattgcgaaatttggtacagcatttaaagctgtaaataatagcttgaatgtaaacttcggcgcaatcagtgaagggaaa
atgcaagaagaagtcattagtttttaaacaaatttactataacgtgaatgttaatgaacctacaagaccttccagattttcggcaaagctgtt
actaaagagcagttgcaagcgcttggagtgaatgcagaaaatcctcctgcatatatctcaagtgtggcgtatggccgtcaagtttatttga
aattatcaactaattcccatagtactaaagtaaaagctgcttttgatgctgccgtaagcggaaaatctgtctcaggtgatgtagaactaaca
aatatcatcaaaaattcttccttcaaagccgtaatttacggaggttccgcaaaagatgaagttcaaatcatcgacggcaacctcggagac
ttacgcgatattttgaaaaaaggcgctacttttaatcgagaaacaccaggagttcccattgcttatacaacaaacttcctaaaagacaatg
aattagctgttattaaaaacaactcagaatatattgaaacaacttcaaaagcttatacagatggaaaaattaacatcgatcactctggagga
tacgttgctcaattcaacatttcttgggatgaagtaaattatgatctcgag<ins>attgtgggaggctgggagtgcgagaagcattcccaaccct</ins>
<ins>ggcaggtgcttgtggcctctcgtggcagggcagtctgcggcggtgttctggtgcaccccagtgggtcctcacagctgcccactgcat</ins>
<ins>caggaacaaaagcgtgatcttgctgggtcggcacagcctgtttcatcctgaagacacaggccaggtatttcaggtcagccacagcttc</ins>
<ins>ccacacccgctctacgatatgagcctcctgaagaatcgattcctcaggccaggtgatgactccagccacgacctcatgctgctccgcct</ins>
<ins>gtcagagcctgccgagctcacggatgctgtgaaggtcatggacctgcccacccaggagccagcactggggaccacctgctacgcct</ins>
<ins>caggctggggcagcattgaaccagaggagttcttgaccccaaagaaacttcagtgtgtggacctccatgttatttccaatgacgtgtgtg</ins>
<ins>cgcaagttcaccctcagaaggtgaccaagttcatgctgtgtgctggacgctggacagggggcaaaagcacctgctcgggtgattctg</ins>
<ins>ggggcccacttgtctgttatggtgtgcttcaaggtatcacgtcatggggcagtgaaccatgtgccctgcccgaaaggccttccctgtaca</ins>
<ins>ccaaggtggtgcattaccggaagtggatcaaggacaccatcgtgccaaccccTAA</ins>cccgggccactaactcaacgctagtagtg
gatttaatcccaaatgagccaacagaaccagaaccagaaacagaacaagtaacattggagttagaaatggaagaagaaaaaagcaat
gatttcgtgtgaataatgcacgaaatcattgcttattttttaaaaagcgatatactagatataacgaaacaacgaactgaataaagaataca
aaaaaagagccacgaccagttaaagcctgagaaactttaactgcgagccttaattgattaccaccaatcaattaaagaagtcgagaccc
aaaatttggtaaagtatttaattactttattaatcagatacttaaatatctgtaaacccattatatcgggttttgagggggatttcaagtctttaag
aagataccaggcaatcaattaagaaaaacttagttgattgccttttttgttgtgattcaactttgatcgtagcttctaactaattaattttcgtaa
gaaaggagaacagctgaatgaatatccctttgttgtagaaactgtgcttcatgacggcttgttaaagtacaaatttaaaaatagtaaaatt
cgctcaatcactaccaagccaggtaaaagtaaaggggctattttgcgtatcgctcaaaaaaagcatgattggcggacgtggcgttgtt
ctgacttccgaagaagcgattcacgaaatcaagatacatttacgcattggacaccaaacgtttatcgttatggtacgtatgcagacgaa
aaccgttcatacactaaaggacattctgaaaacaatttaagacaaatcaataccttctttattgatttgatattcacacggaaaaagaaact
atttcagcaagcgatattttaacaacagctattgattaggttttatgcctacgttaattatcaaatctgataaaggttatcaagcatattttgttt
tagaaacgccagtctatgtgacttcaaaatcagaatttaaatctgtcaaagcagccaaaataatctcgcaaaatatccgagaatattttgg
aaagtctttgccagttgatctaacgtgcaatcattttgggattgctcgtataccaagaacggacaatgtagaatttttgatcccaattaccgt
tattctttcaaagaatggcaagattggtctttcaaacaaacagataataagggctttactcgttcaagtctaacggttttaagcggtacaga Figure 9C (continued)

aggcaaaaaacaagtagatgaaccctggtttaatctcttattgcacgaaacgaaattttcaggagaaaagggtttagtagggcgcaata
gcgttatgtttaccctctctttagcctactttagttcaggctattcaatcgaaacgtgcgaatataatatgtttgagtttaataatcgattagatc
aacccttagaagaaaaagaagtaatcaaaattgttagaagtgcctattcagaaaactatcaaggggctaataggggaatacattaccattc
tttgcaaagcttgggtatcaagtgatttaaccagtaaagatttatttgtccgtcaagggtggtttaaattcaagaaaaaaagaagcgaacgt
caacgtgttcatttgtcagaatggaaagaagatttaatggcttatattagcgaaaaaagcgatgtatacaagccttatttagcgacgacca
aaaaagagattagagaagtgctaggcattcctgaacggacattagataaattgctgaaggtactgaaggcgaatcaggaaattttcttta
agattaaaccaggaagaaatggtggcattcaacttgctagtgttaaatcattgttgctatcgatcattaaattaaaaaaagaagaacgaga
aagctatataaaggcgctgacagcttcgtttaatttagaacgtacatttattcaagaaactctaaacaaattggcagaacgccccaaaacg
gacccacaactcgatttgtttagctacgatacaggctgaaaataaaacccgcactatgccattacatttatatctatgatacgtgtttgttttt
ctttgctggctagcttaattgcttatatttacctgcaataaaggatttcttacttccattatactcccattttccaaaaacatacggggaacacg
ggaacttattgtacaggccacctcatagttaatggtttcgagccttcctgcaatctcatccatggaaatatattcatcccctgccggcctat
taatgtgacttttgtgcccggcggatattcctgatccagctccaccataaattggtccatgcaaattcggccggcaattttcaggcgttttcc
cttcacaaggatgtcggtccctttcaattttcggagccagccgtccgcatagcctacaggcaccgtcccgatccatgtgtcttttccgct
gtgtactcggctccgtagctgacgctctcgccttttctgatcagtttgacatgtgacagtgtcgaatgcagggtaaatgccggacgcagc
tgaaacggtatctcgtccgacatgtcagcagacgggcgaaggccatacatgccgatgccgaatctgactgcattaaaaaagccttttt
cagccggagtccagcggcgctgttcgcgcagtggaccattagattctttaacggcagcggagcaatcagctctttaaagcgctcaaac
tgcattaagaaatagcctctttcttttcatccgctgtcgcaaaatgggtaaataccccctttgcactttaaacgagggttgcggtcaagaatt
gccatcacgttctgaacttcttcctctgttttacaccaagtctgttcatccccgtatcgaccttcagatgaaaatgaagagaacctttttcgt
gtggcgggctgcctcctgaagccattcaacagaataacctgttaaggtcacgtcatactcagcagcgattgccacatactccggggga
accgcgccaagcaccaatataggcgccttcaatccctttttgcgcagtgaaatcgcttcatccaaaatggccacggccaagcatgaag
cacctgcgtcaagagcagccttgctgtttctgcatcaccatgcccgtaggcgtttgctttcacaactgccatcaagtggacatgttcacc
gatatgtttttcatattgctgacattttcctttatcgcggacaagtcaatttccgcccacgtatctctgtaaaaaggttttgtgctcatggaaaa
ctcctctcttttttcagaaaatcccagtacgtaattaagtatttgagaattaattttatattgattaatactaagtttacccagttttcacctaaaaa
acaaatgatgagataatagctccaaaggctaaagaggactataccaactatttgttaattaa Sample Size= 21 ; Target Toxicity Probability = 0.25 ; epsilon 1 = 0.05 ; epsilon 2 = 0.05

Sample Size= 21 ; Target Toxicity Probability = 0.3 ; epsilon 1 = 0.05 ; epsilon 2 = 0.05

SEQUENCE LISTING

```
<160> NUMBER OF SEQ ID NOS: 66

<210> SEQ ID NO 1
<211> LENGTH: 15
<212> TYPE: PRT
<213> ORGANISM: Artificial Sequence
<220> FEATURE:
<223> OTHER INFORMATION: Antibody Light Chain CDR

<400> SEQUENCE: 1

Arg Ala Ser Lys Ser Val Ser Thr Ser Gly Phe Ser Tyr Leu His
1               5                   10                  15

<210> SEQ ID NO 2
<211> LENGTH: 7
<212> TYPE: PRT
<213> ORGANISM: Artificial Sequence
<220> FEATURE:
<223> OTHER INFORMATION: Antibody Light Chain CDR
```

<400> SEQUENCE: 2

Leu Ala Ser Asn Leu Glu Ser
1               5

<210> SEQ ID NO 3
<211> LENGTH: 9
<212> TYPE: PRT
<213> ORGANISM: Artificial Sequence
<220> FEATURE:
<223> OTHER INFORMATION: Antibody Light Chain CDR

<400> SEQUENCE: 3

Gln His Ser Trp Glu Leu Pro Leu Thr
1               5

<210> SEQ ID NO 4
<211> LENGTH: 5
<212> TYPE: PRT
<213> ORGANISM: Artificial Sequence
<220> FEATURE:
<223> OTHER INFORMATION: Antibody Heavy Chain CDR

<400> SEQUENCE: 4

Ser Tyr Tyr Leu Tyr
1               5

<210> SEQ ID NO 5
<211> LENGTH: 17
<212> TYPE: PRT
<213> ORGANISM: Artificial Sequence
<220> FEATURE:
<223> OTHER INFORMATION: Antibody Heavy Chain CDR

<400> SEQUENCE: 5

Gly Val Asn Pro Ser Asn Gly Gly Thr Asn Phe Ser Glu Lys Phe Lys
1               5                   10                  15

Ser

<210> SEQ ID NO 6
<211> LENGTH: 11
<212> TYPE: PRT
<213> ORGANISM: Artificial Sequence
<220> FEATURE:
<223> OTHER INFORMATION: Antibody Heavy Chain CDR

<400> SEQUENCE: 6

Arg Asp Ser Asn Tyr Asp Gly Gly Phe Asp Tyr
1               5                   10

<210> SEQ ID NO 7
<211> LENGTH: 15
<212> TYPE: PRT
<213> ORGANISM: Artificial Sequence
<220> FEATURE:
<223> OTHER INFORMATION: Antibody Light Chain CDR

<400> SEQUENCE: 7

Arg Ala Ser Lys Gly Val Ser Thr Ser Gly Tyr Ser Tyr Leu His
1               5                   10                  15

<210> SEQ ID NO 8
<211> LENGTH: 7
<212> TYPE: PRT
<213> ORGANISM: Artificial Sequence
<220> FEATURE:

<223> OTHER INFORMATION: Antibody Light Chain CDR

<400> SEQUENCE: 8

Leu Ala Ser Tyr Leu Glu Ser
1               5

<210> SEQ ID NO 9
<211> LENGTH: 9
<212> TYPE: PRT
<213> ORGANISM: Artificial Sequence
<220> FEATURE:
<223> OTHER INFORMATION: Antibody Light Chain CDR

<400> SEQUENCE: 9

Gln His Ser Arg Asp Leu Pro Leu Thr
1               5

<210> SEQ ID NO 10
<211> LENGTH: 5
<212> TYPE: PRT
<213> ORGANISM: Artificial Sequence
<220> FEATURE:
<223> OTHER INFORMATION: Antibody Heavy Chain CDR

<400> SEQUENCE: 10

Asn Tyr Tyr Met Tyr
1               5

<210> SEQ ID NO 11
<211> LENGTH: 17
<212> TYPE: PRT
<213> ORGANISM: Artificial Sequence
<220> FEATURE:
<223> OTHER INFORMATION: Antibody Heavy Chain CDR

<400> SEQUENCE: 11

Gly Ile Asn Pro Ser Asn Gly Gly Thr Asn Phe Asn Glu Lys Phe Lys
1               5                   10                  15

Asn

<210> SEQ ID NO 12
<211> LENGTH: 11
<212> TYPE: PRT
<213> ORGANISM: Artificial Sequence
<220> FEATURE:
<223> OTHER INFORMATION: Antibody Heavy Chain CDR

<400> SEQUENCE: 12

Arg Asp Tyr Arg Phe Asp Met Gly Phe Asp Tyr
1               5                   10

<210> SEQ ID NO 13
<211> LENGTH: 120
<212> TYPE: PRT
<213> ORGANISM: Artificial Sequence
<220> FEATURE:
<223> OTHER INFORMATION: Humanized Antibody Heavy Chain Variable Region

<400> SEQUENCE: 13

Gln Val Gln Leu Val Gln Ser Gly Val Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Tyr Met Tyr Trp Val Arg Gln Ala Pro Gly Gln Gly Leu Glu Trp Met
        35                  40                  45

Gly Gly Ile Asn Pro Ser Asn Gly Gly Thr Asn Phe Asn Glu Lys Phe
            50                  55                  60

Lys Asn Arg Val Thr Leu Thr Thr Asp Ser Ser Thr Thr Thr Ala Tyr
 65                  70                  75                  80

Met Glu Leu Lys Ser Leu Gln Phe Asp Asp Thr Ala Val Tyr Tyr Cys
                 85                  90                  95

Ala Arg Arg Asp Tyr Arg Phe Asp Met Gly Phe Asp Tyr Trp Gly Gln
                100                 105                 110

Gly Thr Thr Val Thr Val Ser Ser
                115                 120

<210> SEQ ID NO 14
<211> LENGTH: 447
<212> TYPE: PRT
<213> ORGANISM: Artificial Sequence
<220> FEATURE:
<223> OTHER INFORMATION: Humanized Antibody Heavy Chain

<400> SEQUENCE: 14

Gln Val Gln Leu Val Gln Ser Gly Val Glu Val Lys Lys Pro Gly Ala
 1               5                  10                  15

Ser Val Lys Val Ser Cys Lys Ala Ser Gly Tyr Thr Phe Thr Asn Tyr
                 20                  25                  30

Tyr Met Tyr Trp Val Arg Gln Ala Pro Gly Gln Gly Leu Glu Trp Met
             35                  40                  45

Gly Gly Ile Asn Pro Ser Asn Gly Gly Thr Asn Phe Asn Glu Lys Phe
         50                  55                  60

Lys Asn Arg Val Thr Leu Thr Thr Asp Ser Ser Thr Thr Thr Ala Tyr
 65                  70                  75                  80

Met Glu Leu Lys Ser Leu Gln Phe Asp Asp Thr Ala Val Tyr Tyr Cys
                 85                  90                  95

Ala Arg Arg Asp Tyr Arg Phe Asp Met Gly Phe Asp Tyr Trp Gly Gln
                100                 105                 110

Gly Thr Thr Val Thr Val Ser Ser Ala Ser Thr Lys Gly Pro Ser Val
                115                 120                 125

Phe Pro Leu Ala Pro Cys Ser Arg Ser Thr Ser Glu Ser Thr Ala Ala
            130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
                180                 185                 190

Ser Ser Ser Leu Gly Thr Lys Thr Tyr Thr Cys Asn Val Asp His Lys
            195                 200                 205

Pro Ser Asn Thr Lys Val Asp Lys Arg Val Glu Ser Lys Tyr Gly Pro
        210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

```
Thr Lys Pro Arg Glu Glu Gln Phe Asn Ser Thr Tyr Arg Val Val Ser
    290                 295                 300
Val Leu Thr Val Leu His Gln Asp Trp Leu Asn Gly Lys Glu Tyr Lys
305                 310                 315                 320
Cys Lys Val Ser Asn Lys Gly Leu Pro Ser Ser Ile Glu Lys Thr Ile
                325                 330                 335
Ser Lys Ala Lys Gly Gln Pro Arg Glu Pro Gln Val Tyr Thr Leu Pro
            340                 345                 350
Pro Ser Gln Glu Glu Met Thr Lys Asn Gln Val Ser Leu Thr Cys Leu
        355                 360                 365
Val Lys Gly Phe Tyr Pro Ser Asp Ile Ala Val Glu Trp Glu Ser Asn
370                 375                 380
Gly Gln Pro Glu Asn Asn Tyr Lys Thr Thr Pro Pro Val Leu Asp Ser
385                 390                 395                 400
Asp Gly Ser Phe Phe Leu Tyr Ser Arg Leu Thr Val Asp Lys Ser Arg
                405                 410                 415
Trp Gln Glu Gly Asn Val Phe Ser Cys Ser Val Met His Glu Ala Leu
            420                 425                 430
His Asn His Tyr Thr Gln Lys Ser Leu Ser Leu Ser Leu Gly Lys
        435                 440                 445

<210> SEQ ID NO 15
<211> LENGTH: 111
<212> TYPE: PRT
<213> ORGANISM: Artificial Sequence
<220> FEATURE:
<223> OTHER INFORMATION: Humanized Antibody Light Chain Variable Region

<400> SEQUENCE: 15

Glu Ile Val Leu Thr Gln Ser Pro Ala Thr Leu Ser Leu Ser Pro Gly
1               5                   10                  15
Glu Arg Ala Thr Leu Ser Cys Arg Ala Ser Lys Gly Val Ser Thr Ser
            20                  25                  30
Gly Tyr Ser Tyr Leu His Trp Tyr Gln Gln Lys Pro Gly Gln Ala Pro
        35                  40                  45
Arg Leu Leu Ile Tyr Leu Ala Ser Tyr Leu Glu Ser Gly Val Pro Ala
    50                  55                  60
Arg Phe Ser Gly Ser Gly Ser Gly Thr Asp Phe Thr Leu Thr Ile Ser
65                  70                  75                  80
Ser Leu Glu Pro Glu Asp Phe Ala Val Tyr Tyr Cys Gln His Ser Arg
                85                  90                  95
Asp Leu Pro Leu Thr Phe Gly Gly Gly Thr Lys Val Glu Ile Lys
            100                 105                 110

<210> SEQ ID NO 16
<211> LENGTH: 111
<212> TYPE: PRT
<213> ORGANISM: Artificial Sequence
<220> FEATURE:
<223> OTHER INFORMATION: Humanized Antibody Light Chain Variable Region

<400> SEQUENCE: 16

Glu Ile Val Leu Thr Gln Ser Pro Leu Ser Leu Pro Val Thr Pro Gly
1               5                   10                  15
Glu Pro Ala Ser Ile Ser Cys Arg Ala Ser Lys Gly Val Ser Thr Ser
            20                  25                  30
Gly Tyr Ser Tyr Leu His Trp Tyr Leu Gln Lys Pro Gly Gln Ser Pro
```

```
            35                  40                  45

Gln Leu Leu Ile Tyr Leu Ala Ser Tyr Leu Glu Ser Gly Val Pro Asp
         50                  55                  60

Arg Phe Ser Gly Ser Gly Ser Gly Thr Asp Phe Thr Leu Lys Ile Ser
 65                  70                  75                  80

Arg Val Glu Ala Glu Asp Val Gly Val Tyr Tyr Cys Gln His Ser Arg
                 85                  90                  95

Asp Leu Pro Leu Thr Phe Gly Gln Gly Thr Lys Leu Glu Ile Lys
            100                 105                 110

<210> SEQ ID NO 17
<211> LENGTH: 111
<212> TYPE: PRT
<213> ORGANISM: Artificial Sequence
<220> FEATURE:
<223> OTHER INFORMATION: Humanized Antibody Light Chain Variable Region

<400> SEQUENCE: 17

Asp Ile Val Met Thr Gln Thr Pro Leu Ser Leu Pro Val Thr Pro Gly
 1               5                  10                  15

Glu Pro Ala Ser Ile Ser Cys Arg Ala Ser Lys Gly Val Ser Thr Ser
                 20                  25                  30

Gly Tyr Ser Tyr Leu His Trp Tyr Leu Gln Lys Pro Gly Gln Ser Pro
            35                  40                  45

Gln Leu Leu Ile Tyr Leu Ala Ser Tyr Leu Glu Ser Gly Val Pro Asp
         50                  55                  60

Arg Phe Ser Gly Ser Gly Ser Gly Thr Ala Phe Thr Leu Lys Ile Ser
 65                  70                  75                  80

Arg Val Glu Ala Glu Asp Val Gly Leu Tyr Tyr Cys Gln His Ser Arg
                 85                  90                  95

Asp Leu Pro Leu Thr Phe Gly Gln Gly Thr Lys Leu Glu Ile Lys
            100                 105                 110

<210> SEQ ID NO 18
<211> LENGTH: 218
<212> TYPE: PRT
<213> ORGANISM: Artificial Sequence
<220> FEATURE:
<223> OTHER INFORMATION: Humanized Antibody Light Chain

<400> SEQUENCE: 18

Glu Ile Val Leu Thr Gln Ser Pro Ala Thr Leu Ser Leu Ser Pro Gly
 1               5                  10                  15

Glu Arg Ala Thr Leu Ser Cys Arg Ala Ser Lys Gly Val Ser Thr Ser
                 20                  25                  30

Gly Tyr Ser Tyr Leu His Trp Tyr Gln Gln Lys Pro Gly Gln Ala Pro
            35                  40                  45

Arg Leu Leu Ile Tyr Leu Ala Ser Tyr Leu Glu Ser Gly Val Pro Ala
         50                  55                  60

Arg Phe Ser Gly Ser Gly Ser Gly Thr Asp Phe Thr Leu Thr Ile Ser
 65                  70                  75                  80

Ser Leu Glu Pro Glu Asp Phe Ala Val Tyr Tyr Cys Gln His Ser Arg
                 85                  90                  95

Asp Leu Pro Leu Thr Phe Gly Gly Gly Thr Lys Val Glu Ile Lys Arg
            100                 105                 110

Thr Val Ala Ala Pro Ser Val Phe Ile Phe Pro Pro Ser Asp Glu Gln
            115                 120                 125
```

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
                180                 185                 190

His Lys Val Tyr Ala Cys Glu Val Thr His Gln Gly Leu Ser Ser Pro
                195                 200                 205

Val Thr Lys Ser Phe Asn Arg Gly Glu Cys
    210                 215

<210> SEQ ID NO 19
<211> LENGTH: 218
<212> TYPE: PRT
<213> ORGANISM: Artificial Sequence
<220> FEATURE:
<223> OTHER INFORMATION: Humanized Antibody Light Chain

<400> SEQUENCE: 19

Glu Ile Val Leu Thr Gln Ser Pro Leu Ser Leu Pro Val Thr Pro Gly
1               5                   10                  15

Glu Pro Ala Ser Ile Ser Cys Arg Ala Ser Lys Gly Val Ser Thr Ser
                20                  25                  30

Gly Tyr Ser Tyr Leu His Trp Tyr Leu Gln Lys Pro Gly Gln Ser Pro
            35                  40                  45

Gln Leu Leu Ile Tyr Leu Ala Ser Tyr Leu Glu Ser Gly Val Pro Asp
    50                  55                  60

Arg Phe Ser Gly Ser Gly Ser Gly Thr Asp Phe Thr Leu Lys Ile Ser
65                  70                  75                  80

Arg Val Glu Ala Glu Asp Val Gly Val Tyr Tyr Cys Gln His Ser Arg
                85                  90                  95

Asp Leu Pro Leu Thr Phe Gly Gln Gly Thr Lys Leu Glu Ile Lys Arg
                100                 105                 110

Thr Val Ala Ala Pro Ser Val Phe Ile Phe Pro Pro Ser Asp Glu Gln
            115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
                180                 185                 190

His Lys Val Tyr Ala Cys Glu Val Thr His Gln Gly Leu Ser Ser Pro
                195                 200                 205

Val Thr Lys Ser Phe Asn Arg Gly Glu Cys
    210                 215

<210> SEQ ID NO 20
<211> LENGTH: 218
<212> TYPE: PRT
<213> ORGANISM: Artificial Sequence
<220> FEATURE:
<223> OTHER INFORMATION: Humanized Antibody Light Chain

<400> SEQUENCE: 20

-continued

```
Asp Ile Val Met Thr Gln Thr Pro Leu Ser Leu Pro Val Thr Pro Gly
1               5                   10                  15

Glu Pro Ala Ser Ile Ser Cys Arg Ala Ser Lys Gly Val Ser Thr Ser
            20                  25                  30

Gly Tyr Ser Tyr Leu His Trp Tyr Leu Gln Lys Pro Gly Gln Ser Pro
        35                  40                  45

Gln Leu Leu Ile Tyr Leu Ala Ser Tyr Leu Glu Ser Gly Val Pro Asp
    50                  55                  60

Arg Phe Ser Gly Ser Gly Ser Gly Thr Ala Phe Thr Leu Lys Ile Ser
65                  70                  75                  80

Arg Val Glu Ala Glu Asp Val Gly Leu Tyr Tyr Cys Gln His Ser Arg
                85                  90                  95

Asp Leu Pro Leu Thr Phe Gly Gln Gly Thr Lys Leu Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 21
<211> LENGTH: 447
<212> TYPE: PRT
<213> ORGANISM: Artificial Sequence
<220> FEATURE:
<223> OTHER INFORMATION: Humanized Antibody Heavy Chain

<400> SEQUENCE: 21

Gln Val Gln Leu Val Gln Ser Gly Val Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Tyr Met Tyr Trp Val Arg Gln Ala Pro Gly Gln Gly Leu Glu Trp Met
        35                  40                  45

Gly Gly Ile Asn Pro Ser Gly Gly Thr Asn Phe Asn Glu Lys Phe
    50                  55                  60

Lys Asn Arg Val Thr Leu Thr Thr Asp Ser Ser Thr Thr Thr Ala Tyr
65                  70                  75                  80

Met Glu Leu Lys Ser Leu Gln Phe Asp Thr Ala Val Tyr Tyr Cys
                85                  90                  95

Ala Arg Arg Asp Tyr Arg Phe Asp Met Gly Phe Asp Tyr Trp Gly Gln
            100                 105                 110

Gly Thr Thr Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140
```

```
Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
    210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Leu Gly Lys
        435                 440                 445

<210> SEQ ID NO 22
<211> LENGTH: 218
<212> TYPE: PRT
<213> ORGANISM: Artificial Sequence
<220> FEATURE:
<223> OTHER INFORMATION: Humanized Antibody Light Chain

<400> SEQUENCE: 22

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Lys Gly Val Ser Thr Ser
            20                  25                  30

Gly Tyr Ser Tyr Leu His Trp Tyr Gln Gln Lys Pro Gly Gln Ala Pro
        35                  40                  45

Arg Leu Leu Ile Tyr Leu Ala Ser Tyr Leu Glu Ser Gly Val Pro Ala
    50                  55                  60
```

Arg Phe Ser Gly Ser Gly Ser Gly Thr Asp Phe Thr Leu Thr Ile Ser
65                  70                  75                  80

Ser Leu Glu Pro Glu Asp Phe Ala Val Tyr Tyr Cys Gln His Ser Arg
            85                  90                  95

Asp Leu Pro Leu Thr Phe Gly Gly Gly Thr Lys Val Glu Ile Lys Arg
            100                 105                 110

Thr Val Ala Ala Pro Ser Val Phe Ile Phe Pro Pro Ser Asp Glu Gln
            115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
            195                 200                 205

Val Thr Lys Ser Phe Asn Arg Gly Glu Cys
    210                 215

<210> SEQ ID NO 23
<211> LENGTH: 440
<212> TYPE: PRT
<213> ORGANISM: Homo sapiens

<400> SEQUENCE: 23

Gln Val Gln Leu Val Glu Ser Gly Gly Gly Val Val Gln Pro Gly Arg
1               5                   10                  15

Ser Leu Arg Leu Asp Cys Lys Ala Ser Gly Ile Thr Phe Ser Asn Ser
            20                  25                  30

Gly Met His Trp Val Arg Gln Ala Pro Gly Lys Gly Leu Glu Trp Val
        35                  40                  45

Ala Val Ile Trp Tyr Asp Gly Ser Lys Arg Tyr Tyr Ala Asp Ser Val
    50                  55                  60

Lys Gly Arg Phe Thr Ile Ser Arg Asp Asn Ser Lys Asn Thr Leu Phe
65                  70                  75                  80

Leu Gln Met Asn Ser Leu Arg Ala Glu Asp Thr Ala Val Tyr Tyr Cys
            85                  90                  95

Ala Thr Asn Asp Asp Tyr Trp Gly Gln Gly Thr Leu Val Thr Val Ser
            100                 105                 110

Ser Ala Ser Thr Lys Gly Pro Ser Val Phe Pro Leu Ala Pro Cys Ser
            115                 120                 125

Arg Ser Thr Ser Glu Ser Thr Ala Ala Leu Gly Cys Leu Val Lys Asp
    130                 135                 140

Tyr Phe Pro Glu Pro Val Thr Val Ser Trp Asn Ser Gly Ala Leu Thr
145                 150                 155                 160

Ser Gly Val His Thr Phe Pro Ala Val Leu Gln Ser Ser Gly Leu Tyr
                165                 170                 175

Ser Leu Ser Ser Val Val Thr Val Pro Ser Ser Ser Leu Gly Thr Lys
            180                 185                 190

Thr Tyr Thr Cys Asn Val Asp His Lys Pro Ser Asn Thr Lys Val Asp
            195                 200                 205

Lys Arg Val Glu Ser Lys Tyr Gly Pro Pro Cys Pro Pro Cys Pro Ala

```
                210                 215                 220
Pro Glu Phe Leu Gly Gly Pro Ser Val Phe Leu Phe Pro Pro Lys Pro
225                 230                 235                 240

Lys Asp Thr Leu Met Ile Ser Arg Thr Pro Glu Val Thr Cys Val Val
                245                 250                 255

Val Asp Val Ser Gln Glu Asp Pro Glu Val Gln Phe Asn Trp Tyr Val
                260                 265                 270

Asp Gly Val Glu Val His Asn Ala Lys Thr Lys Pro Arg Glu Glu Gln
                275                 280                 285

Phe Asn Ser Thr Tyr Arg Val Val Ser Val Leu Thr Val Leu His Gln
                290                 295                 300

Asp Trp Leu Asn Gly Lys Glu Tyr Lys Cys Lys Val Ser Asn Lys Gly
305                 310                 315                 320

Leu Pro Ser Ser Ile Glu Lys Thr Ile Ser Lys Ala Lys Gly Gln Pro
                325                 330                 335

Arg Glu Pro Gln Val Tyr Thr Leu Pro Pro Ser Gln Glu Glu Met Thr
                340                 345                 350

Lys Asn Gln Val Ser Leu Thr Cys Leu Val Lys Gly Phe Tyr Pro Ser
                355                 360                 365

Asp Ile Ala Val Glu Trp Glu Ser Asn Gly Gln Pro Glu Asn Asn Tyr
                370                 375                 380

Lys Thr Thr Pro Pro Val Leu Asp Ser Asp Gly Ser Phe Phe Leu Tyr
385                 390                 395                 400

Ser Arg Leu Thr Val Asp Lys Ser Arg Trp Gln Glu Gly Asn Val Phe
                405                 410                 415

Ser Cys Ser Val Met His Glu Ala Leu His Asn His Tyr Thr Gln Lys
                420                 425                 430

Ser Leu Ser Leu Ser Leu Gly Lys
                435                 440

<210> SEQ ID NO 24
<211> LENGTH: 214
<212> TYPE: PRT
<213> ORGANISM: Homo sapiens

<400> SEQUENCE: 24

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
                20                  25                  30

Leu Ala Trp Tyr Gln Gln Lys Pro Gly Gln Ala Pro Arg Leu Leu Ile
            35                  40                  45

Tyr Asp Ala Ser Asn Arg Ala Thr Gly Ile Pro Ala Arg Phe Ser Gly
        50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Ser Ser Asn Trp Pro Arg
                85                  90                  95

Thr Phe Gly Gln Gly Thr Lys Val Glu Ile Lys Arg Thr Val Ala Ala
                100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140
```

```
Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 25
<211> LENGTH: 261
<212> TYPE: PRT
<213> ORGANISM: Homo sapiens

<400> SEQUENCE: 25

Met Trp Val Pro Val Val Phe Leu Thr Leu Ser Val Thr Trp Ile Gly
1               5                   10                  15

Ala Ala Pro Leu Ile Leu Ser Arg Ile Val Gly Gly Trp Glu Cys Glu
            20                  25                  30

Lys His Ser Gln Pro Trp Gln Val Leu Val Ala Ser Arg Gly Arg Ala
        35                  40                  45

Val Cys Gly Gly Val Leu Val His Pro Gln Trp Val Leu Thr Ala Ala
    50                  55                  60

His Cys Ile Arg Asn Lys Ser Val Ile Leu Leu Gly Arg His Ser Leu
65                  70                  75                  80

Phe His Pro Glu Asp Thr Gly Gln Val Phe Gln Val Ser His Ser Phe
                85                  90                  95

Pro His Pro Leu Tyr Asp Met Ser Leu Leu Lys Asn Arg Phe Leu Arg
            100                 105                 110

Pro Gly Asp Asp Ser Ser His Asp Leu Met Leu Leu Arg Leu Ser Glu
        115                 120                 125

Pro Ala Glu Leu Thr Asp Ala Val Lys Val Met Asp Leu Pro Thr Gln
    130                 135                 140

Glu Pro Ala Leu Gly Thr Thr Cys Tyr Ala Ser Gly Trp Gly Ser Ile
145                 150                 155                 160

Glu Pro Glu Glu Phe Leu Thr Pro Lys Lys Leu Gln Cys Val Asp Leu
                165                 170                 175

His Val Ile Ser Asn Asp Val Cys Ala Gln Val His Pro Gln Lys Val
            180                 185                 190

Thr Lys Phe Met Leu Cys Ala Gly Arg Trp Thr Gly Gly Lys Ser Thr
        195                 200                 205

Cys Ser Gly Asp Ser Gly Gly Pro Leu Val Cys Asn Gly Val Leu Gln
    210                 215                 220

Gly Ile Thr Ser Trp Gly Ser Glu Pro Cys Ala Leu Pro Glu Arg Pro
225                 230                 235                 240

Ser Leu Tyr Thr Lys Val Val His Tyr Arg Lys Trp Ile Lys Asp Thr
                245                 250                 255

Ile Val Ala Asn Pro
            260

<210> SEQ ID NO 26
<211> LENGTH: 237
<212> TYPE: PRT
<213> ORGANISM: Homo sapiens
```

<400> SEQUENCE: 26

```
Ile Val Gly Gly Trp Glu Cys Glu Lys His Ser Gln Pro Trp Gln Val
1               5                   10                  15

Leu Val Ala Ser Arg Gly Arg Ala Val Cys Gly Gly Val Leu Val His
            20                  25                  30

Pro Gln Trp Val Leu Thr Ala Ala His Cys Ile Arg Asn Lys Ser Val
        35                  40                  45

Ile Leu Leu Gly Arg His Ser Leu Phe His Pro Glu Asp Thr Gly Gln
    50                  55                  60

Val Phe Gln Val Ser His Ser Phe Pro His Pro Leu Tyr Asp Met Ser
65                  70                  75                  80

Leu Leu Lys Asn Arg Phe Leu Arg Pro Gly Asp Asp Ser Ser His Asp
                85                  90                  95

Leu Met Leu Leu Arg Leu Ser Glu Pro Ala Glu Leu Thr Asp Ala Val
            100                 105                 110

Lys Val Met Asp Leu Pro Thr Gln Glu Pro Ala Leu Gly Thr Thr Cys
        115                 120                 125

Tyr Ala Ser Gly Trp Gly Ser Ile Glu Pro Glu Glu Phe Leu Thr Pro
    130                 135                 140

Lys Lys Leu Gln Cys Val Asp Leu His Val Ile Ser Asn Asp Val Cys
145                 150                 155                 160

Ala Gln Val His Pro Gln Lys Val Thr Lys Phe Met Leu Cys Ala Gly
                165                 170                 175

Arg Trp Thr Gly Gly Lys Ser Thr Cys Ser Gly Asp Ser Gly Gly Pro
            180                 185                 190

Leu Val Cys Tyr Gly Val Leu Gln Gly Ile Thr Ser Trp Gly Ser Glu
        195                 200                 205

Pro Cys Ala Leu Pro Glu Arg Pro Ser Leu Tyr Thr Lys Val Val His
    210                 215                 220

Tyr Arg Lys Trp Ile Lys Asp Thr Ile Val Ala Asn Pro
225                 230                 235
```

<210> SEQ ID NO 27
<211> LENGTH: 237
<212> TYPE: PRT
<213> ORGANISM: Homo sapiens

<400> SEQUENCE: 27

```
Ile Val Gly Gly Trp Glu Cys Glu Lys His Ser Gln Pro Trp Gln Val
1               5                   10                  15

Leu Val Ala Ser Arg Gly Arg Ala Val Cys Gly Gly Val Leu Val His
            20                  25                  30

Pro Gln Trp Val Leu Thr Ala Ala His Cys Ile Arg Asn Lys Ser Val
        35                  40                  45

Ile Leu Leu Gly Arg His Ser Leu Phe His Pro Glu Asp Thr Gly Gln
    50                  55                  60

Val Phe Gln Val Ser His Ser Phe Pro His Pro Leu Tyr Asp Met Ser
65                  70                  75                  80

Leu Leu Lys Asn Arg Phe Leu Arg Pro Gly Asp Asp Ser Ser His Asp
                85                  90                  95

Leu Met Leu Leu Arg Leu Ser Glu Pro Ala Glu Leu Thr Asp Ala Val
            100                 105                 110

Lys Val Met Asp Leu Pro Thr Gln Glu Pro Ala Leu Gly Thr Thr Cys
        115                 120                 125
```

```
Tyr Ala Ser Gly Trp Gly Ser Ile Glu Pro Glu Phe Leu Thr Pro
    130                 135                 140

Lys Lys Leu Gln Cys Val Asp Leu His Val Ile Ser Asn Asp Val Cys
145             150                 155                 160

Ala Gln Val His Pro Gln Lys Val Thr Lys Phe Met Leu Cys Ala Gly
                165                 170                 175

Arg Trp Thr Gly Gly Lys Ser Thr Cys Ser Gly Asp Ser Gly Gly Pro
            180                 185                 190

Leu Val Cys Asn Gly Val Leu Gln Gly Ile Thr Ser Trp Gly Ser Glu
        195                 200                 205

Pro Cys Ala Leu Pro Glu Arg Pro Ser Leu Tyr Thr Lys Val Val His
    210                 215                 220

Tyr Arg Lys Trp Ile Lys Asp Thr Ile Val Ala Asn Pro
225                 230                 235

<210> SEQ ID NO 28
<211> LENGTH: 5873
<212> TYPE: DNA
<213> ORGANISM: Homo sapiens

<400> SEQUENCE: 28
ggtgtcttag gcacactggt cttggagtgc aaaggatcta ggcacgtgag gctttgtatg      60
aagaatcggg gatcgtaccc accccctgtt tctgtttcat cctgggcatg tctcctctgc    120
ctttgtcccc tagatgaagt ctccatgagc tacaagggcc tggtgcatcc agggtgatct    180
agtaattgca gaacagcaag tgctagctct ccctcccctt ccacagctct gggtgtggga    240
gggggttgtc cagcctccag cagcatgggg agggccttgg tcagcctctg ggtgccagca    300
gggcagggge ggagtcctgg ggaatgaagg ttttataggg ctcctggggg aggctcccca    360
gccccaagct taccacctgc acccggagag ctgtgtcacc atgtgggtcc cggttgtctt    420
cctcaccctg tccgtgacgt ggattggtga gaggggccat ggttgggggg atgcaggaga    480
gggagccagc cctgactgtc aagctgaggc tctttccccc caacccagc accccagccc     540
agacagggag ctgggctctt ttctgtctct cccagcccca cttcaagccc ataccccag     600
tcccctccat attgcaacag tcctcactcc cacaccaggt cccgctcccc tcccacttac    660
cccagaactt tcttcccatt tgcccagcca gctccctgct cccagctgct ttactaaagg    720
ggaagttcct gggcatctcc gtgtttctct ttgtggggct caaaacctcc aaggacctct    780
ctcaatgcca ttggttcctt ggaccgtatc actggtccat ctcctgagcc ctcaatcct    840
atcacagtct actgacttt cccattcagc tgtgagtgtc caaccctatc ccagagacct    900
tgatgcttgg cctcccaatc ttgccctagg atacccagat gccaaccaga cacctccttc    960
tttcctagcc aggctatctg gcctgagaca acaaatgggt ccctcagtct ggcaatggga   1020
ctctgagaac tcctcattcc ctgactctta gccccagact cttcattcag tggcccacat   1080
tttccttagg aaaaacatga gcatccccag ccacaactgc cagctctctg agtccccaaa   1140
tctgcatcct tttcaaaacc taaaacaaa agaaaaaca aataaaacaa aaccaactca     1200
gaccagaact gttttctcaa cctgggactt cctaaactt ccaaaacctt cctcttccag    1260
caactgaacc tcgccataag gcacttatcc ctggttccta gcacccctta tccctcaga    1320
atccacaact gtaccaagt ttccttctc ccagtccaag accccaaatc accacaaagg     1380
acccaatccc cagactcaag atatggtctg ggcgctgtct tgtgtctcct accctgatcc   1440
ctgggttcaa ctctgctccc agagcatgaa gcctctccac cagcaccagc caccaacctg   1500
```

```
caaacctagg gaagattgac agaattccca gcctttccca gctcccctg cccatgtccc      1560
aggactccca gccttggttc tctgcccccg tgtcttttca aacccacatc ctaaatccat     1620
ctcctatccg agtccccag ttcccctgt caaccctgat tccctgatc tagcacccc        1680
tctgcaggcg ctgcgcccct catcctgtct cggattgtgg gaggctggga gtgcgagaag    1740
cattcccaac cctggcaggt gcttgtggcc tctcgtggca gggcagtctg cggcggtgtt    1800
ctggtgcacc cccagtgggt cctcacagct gcccactgca tcaggaagtg agtaggggcc    1860
tggggtctgg ggagcaggtg tctgtgtccc agaggaataa cagctgggca ttttccccag    1920
gataacctct aaggccagcc ttgggactgg gggagagagg gaaagttctg gttcaggtca    1980
catggggagg cagggttggg gctggaccac cctccccatg gctgcctggg tctccatctg    2040
tgtccctcta tgtctctttg tgtcgctttc attatgtctc ttggtaactg gcttcggttg    2100
tgtctctccg tgtgactatt ttgttctctc tctccctctc ttctctgtct tcagtctcca    2160
tatctccccc tctctctgtc cttctctggt ccctctctag ccagtgtgtc tcaccctgta    2220
tctctctgcc aggctctgtc tctcggtctc tgtctcacct gtgccttctc cctactgaac    2280
acacgcacgg gatgggcctg ggggaccctg agaaaaggaa gggctttggc tgggcgcggt    2340
ggctcacacc tgtaatccca gcactttggg aggccaaggc aggtagatca cctgaggtca    2400
ggagttcgag accagcctgg ccaactggtg aaacccatc tctactaaaa atacaaaaaa    2460
ttagccaggc gtggtggcgc atgcctgtag tcccagctac tcaggagctg agggaggaga    2520
attgcattga acctggaggt tgaggttgca gtgagccgag accgtgccac tgcactccag    2580
cctgggtgac agagtgagac tccgcctcaa aaaaaaaaaa aaaaaaaaaa aaaaaaaga    2640
aaagaaaaga aaagaaaagg aagtgtttta tccctgatgt gtgtgggtat gagggtatga    2700
gagggcccct ctcactccat tccttctcca ggacatccct ccactcttgg gagacacaga    2760
gaagggctgg ttccagctgg agctggggagg ggcaattgag ggaggaggaa ggagaagggg    2820
gaaggaaaac agggtatggg ggaaaggacc ctggggagcg aagtggagga tacaaccttg    2880
ggcctgcagg caggctacct acccacttgg aaacccacgc caaagccgca tctacagctg    2940
agccactctg aggcctcccc tccccggcgg tccccactca gctccaaagt ctctctccct    3000
tttctctccc cactttatc atcccccgga ttcctctcta cttggttctc attcttcctt    3060
tgacttcctg cttcccttc tcattcatct gtttctcact ttctgcctgg ttttgttctt    3120
ctctctctct ttctctggcc catgtctgtt tctctatgtt tctgtctttt ctttctcatc    3180
ctgtgtattt tcggctcacc ttgtttgtca ctgttctccc ctctgccctt tcattctctc    3240
tgcccttta ccctcttcct tttcccttgg ttctctcagt tctgtatctg cccttcaccc    3300
tctcacactg ctgtttccca actcgttgtc tgtattttgg cctgaactgt gtcttcccaa    3360
ccctgtgttt tctcactgtt tcttttttctc ttttggagcc tcctccttgc tcctctgtcc    3420
cttctctctt tccttatcat cctcgctcct cattcctgcg tctgcttcct ccccagcaaa    3480
agcgtgatct tgctgggtcg gcacagcctg tttcatcctg aagacacagg ccaggtattt    3540
caggtcagcc acagcttccc acacccgctc tacgatatga gcctcctgaa gaatcgattc    3600
ctcaggccag gtgatgactc cagccacgac ctcatgctgc tccgcctgtc agagcctgcc    3660
gagctcacgg atgctgtgaa ggtcatggac ctgcccaccc aggagccagc actggggacc    3720
acctgctacg cctcaggctg gggcagcatt gaaccagagg agtgtacgcc tgggccagat    3780
ggtgcagccg ggagcccaga tgcctgggtc tgagggagga ggggacagga ctcctgggtc    3840
```

| | | |
|---|---|---|
| tgagggagga gggccaagga accaggtggg gtccagccca caacagtgtt tttgcctggc | 3900 | |
| ccgtagtctt gaccccaaag aaacttcagt gtgtggacct ccatgttatt tccaatgacg | 3960 | |
| tgtgtgcgca agttcaccct cagaaggtga ccaagttcat gctgtgtgct ggacgctgga | 4020 | |
| caggggggcaa aagcacctgc tcggtgagtc atccctactc ccaagatctt gagggaaagg | 4080 | |
| tgagtgggac cttaattctg ggctggggtc tagaagccaa caaggcgtct gcctcccctg | 4140 | |
| ctccccagct gtagccatgc cacctccccg tgtctcatct cattccctcc ttccctcttc | 4200 | |
| tttgactccc tcaaggcaat aggttattct tacagcacaa ctcatctgtt cctgcgttca | 4260 | |
| gcacacggtt actaggcacc tgctatgcac ccagcactgc cctagagcct gggacatagc | 4320 | |
| agtgaacaga cagagagcag cccctccctt ctgtagcccc caagccagtg aggggcacag | 4380 | |
| gcaggaacag ggaccacaac acagaaaagc tggagggtgt caggaggtga tcaggctctc | 4440 | |
| ggggagggag aaggggtggg gagtgtgact gggaggagac atcctgcaga aggtgggagt | 4500 | |
| gagcaaacac ctgcgcaggg gaggggaggg cctgcggcac ctgggggagc agagggaaca | 4560 | |
| gcatctggcc aggcctggga ggaggggcct agagggcgtc aggagcagag aggaggttgc | 4620 | |
| ctggctggag tgaaggatcg gggcagggtg cgagagggaa caaaggaccc ctcctgcagg | 4680 | |
| gcctcacctg ggccacagga ggacactgct tttcctctga ggagtcagga actgtggatg | 4740 | |
| gtgctggaca gaagcaggac agggcctggc tcaggtgtcc agaggctgcg ctggcctcct | 4800 | |
| atgggatcag actgcaggga gggagggcag caggatgtg agggagtga tgatgggggct | 4860 | |
| gacctggggg tggctccagg cattgtcccc acctgggccc ttacccagcc tccctcacag | 4920 | |
| gctcctggcc ctcagtctct ccctccact ccattctcca cctacccaca gtgggtcatt | 4980 | |
| ctgatcaccg aactgaccat gccagccctg ccgatggtcc tccatggctc cctagtgccc | 5040 | |
| tggagaggag gtgtctagtc agagagtagt cctggaaggt ggcctctgtg aggagccacg | 5100 | |
| gggacagcat cctgcagatg gtcctggccc ttgtcccacc gacctgtcta caaggactgt | 5160 | |
| cctcgtggac cctccctct gcacaggagc tggaccctga agtcccttcc taccggccag | 5220 | |
| gactggagcc cctacccctc tgttggaatc cctgccacc ttcttctgga agtcggctct | 5280 | |
| ggagacattt ctctcttctt ccaaagctgg gaactgctat ctgttatctg cctgtccagg | 5340 | |
| tctgaaagat aggattgccc aggcagaaac tgggactgac ctatctcact ctctccctgc | 5400 | |
| ttttacccctt agggtgattc tgggggcccca cttgtctgta atggtgtgct tcaaggtatc | 5460 | |
| acgtcatggg gcagtgaacc atgtgccctg cccgaaaggc cttccctgta caccaaggtg | 5520 | |
| gtgcattacc ggaagtggat caaggacacc atcgtggcca accctgagc accctatca | 5580 | |
| agtccctatt gtagtaaact tggaaccttg gaaatgacca ggccaagact caagcctccc | 5640 | |
| cagttctact gacctttgtc cttaggtgtg aggtccaggg ttgctaggaa aagaaatcag | 5700 | |
| cagacacagg tgtagaccag agtgtttctt aaatggtgta attttgtcct ctctgtgtcc | 5760 | |
| tggggaatac tggccatgcc tggagacata tcactcaatt tctctgagga cacagttagg | 5820 | |
| atggggtgtc tgtgttattt gtgggataca gagatgaaag aggggtggga tcc | 5873 | |

<210> SEQ ID NO 29
<211> LENGTH: 238
<212> TYPE: PRT
<213> ORGANISM: Homo sapiens

<400> SEQUENCE: 29

Met Trp Val Pro Val Val Phe Leu Thr Leu Ser Val Thr Trp Ile Gly
1               5                   10                  15

```
Ala Ala Pro Leu Ile Leu Ser Arg Ile Val Gly Gly Trp Glu Cys Glu
             20                  25                  30

Lys His Ser Gln Pro Trp Gln Val Leu Val Ala Ser Arg Gly Arg Ala
         35                  40                  45

Val Cys Gly Gly Val Leu Val His Pro Gln Trp Val Leu Thr Ala Ala
     50                  55                  60

His Cys Ile Arg Asn Lys Ser Val Ile Leu Leu Gly Arg His Ser Leu
 65                  70                  75                  80

Phe His Pro Glu Asp Thr Gly Gln Val Phe Gln Val Ser His Ser Phe
                 85                  90                  95

Pro His Pro Leu Tyr Asp Met Ser Leu Leu Lys Asn Arg Phe Leu Arg
            100                 105                 110

Pro Gly Asp Asp Ser Ser His Asp Leu Met Leu Leu Arg Leu Ser Glu
        115                 120                 125

Pro Ala Glu Leu Thr Asp Ala Val Lys Val Met Asp Leu Pro Thr Gln
    130                 135                 140

Glu Pro Ala Leu Gly Thr Thr Cys Tyr Ala Ser Gly Trp Gly Ser Ile
145                 150                 155                 160

Glu Pro Glu Glu Phe Leu Thr Pro Lys Lys Leu Gln Cys Val Asp Leu
                165                 170                 175

His Val Ile Ser Asn Asp Val Cys Ala Gln Val His Pro Gln Lys Val
            180                 185                 190

Thr Lys Phe Met Leu Cys Ala Gly Arg Trp Thr Gly Gly Lys Ser Thr
        195                 200                 205

Cys Ser Trp Val Ile Leu Ile Thr Glu Leu Thr Met Pro Ala Leu Pro
    210                 215                 220

Met Val Leu His Gly Ser Leu Val Pro Trp Arg Gly Val
225                 230                 235

<210> SEQ ID NO 30
<211> LENGTH: 1906
<212> TYPE: DNA
<213> ORGANISM: Homo sapiens

<400> SEQUENCE: 30
agccccaagc ttaccacctg cacccggaga gctgtgtcac catgtgggtc ccggttgtct      60
tcctcaccct gtccgtgacg tggattggtg ctgcacccct catcctgtct cggattgtgg     120
gaggctggga gtgcgagaag cattcccaac cctggcaggt gcttgtggcc tctcgtggca     180
gggcagtctg cggcggtgtt ctggtgcacc ccagtgggt cctcacagct gcccactgca     240
tcaggaacaa aagcgtgatc ttgctgggtc ggcacagcct gtttcatcct gaagacacag     300
gccaggtatt tcaggtcagc cacagcttcc cacacccgct ctacgatatg agcctcctga     360
agaatcgatt cctcaggcca ggtgatgact ccagccacga cctcatgctg ctccgcctgt     420
cagagcctgc cgagctcacg gatgctgtga aggtcatgga cctgcccacc caggagccag     480
cactggggac cacctgctac gcctcaggct ggggcagcat tgaaccagag gagttcttga     540
ccccaaagaa acttcagtgt gtggacctcc atgttatttc caatgacgtg tgtgcgcaag     600
ttcaccctca gaaggtgacc aagttcatgc tgtgtgctgg acgctggaca ggggcaaaa     660 gcacctgctc gtgggtcatt ctgatcaccg aactgaccat gccagccctg ccgatggtcc     720
tccatggctc cctagtgccc tggagaggag gtgtctagtc agagagtagt cctggaaggt     780
ggcctctgtg aggagccacg gggacagcat cctgcagatg gtcctggccc ttgtcccacc     840
gacctgtcta caaggactgt cctcgtggac cctcccctct gcacaggagc tggaccctga     900
```

```
agtcccttcc ccaccggcca ggactggagc ccctacccct ctgttggaat ccctgcccac    960
cttcttctgg aagtcggctc tggagacatt tctctcttct tccaaagctg ggaactgcta   1020
tctgttatct gcctgtccag gtctgaaaga taggattgcc caggcagaaa ctgggactga   1080
cctatctcac tctctccctg cttttaccct tagggtgatt ctgggggccc acttgtctgt   1140
aatggtgtgc ttcaaggtat cacgtcatgg ggcagtgaac catgtgccct gcccgaaagg   1200
ccttccctgt acaccaaggt ggtgcattac cggaagtgga tcaaggacac catcgtggcc   1260
aacccctgag cacccctatc aaccccctat tgtagtaaac ttggaacctt ggaaatgacc   1320
aggccaagac tcaagcctcc ccagttctac tgacctttgt ccttaggtgt gaggtccagg   1380
gttgctagga aagaaatca gcagacacag gtgtagacca gagtgtttct taaatggtgt   1440
aattttgtcc tctctgtgtc ctggggaata ctggccatgc ctggagacat atcactcaat   1500
ttctctgagg acacagatag gatggggtgt ctgtgttatt tgtggggtac agagatgaaa   1560
gaggggtggg atccacactg agagagtgga gagtgacatg tgctgacac tgtccatgaa    1620 gcactgagca gaagctggag gcacaacgca ccagacactc acagcaagga tggagctgaa   1680
aacataaccc actctgtcct ggaggcactg ggaagcctag agaaggctgt gagccaagga   1740
gggagggtct tcctttggca tgggatgggg atgaagtaag gagagggact ggacccctg    1800 gaagctgatt cactatgggg ggaggtgtat tgaagtcctc cagacaaccc tcagatttga   1860
tgatttccta gtagaactca cagaaataaa gagctgttat actgtg                  1906
```

<210> SEQ ID NO 31
<211> LENGTH: 69
<212> TYPE: PRT
<213> ORGANISM: Homo sapiens

<400> SEQUENCE: 31

```
Met Trp Val Pro Val Val Phe Leu Thr Leu Ser Val Thr Trp Ile Gly
1               5                   10                  15

Ala Ala Pro Leu Ile Leu Ser Arg Ile Val Gly Gly Trp Glu Cys Glu
            20                  25                  30

Lys His Ser Gln Pro Trp Gln Val Leu Val Ala Ser Arg Gly Arg Ala
        35                  40                  45

Val Cys Gly Gly Val Leu Val His Pro Gln Trp Val Leu Thr Ala Ala
    50                  55                  60

His Cys Ile Arg Lys
65
```

<210> SEQ ID NO 32
<211> LENGTH: 554
<212> TYPE: DNA
<213> ORGANISM: Homo sapiens

<400> SEQUENCE: 32

```
agccccaagc ttaccacctg cacccggaga gctgtgtcac catgtgggtc ccggttgtct     60
tcctcaccct tccgtgacgt ggattggtgc tgcacccctc atcctgtctc ggattgtggg    120
aggctgggag tgcgagaagc attcccaacc ctggcaggtg cttgtggcct ctcgtggcag    180
ggcagtctgc ggcggtgttc tggtgcaccc ccagtgggtc ctcacagctg cccactgcat    240
caggaagtga gtaggggcct ggggtctggg gagcaggtgt ctgtgtccca gaggaataac    300
agctgggcat tttccccagg ataacctcta aggccagcct tgggactggg ggagagaggg    360
aaagttctgg ttcaggtcac atggggaggc agggttgggg ctggaccacc ctccccatgg    420
```

```
ctgcctgggt ctccatctgt gttcctctat gtctctttgt gtcgctttca ttatgtctct    480
tggtaactgg cttcggttgt gtctctccgt gtgactattt tgttctctct ctccctctct    540
tctctgtctt cagt                                                       554
```

<210> SEQ ID NO 33
<211> LENGTH: 220
<212> TYPE: PRT
<213> ORGANISM: Homo sapiens

<400> SEQUENCE: 33

```
Met Trp Val Pro Val Val Phe Leu Thr Leu Ser Val Thr Trp Ile Gly
1               5                   10                  15

Ala Ala Pro Leu Ile Leu Ser Arg Ile Val Gly Gly Trp Glu Cys Glu
            20                  25                  30

Lys His Ser Gln Pro Trp Gln Val Leu Val Ala Ser Arg Gly Arg Ala
        35                  40                  45

Val Cys Gly Gly Val Leu Val His Pro Gln Trp Val Leu Thr Ala Ala
    50                  55                  60

His Cys Ile Arg Asn Lys Ser Val Ile Leu Leu Gly Arg His Ser Leu
65                  70                  75                  80

Phe His Pro Glu Asp Thr Gly Gln Val Phe Gln Val Ser His Ser Phe
                85                  90                  95

Pro His Pro Leu Tyr Asp Met Ser Leu Leu Lys Asn Arg Phe Leu Arg
            100                 105                 110

Pro Gly Asp Asp Ser Ser Ile Glu Pro Glu Glu Phe Leu Thr Pro Lys
        115                 120                 125

Lys Leu Gln Cys Val Asp Leu His Val Ile Ser Asn Asp Val Cys Ala
    130                 135                 140

Gln Val His Pro Gln Lys Val Thr Lys Phe Met Leu Cys Ala Gly Arg
145                 150                 155                 160

Trp Thr Gly Gly Lys Ser Thr Cys Ser Gly Asp Ser Gly Gly Pro Leu
                165                 170                 175

Val Cys Asn Gly Val Leu Gln Gly Ile Thr Ser Trp Gly Ser Glu Pro
            180                 185                 190

Cys Ala Leu Pro Glu Arg Pro Ser Leu Tyr Thr Lys Val Val His Tyr
        195                 200                 205

Arg Lys Trp Ile Lys Asp Thr Ile Val Ala Asn Pro
    210                 215                 220
```

<210> SEQ ID NO 34
<211> LENGTH: 1341
<212> TYPE: DNA
<213> ORGANISM: Homo sapiens

<400> SEQUENCE: 34

```
agccccaagc ttaccacctg cacccggaga gctgtgtcac catgtgggtc ccggttgtct    60
tcctcaccct gtccgtgacg tggattggtg ctgcaccct catcctgtct cggattgtgg    120
gaggctggga gtgcgagaag cattcccaac cctggcaggt gcttgtggcc tctcgtggca    180
gggcagtctg cggcggtgtt ctggtgcacc ccagtgggg cctcacagct gcccactgca    240
tcaggaacaa aagcgtgatc ttgctgggtc ggcacagcct gtttcatcct gaagacacag    300
gccaggtatt tcaggtcagc cacagcttcc cacacccgct ctacgatatg agcctcctga    360
agaatcgatt cctcaggcca ggtgatgact ccagcattga accagaggag ttcttgaccc    420
```

-continued

```
caaagaaact tcagtgtgtg gacctccatg ttatttccaa tgacgtgtgt gcgcaagttc    480
accctcagaa ggtgaccaag ttcatgctgt gtgctggacg ctggacaggg ggcaaaagca    540
cctgctcggg tgattctggg ggcccacttg tctgtaatgg tgtgcttcaa ggtatcacgt    600
catggggcag tgaaccatgt gccctgcccg aaaggccttc cctgtacacc aaggtggtgc    660
attaccggaa gtggatcaag gacaccatcg tggccaaccc ctgagcaccc ctatcaaccc    720
cctattgtag taaacttgga accttggaaa tgaccaggcc aagactcaag cctccccagt    780
tctactgacc tttgtcctta ggtgtgaggt ccagggttgc taggaaaaga aatcagcaga    840
cacaggtgta gaccagagtg tttcttaaat ggtgtaattt tgtcctctct gtgtcctggg    900
gaatactggc catgcctgga gacatatcac tcaatttctc tgaggacaca gataggatgg    960
ggtgtctgtg ttatttgtgg ggtacagaga tgaaagaggg gtgggatcca cactgagaga   1020
gtggagagtg acatgtgctg gacactgtcc atgaagcact gagcagaagc tggaggcaca   1080
acgcaccaga cactcacagc aaggatggag ctgaaaacat aacccactct gtcctggagg   1140
cactgggaag cctagagaag gctgtgagcc aaggaggag ggtcttcctt tggcatggga    1200
tggggatgaa gtaaggagag ggactggacc ccctggaagc tgattcacta tggggggagg   1260
tgtattgaag tcctccagac aaccctcaga tttgatgatt tcctagtaga actcacagaa   1320
ataaagagct gttatactgt g                                            1341
```

<210> SEQ ID NO 35
<211> LENGTH: 218
<212> TYPE: PRT
<213> ORGANISM: Homo sapiens

<400> SEQUENCE: 35

```
Met Trp Val Pro Val Val Phe Leu Thr Leu Ser Val Thr Trp Ile Gly
 1               5                   10                  15

Ala Ala Pro Leu Ile Leu Ser Arg Ile Val Gly Gly Trp Glu Cys Glu
                20                  25                  30

Lys His Ser Gln Pro Trp Gln Val Leu Val Ala Ser Arg Gly Arg Ala
            35                  40                  45

Val Cys Gly Gly Val Leu Val His Pro Gln Trp Val Leu Thr Ala Ala
        50                  55                  60

His Cys Ile Arg Lys Pro Gly Asp Asp Ser Ser His Asp Leu Met Leu
 65                  70                  75                  80

Leu Arg Leu Ser Glu Pro Ala Glu Leu Thr Asp Ala Val Lys Val Met
                85                  90                  95

Asp Leu Pro Thr Gln Glu Pro Ala Leu Gly Thr Thr Cys Tyr Ala Ser
            100                 105                 110

Gly Trp Gly Ser Ile Glu Pro Glu Glu Phe Leu Thr Pro Lys Lys Leu
        115                 120                 125

Gln Cys Val Asp Leu His Val Ile Ser Asn Asp Val Cys Ala Gln Val
    130                 135                 140

His Pro Gln Lys Val Thr Lys Phe Met Leu Cys Ala Gly Arg Trp Thr
145                 150                 155                 160

Gly Gly Lys Ser Thr Cys Ser Gly Asp Ser Gly Gly Pro Leu Val Cys
                165                 170                 175

Asn Gly Val Leu Gln Gly Ile Thr Ser Trp Gly Ser Glu Pro Cys Ala
            180                 185                 190

Leu Pro Glu Arg Pro Ser Leu Tyr Thr Lys Val Val His Tyr Arg Lys
        195                 200                 205
```

```
Trp Ile Lys Asp Thr Ile Val Ala Asn Pro
    210                 215
```

<210> SEQ ID NO 36
<211> LENGTH: 1325
<212> TYPE: DNA
<213> ORGANISM: Homo sapiens

<400> SEQUENCE: 36

```
agccccaagc ttaccacctg cacccggaga gctgtgtcac catgtgggtc ccggttgtct      60
tcctcaccct gtccgtgacg tggattggtg ctgcacccct catcctgtct cggattgtgg     120
gaggctggga gtgcgagaag cattcccaac cctggcaggt gcttgtggcc tctcgtggca     180
ggcagtctg cggcggtgtt ctggtgcacc ccagtgggt cctcacagct gcccactgca       240
tcaggaagcc aggtgatgac tccagccacg acctcatgct gctccgcctg tcagagcctg     300
ccgagctcac ggatgctgtg aaggtcatgg acctgccacc ccaggagcca gcactgggga    360
ccacctgcta cgcctcaggc tggggcagca ttgaaccaga ggagttcttg accccaaaga    420
aacttcagtg tgtggacctc catgttattt ccaatgacgt gtgtgcgcaa gttcaccctc    480
agaaggtgac caagttcatg ctgtgtgctg acgctggac aggggcaaa agcacctgct      540
cgggtgattc tgggggccca cttgtctgta atggtgtgct tcaaggtatc acgtcatggg    600
gcagtgaacc atgtgccctg cccgaaaggc cttccctgta caccaaggtg gtgcattacc    660
caaggacacc atcgtggcca acccctgagc accctatca accccctatt gtagtaaact    720
tggaaccttg gaaatgacca ggccaagact caagcctccc cagttctact gacctttgtc    780
cttaggtgtg aggtccaggg ttgctaggaa agaaatcag cagacacagg tgtagaccag    840
agtgtttctt aaatggtgta attttgtcct ctctgtgtcc tggggaatac tggccatgcc    900
tggagacata tcactcaatt tctctgagga cacagatagg atggggtgtc tgtgttattt    960
gtggggtaca gagatgaaag aggggtggga tccacactga gagagtggag agtgacatgt   1020
gctggacact gtccatgaag cactgagcag aagctggagg cacaacgcac cagacactca   1080
cagcaaggat ggagctgaaa acataaccca ctctgtcctg gaggcactgg gaagcctaga   1140
gaaggctgtg agccaaggag ggagggtctt cctttggcat gggatgggga tgaagtaagg   1200
agagggactg gaccccctgg aagctgattc actatggggg gaggtgtatt gaagtcctcc   1260
agacaaccct cagatttgat gatttcctag tagaactcac agaaataaag agctgttata   1320
ctgtg                                                              1325
```

<210> SEQ ID NO 37
<211> LENGTH: 261
<212> TYPE: PRT
<213> ORGANISM: Homo sapiens

<400> SEQUENCE: 37

```
Met Trp Val Pro Val Val Phe Leu Thr Leu Ser Val Thr Trp Ile Gly
1               5                   10                  15

Ala Ala Pro Leu Ile Leu Ser Arg Ile Val Gly Gly Trp Glu Cys Glu
            20                  25                  30

Lys His Ser Gln Pro Trp Gln Val Leu Val Ala Ser Arg Gly Arg Ala
        35                  40                  45

Val Cys Gly Gly Val Leu Val His Pro Gln Trp Val Leu Thr Ala Ala
    50                  55                  60

His Cys Ile Arg Asn Lys Ser Val Ile Leu Leu Gly Arg His Ser Leu
65                  70                  75                  80
```

Phe His Pro Glu Asp Thr Gly Gln Val Phe Gln Val Ser His Ser Phe
             85                  90                  95

Pro His Pro Leu Tyr Asp Met Ser Leu Leu Lys Asn Arg Phe Leu Arg
            100                 105                 110

Pro Gly Asp Asp Ser Ser His Asp Leu Met Leu Leu Arg Leu Ser Glu
            115                 120                 125

Pro Ala Glu Leu Thr Asp Ala Val Lys Val Met Asp Leu Pro Thr Gln
            130                 135                 140

Glu Pro Ala Leu Gly Thr Thr Cys Tyr Ala Ser Gly Trp Gly Ser Ile
145                 150                 155                 160

Glu Pro Glu Glu Phe Leu Thr Pro Lys Lys Leu Gln Cys Val Asp Leu
            165                 170                 175

His Val Ile Ser Asn Asp Val Cys Ala Gln Val His Pro Gln Lys Val
            180                 185                 190

Thr Lys Phe Met Leu Cys Ala Gly Arg Trp Thr Gly Gly Lys Ser Thr
            195                 200                 205

Cys Ser Gly Asp Ser Gly Gly Pro Leu Val Cys Asn Gly Val Leu Gln
            210                 215                 220

Gly Ile Thr Ser Trp Gly Ser Glu Pro Cys Ala Leu Pro Glu Arg Pro
225                 230                 235                 240

Ser Leu Tyr Thr Lys Val Val His Tyr Arg Lys Trp Ile Lys Asp Thr
            245                 250                 255

Ile Val Ala Asn Pro
            260

<210> SEQ ID NO 38
<211> LENGTH: 1464
<212> TYPE: DNA
<213> ORGANISM: Homo sapiens

<400> SEQUENCE: 38

```
agccccaagc ttaccacctg cacccggaga gctgtgtcac catgtgggtc ccggttgtct    60
tcctcaccct gtccgtgacg tggattggtg ctgcacccct catcctgtct cggattgtgg   120
gaggctggga gtgcgagaag cattcccaac cctggcaggt gcttgtggcc tctcgtggca   180
gggcagtctg cggcggtgtt ctggtgcacc ccagtgggt cctcacagct gcccactgca   240
tcaggaacaa aagcgtgatc ttgctgggtc ggcacagcct gtttcatcct gaagacacag   300
gccaggtatt tcaggtcagc cacagcttcc cacacccgct ctacgatatg agcctcctga   360
agaatcgatt cctcaggcca ggtgatgact ccagccacga cctcatgctg ctccgcctgt   420
cagagcctgc cgagctcacg gatgctgtga aggtcatgga cctgcccacc caggagccag   480
cactggggac cacctgctac gcctcaggct ggggcagcat tgaaccagag gagttcttga   540
ccccaaagaa acttcagtgt gtggacctcc atgttatttc aatgacgtg tgtgcgcaag   600 ttcaccctca gaaggtgacc aagttcatgc tgtgtgctgg acgctggaca ggggcaaaa   660 gcacctgctc gggtgattct gggggcccac ttgtctgtaa tggtgtgctt caaggtatca   720
cgtcatgggg cagtgaacca tgtgccctgc ccgaaaggcc ttccctgtac accaaggtgg   780
tgcattaccg gaagtggatc aaggacacca tcgtggccaa ccctgagca cccctatcaa   840 ccccctattg tagtaaactt ggaaccttgg aaatgaccag gccaagactc aagcctcccc   900
agttctactg acctttgtcc ttaggtgtga ggtccagggt tgctaggaaa agaaatcagc   960
agacacaggt gtagaccaga gtgtttctta aatggtgtaa ttttgtcctc tctgtgtcct  1020
```

-continued

```
ggggaatact ggccatgcct ggagacatat cactcaattt ctctgaggac acagatagga    1080
tggggtgtct gtgttatttg tggggtacag agatgaaaga ggggtgggat ccacactgag    1140
agagtggaga gtgacatgtg ctggacactg tccatgaagc actgagcaga agctggaggc    1200
acaacgcacc agacactcac agcaaggatg gagctgaaaa cataacccac tctgtcctgg    1260
aggcactggg aagcctagag aaggctgtga gccaaggagg gagggtcttc ctttggcatg    1320
ggatggggat gaagtaagga gagggactgg accccctgga agctgattca ctatgggggg    1380
aggtgtattg aagtcctcca gacaaccctc agatttgatg atttcctagt agaactcaca    1440
gaaataaaga gctgttatac tgtg                                           1464
```

<210> SEQ ID NO 39
<211> LENGTH: 261
<212> TYPE: PRT
<213> ORGANISM: Artificial Sequence
<220> FEATURE:
<223> OTHER INFORMATION: kallikrein 3, partial

<400> SEQUENCE: 39

```
Met Trp Val Pro Val Val Phe Leu Thr Leu Ser Val Thr Trp Ile Gly
 1               5                  10                  15

Ala Ala Pro Leu Ile Leu Ser Arg Ile Val Gly Gly Trp Glu Cys Glu
            20                  25                  30

Lys His Ser Gln Pro Trp Gln Val Leu Val Ala Ser Arg Gly Arg Ala
        35                  40                  45

Val Cys Gly Gly Val Leu Val His Pro Gln Trp Val Leu Thr Ala Ala
    50                  55                  60

His Cys Ile Arg Asn Lys Ser Val Ile Leu Leu Gly Arg His Ser Leu
65                  70                  75                  80

Phe His Pro Glu Asp Thr Gly Gln Val Phe Gln Val Ser His Ser Phe
                85                  90                  95

Pro His Pro Leu Tyr Asp Met Ser Leu Leu Lys Asn Arg Phe Leu Arg
            100                 105                 110

Pro Gly Asp Asp Ser Ser His Asp Leu Met Leu Leu Arg Leu Ser Glu
        115                 120                 125

Pro Ala Glu Leu Thr Asp Ala Val Lys Val Met Asp Leu Pro Thr Gln
    130                 135                 140

Glu Pro Ala Leu Gly Thr Thr Cys Tyr Ala Ser Gly Trp Gly Ser Ile
145                 150                 155                 160

Glu Pro Glu Glu Phe Leu Thr Pro Lys Lys Leu Gln Cys Val Asp Leu
                165                 170                 175

His Val Ile Ser Asn Asp Val Cys Ala Gln Val His Pro Gln Lys Val
            180                 185                 190

Thr Lys Phe Met Leu Cys Ala Gly Arg Trp Thr Gly Gly Lys Ser Thr
        195                 200                 205

Cys Ser Gly Asp Ser Gly Gly Pro Leu Val Cys Asn Gly Val Leu Gln
    210                 215                 220

Gly Ile Thr Ser Trp Gly Ser Glu Pro Cys Ala Leu Pro Glu Arg Pro
225                 230                 235                 240

Ser Leu Tyr Thr Lys Val Val His Tyr Arg Lys Trp Ile Lys Asp Thr
                245                 250                 255

Ile Val Ala Asn Pro
            260
```

<210> SEQ ID NO 40

<211> LENGTH: 1495
<212> TYPE: DNA
<213> ORGANISM: Homo sapiens

<400> SEQUENCE: 40

```
gggggagccc caagcttacc acctgcaccc ggagagctgt gtcaccatgt gggtcccggt      60
tgtcttcctc accctgtccg tgacgtggat tggtgctgca cccctcatcc tgtctcggat     120
tgtgggaggc tgggagtgcg agaagcattc ccaaccctgg caggtgcttg tggcctctcg     180
tggcagggca gtctgcggcg gtgttctggt gcaccccag tgggtcctca cagctgccca     240
ctgcatcagg aacaaaagcg tgatcttgct gggtcggcac agcctgtttc atcctgaaga     300
cacaggccag gtatttcagg tcagccacag cttcccacac ccgctctacg atatgagcct     360
cctgaagaat cgattcctca ggccaggtga tgactccagc cacgacctca tgctgctccg     420
cctgtcagag cctgccgagc tcacggatgc tgtgaaggtc atggacctgc ccacccagga     480
gccagcactg gggaccacct gctacgcctc aggctgggc agcattgaac cagaggagtt     540
cttgacccca agaaacttc agtgtgtgga cctccatgtt atttccaatg acgtgtgtgc     600
gcaagttcac cctcagaagg tgaccaagtt catgctgtgt gctggacgct ggacaggggg     660
caaaagcacc tgctcgggtg attctggggg cccacttgtc tgtaatggtg tgcttcaagg     720
tatcacgtca tggggcagtg aaccatgtgc cctgcccgaa aggccttccc tgtacaccaa     780
ggtggtgcat taccggaagt ggatcaagga caccatcgtg gccaacccct gagcaccct     840
atcaactccc tattgtagta aacttggaac cttggaaatg accaggccaa gactcaggcc     900
tccccagttc tactgacctt tgtccttagg tgtgaggtcc agggttgcta ggaaaagaaa     960
tcagcagaca caggtgtaga ccagagtgtt tcttaaatgg tgtaattttg tcctctctgt    1020
gtcctgggga atactggcca tgcctggaga catatcactc aatttctctg aggacacaga    1080
taggatgggg tgtctgtgtt atttgtgggg tacagagatg aaagaggggt gggatccaca    1140
ctgagagagt ggagagtgac atgtgctgga cactgtccat gaagcactga gcagaagctg    1200
gaggcacaac gcaccagaca ctcacagcaa ggatggagct gaaaacataa cccactctgt    1260
cctggaggca ctgggaagcc tagagaaggc tgtgagccaa ggagggaggg tcttcctttg    1320
gcatgggatg gggatgaagt agggagaggg actggacccc ctggaagctg attcactatg    1380
ggggaggtg tattgaagtc ctccagacaa ccctcagatt tgatgatttc ctagtagaac    1440
tcacagaaat aaagagctgt tatactgcga aaaaaaaaa aaaaaaaaa aaaaa           1495
```

<210> SEQ ID NO 41
<211> LENGTH: 218
<212> TYPE: PRT
<213> ORGANISM: Homo sapiens

<400> SEQUENCE: 41

```
Met Trp Val Pro Val Val Phe Leu Thr Leu Ser Val Thr Trp Ile Gly
1               5                   10                  15

Ala Ala Pro Leu Ile Leu Ser Arg Ile Val Gly Gly Trp Glu Cys Glu
            20                  25                  30

Lys His Ser Gln Pro Trp Gln Val Leu Val Ala Ser Arg Gly Arg Ala
        35                  40                  45

Val Cys Gly Gly Val Leu Val His Pro Gln Trp Val Leu Thr Ala Ala
    50                  55                  60

His Cys Ile Arg Asn Lys Ser Val Ile Leu Leu Gly Arg His Ser Leu
65                  70                  75                  80
```

```
Phe His Pro Glu Asp Thr Gly Gln Val Phe Gln Val Ser His Ser Phe
                 85                  90                  95

Pro His Pro Leu Tyr Asp Met Ser Leu Leu Lys Asn Arg Phe Leu Arg
            100                 105                 110

Pro Gly Asp Asp Ser Ser Ile Glu Pro Glu Phe Leu Thr Pro Lys
        115                 120                 125

Lys Leu Gln Cys Val Asp Leu His Val Ile Ser Asn Asp Val Cys Ala
130             135                 140

Gln Val His Pro Gln Lys Val Thr Lys Phe Met Leu Cys Ala Gly Arg
145             150                 155                 160

Trp Thr Gly Gly Lys Ser Thr Cys Ser Gly Asp Ser Gly Gly Pro Leu
                165                 170                 175

Val Cys Asn Gly Val Leu Gln Gly Ile Thr Ser Trp Gly Ser Glu Pro
            180                 185                 190

Cys Ala Leu Pro Glu Arg Pro Ser Leu Tyr Thr Lys Val Val His Tyr
        195                 200                 205

Arg Lys Trp Ile Lys Asp Thr Ile Val Ala
210                 215

<210> SEQ ID NO 42
<211> LENGTH: 227
<212> TYPE: PRT
<213> ORGANISM: Homo sapiens

<400> SEQUENCE: 42

Met Trp Val Pro Val Val Phe Leu Thr Leu Ser Val Thr Trp Ile Gly
1               5                   10                  15

Ala Ala Pro Leu Ile Leu Ser Arg Ile Val Gly Gly Trp Glu Cys Glu
                20                  25                  30

Lys His Ser Gln Pro Trp Gln Val Leu Val Ala Ser Arg Gly Arg Ala
            35                  40                  45

Val Cys Gly Gly Val Leu Val His Pro Gln Trp Val Leu Thr Ala Ala
        50                  55                  60

His Cys Ile Arg Asn Lys Ser Val Ile Leu Leu Gly Arg His Ser Leu
65                  70                  75                  80

Phe His Pro Glu Asp Thr Gly Gln Val Phe Gln Val Ser His Ser Phe
                85                  90                  95

Pro His Pro Leu Tyr Asp Met Ser Leu Leu Lys Asn Arg Phe Leu Arg
            100                 105                 110

Pro Gly Asp Asp Ser Ser His Asp Leu Met Leu Leu Arg Leu Ser Glu
        115                 120                 125

Pro Ala Glu Leu Thr Asp Ala Val Lys Val Met Asp Leu Pro Thr Gln
130             135                 140

Glu Pro Ala Leu Gly Thr Thr Cys Tyr Ala Ser Gly Trp Gly Ser Ile
145             150                 155                 160

Glu Pro Glu Glu Phe Leu Thr Pro Lys Lys Leu Gln Cys Val Asp Leu
                165                 170                 175

His Val Ile Ser Asn Asp Val Cys Ala Gln Val His Pro Gln Lys Val
            180                 185                 190

Thr Lys Phe Met Leu Cys Ala Gly Arg Trp Thr Gly Gly Lys Ser Thr
        195                 200                 205

Cys Ser Val Ser His Pro Tyr Ser Gln Asp Leu Glu Gly Lys Gly Glu
    210                 215                 220

Trp Gly Pro
225
```

<210> SEQ ID NO 43
<211> LENGTH: 104
<212> TYPE: PRT
<213> ORGANISM: Homo sapiens

<400> SEQUENCE: 43

```
Met Trp Val Pro Val Val Phe Leu Thr Leu Ser Val Thr Trp Ile Gly
1               5                   10                  15

Glu Arg Gly His Gly Trp Gly Asp Ala Gly Glu Gly Ala Ser Pro Asp
            20                  25                  30

Cys Gln Ala Glu Ala Leu Ser Pro Pro Thr Gln His Pro Ser Pro Asp
        35                  40                  45

Arg Glu Leu Gly Ser Phe Leu Ser Leu Pro Ala Pro Leu Gln Ala His
    50                  55                  60

Thr Pro Ser Pro Ser Ile Leu Gln Gln Ser Ser Leu Pro His Gln Val
65                  70                  75                  80

Pro Ala Pro Ser His Leu Pro Gln Asn Phe Leu Pro Ile Ala Gln Pro
                85                  90                  95

Ala Pro Cys Ser Gln Leu Leu Tyr
            100
```

<210> SEQ ID NO 44
<211> LENGTH: 261
<212> TYPE: PRT
<213> ORGANISM: Homo sapiens

<400> SEQUENCE: 44

```
Met Trp Val Pro Val Val Phe Leu Thr Leu Ser Val Thr Trp Ile Gly
1               5                   10                  15

Ala Ala Pro Leu Ile Leu Ser Arg Ile Val Gly Gly Trp Glu Cys Glu
            20                  25                  30

Lys His Ser Gln Pro Trp Gln Val Leu Val Ala Ser Arg Gly Arg Ala
        35                  40                  45

Val Cys Gly Gly Val Leu Val His Pro Gln Trp Val Leu Thr Ala Ala
    50                  55                  60

His Cys Ile Arg Asn Lys Ser Val Ile Leu Leu Gly Arg His Ser Leu
65                  70                  75                  80

Phe His Pro Glu Asp Thr Gly Gln Val Phe Gln Val Ser His Ser Phe
                85                  90                  95

Pro His Pro Leu Tyr Asp Met Ser Leu Leu Lys Asn Arg Phe Leu Arg
            100                 105                 110

Pro Gly Asp Asp Ser Ser His Asp Leu Met Leu Leu Arg Leu Ser Glu
        115                 120                 125

Pro Ala Glu Leu Thr Asp Ala Val Lys Val Met Asp Leu Pro Thr Gln
    130                 135                 140

Glu Pro Ala Leu Gly Thr Thr Cys Tyr Ala Ser Gly Trp Gly Ser Ile
145                 150                 155                 160

Glu Pro Glu Glu Phe Leu Thr Pro Lys Lys Leu Gln Cys Val Asp Leu
                165                 170                 175

His Val Ile Ser Asn Asp Val Cys Ala Gln Val His Pro Gln Lys Val
            180                 185                 190

Thr Lys Phe Met Leu Cys Ala Gly Arg Trp Thr Gly Gly Lys Ser Thr
        195                 200                 205

Cys Ser Gly Asp Ser Gly Gly Pro Leu Val Cys Asn Gly Val Leu Gln
    210                 215                 220
```

Gly Ile Thr Ser Trp Gly Ser Glu Pro Cys Ala Leu Pro Glu Arg Pro
225                 230                 235                 240

Ser Leu Tyr Thr Lys Val Val His Tyr Arg Lys Trp Ile Lys Asp Thr
                245                 250                 255

Ile Val Ala Asn Pro
            260

<210> SEQ ID NO 45
<211> LENGTH: 1729
<212> TYPE: DNA
<213> ORGANISM: Homo sapiens

<400> SEQUENCE: 45

```
aagtttccct tctcccagtc caagacccca atcaccaca aaggacccaa tccccagact      60
caagatatgg tctgggcgct gtcttgtgtc tcctaccctg atccctgggt tcaactctgc    120
tcccagagca tgaagcctct ccaccagcac cagccaccaa cctgcaaacc tagggaagat    180
tgacagaatt cccagccttt cccagctccc cctgcccatg tcccaggact cccagccttg    240
gttctctgcc ccgtgtctt ttcaaaccca catcctaaat ccatctccta tccgagtccc     300
ccagttcctc ctgtcaaccc tgattcccct gatctagcac ccctctgca ggtgctgcac     360
ccctcatcct gtctcggatt gtgggaggct gggagtgcga aagcattcc caaccctggc    420
aggtgcttgt agcctctcgt ggcagggcag tctgcggcgg tgttctggtg cacccccagt    480
gggtcctcac agctacccac tgcatcagga caaaagcgt gatcttgctg gtcggcaca     540
gcctgtttca tcctgaagac acaggccagg tatttcaggt cagccacagc ttcccacacc    600
cgctctacga tatgagcctc ctgaagaatc gattcctcag gccaggtgat gactccagcc    660
acgacctcat gctgctccgc ctgtcagagc ctgccgagct cacggatgct atgaaggtca    720
tggacctgcc cacccaggag ccagcactgg ggaccacctg ctacgcctca ggctggggca    780
gcattgaacc agaggagttc ttgaccccaa agaaacttca gtgtgtggac ctccatgtta    840
tttccaatga cgtgtgtgcg caagttcacc ctcagaaggt gaccaagttc atgctgtgtg    900
ctggacgctg gacaggggggc aaaagcacct gctcggtga ttctggggc ccacttgtct     960
gtaatggtgt gcttcaaggt atcacgtcat ggggcagtga accatgtgcc ctgcccgaaa   1020
ggccttccct gtacaccaag gtggtgcatt accggaagtg gatcaaggac catcgtgg    1080
ccaaccctg agcaccccta tcaactccct attgtagtaa acttggaacc ttggaaatga   1140
ccaggccaag actcaggcct ccccagttct actgacccttt gtccttaggt gtgaggtcca   1200
gggttgctag gaaaagaaat cagcagacac aggtgtagac cagagtgttt cttaaatggt   1260
gtaattttgt cctctctgtg tcctggggaa tactggccat gcctgagac atatcactca    1320
atttctctga ggacacagat aggatggggt gtctgtgtta tttgtggggt acagagatga   1380
aagaggggtg ggatccacac tgagagagtg gagagtgaca tgtgctggac actgtccatg   1440
aagcactgag cagaagctgg aggcacaacg caccagacac tcacagcaag gatggagctg   1500
aaaacataac ccactctgtc ctggaggcac tgggaagcct agagaaggct gtgaaccaag   1560
gagggagggt cttcctttgg catgggatgg ggatgaagta aggagaggga ctgacccccct   1620
ggaagctgat tcactatggg gggaggtgta ttgaagtcct ccagacaacc ctcagatttg   1680
atgatttcct agtagaactc acagaaataa agagctgtta tactgtgaa                1729
```

<210> SEQ ID NO 46
<211> LENGTH: 29

```
<212> TYPE: DNA
<213> ORGANISM: Homo sapiens

<400> SEQUENCE: 46
gtgctcgaga ttgtgggagg ctgggagtg                                       29

<210> SEQ ID NO 47
<211> LENGTH: 29
<212> TYPE: DNA
<213> ORGANISM: Homo sapiens

<400> SEQUENCE: 47
gatactagtt taggggttgg ccacgatgg                                       29

<210> SEQ ID NO 48
<211> LENGTH: 680
<212> TYPE: PRT
<213> ORGANISM: Listeria monocytogenes

<400> SEQUENCE: 48
```

Met Lys Lys Ile Met Leu Val Phe Ile Thr Leu Ile Leu Val Ser Leu
1               5                   10                  15

Pro Ile Ala Gln Gln Thr Glu Ala Lys Asp Ala Ser Ala Phe Asn Lys
            20                  25                  30

Glu Asn Ser Ile Ser Ser Met Ala Pro Pro Ala Ser Pro Pro Ala Ser
        35                  40                  45

Pro Lys Thr Pro Ile Glu Lys Lys His Ala Asp Glu Ile Asp Lys Tyr
    50                  55                  60

Ile Gln Gly Leu Asp Tyr Asn Lys Asn Asn Val Leu Val Tyr His Gly
65                  70                  75                  80

Asp Ala Val Thr Asn Val Pro Pro Arg Lys Gly Tyr Lys Asp Gly Asn
                85                  90                  95

Glu Tyr Ile Val Val Glu Lys Lys Lys Ser Ile Asn Gln Asn Asn
            100                 105                 110

Ala Asp Ile Gln Val Val Asn Ala Ile Ser Ser Leu Thr Tyr Pro Gly
        115                 120                 125

Ala Leu Val Lys Ala Asn Ser Glu Leu Val Glu Asn Gln Pro Asp Val
    130                 135                 140

Leu Pro Val Lys Arg Asp Ser Leu Thr Leu Ser Ile Asp Leu Pro Gly
145                 150                 155                 160

Met Thr Asn Gln Asp Asn Lys Ile Val Val Lys Asn Ala Thr Lys Ser
                165                 170                 175

Asn Val Asn Asn Ala Val Asn Thr Leu Val Glu Arg Trp Asn Glu Lys
            180                 185                 190

Tyr Ala Gln Ala Tyr Pro Asn Val Ser Ala Lys Ile Asp Tyr Asp Asp
        195                 200                 205

Glu Met Ala Tyr Ser Glu Ser Gln Leu Ile Ala Lys Phe Gly Thr Ala
    210                 215                 220

Phe Lys Ala Val Asn Asn Ser Leu Asn Val Asn Phe Gly Ala Ile Ser
225                 230                 235                 240

Glu Gly Lys Met Gln Glu Glu Val Ile Ser Phe Lys Gln Ile Tyr Tyr
                245                 250                 255

Asn Val Asn Val Asn Glu Pro Thr Arg Pro Ser Arg Phe Phe Gly Lys
            260                 265                 270

Ala Val Thr Lys Glu Gln Leu Gln Ala Leu Gly Val Asn Ala Glu Asn
        275                 280                 285

Pro Pro Ala Tyr Ile Ser Ser Val Ala Tyr Gly Arg Gln Val Tyr Leu
            290                 295                 300
Lys Leu Ser Thr Asn Ser His Ser Thr Lys Val Lys Ala Ala Phe Asp
305                 310                 315                 320
Ala Ala Val Ser Gly Lys Ser Val Ser Gly Asp Val Glu Leu Thr Asn
                325                 330                 335
Ile Ile Lys Asn Ser Ser Phe Lys Ala Val Ile Tyr Gly Gly Ser Ala
            340                 345                 350
Lys Asp Glu Val Gln Ile Ile Asp Gly Asn Leu Gly Asp Leu Arg Asp
        355                 360                 365
Ile Leu Lys Lys Gly Ala Thr Phe Asn Arg Glu Thr Pro Gly Val Pro
370                 375                 380
Ile Ala Tyr Thr Thr Asn Phe Leu Lys Asp Asn Glu Leu Ala Val Ile
385                 390                 395                 400
Lys Asn Asn Ser Glu Tyr Ile Glu Thr Thr Ser Lys Ala Tyr Thr Asp
                405                 410                 415
Gly Lys Ile Asn Ile Asp His Ser Gly Gly Tyr Val Ala Gln Phe Asn
            420                 425                 430
Ile Ser Trp Asp Glu Val Asn Tyr Asp Leu Glu Ile Val Gly Gly Trp
        435                 440                 445
Glu Cys Glu Lys His Ser Gln Pro Trp Gln Val Leu Val Ala Ser Arg
450                 455                 460
Gly Arg Ala Val Cys Gly Gly Val Leu Val His Pro Gln Trp Val Leu
465                 470                 475                 480
Thr Ala Ala His Cys Ile Arg Asn Lys Ser Val Ile Leu Leu Gly Arg
                485                 490                 495
His Ser Leu Phe His Pro Glu Asp Thr Gly Gln Val Phe Gln Val Ser
            500                 505                 510
His Ser Phe Pro His Pro Leu Tyr Asp Met Ser Leu Leu Lys Asn Arg
        515                 520                 525
Phe Leu Arg Pro Gly Asp Asp Ser Ser His Asp Leu Met Leu Leu Arg
530                 535                 540
Leu Ser Glu Pro Ala Glu Leu Thr Asp Ala Val Lys Val Met Asp Leu
545                 550                 555                 560
Pro Thr Gln Glu Pro Ala Leu Gly Thr Thr Cys Tyr Ala Ser Gly Trp
                565                 570                 575
Gly Ser Ile Glu Pro Glu Glu Phe Leu Thr Pro Lys Lys Leu Gln Cys
            580                 585                 590
Val Asp Leu His Val Ile Ser Asn Asp Val Cys Ala Gln Val His Pro
        595                 600                 605
Gln Lys Val Thr Lys Phe Met Leu Cys Ala Gly Arg Trp Thr Gly Gly
610                 615                 620
Lys Ser Thr Cys Ser Gly Asp Ser Gly Gly Pro Leu Val Cys Tyr Gly
625                 630                 635                 640
Val Leu Gln Gly Ile Thr Ser Trp Gly Ser Glu Pro Cys Ala Leu Pro
                645                 650                 655
Glu Arg Pro Ser Leu Tyr Thr Lys Val Val His Tyr Arg Lys Trp Ile
            660                 665                 670
Lys Asp Thr Ile Val Ala Asn Pro
        675                 680

<210> SEQ ID NO 49
<211> LENGTH: 32
<212> TYPE: PRT

<213> ORGANISM: Listeria monocytogenes

<400> SEQUENCE: 49

Lys Glu Asn Ser Ile Ser Ser Met Ala Pro Ala Ser Pro Pro Ala
1               5                   10                  15

Ser Pro Lys Thr Pro Ile Glu Lys Lys His Ala Asp Glu Ile Asp Lys
            20                  25                  30

<210> SEQ ID NO 50
<211> LENGTH: 227
<212> TYPE: PRT
<213> ORGANISM: Homo sapiens

<400> SEQUENCE: 50

Met Trp Val Pro Val Val Phe Leu Thr Leu Ser Val Thr Trp Ile Gly
1               5                   10                  15

Ala Ala Pro Leu Ile Leu Ser Arg Ile Val Gly Gly Trp Glu Cys Glu
            20                  25                  30

Lys His Ser Gln Pro Trp Gln Val Leu Val Ala Ser Arg Gly Arg Ala
        35                  40                  45

Val Cys Gly Gly Val Leu Val His Pro Gln Trp Val Leu Thr Ala Ala
    50                  55                  60

His Cys Ile Arg Asn Lys Ser Val Ile Leu Leu Gly Arg His Ser Leu
65                  70                  75                  80

Phe His Pro Glu Asp Thr Gly Gln Val Phe Gln Val Ser His Ser Phe
                85                  90                  95

Pro His Pro Leu Tyr Asp Met Ser Leu Leu Lys Asn Arg Phe Leu Arg
            100                 105                 110

Pro Gly Asp Asp Ser Ser His Asp Leu Met Leu Leu Arg Leu Ser Glu
        115                 120                 125

Pro Ala Glu Leu Thr Asp Ala Val Lys Val Met Asp Leu Pro Thr Gln
    130                 135                 140

Glu Pro Ala Leu Gly Thr Thr Cys Tyr Ala Ser Gly Trp Gly Ser Ile
145                 150                 155                 160

Glu Pro Glu Glu Phe Leu Thr Pro Lys Lys Leu Gln Cys Val Asp Leu
                165                 170                 175

His Val Ile Ser Asn Asp Val Cys Ala Gln Val His Pro Gln Lys Val
            180                 185                 190

Thr Lys Phe Met Leu Cys Ala Gly Arg Trp Thr Gly Gly Lys Ser Thr
        195                 200                 205

Cys Ser Val Ser His Pro Tyr Ser Gln Asp Leu Glu Gly Lys Gly Glu
    210                 215                 220

Trp Gly Pro
225

<210> SEQ ID NO 51
<211> LENGTH: 104
<212> TYPE: PRT
<213> ORGANISM: Homo sapiens

<400> SEQUENCE: 51

Met Trp Val Pro Val Val Phe Leu Thr Leu Ser Val Thr Trp Ile Gly
1               5                   10                  15

Glu Arg Gly His Gly Trp Gly Asp Ala Gly Glu Gly Ala Ser Pro Asp
            20                  25                  30

Cys Gln Ala Glu Ala Leu Ser Pro Thr Gln His Pro Ser Pro Asp
        35                  40                  45

```
Arg Glu Leu Gly Ser Phe Leu Ser Leu Pro Ala Pro Leu Gln Ala His
    50                  55                  60

Thr Pro Ser Pro Ser Ile Leu Gln Gln Ser Ser Leu Pro His Gln Val
65                  70                  75                  80

Pro Ala Pro Ser His Leu Pro Gln Asn Phe Leu Pro Ile Ala Gln Pro
                85                  90                  95

Ala Pro Cys Ser Gln Leu Leu Tyr
            100

<210> SEQ ID NO 52
<211> LENGTH: 24
<212> TYPE: PRT
<213> ORGANISM: Homo sapiens

<400> SEQUENCE: 52

Met Trp Val Pro Val Phe Leu Thr Leu Ser Val Thr Trp Ile Gly
1               5                   10                  15

Ala Ala Pro Leu Ile Leu Ser Arg
            20

<210> SEQ ID NO 53
<211> LENGTH: 529
<212> TYPE: PRT
<213> ORGANISM: Listeria monocytogenes

<400> SEQUENCE: 53

Met Lys Lys Ile Met Leu Val Phe Ile Thr Leu Ile Leu Val Ser Leu
1               5                   10                  15

Pro Ile Ala Gln Gln Thr Glu Ala Lys Asp Ala Ser Ala Phe Asn Lys
            20                  25                  30

Glu Asn Ser Ile Ser Ser Met Ala Pro Pro Ala Ser Pro Pro Ala Ser
            35                  40                  45

Pro Lys Thr Pro Ile Glu Lys Lys His Ala Asp Glu Ile Asp Lys Tyr
    50                  55                  60

Ile Gln Gly Leu Asp Tyr Asn Lys Asn Asn Val Leu Val Tyr His Gly
65                  70                  75                  80

Asp Ala Val Thr Asn Val Pro Pro Arg Lys Gly Tyr Lys Asp Gly Asn
                85                  90                  95

Glu Tyr Ile Val Val Glu Lys Lys Lys Ser Ile Asn Gln Asn Asn
            100                 105                 110

Ala Asp Ile Gln Val Val Asn Ala Ile Ser Ser Leu Thr Tyr Pro Gly
            115                 120                 125

Ala Leu Val Lys Ala Asn Ser Glu Leu Val Glu Asn Gln Pro Asp Val
        130                 135                 140

Leu Pro Val Lys Arg Asp Ser Leu Thr Leu Ser Ile Asp Leu Pro Gly
145                 150                 155                 160

Met Thr Asn Gln Asp Asn Lys Ile Val Val Lys Asn Ala Thr Lys Ser
                165                 170                 175

Asn Val Asn Asn Ala Val Asn Thr Leu Val Glu Arg Trp Asn Glu Lys
            180                 185                 190

Tyr Ala Gln Ala Tyr Pro Asn Val Ser Ala Lys Ile Asp Tyr Asp Asp
            195                 200                 205

Glu Met Ala Tyr Ser Glu Ser Gln Leu Ile Ala Lys Phe Gly Thr Ala
        210                 215                 220

Phe Lys Ala Val Asn Asn Ser Leu Asn Val Asn Phe Gly Ala Ile Ser
225                 230                 235                 240
```

```
Glu Gly Lys Met Gln Glu Val Ile Ser Phe Lys Gln Ile Tyr Tyr
                245                 250                 255

Asn Val Asn Val Asn Glu Pro Thr Arg Pro Ser Arg Phe Phe Gly Lys
            260                 265                 270

Ala Val Thr Lys Glu Gln Leu Gln Ala Leu Gly Val Asn Ala Glu Asn
            275                 280                 285

Pro Pro Ala Tyr Ile Ser Ser Val Ala Tyr Gly Arg Gln Val Tyr Leu
            290                 295                 300

Lys Leu Ser Thr Asn Ser His Ser Thr Lys Val Lys Ala Ala Phe Asp
305                 310                 315                 320

Ala Ala Val Ser Gly Lys Ser Val Ser Gly Asp Val Glu Leu Thr Asn
                325                 330                 335

Ile Ile Lys Asn Ser Ser Phe Lys Ala Val Ile Tyr Gly Gly Ser Ala
                340                 345                 350

Lys Asp Glu Val Gln Ile Ile Asp Gly Asn Leu Gly Asp Leu Arg Asp
                355                 360                 365

Ile Leu Lys Lys Gly Ala Thr Phe Asn Arg Glu Thr Pro Gly Val Pro
            370                 375                 380

Ile Ala Tyr Thr Thr Asn Phe Leu Lys Asp Asn Glu Leu Ala Val Ile
385                 390                 395                 400

Lys Asn Asn Ser Glu Tyr Ile Glu Thr Thr Ser Lys Ala Tyr Thr Asp
                405                 410                 415

Gly Lys Ile Asn Ile Asp His Ser Gly Gly Tyr Val Ala Gln Phe Asn
            420                 425                 430

Ile Ser Trp Asp Glu Val Asn Tyr Asp Pro Gly Gly Asn Glu Ile Val
            435                 440                 445

Gln His Lys Asn Trp Ser Glu Asn Asn Lys Ser Lys Leu Ala His Phe
450                 455                 460

Thr Ser Ser Ile Tyr Leu Pro Gly Asn Ala Arg Asn Ile Asn Val Tyr
465                 470                 475                 480

Ala Lys Glu Cys Thr Gly Leu Ala Trp Glu Trp Trp Arg Thr Val Ile
                485                 490                 495

Asp Asp Arg Asn Leu Pro Leu Val Lys Asn Arg Asn Ile Ser Ile Trp
            500                 505                 510

Gly Thr Thr Leu Tyr Pro Lys Tyr Ser Asn Lys Val Asp Asn Pro Ile
            515                 520                 525

Glu

<210> SEQ ID NO 54
<211> LENGTH: 441
<212> TYPE: PRT
<213> ORGANISM: Listeria monocytogenes

<400> SEQUENCE: 54

Met Lys Lys Ile Met Leu Val Phe Ile Thr Leu Ile Leu Val Ser Leu
1               5                   10                  15

Pro Ile Ala Gln Gln Thr Glu Ala Lys Asp Ala Ser Ala Phe Asn Lys
            20                  25                  30

Glu Asn Ser Ile Ser Ser Val Ala Pro Pro Ala Ser Pro Pro Ala Ser
        35                  40                  45

Pro Lys Thr Pro Ile Glu Lys Lys His Ala Asp Glu Ile Asp Lys Tyr
    50                  55                  60

Ile Gln Gly Leu Asp Tyr Asn Lys Asn Asn Val Leu Val Tyr His Gly
65                  70                  75                  80
```

Asp Ala Val Thr Asn Val Pro Pro Arg Lys Gly Tyr Lys Asp Gly Asn
                85                  90                  95

Glu Tyr Ile Val Val Glu Lys Lys Lys Ser Ile Asn Gln Asn Asn
            100                 105                 110

Ala Asp Ile Gln Val Val Asn Ala Ile Ser Ser Leu Thr Tyr Pro Gly
        115                 120                 125

Ala Leu Val Lys Ala Asn Ser Glu Leu Val Glu Asn Gln Pro Asp Val
    130                 135                 140

Leu Pro Val Lys Arg Asp Ser Leu Thr Leu Ser Ile Asp Leu Pro Gly
145                 150                 155                 160

Met Thr Asn Gln Asp Asn Lys Ile Val Lys Asn Ala Thr Lys Ser
                165                 170                 175

Asn Val Asn Asn Ala Val Asn Thr Leu Val Glu Arg Trp Asn Glu Lys
            180                 185                 190

Tyr Ala Gln Ala Tyr Ser Asn Val Ser Ala Lys Ile Asp Tyr Asp Asp
        195                 200                 205

Glu Met Ala Tyr Ser Glu Ser Gln Leu Ile Ala Lys Phe Gly Thr Ala
    210                 215                 220

Phe Lys Ala Val Asn Asn Ser Leu Asn Val Asn Phe Gly Ala Ile Ser
225                 230                 235                 240

Glu Gly Lys Met Gln Glu Val Ile Ser Phe Lys Gln Ile Tyr Tyr
                245                 250                 255

Asn Val Asn Val Asn Glu Pro Thr Arg Pro Ser Arg Phe Phe Gly Lys
            260                 265                 270

Ala Val Thr Lys Glu Gln Leu Gln Ala Leu Gly Val Asn Ala Glu Asn
        275                 280                 285

Pro Pro Ala Tyr Ile Ser Ser Val Ala Tyr Gly Arg Gln Val Tyr Leu
    290                 295                 300

Lys Leu Ser Thr Asn Ser His Ser Thr Lys Val Lys Ala Ala Phe Asp
305                 310                 315                 320

Ala Ala Val Ser Gly Lys Ser Val Ser Gly Asp Val Glu Leu Thr Asn
                325                 330                 335

Ile Ile Lys Asn Ser Ser Phe Lys Ala Val Ile Tyr Gly Gly Ser Ala
            340                 345                 350

Lys Asp Glu Val Gln Ile Ile Asp Gly Asn Leu Gly Asp Leu Arg Asp
        355                 360                 365

Ile Leu Lys Lys Gly Ala Thr Phe Asn Arg Glu Thr Pro Gly Val Pro
370                 375                 380

Ile Ala Tyr Thr Thr Asn Phe Leu Lys Asp Asn Glu Leu Ala Val Ile
385                 390                 395                 400

Lys Asn Asn Ser Glu Tyr Ile Glu Thr Thr Ser Lys Ala Tyr Thr Asp
                405                 410                 415

Gly Lys Ile Asn Ile Asp His Ser Gly Gly Tyr Val Ala Gln Phe Asn
            420                 425                 430

Ile Ser Trp Asp Glu Val Asn Tyr Asp
        435                 440

<210> SEQ ID NO 55
<211> LENGTH: 416
<212> TYPE: PRT
<213> ORGANISM: Listeria monocytogenes

<400> SEQUENCE: 55

Met Lys Lys Ile Met Leu Val Phe Ile Thr Leu Ile Leu Val Ser Leu

```
1               5                   10                  15
Pro Ile Ala Gln Gln Thr Glu Ala Lys Asp Ala Ser Ala Phe Asn Lys
            20                  25                  30

Glu Asn Ser Ile Ser Ser Val Ala Pro Pro Ala Ser Pro Pro Ala Ser
            35                  40                  45

Pro Lys Thr Pro Ile Glu Lys Lys His Ala Asp Glu Ile Asp Lys Tyr
    50                  55                  60

Ile Gln Gly Leu Asp Tyr Asn Lys Asn Val Leu Val Tyr His Gly
65                  70                  75                  80

Asp Ala Val Thr Asn Val Pro Pro Arg Lys Gly Tyr Lys Asp Gly Asn
                85                  90                  95

Glu Tyr Ile Val Val Glu Lys Lys Lys Ser Ile Asn Gln Asn Asn
                    100                 105                 110

Ala Asp Ile Gln Val Val Asn Ala Ile Ser Ser Leu Thr Tyr Pro Gly
            115                 120                 125

Ala Leu Val Lys Ala Asn Ser Glu Leu Val Glu Asn Gln Pro Asp Val
    130                 135                 140

Leu Pro Val Lys Arg Asp Ser Leu Thr Leu Ser Ile Asp Leu Pro Gly
145                 150                 155                 160

Met Thr Asn Gln Asp Asn Lys Ile Val Val Lys Asn Ala Thr Lys Ser
                165                 170                 175

Asn Val Asn Asn Ala Val Asn Thr Leu Val Glu Arg Trp Asn Glu Lys
                180                 185                 190

Tyr Ala Gln Ala Tyr Ser Asn Val Ser Ala Lys Ile Asp Tyr Asp Asp
            195                 200                 205

Glu Met Ala Tyr Ser Glu Ser Gln Leu Ile Ala Lys Phe Gly Thr Ala
    210                 215                 220

Phe Lys Ala Val Asn Asn Ser Leu Asn Val Asn Phe Gly Ala Ile Ser
225                 230                 235                 240

Glu Gly Lys Met Gln Glu Val Ile Ser Phe Lys Gln Ile Tyr Tyr
                245                 250                 255

Asn Val Asn Val Asn Glu Pro Thr Arg Pro Ser Arg Phe Phe Gly Lys
                260                 265                 270

Ala Val Thr Lys Glu Gln Leu Gln Ala Leu Gly Val Asn Ala Glu Asn
            275                 280                 285

Pro Pro Ala Tyr Ile Ser Ser Val Ala Tyr Gly Arg Gln Val Tyr Leu
    290                 295                 300

Lys Leu Ser Thr Asn Ser His Ser Thr Lys Val Lys Ala Ala Phe Asp
305                 310                 315                 320

Ala Ala Val Ser Gly Lys Ser Val Ser Gly Asp Val Glu Leu Thr Asn
            325                 330                 335

Ile Ile Lys Asn Ser Ser Phe Lys Ala Val Ile Tyr Gly Gly Ser Ala
            340                 345                 350

Lys Asp Glu Val Gln Ile Ile Asp Gly Asn Leu Gly Asp Leu Arg Asp
    355                 360                 365

Ile Leu Lys Lys Gly Ala Thr Phe Asn Arg Glu Thr Pro Gly Val Pro
    370                 375                 380

Ile Ala Tyr Thr Thr Asn Phe Leu Lys Asp Asn Glu Leu Ala Val Ile
385                 390                 395                 400

Lys Asn Asn Ser Glu Tyr Ile Glu Thr Thr Ser Lys Ala Tyr Thr Asp
                405                 410                 415

<210> SEQ ID NO 56
```

-continued

```
<211> LENGTH: 14
<212> TYPE: PRT
<213> ORGANISM: Listeria monocytogenes

<400> SEQUENCE: 56

Lys Thr Glu Glu Gln Pro Ser Glu Val Asn Thr Gly Pro Arg
1               5                   10

<210> SEQ ID NO 57
<211> LENGTH: 28
<212> TYPE: PRT
<213> ORGANISM: Listeria monocytogenes

<400> SEQUENCE: 57

Lys Ala Ser Val Thr Asp Thr Ser Glu Gly Asp Leu Asp Ser Ser Met
1               5                   10                  15

Gln Ser Ala Asp Glu Ser Thr Pro Gln Pro Leu Lys
            20                  25

<210> SEQ ID NO 58
<211> LENGTH: 20
<212> TYPE: PRT
<213> ORGANISM: Listeria monocytogenes

<400> SEQUENCE: 58

Lys Asn Glu Glu Val Asn Ala Ser Asp Phe Pro Pro Pro Pro Thr Asp
1               5                   10                  15

Glu Glu Leu Arg
            20

<210> SEQ ID NO 59
<211> LENGTH: 33
<212> TYPE: PRT
<213> ORGANISM: Listeria monocytogenes

<400> SEQUENCE: 59

Arg Gly Gly Ile Pro Thr Ser Glu Glu Phe Ser Ser Leu Asn Ser Gly
1               5                   10                  15

Asp Phe Thr Asp Asp Glu Asn Ser Glu Thr Thr Glu Glu Glu Ile Asp
            20                  25                  30

Arg

<210> SEQ ID NO 60
<211> LENGTH: 17
<212> TYPE: PRT
<213> ORGANISM: Streptococcus pyogenes

<400> SEQUENCE: 60

Lys Gln Asn Thr Ala Ser Thr Glu Thr Thr Thr Thr Asn Glu Gln Pro
1               5                   10                  15

Lys

<210> SEQ ID NO 61
<211> LENGTH: 17
<212> TYPE: PRT
<213> ORGANISM: Streptococcus equisimilis

<400> SEQUENCE: 61

Lys Gln Asn Thr Ala Asn Thr Glu Thr Thr Thr Thr Asn Glu Gln Pro
1               5                   10                  15

Lys
```

<210> SEQ ID NO 62
<211> LENGTH: 6523
<212> TYPE: DNA
<213> ORGANISM: Homo sapiens

<400> SEQUENCE: 62

```
cggagtgtat actggcttac tatgttggca ctgatgaggg tgtcagtgaa gtgcttcatg      60
tggcaggaga aaaaaggctg caccggtgcg tcagcagaat atgtgataca ggatatattc     120
cgcttcctcg ctcactgact cgctacgctc ggtcgttcga ctgcggcgag cggaaatggc     180
ttacgaacgg ggcggagatt tcctggaaga tgccaggaag atacttaaca gggaagtgag     240
agggccgcgg caaagccgtt tttccatagg ctccgccccc ctgacaagca tcacgaaatc     300
tgacgctcaa atcagtggtg gcgaaacccg acaggactat aaagatacca ggcgtttccc     360
cctggcggct ccctcgtgcg ctctcctgtt cctgcctttc ggtttaccgg tgtcattccg     420
ctgttatggc cgcgtttgtc tcattccacg cctgacactc agttccgggt aggcagttcg     480
ctccaagctg gactgtatgc acgaaccccc cgttcagtcc gaccgctgcg ccttatccgg     540
taactatcgt cttgagtcca acccggaaag acatgcaaaa gcaccactgg cagcagccac     600
tggtaattga tttagaggag ttagtcttga agtcatgcgc cggttaaggc taaactgaaa     660
ggacaagttt tggtgactgc gctcctccaa gccagttacc tcggttcaaa gagttggtag     720
ctcagagaac cttcgaaaaa ccgccctgca aggcggtttt ttcgttttca gagcaagaga     780
ttacgcgcag accaaaacga tctcaagaag atcatcttat taatcagata aaatatttct     840
agccctcctt tgattagtat attcctatct taaagttact tttatgtgga ggcattaaca     900
tttgttaatg acgtcaaaag gatagcaaga ctagaataaa gctataaagc aagcatataa     960
tattgcgttt catctttaga agcgaatttc gccaatatta taattatcaa agagagggg    1020 tggcaaacgg tatttggcat tattaggtta aaaaatgtag aaggagagtg aaacccatga    1080
aaaaaataat gctagttttt attacactta tattagttag tctaccaatt gcgcaacaaa    1140
ctgaagcaaa ggatgcatct gcattcaata agaaaattc aatttcatcc atggcaccac    1200
cagcatctcc gcctgcaagt cctaagacgc caatcgaaaa gaaacacgcg gatgaaatcg    1260
ataagtatat acaaggattg gattacaata aaaacaatgt attagtatac cacggagatg    1320
cagtgacaaa tgtgccgcca agaaaaggtt acaaagatgg aaatgaatat attgttgtgg    1380
agaaaaagaa gaaatccatc aatcaaaata atgcagacat tcaagttgtg aatgcaattt    1440
cgagcctaac ctatccaggt gctctcgtaa aagcgaattc ggaattagta gaaaatcaac    1500
cagatgttct ccctgtaaaa cgtgattcat taacactcag cattgatttg ccaggtatga    1560
ctaatcaaga caataaaata gttgtaaaaa atgccactaa atcaaacgtt aacaacgcag    1620
taaatacatt agtggaaaga tggaatgaaa aatatgctca agcttatcca aatgtaagtg    1680
caaaaattga ttatgatgac gaaatggctt acagtgaatc acaattaatt gcgaaatttg    1740
gtacagcatt taaagctgta aataatagct tgaatgtaaa cttcggcgca atcagtgaag    1800
ggaaaatgca agaagaagtc attagtttta acaaatttta ctataacgtg aatgttaatg    1860
aacctacaag accttccaga ttttcggca agctgttac taaagagcag ttgcaagcgc    1920
ttggagtgaa tgcagaaaat cctcctgcat atatctcaag tgtggcgtat ggccgtcaag    1980
tttatttgaa attatcaact aattcccata gtactaaagt aaaagctgct tttgatgctg    2040
ccgtaagcgg aaaatctgtc tcaggtgatg tagaactaac aaatatcatc aaaaattctt    2100
ccttcaaagc cgtaatttac ggaggttccg caaaagatga agttcaaatc atcgacggca    2160
```

```
acctcggaga cttacgcgat attttgaaaa aaggcgctac ttttaatcga gaaacaccag    2220
gagttcccat tgcttataca acaaacttcc taaaagacaa tgaattagct gttattaaaa    2280
acaactcaga atatattgaa acaacttcaa aagcttatac agatggaaaa attaacatcg    2340
atcactctgg aggatacgtt gctcaattca acatttcttg ggatgaagta aattatgatc    2400
tcgagattgt gggaggctgg gagtgcgaga agcattccca accctggcag gtgcttgtgg    2460
cctctcgtgg cagggcagtc tgcggcggtg ttctggtgca cccccagtgg gtcctcacag    2520
ctgcccactg catcaggaac aaaagcgtga tcttgctggg tcggcacagc ctgtttcatc    2580
ctgaagacac aggccaggta tttcaggtca gccacagctt cccacacccg ctctacgata    2640
tgagcctcct gaagaatcga ttcctcaggc caggtgatga ctccagccac gacctcatgc    2700
tgctccgcct gtcagagcct gccgagctca cggatgctgt gaaggtcatg acctgcccca    2760
cccaggagcc agcactgggg accacctgct acgcctcagg ctggggcagc attgaaccag    2820
aggagttctt gaccccaaag aaacttcagt gtgtggacct ccatgttatt ccaatgacg     2880 tgtgtgcgca agttcaccct cagaaggtga ccaagttcat gctgtgtgct ggacgctgga    2940
cagggggcaa aagcacctgc tcgggtgatt ctggggccc acttgtctgt tatggtgtgc     3000
ttcaaggtat cacgtcatgg ggcagtgaac catgtgccct gcccgaaagg ccttccctgt    3060
acaccaaggt ggtgcattac cggaagtgga tcaaggacac catcgtggcc aaccctaac     3120 ccgggccact aactcaacgc tagtagtgga tttaatccca aatgagccaa cagaaccaga    3180
accagaaaca gaacaagtaa cattggagtt agaaatggaa gaagaaaaa gcaatgattt     3240 cgtgtgaata atgcacgaaa tcattgctta tttttttaaa aagcgatata ctagatataa    3300
cgaaacaacg aactgaataa agaatacaaa aaaagagcca cgaccagtta aagcctgaga    3360
aactttaact gcgagcctta attgattacc accaatcaat taaagaagtc gagacccaaa    3420
atttggtaaa gtatttaatt actttattaa tcagatactt aaatatctgt aaacccatta    3480
tatcgggttt ttgagggat ttcaagtctt taagaagata ccaggcaatc aattaagaaa     3540
aacttagttg attgccttt ttgttgtgat tcaactttga tcgtagcttc taactaatta     3600
attttcgtaa gaaaggagaa cagctgaatg aatatccctt ttgttgtaga aactgtgctt    3660
catgacggct tgttaaagta caaatttaaa aatagtaaaa ttcgctcaat cactaccaag    3720
ccaggtaaaa gtaaagggc tatttttgcg tatcgctcaa aaaaaagcat gattggcgga    3780
cgtggcgttg ttctgacttc cgaagaagcg attcacgaaa tcaagatac atttacgcat    3840 tggacaccaa acgtttatcg ttatggtacg tatgcagacg aaaaccgttc atacactaaa    3900
ggacattctg aaaacaattt aagacaaatc aataccttct ttattgattt tgatattcac    3960
acggaaaaag aaactatttc agcaagcgat attttaacaa cagctattga tttaggtttt    4020
atgcctacgt taattatcaa atctgataaa ggttatcaag catattttgt tttagaaacg    4080
ccagtctatg tgacttcaaa atcagaattt aaatctgtca agcagccaa ataatctcg     4140 caaaatatcc gagaatattt tggaaagtct ttgccagttg atctaacgtg caatcatttt    4200
gggattgctc gtataccaag aacggacaat gtagaatttt tgatcccaa ttaccgttat     4260 tctttcaaag aatggcaaga ttggtctttc aaacaaacag ataataaggg ctttactcgt    4320
tcaagtctaa cggttttaag cggtacagaa ggcaaaaaac aagtagatga accctggttt    4380
aatctcttat tgcacgaaac gaaatttca ggagaaaagg gtttagtagg gcgcaatagc     4440
gttatgttta ccctctcttt agcctacttt agttcaggct attcaatcga aacgtgcgaa    4500
```

| | | | | |
|---|---|---|---|---|
| tataatatgt | ttgagtttaa | taatcgatta | gatcaaccct | tagaagaaaa agaagtaatc | 4560 |
| aaaattgtta | gaagtgccta | ttcagaaaac | tatcaagggg | ctaataggga atacattacc | 4620 |
| attctttgca | aagcttgggt | atcaagtgat | ttaaccagta | aagatttatt tgtccgtcaa | 4680 |
| gggtggttta | aattcaagaa | aaaagaagc | gaacgtcaac | gtgttcattt gtcagaatgg | 4740 |
| aaagaagatt | taatggctta | tattagcgaa | aaaagcgatg | tatacaagcc ttatttagcg | 4800 |
| acgaccaaaa | aagagattag | agaagtgcta | ggcattcctg | aacggacatt agataaattg | 4860 |
| ctgaaggtac | tgaaggcgaa | tcaggaaatt | ttctttaaga | ttaaaccagg aagaaatggt | 4920 |
| ggcattcaac | ttgctagtgt | taaatcattg | ttgctatcga | tcattaaatt aaaaaaagaa | 4980 |
| gaacgagaaa | gctatataaa | ggcgctgaca | gcttcgttta | atttagaacg tacatttatt | 5040 |
| caagaaactc | taaacaaatt | ggcagaacgc | cccaaaacgg | acccacaact cgatttgttt | 5100 |
| agctacgata | caggctgaaa | ataaaacccg | cactatgcca | ttacatttat atctatgata | 5160 |
| cgtgtttgtt | tttctttgct | ggctagctta | attgcttata | tttacctgca ataaaggatt | 5220 |
| tcttacttcc | attatactcc | cattttccaa | aaacatacgg | ggaacacggg aacttattgt | 5280 |
| acaggccacc | tcatagttaa | tggtttcgag | ccttcctgca | atctcatcca tggaaatata | 5340 |
| ttcatccccc | tgccggccta | ttaatgtgac | ttttgtgccc | ggcggatatt cctgatccag | 5400 |
| ctccaccata | aattggtcca | tgcaaattcg | gccggcaatt | tcaggcgtt ttcccttcac | 5460 |
| aaggatgtcg | gtccctttca | attttcggag | ccagccgtcc | gcatagccta caggcaccgt | 5520 |
| cccgatccat | gtgtcttttt | ccgctgtgta | ctcggctccg | tagctgacgc tctcgccttt | 5580 |
| tctgatcagt | ttgacatgtg | acagtgtcga | atgcagggta | aatgccggac gcagctgaaa | 5640 |
| cggtatctcg | tccgacatgt | cagcagacgg | gcgaaggcca | tacatgccga tgccgaatct | 5700 |
| gactgcatta | aaaaagcctt | ttttcagccg | gagtccagcg | gcgctgttcg cgcagtggac | 5760 |
| cattagattc | tttaacggca | gcggagcaat | cagctcttta | aagcgctcaa actgcattaa | 5820 |
| gaaatagcct | ctttcttttt | catccgctgt | cgcaaaatgg | gtaaataccc ctttgcactt | 5880 |
| taaacgaggg | ttgcggtcaa | gaattgccat | cacgttctga | acttcttcct ctgttttac | 5940 |
| accaagtctg | ttcatccccg | tatcgacctt | cagatgaaaa | tgaagagaac cttttttcgt | 6000 |
| gtggcgggct | gcctcctgaa | gccattcaac | agaataacct | gttaaggtca cgtcatactc | 6060 |
| agcagcgatt | gccacatact | ccgggggaac | cgcgccaagc | accaatatag gcgccttcaa | 6120 |
| tcccttttg | cgcagtgaaa | tcgcttcatc | caaaatggcc | acggccaagc atgaagcacc | 6180 |
| tgcgtcaaga | gcagcctttg | ctgtttctgc | atcaccatgc | ccgtaggcgt ttgctttcac | 6240 |
| aactgccatc | aagtggacat | gttcaccgat | atgttttttc | atattgctga cattttcctt | 6300 |
| tatcgcggac | aagtcaattt | ccgcccacgt | atctctgtaa | aaaggtttg tgctcatgga | 6360 |
| aaactcctct | cttttttcag | aaaatcccag | tacgtaatta | agtatttgag aattaatttt | 6420 |
| atattgatta | atactaagtt | tacccagttt | tcacctaaaa | aacaaatgat gagataaatag | 6480 |
| ctccaaaggc | taaagaggac | tataccaact | atttgttaat | taa | 6523 |

<210> SEQ ID NO 63
<211> LENGTH: 69
<212> TYPE: PRT
<213> ORGANISM: Homo sapiens

<400> SEQUENCE: 63

Met Trp Val Pro Val Val Phe Leu Thr Leu Ser Val Thr Trp Ile Gly
1               5                   10                  15

```
Ala Ala Pro Leu Ile Leu Ser Arg Ile Val Gly Gly Trp Glu Cys Glu
            20                  25                  30

Lys His Ser Gln Pro Trp Gln Val Leu Val Ala Ser Arg Gly Arg Ala
        35                  40                  45

Val Cys Gly Gly Val Leu Val His Pro Gln Trp Val Leu Thr Ala Ala
    50                  55                  60

His Cys Ile Arg Lys
65

<210> SEQ ID NO 64
<211> LENGTH: 220
<212> TYPE: PRT
<213> ORGANISM: Oryza sativa

<400> SEQUENCE: 64

Met Trp Val Pro Val Val Phe Leu Thr Leu Ser Val Thr Trp Ile Gly
1               5                   10                  15

Ala Ala Pro Leu Ile Leu Ser Arg Ile Val Gly Gly Trp Glu Cys Glu
            20                  25                  30

Lys His Ser Gln Pro Trp Gln Val Leu Val Ala Ser Arg Gly Arg Ala
        35                  40                  45

Val Cys Gly Gly Val Leu Val His Pro Gln Trp Val Leu Thr Ala Ala
    50                  55                  60

His Cys Ile Arg Asn Lys Ser Val Ile Leu Leu Gly Arg His Ser Leu
65                  70                  75                  80

Phe His Pro Glu Asp Thr Gly Gln Val Phe Gln Val Ser His Ser Phe
                85                  90                  95

Pro His Pro Leu Tyr Asp Met Ser Leu Leu Lys Asn Arg Phe Leu Arg
            100                 105                 110

Pro Gly Asp Asp Ser Ser Ile Glu Pro Glu Phe Leu Thr Pro Lys
        115                 120                 125

Lys Leu Gln Cys Val Asp Leu His Val Ile Ser Asn Asp Val Cys Ala
    130                 135                 140

Gln Val His Pro Gln Lys Val Thr Lys Phe Met Leu Cys Ala Gly Arg
145                 150                 155                 160

Trp Thr Gly Gly Lys Ser Thr Cys Ser Gly Asp Ser Gly Gly Pro Leu
                165                 170                 175

Val Cys Asn Gly Val Leu Gln Gly Ile Thr Ser Trp Gly Ser Glu Pro
            180                 185                 190

Cys Ala Leu Pro Glu Arg Pro Ser Leu Tyr Thr Lys Val Val His Tyr
        195                 200                 205

Arg Lys Trp Ile Lys Asp Thr Ile Val Ala Asn Pro
    210                 215                 220

<210> SEQ ID NO 65
<211> LENGTH: 218
<212> TYPE: PRT
<213> ORGANISM: Homo sapiens

<400> SEQUENCE: 65

Met Trp Val Pro Val Val Phe Leu Thr Leu Ser Val Thr Trp Ile Gly
1               5                   10                  15

Ala Ala Pro Leu Ile Leu Ser Arg Ile Val Gly Gly Trp Glu Cys Glu
            20                  25                  30

Lys His Ser Gln Pro Trp Gln Val Leu Val Ala Ser Arg Gly Arg Ala
        35                  40                  45
```

Val Cys Gly Gly Val Leu Val His Pro Gln Trp Val Leu Thr Ala Ala
    50                  55                  60

His Cys Ile Arg Lys Pro Gly Asp Ser Ser His Asp Leu Met Leu
65                  70                  75                  80

Leu Arg Leu Ser Glu Pro Ala Glu Leu Thr Asp Ala Val Lys Val Met
                85                  90                  95

Asp Leu Pro Thr Gln Glu Pro Ala Leu Gly Thr Thr Cys Tyr Ala Ser
            100                 105                 110

Gly Trp Gly Ser Ile Glu Pro Glu Phe Leu Thr Pro Lys Lys Leu
        115                 120                 125

Gln Cys Val Asp Leu His Val Ile Ser Asn Asp Val Cys Ala Gln Val
130                 135                 140

His Pro Gln Lys Val Thr Lys Phe Met Leu Cys Ala Gly Arg Trp Thr
145                 150                 155                 160

Gly Gly Lys Ser Thr Cys Ser Gly Asp Ser Gly Gly Pro Leu Val Cys
                165                 170                 175

Asn Gly Val Leu Gln Gly Ile Thr Ser Trp Gly Ser Glu Pro Cys Ala
            180                 185                 190

Leu Pro Glu Arg Pro Ser Leu Tyr Thr Lys Val Val His Tyr Arg Lys
        195                 200                 205

Trp Ile Lys Asp Thr Ile Val Ala Asn Pro
    210                 215

<210> SEQ ID NO 66
<211> LENGTH: 218
<212> TYPE: PRT
<213> ORGANISM: Homo sapiens

<400> SEQUENCE: 66

Met Trp Val Pro Val Val Phe Leu Thr Leu Ser Val Thr Trp Ile Gly
1               5                   10                  15

Ala Ala Pro Leu Ile Leu Ser Arg Ile Val Gly Gly Trp Glu Cys Glu
            20                  25                  30

Lys His Ser Gln Pro Trp Gln Val Leu Val Ala Ser Arg Gly Arg Ala
        35                  40                  45

Val Cys Gly Gly Val Leu Val His Pro Gln Trp Val Leu Thr Ala Ala
    50                  55                  60

His Cys Ile Arg Asn Lys Ser Val Ile Leu Leu Gly Arg His Ser Leu
65                  70                  75                  80

Phe His Pro Glu Asp Thr Gly Gln Val Phe Gln Val Ser His Ser Phe
                85                  90                  95

Pro His Pro Leu Tyr Asp Met Ser Leu Leu Lys Asn Arg Phe Leu Arg
            100                 105                 110

Pro Gly Asp Asp Ser Ser Ile Glu Pro Glu Glu Phe Leu Thr Pro Lys
        115                 120                 125

Lys Leu Gln Cys Val Asp Leu His Val Ile Ser Asn Asp Val Cys Ala
130                 135                 140

Gln Val His Pro Gln Lys Val Thr Lys Phe Met Leu Cys Ala Gly Arg
145                 150                 155                 160

Trp Thr Gly Gly Lys Ser Thr Cys Ser Gly Asp Ser Gly Gly Pro Leu
                165                 170                 175

Val Cys Asn Gly Val Leu Gln Gly Ile Thr Ser Trp Gly Ser Glu Pro
            180                 185                 190

```
Cys Ala Leu Pro Glu Arg Pro Ser Leu Tyr Thr Lys Val Val His Tyr
        195                 200                 205

Arg Lys Trp Ile Lys Asp Thr Ile Val Ala
    210                 215
```

COMBINATION OF A PD-1 ANTAGONIST AND A LISTERIA-BASED VACCINE FOR TREATING PROSTATE CANCER

CROSS REFERENCE TO RELATED APPLICATIONS

This application claims the benefit of U.S. Provisional Patent Application No. 62/026,221, filed Jul. 18, 2014 and U.S. Provisional Patent Application No. 62/039,011, filed Aug. 19, 2014, both of which are incorporated in their entirety herein by reference.

FIELD OF THE INVENTION

The present invention relates to combination therapies useful for the treatment of cancer. In particular, the invention relates to the treatment of prostate cancer using an antagonist of a Programmed Death 1 protein (PD-1) in combination with a live attenuated recombinant *Listeria* strain comprising a fusion protein of a PEST sequence-containing polypeptide or PEST-sequence containing peptide fused to a tumor-associated antigen.

BACKGROUND OF THE INVENTION

PD-1 is recognized as an important player in immune regulation and the maintenance of peripheral tolerance. PD-1 is moderately expressed on naive T, B and NKT cells and up-regulated by T/B cell receptor signaling on lymphocytes, monocytes and myeloid cells (1).

Two known ligands for PD-1, PD-L1 (B7-H1) and PD-L2 (B7-DC), are expressed in human cancers arising in various tissues. In large sample sets of e.g. ovarian, renal, colorectal, pancreatic, liver cancers and melanoma, it was shown that PD-L1 expression correlated with poor prognosis and reduced overall survival irrespective of subsequent treatment (2-13). Similarly, PD-1 expression on tumor infiltrating lymphocytes was found to mark dysfunctional T cells in breast cancer and melanoma (14-15) and to correlate with poor prognosis in renal cancer (16). Thus, it has been proposed that PD-L1 expressing tumor cells interact with PD-1 expressing T cells to attenuate T cell activation and evasion of immune surveillance, thereby contributing to an impaired immune response against the tumor.

Several monoclonal antibodies that inhibit the interaction between PD-1 and one or both of its ligands PD-L1 and PD-L2 are in clinical development for treating cancer. It has been proposed that the efficacy of such antibodies might be enhanced if administered in combination with other approved or experimental cancer therapies, e.g., radiation, surgery, chemotherapeutic agents, targeted therapies, agents that inhibit other signaling pathways that are disregulated in tumors, and other immune enhancing agents.

*Listeria monocytogenes* (Lm) is a Gram-positive facultative intracellular pathogen that causes listeriolysis. Once invading a host cell, Lm can escape from the phagolysosome through production of a pore-forming protein listeriolysin O (LLO) to lyse the vascular membrane, allowing it to enter the cytoplasm, where it replicates and spreads to adjacent cells based on the mobility of actin-polymerizing protein (ActA). In the cytoplasm, Lm-secreting proteins are degraded by the proteasome and processed into peptides that associate with MHC class I molecules in the endoplasmic reticulum.

SUMMARY OF THE INVENTION

In one embodiment, the invention provides a method for treating a prostate cancer in a human individual comprising administering to the individual a combination therapy which comprises a PD-1 antagonist and a live-attenuated bacterial strain that is used to stimulate Antigen Presenting Cells (APCs) capable of driving a cellular immune response to Prostate Specific Antigen (PSA) expressing cells.

In another embodiment, the invention provides a method for treating a prostate cancer in a human individual comprising administering to the individual a combination therapy which comprises a PD-1 antagonist and a live-attenuated *Listeria monocytogenes* strain bioengineered, by transforming it with an expression vector to express a PSA antigen fused to a truncated Listeriolysin O (tLLO).

In yet another embodiment, the invention provides a method for treating a prostate cancer in a human individual comprising administering to the individual a combination therapy, which comprises a PD-1 antagonist and an LmddA-142 (10403S dal$^{(-)}$ dat$^{(-)}$ actA$^{(-)}$ pADV142) strain.

In a further embodiment, the invention provides a method for treating a prostate cancer in a human individual comprising administering to the individual a combination therapy, which comprises a PD-1 antagonist and an LmddA-143 (10403S dal$^{(-)}$ dat$^{(-)}$ actA$^{(-)}$ with klk3 fused to the hly gene in the chromosome) strain.

In another embodiment, the invention provides a medicament comprising a PD-1 antagonist for use in combination with a live-attenuated bacterial strain that is used to stimulate Antigen Presenting Cells (APCs) capable of driving a cellular immune response to PSA expressing cells, for treating a prostate cancer in a patient.

In yet another embodiment, the invention provides a medicament comprising a PD-1 antagonist for use in combination with a live-attenuated *Listeria monocytogenes* strain bioengineered, by transforming it with an expression vector to express a PSA antigen fused to a truncated Listeriolysin O (tLLO), for treating a prostate cancer in a patient.

In still another embodiment, the invention provides a medicament comprising a PD-1 antagonist for use in combination with an LmddA-142 (10403S dal$^{(-)}$ dat$^{(-)}$ actA$^{(-)}$ pADV142) strain, for treating a prostate cancer in a patient.

In a further embodiment, the invention provides a medicament comprising a PD-1 antagonist for use in combination with an LmddA-143 (10403S dal$^{(-)}$ dat$^{(-)}$ actA$^{(-)}$ with klk3 fused to the hly gene in the chromosome) strain, for treating a prostate cancer in a patient.

In yet another embodiment, the invention provides a medicament comprising a live-attenuated bacterial strain that is used to stimulate Antigen Presenting Cells (APCs) capable of driving a cellular immune response to PSA expressing cells for use in combination with a PD-1 antagonist for treating a prostate cancer in a patient.

In yet another embodiment, the invention provides a medicament comprising a live-attenuated *Listeria monocytogenes* strain bioengineered, by transforming it with an expression vector to express a PSA antigen fused to a truncated Listeriolysin O (tLLO) for use in combination with a PD-1 antagonist for treating a prostate cancer in a patient.

In another embodiment, the invention provides a medicament comprising an LmddA-142 (10403S dal$^{(-)}$ dat$^{(-)}$ actA$^{(-)}$ pADV142) strain for use in combination with a PD-1 antagonist for treating a prostate cancer in a patient.

In yet embodiment, the invention provides a medicament comprising an LmddA-143 (10403S dal$^{(-)}$ dat$^{(-)}$ actA$^{(-)}$ with klk3 fused to the hly gene in the chromosome) strain for use in combination with a PD-1 antagonist for treating a prostate cancer in a patient.

Other embodiments provide for use of a PD-1 antagonist in the manufacture of medicament for treating a prostate cancer in a human when administered in combination with a live-attenuated bacterial strain that is used to stimulate Antigen Presenting Cells (APCs) capable of driving a cellular immune response to PSA expressing cells and use of a live-attenuated bacterial strain that is used to stimulate Antigen Presenting Cells (APCs) capable of driving a cellular immune response to PSA expressing cells in the manufacture of a medicament for treating a prostate cancer in a patient when administered in combination with a PD-1 antagonist.

Other embodiments provide for use of a PD-1 antagonist in the manufacture of a medicament for treating a prostate cancer in a human when administered in combination with a live-attenuated *Listeria monocytogenes* strain bioengineered, by transforming it with an expression vector to express a PSA antigen fused to a truncated Listeriolysin O (tLLO) and use of a live-attenuated *Listeria monocytogenes* strain bioengineered, by transforming it with an expression vector to express a PSA antigen fused to a truncated Listeriolysin O (tLLO) in the manufacture of a medicament for treating a prostate cancer in a patient when administered in combination with a PD-1 antagonist.

Other embodiments provide for use of a PD-1 antagonist in the manufacture of medicament for treating a prostate cancer in a human when administered in combination with an LmddA-142 (10403S dal$^{(-)}$ dat$^{(-)}$ actA$^{(-)}$ pADV142) strain and use of an LmddA-142 (10403S dal$^{(-)}$ dat$^{(-)}$ actA$^{(-)}$ pADV142) strain in the manufacture of a medicament for treating a prostate cancer in a patient when administered in combination with a PD-1 antagonist.

Other embodiments provide for use of a PD-1 antagonist in the manufacture of medicament for treating a prostate cancer in a human when administered in combination with an LmddA-143 (10403S dal$^{(-)}$ dat$^{(-)}$ actA$^{(-)}$ with klk3 fused to the hly gene in the chromosome) strain and use of an LmddA-143 (10403S dal$^{(-)}$ dat$^{(-)}$ actA$^{(-)}$ with klk3 fused to the hly gene in the chromosome) strain in the manufacture of a medicament for treating a prostate cancer in a patient when administered in combination with a PD-1 antagonist.

In a still further embodiment, the invention provides for use of a PD-1 antagonist and a live-attenuated bacterial strain that is used to stimulate Antigen Presenting Cells (APCs) capable of driving a cellular immune response to PSA-expressing cells in the manufacture of medicaments for treating a prostate cancer in a patient. In some embodiments, the medicaments comprise a kit, and the kit also comprises a package insert comprising instructions for using the PD-1 antagonist in combination with an a live-attenuated bacterial strain that is used to stimulate Antigen Presenting Cells (APCs) capable of driving a cellular immune response to PSA expressing cells to treat a prostate cancer in a patient.

In another embodiment, the invention provides for use of a PD-1 antagonist and a live-attenuated *Listeria monocytogenes* strain bioengineered, by transforming it with an expression vector to express a PSA antigen fused to a truncated Listeriolysin O (tLLO) in the manufacture of medicaments for treating a prostate cancer in a patient. In some embodiments, the medicaments comprise a kit, and the kit also comprises a package insert comprising instructions for using the PD-1 antagonist in combination with a live-attenuated *Listeria monocytogenes* strain bioengineered, by transforming it with an expression vector to express a PSA antigen fused to a truncated Listeriolysin O (tLLO) to treat a prostate cancer in a patient.

In yet another embodiment, the invention provides for use of a PD-1 antagonist and an LmddA-142 (10403S dal$^{(-)}$ dat$^{(-)}$ actA$^{(-)}$ pADV142) strain in the manufacture of medicaments for treating a prostate cancer in a patient. In some embodiments, the medicaments comprise a kit, and the kit also comprises a package insert comprising instructions for using the PD-1 antagonist in combination with an LmddA-142 (10403S dal$^{(-)}$ dat$^{(-)}$ actA$^{(-)}$ pADV142) strain to treat a prostate cancer in a patient.

In still another embodiment, the invention provides for use of a PD-1 antagonist and an LmddA-143 (10403S dal$^{(-)}$ dat$^{(-)}$ actA$^{(-)}$ with klk3 fused to the hly gene in the chromosome) strain in the manufacture of medicaments for treating a prostate cancer in a patient. In some embodiments, the medicaments comprise a kit, and the kit also comprises a package insert comprising instructions for using the PD-1 antagonist in combination with an LmddA-143 (10403S dal$^{(-)}$ dat$^{(-)}$ actA$^{(-)}$ with klk3 fused to the hly gene in the chromosome) strain to treat a prostate cancer in a patient.

In all of the above treatment method, medicaments and uses, the PD-1 antagonist inhibits the binding of PD-L1 to PD-1, and preferably also inhibits the binding of PD-L2 to PD-1. In some embodiments of the above treatment method, medicaments and uses, the PD-1 antagonist is a monoclonal antibody, or antigen binding fragment thereof, which specifically binds to PD-1 or to PD-L1 and blocks the binding of PD-L1 to PD-1. In one embodiment, the PD-1 antagonist is an anti-PD-1 antibody which comprises a heavy chain and a light chain, and wherein the heavy and light chains comprise the amino acid sequences shown in FIG. 6 (SEQ ID NO:21 and SEQ ID NO:22).

In all of the above embodiments of the treatment method, medicaments and uses, the live-attenuated bacterial strain comprises a recombinant *Listeria* that is an attenuated auxotrophic strain. In one embodiment, the attenuated strain is Lm dal(-)dat(-) (Lmdd). In another embodiment, the attenuated strains is Lm dal(-)dat(-)ΔactA (LmddA). LmddA is based on a *Listeria* strain vector which is attenuated due to the deletion of virulence gene actA and retains a plasmid for expression of a trunctated LLO (tLLO) fused to a PSA antigen polypeptide in vivo and in vitro by complementation of dal gene. In some embodiments, the klk3 gene is fused to the hly gene in the chromosome for expression of a tLLO-PSA fusion polypeptide. In some of the above embodiments of the treatment method, medicaments and uses, the *Listeria* strain is a *Listeria monocytogenes*. In some of the above embodiments of the treatment method, medicaments and uses, the PSA antigen is fused to a truncated Listeriolysin O (tLLO). In one embodiment, the tLLO is an N-terminal LLO protein fragment. In one embodiment, the N-terminal LLO protein fragment and the PSA antigen are fused directly to one another. In another embodiment, the N-terminal LLO protein fragment and the PSA antigen are operably attached via a linker peptide. In another embodiment, the N-terminal LLO protein fragment and the PSA antigen are attached via a heterologous peptide. In another embodiment, the N-terminal LLO protein fragment is N-terminal to the PSA antigen. In another embodiment, the N-terminal LLO protein fragment is the N-terminal-most portion of the fusion protein. In another embodiment, a truncated LLO is truncated at the C-terminal to arrive at an N-terminal LLO. In all of the above embodiments of the treatment method, medicaments and uses, PSA is a kallikrein serine protease (KLK3) secreted by prostatic epithelial cells, which in one embodiment, is widely used as a marker for prostate cancer. In some embodiments, PSA is the full-length polypeptide. In other embodiment, PSA is a fraction of the full-length polypeptide. In one embodiment, a PSA antigen is encoded by the klk3 gene.

In some embodiments of the above treatment method, medicaments and uses, the live-attenuated bacterial strain is a dal$^{(-)}$ dat$^{(-)}$ actA$^{(-)}$ *Listeria monocytogenes* strain that episomally expresses the tLLO-PSA fusion protein. In one embodiment, the tLLO consists of about the first 441 AA of the LLO protein. In another embodiment, the LLO fragment is a non-hemolytic form of the LLO protein. In one embodiment, the PSA consists of a full-length protein. In another embodiment, the PSA consists of less than the full-length protein.

In some embodiments of the above treatment method, medicaments and uses of the invention, the prostate cancer is metastatic.

In other embodiments of the above treatment method, medicaments and uses of the invention, the prostate cancer is Castration-Resistant Prostate Cancer (mCRPC).

In still other embodiments of the above treatment method, medicaments and uses of the invention, the patient has been diagnosed with metastatic Castration-Resistant Prostate Cancer (mCRPC) following treatment with at least one previous therapeutic agent.

Also, in some embodiments of any of the above treatment method, medicaments and uses, the prostate cancer tests positive for the expression of one or both of PD-L1 and PD-L2. In some embodiments, the prostate cancer has elevated PD-L1 expression.

BRIEF DESCRIPTION OF THE DRAWINGS

FIG. 1 shows amino acid sequences of the light chain and heavy chain CDRs for an exemplary anti-PD-1 monoclonal antibody useful in the present invention (SEQ ID NOs:1-6).

FIG. 2 shows amino acid sequences of the light chain and heavy chain CDRs for another exemplary anti-PD-1 monoclonal antibody useful in the present invention (SEQ ID NOs:7-12).

FIG. 3 shows amino acid sequences of the heavy chain variable region and full length heavy chain for an exemplary anti-PD-1 monoclonal antibody useful in the present invention (SEQ ID NO:13 and SEQ ID NO:14).

FIG. 4 shows amino acid sequences of alternative light chain variable regions for an exemplary anti-PD-1 monoclonal antibody useful in the present invention (SEQ ID NOs:15-17).

FIGS. 5A and 5B show amino acid sequences of alternative light chains for an exemplary anti-PD-1 monoclonal antibody useful in the present invention (SEQ ID NOs:18-20). FIG. 5A shows the full length sequence of K09A-L-11 light chain (SEQ ID NO: 18) and K09A-L-16 light chain (SEQ ID NO: 19). FIG. 5B shows the full length sequence of K09A-L-17 light chain (SEQ ID NO: 20).

FIG. 6 shows amino acid sequences of the heavy and light chains for MK-3475 (SEQ ID NOs. 21 and 22, respectively).

FIG. 7 shows amino acid sequences of the heavy and light chains for nivolumab (SEQ ID NOs. 23 and 24, respectively).

FIGS. 9A-9C. FIG. 9A shows a map of the pADV134 plasmid.

FIGS. 9B and 9C show a map of the antibiotic-independent episomal expression vector for PSA delivery, pADV142 plasmid, wherein the antigen expression cassette consists of a hly promoter and LLO-PSA fusion protein (FIG. 9B) and the nucleotide sequence of pADV142 plasmid, wherein the underline section encodes a *Homo sapiens* kallikrein 3, (prostate specific antigen) (FIG. 9C).

DETAILED DESCRIPTION

Figure 8:
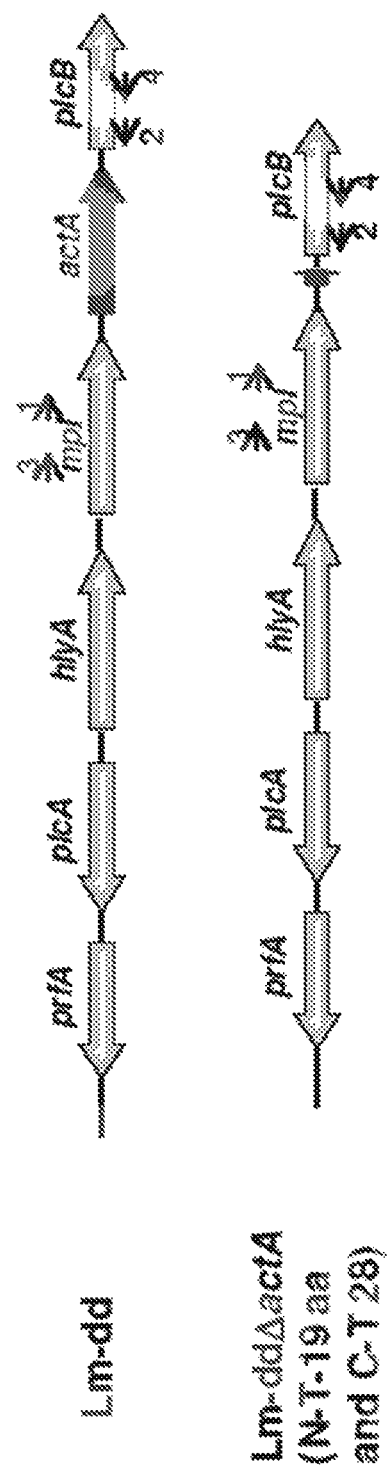
FIG. 8 shows a schematic representation of the chromosomal region of the Lmdd-143 and LmddA-143 after klk3 integration and actA deletion.

Abbreviations. Throughout the detailed description and examples of the invention the following abbreviations will be used:

| | |
|---|---|
| APC | antigen presenting cell |
| BID | One dose twice daily |
| CBD | Cholesterol Binding Domain |
| CDR | Complementarity determining region |
| CFU | Colony-forming units |
| CHO | Chinese hamster ovary |
| DFS | Disease free survival |
| DTR | Dose limiting toxicity |
| FFPE | formalin-fixed, paraffin-embedded |
| FR | Framework region |
| IgG | Immunoglobulin G |
| IHC | Immunohistochemistry or immunohistochemical |
| KLK3 | Kallikrein-related peptidase 3; also known as APS; PSA; hK3; KLK2A1 |
| LLO | Listeriolysin O polypeptide |
| tLLO | truncated Listeriolysin O polypeptide |
| Lm | *Listeria monocytogenes* |
| LmddA-142 | *Listeria monocytogenes* (10403S dal$^{(-)}$ dat$^{(-)}$ actA$^{(-)}$ pADV142); also known as ADXS31-142 |
| LmddA-143 | *Listeria monocytogenes* (10403S dal$^{(-)}$ dat$^{(-)}$ actA$^{(-)}$ with klk3 fused to the hly gene in the chromosome) |
| MTD | Maximum tolerated dose |
| NCBI | National Center for Biotechnology Information |
| NCI | National Cancer Institute |
| OR | Overall response |
| ORF | Open reading frame |
| OS | Overall survival |
| PCR | Polymerase chain reaction |
| PD | Progressive disease |
| PSA | Prostate specific antigen |
| PFS | Progression free survival |
| PR | Partial response |
| Q2W | One dose every two weeks |
| Q3W | One dose every three weeks |
| Q4W | One dose every four weeks |
| QD | One dose per day |
| RECIST | Response Evaluation Criteria in Solid Tumors |
| SD | Stable disease |
| SDS-PAGE | Sodium dodecyl sulfate-Polyacrylamide gel electrophoresis |
| TILs | Tumor infiltrating lymphocytes |
| VH | Immunoglobulin heavy chain variable region |
| VK | Immunoglobulin kappa light chain variable region |

I. Definitions

So that the invention n may be more readily understood, certain technical and scientific terms are specifically defined below. Unless specifically defined elsewhere in this document, all other technical and scientific terms used herein have the meaning commonly understood by one of ordinary skill in the art to which this invention belongs.

"About" when used to modify a numerically defined parameter (e.g., the dose of a PD-1 antagonist or a live-attenuated bacterial strain that is used to stimulate Antigen Presenting Cells (APCs) capable of driving a cellular immune response to PSA expressing cells or a live-attenuated *Listeria monocytogenes* strain bioengineered, by transforming it with an expression vector to express a PSA antigen fused to a truncated Listeriolysin O (tLLO) or an LmddA-142 (10403S dal$^{(-)}$ dat$^{(-)}$ actA$^{(-)}$ pADV142) strain or an LmddA-143 (10403S dal$^{(-)}$ dat$^{(-)}$ actA$^{(-)}$ with klk3 fused to the hly gene in the chromosome) strain, or the length of treatment time with a combination therapy described herein) means that the parameter may vary by as much as 10% below or above the stated numerical value for that parameter. For example, a dose of about 200 mg of the PD-1 antagonist, i.e., MK-3475, may vary between 180 mg and 220 mg.

As used herein, including the appended claims, the singular forms of words such as "a," "an," and "the," include their corresponding plural references unless the context clearly dictates otherwise.

"Administration" and "treatment," as it applies to an animal, human, experimental subject, cell, tissue, organ, or biological fluid, refers to contact of an exogenous pharmaceutical, therapeutic, diagnostic agent, or composition to the animal, human, subject, cell, tissue, organ, or biological fluid. Treatment of a cell encompasses contact of a reagent to the cell, as well as contact of a reagent to a fluid, where the fluid is in contact with the cell. "Administration" and "treatment" also means in vitro and ex vivo treatments, e.g., of a cell, by a reagent, diagnostic, binding compound, or by another cell. The term "subject" includes any organism, preferably an animal, more preferably a mammal (e.g., rat, mouse, dog, cat, rabbit) and most preferably a human.

The term "pharmaceutically acceptable carrier" refers to any inactive substance that is suitable for use in a formulation for the administration to a human of a PD-1 antagonist or a live-attenuated bacterial strain that is used to stimulate APCs capable of driving a cellular immune response to PSA expressing cells or a live-attenuated *Listeria monocytogenes* strain bioengineered, by transforming it with an expression vector to express a PSA antigen fused to a tLLO or an LmddA-142 (10403S dal$^{(-)}$ dat$^{(-)}$ actA$^{(-)}$ pADV142) strain or an LmddA-143 (10403S dal$^{(-)}$ dat$^{(-)}$ actA$^{(-)}$ with klk3 fused to the hly gene in the chromosome) strain.

As used herein, the term "antibody" refers to any form of immunoglobulin molecule that exhibits the desired biological or binding activity. Thus, it is used in the broadest sense and specifically covers, but is not limited to, monoclonal antibodies (including full length monoclonal antibodies), polyclonal antibodies, multispecific antibodies (e.g., bispecific antibodies), humanized, human antibodies, chimeric antibodies and camelized single domain antibodies. "Parental antibodies" are antibodies obtained by exposure of an immune system to an antigen prior to modification of the antibodies for an intended use, such as humanization of an antibody for use as a human therapeutic. As used herein, the term "antibody" encompasses not only intact polyclonal or monoclonal antibodies, but also, unless otherwise specified, any antigen binding portion thereof that competes with the intact antibody for specific binding, fusion proteins comprising an antigen binding portion, and any other modified configuration of the immunoglobulin molecule that comprises an antigen recognition site. Antigen binding portions include, for example, Fab, Fab', F(ab')$_2$, Fd, Fv, domain antibodies (dAbs, e.g., shark and camelid antibodies), fragments including complementarity determining regions (CDRs), single chain variable fragment antibodies (scFv), maxibodies, minibodies, intrabodies, diabodies, triabodies, tetrabodies, v-NAR and bis-scFv, and polypeptides that contain at least a portion of an immunoglobulin that is sufficient to confer specific antigen binding to the polypeptide. An antibody includes an antibody of any class, such as IgG, IgA, or IgM (or sub-class thereof), and the antibody need not be of any particular class. Depending on the antibody amino acid sequence of the constant region of its heavy chains, immunoglobulins can be assigned to different classes. There are five major classes of immunoglobulins: IgA, IgD, IgE, IgG, and IgM, and several of these may be further divided into subclasses (isotypes), e.g., IgG$_1$, IgG$_2$, IgG$_3$, IgG$_4$, IgA$_1$ and IgA$_2$. The heavy-chain constant regions that correspond to the different classes of immunoglobulins are called alpha, delta, epsilon, gamma, and mu, respectively. The subunit structures and three-dimensional configurations of different classes of immunoglobulins are well known.

"Variable regions" or "V region" as used herein means the segment of IgG chains which is variable in sequence between different antibodies. It extends to Kabat residue 109 in the light chain and 113 in the heavy chain. A "variable region" of an antibody refers to the variable region of the antibody light chain or the variable region of the antibody heavy chain, either alone or in combination. Typically, the variable regions of both the heavy and light chains comprise three hypervariable regions, also called complementarity determining regions (CDRs), which are located within relatively conserved framework regions (FR). The CDRs are usually aligned by the framework regions, enabling binding to a specific epitope. In general, from N-terminal to C-terminal, both light and heavy chains variable domains comprise FR1, CDR1, FR2, CDR2, FR3, CDR3 and FR4. The assignment of amino acids to each domain is, generally, in accordance with the definitions of *Sequences of Proteins of Immunological Interest*, Kabat, et al.; National Institutes of Health, Bethesda, Md.; 5$^{th}$ ed.; NIH Publ. No. 91-3242 (1991); Kabat (1978) *Adv. Prot. Chem.* 32:1-75; Kabat, et al., (1977) J. Biol. Chem. 252:6609-6616; Chothia, et al., (1987) *J Mol. Biol.* 196:901-917 or Chothia et al., (1989) *Nature* 342:878-883.

As used herein, the term "hypervariable region" refers to the amino acid residues of an antibody that are responsible for antigen-binding. The hypervariable region comprises amino acid residues from a "complementarity determining region" or "CDR" (i.e. CDRL1, CDRL2 and CDRL3 in the light chain variable domain and CDRH1, CDRH2 and CDRH3 in the heavy chain variable domain). See Kabat et al. (1991) Sequences of Proteins of Immunological Interest, 5th Ed. Public Health Service, National Institutes of Health, Bethesda, Md. (defining the CDR regions of an antibody by sequence); see also Chothia and Lesk (1987) *J. Mol. Biol.* 196: 901-917 (defining the CDR regions of an antibody by structure). As used herein, the term "framework" or "FR" residues refers to those variable domain residues other than the hypervariable region residues defined herein as CDR residues.

As used herein, unless otherwise indicated, "antibody fragment" or "antigen binding fragment" refers to antigen binding fragments of antibodies, i.e. antibody fragments that retain the ability to bind specifically to the antigen bound by the full-length antibody, e.g. fragments that retain one or more CDR regions. Examples of antibody binding fragments include, but are not limited to, Fab, Fab', F(ab')$_2$, and Fv fragments; diabodies; linear antibodies; single-chain antibody molecules, e.g., sc-Fv; nanobodies and multispecific antibodies formed from antibody fragments.

An antibody that "specifically binds to" a specified target protein is an antibody that exhibits preferential binding to that target as compared to other proteins, but this specificity does not require absolute binding specificity. An antibody is considered "specific" for its intended target if its binding is determinative of the presence of the target protein in a sample, e.g. without producing undesired results such as false positives. Antibodies, or binding fragments thereof, useful in the present invention will bind to the target protein with an affinity that is at least two fold greater, preferably at least ten times greater, more preferably at least 20-times greater, and most preferably at least 100-times greater than the affinity with non-target proteins. As used herein, an antibody is said to bind specifically to a polypeptide comprising a given amino acid sequence, e.g. the amino acid sequence of a mature human PD-1 or human PD-L1 molecule, if it binds to polypeptides comprising that sequence but does not bind to proteins lacking that sequence.

"Chimeric antibody" refers to an antibody in which a portion of the heavy and/or light chain is identical with or homologous to corresponding sequences in an antibody derived from a particular species (e.g., human) or belonging to a particular antibody class or subclass, while the remainder of the chain(s) is identical with or homologous to corresponding sequences in an antibody derived from another species (e.g., mouse) or belonging to another antibody class or subclass, as well as fragments of such antibodies, so long as they exhibit the desired biological activity.

"Human antibody" refers to an antibody that comprises human immunoglobulin protein sequences only. A human antibody may contain murine carbohydrate chains if produced in a mouse, in a mouse cell, or in a hybridoma derived from a mouse cell. Similarly, "mouse antibody" or "rat antibody" refer to an antibody that comprises only mouse or rat immunoglobulin sequences, respectively.

"Humanized antibody" refers to forms of antibodies that contain sequences from non-human (e.g., murine) antibodies as well as human antibodies. Such antibodies contain minimal sequence derived from non-human immunoglobulin. In general, the humanized antibody will comprise substantially all of at least one, and typically two, variable domains, in which all or substantially all of the hypervariable loops correspond to those of a non-human immunoglobulin and all or substantially all of the FR regions are those of a human immunoglobulin sequence. The humanized antibody optionally also will comprise at least a portion of an immunoglobulin constant region (Fc), typically that of a human immunoglobulin. The prefix "hum", "hu" or "h" is added to antibody clone designations when necessary to distinguish humanized antibodies from parental rodent antibodies. The humanized forms of rodent antibodies will generally comprise the same CDR sequences of the parental rodent antibodies, although certain amino acid substitutions may be included to increase affinity, increase stability of the humanized antibody, or for other reasons.

The terms "cancer", "cancerous", or "malignant" refer to or describe the physiological condition in mammals that is typically characterized by unregulated cell growth.

"Biotherapeutic agent" means a biological molecule, such as an antibody or fusion protein, that blocks ligand/receptor signaling in any biological pathway that supports tumor maintenance and/or growth or suppresses the anti-tumor immune response.

"CDR" or "CDRs" as used herein means complementarity determining region(s) in a immunoglobulin variable region, defined using the Kabat numbering system, unless otherwise indicated.

"Chemotherapeutic agent" refers to a chemical or biological substance that can cause death of cancer cells, or interfere with growth, division, repair, and/or function of cancer cells. Classes of chemotherapeutic agents include, but are not limited to: alkylating agents, antimetabolites, kinase inhibitors, spindle poison plant alkaloids, cytoxic/antitumor antibiotics, topisomerase inhibitors, photosensitizers, anti-estrogens and selective estrogen receptor modulators (SERMs), anti-progesterones, estrogen receptor down-regulators (ERDs), estrogen receptor antagonists, leutinizing hormone-releasing hormone agonists, anti-androgens, aromatase inhibitors, EGFR inhibitors, VEGF inhibitors, anti-sense oligonucleotides that inhibit expression of genes implicated in abnormal cell proliferation or tumor growth. Chemotherapeutic agents useful in the treatment methods of the present invention include cytostatic and/or cytotoxic agents.

The antibodies and compositions provided by the present disclosure can be administered via any suitable enteral route or parenteral route of administration. The term "enteral route" of administration refers to the administration via any part of the gastrointestinal tract. Examples of enteral routes include oral, mucosal, buccal, and rectal route, or intragastric route. "Parenteral route" of administration refers to a route of administration other than enteral route. Examples of parenteral routes of administration include intravenous, intramuscular, intradermal, intraperitoneal, intratumor, intravesical, intraarterial, intrathecal, intracapsular, intraorbital, intracardiac, transtracheal, intraarticular, subcapsular, subarachnoid, intraspinal, epidural and intrasternal, subcutaneous, or topical administration. The antibodies and compositions of the disclosure can be administered using any suitable method, such as by oral ingestion, nasogastric tube, gastrostomy tube, injection, infusion, implantable infusion pump, and osmotic pump. The suitable route and method of administration may vary depending on a number of factors such as the specific antibody being used, the rate of absorption desired, specific formulation or dosage form used, type or severity of the disorder being treated, the specific site of action, and conditions of the patient, and can be readily selected by a person skilled in the art.

The term "simultaneous administration" as used herein in relation to the administration of medicaments refers to the administration of medicaments such that the individual medicaments are present within a subject at the same time. In addition to the concomitant administration of medicaments (via the same or alternative routes), simultaneous administration may include the administration of the medicaments (via the same or an alternative route) at different times.

The Bliss independence combined response C for two single compounds with effects A and B is C=A+B−A*B, where each effect is expressed as a fractional inhibition between 0 and 1. (Reference: Bliss (1939) *Annals of Applied Biology*) The Bliss value, defined to be the difference between the experimental response and the calculated Bliss Independence value, indicates whether the two compounds in combination are additive or synergistic.

A Bliss value of zero (0) is considered additive. The term "additive" means that the result of the combination of the two targeted agents is the sum of each agent individually.

"Chothia" as used herein means an antibody numbering system described in Al-Lazikani et al., *JMB* 273:927-948 (1997).

"Conservatively modified variants" or "conservative substitution" refers to substitutions of amino acids in a protein with other amino acids having similar characteristics (e.g.

charge, side-chain size, hydrophobicity/hydrophilicity, backbone conformation and rigidity, etc.), such that the changes can frequently be made without altering the biological activity or other desired property of the protein, such as antigen affinity and/or specificity. Those of skill in this art recognize that, in general, single amino acid substitutions in non-essential regions of a polypeptide do not substantially alter biological activity (see, e.g., Watson et al. (1987) *Molecular Biology of the Gene*, The Benjamin/Cummings Pub. Co., p. 224 (4th Ed.)). In addition, substitutions of structurally or functionally similar amino acids are less likely to disrupt biological activity. Exemplary conservative substitutions are set forth in Table 1 below.

TABLE 1

Exemplary Conservative Amino Acid Substitutions

| Original residue | Conservative substitution |
| --- | --- |
| Ala (A) | Gly; Ser |
| Arg (R) | Lys; His |
| Asn (N) | Gln; His |
| Asp (D) | Glu; Asn |
| Cys (C) | Ser; Ala |
| Gln (Q) | Asn |
| Glu (E) | Asp; Gln |
| Gly (G) | Ala |
| His (H) | Asn; Gln |
| Ile (I) | Leu; Val |
| Leu (L) | Ile; Val |
| Lys (K) | Arg; His |
| Met (M) | Leu; Ile; Tyr |
| Phe (F) | Tyr; Met; Leu |
| Pro (P) | Ala |
| Ser (S) | Thr |
| Thr (T) | Ser |
| Trp (W) | Tyr; Phe |
| Tyr (Y) | Trp; Phe |
| Val (V) | Ile; Leu |

"Consists essentially of," and variations such as "consist essentially of" or "consisting essentially of," as used throughout the specification and claims, indicate the inclusion of any recited elements or group of elements, and the optional inclusion of other elements, of similar or different nature than the recited elements, that do not materially change the basic or novel properties of the specified dosage regimen, method, or composition. As a non-limiting example, an antibody that consists essentially of a recited amino acid sequence may also include the addition and/or substitution of one or more amino acids that do not materially affect the properties of the antibody.

"Diagnostic anti-PD-L monoclonal antibody" means a mAb which specifically binds to the mature form of the designated PD-L (PD-L1 or PDL2) that is expressed on the surface of certain mammalian cells. A mature PD-L lacks the presecretory leader sequence, also referred to as leader peptide The terms "PD-L" and "mature PD-L" are used interchangeably herein, and shall be understood to mean the same molecule unless otherwise indicated or readily apparent from the context.

As used herein, a diagnostic anti-human PD-L1 mAb or anti-hPD-L1 mAb refers to a monoclonal antibody that specifically binds to mature human PD-L1. Specific examples of diagnostic anti-human PD-L1 mAbs useful as diagnostic mAbs for immunohistochemistry (IHC) detection of PD-L1 expression in formalin-fixed, paraffin-embedded (FFPE) tumor tissue sections are antibody 20C3 and antibody 22C3, which are described in WO2014/100079. Another anti-human PD-L1 mAb that has been reported to be useful for IHC detection of PD-L1 expression in FFPE tissue sections (Chen, B. J. et al., *Clin Cancer Res* 19: 3462-3473 (2013)) is a rabbit anti-human PD-L1 mAb publicly available from Sino Biological, Inc. (Beijing, P. R. China; Catalog number 10084-R015).

"Framework region" or "FR" as used herein means the immunoglobulin variable regions excluding the CDR regions.

"Homology" refers to sequence similarity between two polypeptide sequences when they are optimally aligned. When a position in both of the two compared sequences is occupied by the same amino acid monomer subunit, e.g., if a position in a light chain CDR of two different Abs is occupied by alanine, then the two Abs are homologous at that position. The percent of homology is the number of homologous positions shared by the two sequences divided by the total number of positions compared ×100. For example, if 8 of 10 of the positions in two sequences are matched or homologous when the sequences are optimally aligned then the two sequences are 80% homologous. Generally, the comparison is made when two sequences are aligned to give maximum percent homology. For example, the comparison can be performed by a BLAST algorithm wherein the parameters of the algorithm are selected to give the largest match between the respective sequences over the entire length of the respective reference sequences.

The following references relate to BLAST algorithms often used for sequence analysis: BLAST ALGORITHMS: Altschul, S. F., et al., (1990) J. Mol. Biol. 215:403-410; Gish, W., et al., (1993) Nature Genet. 3:266-272; Madden, T. L., et al., (1996) Meth. Enzymol. 266:131-141; Altschul, S. F., et al., (1997) Nucleic Acids Res. 25:3389-3402; Zhang, J., et al., (1997) Genome Res. 7:649-656; Wootton, J. C., et al., (1993) Comput. Chem. 17:149-163; Hancock, J. M. et al., (1994) Comput. Appl. Biosci. 10:67-70; ALIGNMENT SCORING SYSTEMS: Dayhoff, M. O., et al., "A model of evolutionary change in proteins." in Atlas of Protein Sequence and Structure, (1978) vol. 5, suppl. 3. M. O. Dayhoff (ed.), pp. 345-352, Natl. Biomed. Res. Found., Washington, D.C.; Schwartz, R. M., et al., "Matrices for detecting distant relationships." in Atlas of Protein Sequence and Structure, (1978) vol. 5, suppl. 3." M. O. Dayhoff (ed.), pp. 353-358, Natl. Biomed. Res. Found., Washington, D.C.; Altschul, S. F., (1991) J. Mol. Biol. 219:555-565; States, D. J., et al., (1991) Methods 3:66-70; Henikoff, S., et al., (1992) Proc. Natl. Acad. Sci. USA 89:10915-10919; Altschul, S. F., et al., (1993) J. Mol. Evol. 36:290-300; ALIGNMENT STATISTICS: Karlin, S., et al., (1990) Proc. Natl. Acad. Sci. USA 87:2264-2268; Karlin, S., et al., (1993) Proc. Natl. Acad. Sci. USA 90:5873-5877; Dembo, A., et al., (1994) Ann Prob. 22:2022-2039; and Altschul, S. F. "Evaluating the statistical significance of multiple distinct local alignments." in Theoretical and Computational Methods in Genome Research (S. Suhai, ed.), (1997) pp. 1-14, Plenum, New York.

"Isolated antibody" and "isolated antibody fragment" refers to the purification status and in such context means the named molecule is substantially free of other biological molecules such as nucleic acids, proteins, lipids, carbohydrates, or other material such as cellular debris and growth media. Generally, the term "isolated" is not intended to refer to a complete absence of such material or to an absence of water, buffers, or salts, unless they are present in amounts that substantially interfere with experimental or therapeutic use of the binding compound as described herein.

"Kabat" as used herein means an immunoglobulin alignment and numbering system pioneered by Elvin A. Kabat ((1991) Sequences of Proteins of Immunological Interest, 5th Ed. Public Health Service, National Institutes of Health, Bethesda, Md.).

"Monoclonal antibody" or "mAb" or "Mab", as used herein, refers to a population of substantially homogeneous antibodies, i.e., the antibody molecules comprising the population are identical in amino acid sequence except for possible naturally occurring mutations that may be present in minor amounts. In contrast, conventional (polyclonal) antibody preparations typically include a multitude of different antibodies having different amino acid sequences in their variable domains, particularly their CDRs, which are often specific for different epitopes. The modifier "monoclonal" indicates the character of the antibody as being obtained from a substantially homogeneous population of antibodies, and is not to be construed as requiring production of the antibody by any particular method. For example, a monoclonal antibody to be used in accordance with the present invention may be made by the hybridoma method first described by Kohler et al. (1975) *Nature* 256: 495, or may be made by recombinant DNA methods (see, e.g., U.S. Pat. No. 4,816,567). The monoclonal antibody may also be isolated from phage antibody libraries using the techniques described in Clackson et al. (1991) *Nature* 352: 624-628 and Marks et al. (1991) *J. Mol. Biol.* 222: 581-597, for example. See also Presta (2005) *J. Allergy Clin. Immunol.* 116:731.

"Patient" or "subject" refers to any single human subject for which therapy is desired or that is participating in a clinical trial, epidemiological study or used as a control.

"PD-1 antagonist" means any chemical compound or biological molecule that blocks binding of human PD-L1 expressed on a cancer cell to human PD-1 expressed on an immune cell (T cell, B cell or NKT cell) and preferably also blocks binding of human PD-L2 expressed on a cancer cell to the immune-cell expressed PD-1. Alternative names or synonyms for PD-1 and its ligands include: PDCD1, PD1, CD279 and SLEB2 for PD-1; PDCD1L1, PDL1, B7H1, B7-4, CD274 and B7-H for PD-L1; and PDCD1L2, PDL2, B7-DC, Btdc and CD273 for PD-L2. Exemplary human PD-1 amino acid sequences can be found in NCBI Locus No.: NP_005009. Exemplary human PD-L1 and PD-L2 amino acid sequences can be found in NCBI Locus No.: NP_054862 and NP_079515, respectively.

PD-1 antagonists useful in the any of the treatment method, medicaments and uses of the present invention include a monoclonal antibody (mAb), or antigen binding fragment thereof, which specifically binds to human PD-1 or human PD-L1. The mAb may be a human antibody, a humanized antibody or a chimeric antibody, and may include a human constant region. In some embodiments, the human constant region is selected from the group consisting of IgG1, IgG2, IgG3 and IgG4 constant regions, and in some embodiments, the human constant region is an IgG1 or IgG4 constant region. In some embodiments, the antigen binding fragment is selected from the group consisting of Fab, Fab'-SH, F(ab')$_2$, scFv and Fv fragments.

Examples of mAbs that bind to human PD-1, and useful in the treatment method, medicaments and uses of the present invention, are described in U.S. Pat. Nos. 7,488,802, 7,521,051, 8,008,449, 8,354,509, 8,168,757, WO2004/004771, WO2004/072286, WO2004/056875, and US2011/0271358. Specific anti-human PD-1 mAbs useful as the PD-1 antagonist in the treatment method, medicaments and uses of the present invention include: MK-3475, a humanized IgG4 mAb with the structure described in *WHO Drug Information*, Vol. 27, No. 2, pages 161-162 (2013) and which comprises the heavy and light chain amino acid sequences shown in FIG. 6, nivolumab (BMS-936558), a human IgG4 mAb with the structure described in *WHO Drug Information*, Vol. 27, No. 1, pages 68-69 (2013) and which comprises the heavy and light chain amino acid sequences shown in FIG. 7; the humanized antibodies h409A11, h409A16 and h409A17, which are described in WO2008/156712, and AMP-514, which is being developed by MedImmune.

Examples of mAbs that bind to human PD-L1, and useful in the treatment method, medicaments and uses of the present invention, are described in WO2013/019906, WO2010/077634 A1 and U.S. Pat. No. 8,383,796. Specific anti-human PD-L1 mAbs useful as the PD-1 antagonist in the treatment method, medicaments and uses of the present invention include MPDL3280A, BMS-936559, MEDI4736, MSB0010718C and an antibody which comprises the heavy chain and light chain variable regions of SEQ ID NO:24 and SEQ ID NO:21, respectively, of WO2013/019906.

Other PD-1 antagonists useful in the any of the treatment method, medicaments and uses of the present invention include an immunoadhesin that specifically binds to human PD-1 or human PD-L1, e.g., a fusion protein containing the extracellular or PD-1 binding portion of PD-L1 or PD-L2 fused to a constant region such as an Fc region of an immunoglobulin molecule. Examples of immunoadhesion molecules that specifically bind to PD-1 are described in WO2010/027827 and WO2011/066342. Specific fusion proteins useful as the PD-1 antagonist in the treatment method, medicaments and uses of the present invention include AMP-224 (also known as B7-DCIg), which is a PD-L2-FC fusion protein and binds to human PD-1.

In some embodiments of the treatment method, medicaments and uses of the present invention, the PD-1 antagonist is a monoclonal antibody, or antigen binding fragment thereof, which comprises: (a) light chain CDRs SEQ ID NOs: 1, 2 and 3 and heavy chain CDRs SEQ ID NOs: 4, 5 and 6; or (b) light chain CDRs SEQ ID NOs: 7, 8 and 9 and heavy chain CDRs SEQ ID NOs: 10, 11 and 12.

In other embodiments of the treatment method, medicaments and uses of the present invention, the PD-1 antagonist is a monoclonal antibody, or antigen binding fragment thereof, which specifically binds to human PD-1 and comprises (a) a heavy chain variable region comprising SEQ ID NO:13 or a variant thereof, and (b) a light chain variable region comprising an amino acid sequence selected from the group consisting of SEQ ID NO:15 or a variant thereof; SEQ ID NO:16 or a variant thereof; and SEQ ID NO: 17 or a variant thereof. A variant of a heavy chain variable region sequence is identical to the reference sequence except having up to 17 conservative amino acid substitutions in the framework region (i.e., outside of the CDRs), and preferably has less than ten, nine, eight, seven, six or five conservative amino acid substitutions in the framework region. A variant of a light chain variable region sequence is identical to the reference sequence except having up to five conservative amino acid substitutions in the framework region (i.e., outside of the CDRs), and preferably has less than four, three or two conservative amino acid substitution in the framework region.

In another embodiment of the treatment method, medicaments and uses of the present invention, the PD-1 antagonist is a monoclonal antibody which specifically binds to human PD-1 and comprises (a) a heavy chain comprising SEQ ID NO: 14 and (b) a light chain comprising SEQ ID NO:18, SEQ ID NO:19 or SEQ ID NO:20.

In yet another embodiment of the treatment method, medicaments and uses of the present invention, the PD-1 antagonist is a monoclonal antibody which specifically binds to human PD-1 and comprises (a) a heavy chain comprising SEQ ID NO: 14 and (b) a light chain comprising SEQ ID NO:18.

Table 2 below provides a list of the amino acid sequences of exemplary anti-PD-1 mAbs for use in the treatment method, medicaments and uses of the present invention, and the sequences are shown in FIGS. 1-5.

TABLE 2

EXEMPLARY ANTI-HUMAN PD-1 MONOCLONAL ANTIBODIES

A. Comprises light and heavy chain CDRs of hPD-1.08A in WO2008/156712

| | |
|---|---|
| CDRL1 | SEQ ID NO: 1 |
| CDRL2 | SEQ ID NO: 2 |
| CDRL3 | SEQ ID NO: 3 |
| CDRH1 | SEQ ID NO: 4 |
| CDRH2 | SEQ ID NO: 5 |
| CDRH3 | SEQ ID NO: 6 |

B. Comprises light and heavy chain CDRs of hPD-1.09A in WO2008/156712

| | |
|---|---|
| CDRL1 | SEQ ID NO: 7 |
| CDRL2 | SEQ ID NO: 8 |
| CDRL3 | SEQ ID NO: 9 |
| CDRH1 | SEQ ID NO: 10 |
| CDRH2 | SEQ ID NO: 11 |
| CDRH3 | SEQ ID NO: 12 |

C. Comprises the mature h109A heavy chain variable region and one of the mature K09A light chain variable regions in WO2008/156712

| | |
|---|---|
| Heavy chain VR | SEQ ID NO: 13 |
| Light chain VR | SEQ ID NO: 15 or SEQ ID NO: 16 or SEQ ID NO: 17 |

D. Comprises the mature 409 heavy chain and one of the mature K09A light chains in WO2008/156712

| | |
|---|---|
| Heavy chain | SEQ ID NO: 14 |
| Light chain | SEQ ID NO: 18 or SEQ ID NO: 19 or SEQ ID NO: 20 |

"PD-L1" expression or "PD-L2" expression as used herein means any detectable level of expression of the designated PD-L protein on the cell surface or of the designated PD-L mRNA within a cell or tissue. PD-L protein expression may be detected with a diagnostic PD-L antibody in an IHC assay of a tumor tissue section or by flow cytometry. Alternatively, PD-L protein expression by tumor cells may be detected by PET imaging, using a binding agent (e.g., antibody fragment, affibody and the like) that specifically binds to the desired PD-L target, e.g., PD-L1 or PD-L2. Techniques for detecting and measuring PD-L mRNA expression include RT-PCR and realtime quantitative RT-PCR.

Several approaches have been described for quantifying PD-L1 protein expression in IHC assays of tumor tissue sections. See, e.g., Thompson, R. H., et al., *PNAS* 101 (49); 17174-17179 (2004); Thompson, R. H. et al., *Cancer Res.* 66:3381-3385 (2006); Gadiot, J., et al., *Cancer* 117:2192-2201 (2011); Taube, J. M. et al., *Sci Transl Med* 4, 127ra37 (2012); and Toplian, S. L. et al., *New Eng. J Med.* 366 (26): 2443-2454 (2012).

One approach employs a simple binary end-point of positive or negative for PD-L1 expression, with a positive result defined in terms of the percentage of tumor cells that exhibit histologic evidence of cell-surface membrane staining. A tumor tissue section is counted as positive for PD-L1 expression if IHC staining is observed in at least 1%, and preferably 5% of total tumor cells. In an embodiment, a prostate tumor sample is designated as having weak PD-L1 expression if 1% to 49% of the total tumor cells in the sample exhibit membrane staining and is designated as having strong PD-L1 expression if at least 50% of the tumor cells in the sample exhibit membrane staining, in each case as determined by IHC assay using the antibody 22C3 described in WO2014/100079.

In another approach, PD-L1 expression in the tumor tissue section is quantified in the tumor cells as well as in infiltrating immune cells, which predominantly comprise lymphocytes. The percentage of tumor cells and infiltrating immune cells that exhibit membrane staining are separately quantified as <5%, 5 to 9%, and then in 10% increments up to 100%. For tumor cells, PD-L1 expression is counted as negative if the score is <5% score and positive if the score is ≥5%. PD-L1 expression in the immune infiltrate is reported as a semi-quantitative measurement called the adjusted inflammation score (AIS), which is determined by multiplying the percent of membrane staining cells by the intensity of the infiltrate, which is graded as none (0), mild (score of 1, rare lymphocytes), moderate (score of 2, focal infiltration of tumor by lymphohistiocytic aggregates), or severe (score of 3, diffuse infiltration). A tumor tissue section is counted as positive for PD-L1 expression by immune infiltrates if the AIS is ≥5.

The level of PD-L mRNA expression may be compared to the mRNA expression levels of one or more reference genes that are frequently used in quantitative RT-PCR, such as ubiquitin C.

In some embodiments, a level of PD-L1 expression (protein and/or mRNA) by malignant cells and/or by infiltrating immune cells within a tumor is determined to be "overexpressed" or "elevated" based on comparison with the level of PD-L1 expression (protein and/or mRNA) by an appropriate control. For example, a control PD-L1 protein or mRNA expression level may be the level quantified in nonmalignant cells of the same type or in a section from a matched normal tissue. In some embodiments, PD-L1 expression in a tumor sample is determined to be elevated if PD-L1 protein (and/or PD-L1 mRNA) in the sample is at least 10%, 20%, or 30% greater than in the control.

"Prostate Cancer Working Group 2 (PCWG2) criteria" as used herein has the meaning as presented in Scher et al., (2008) "Design and End Points of Clinical Trials for Patients With Progressive Prostate Cancer and Castrate Levels of Testosterone: Recommendations of the Prostate Cancer Clinical Trials Working Group" J. Clin. Oncol. 26(7):1148-159, incorporated in its entirety herein.

"RECIST 1.1 Response Criteria" as used herein means the definitions set forth in Eisenhauer et al., E. A. et al., *Eur. J Cancer* 45:228-247 (2009) for target lesions or nontarget lesions, as appropriate based on the context in which response is being measured.

"Sustained response" means a sustained therapeutic effect after cessation of treatment with a therapeutic agent, or a combination therapy described herein. In some embodiments, the sustained response has a duration that is at least the same as the treatment duration, or at least 1.5, 2.0, 2.5 or 3 times longer than the treatment duration.

The terms "synergy" or "synergistic" are used to mean that the response of the combination of the two agents is more than the sum of each agent's individual response. More specifically, in the in vitro setting one measure of synergy is known as "Bliss synergy." Bliss synergy refers to "excess over Bliss independence", as determined by the Bliss value defined above. When the Bliss value is greater than zero (0), or more preferably greater than 0.2, it is considered indicative of synergy. Of course, the use of "synergy" herein also encompasses in vitro synergy as measured by additional and/or alternate methods. References herein to a combination's in vitro biological effects, including but not limited to anti-cancer effects, being greater than, or equal to, the sum of the combination's components individually, may be correlated to Bliss values. Again, the use of "synergy" herein, including whether a combination of components demonstrates activity equal to or greater than the sum of the components individually, may be measured by additional and/or alternate methods and are known, or will be apparent, to those skilled in this art. In one embodiment, the combination of a *Listeria* based immunotherapy, as described herein, with an anti-PD-1 antibody, as described herein, provides synergistic antitumor activities.

"Tissue Section" refers to a single part or piece of a tissue sample, e.g., a thin slice of tissue cut from a sample of a normal tissue or of a tumor.

"Treat" or "treating" a cancer as used herein means to administer a combination therapy of a PD-1 antagonist and a live-attenuated bacterial strain that is used to stimulate APCs capable of driving a cellular immune response to PSA expressing cells or a live-attenuated *Listeria monocytogenes* strain bioengineered, by transforming it with an expression vector to express a PSA antigen fused to a tLLO or an LmddA-142 (10403S dal$^{(-)}$ dat$^{(-)}$ actA$^{(-)}$ pADV142) strain or an LmddA-143 (10403S dal$^{(-)}$ dat$^{(-)}$ actA$^{(-)}$ with klk3 fused to the hly gene in the chromosome) strain to a subject having a prostate cancer, or diagnosed with a prostate cancer, to achieve at least one positive therapeutic effect, such as for example, reduced number of cancer cells, reduced tumor size, reduced rate of cancer cell infiltration into peripheral organs, or reduced rate of tumor metastasis or tumor growth. Positive therapeutic effects in cancer can be measured in a number of ways (See, W. A. Weber, *J. Nucl. Med.* 50:1S-10S (2009)). For example, with respect to tumor growth inhibition, according to NCI standards, a T/C≤42% is the minimum level of anti-tumor activity. A T/C<10% is considered a high anti-tumor activity level, with T/C (%)=Median tumor volume of the treated/Median tumor volume of the control×100. In some embodiments, the treatment achieved by a combination of the invention is any of PR, CR, OR, PFS, DFS and OS. PFS, also referred to as "Time to Tumor Progression" indicates the length of time during and after treatment that the cancer does not grow, and includes the amount of time patients have experienced a CR or PR, as well as the amount of time patients have experienced SD. DFS refers to the length of time during and after treatment that the patient remains free of disease. OS refers to a prolongation in life expectancy as compared to naive or untreated individuals or patients. In some embodiments, response to a combination of the invention is any of PR, CR, PFS, DFS, OR or OS that is assessed using RECIST 1.1 response criteria. The treatment regimen for a combination of the invention that is effective to treat a cancer patient may vary according to factors such as the disease state, age, and weight of the patient, and the ability of the therapy to elicit an anti-cancer response in the subject. While an embodiment of any of the aspects of the invention may not be effective in achieving a positive therapeutic effect in every subject, it should do so in a statistically significant number of subjects as determined by any statistical test known in the art such as the Student's t-test, the chi$^2$-test, the U-test according to Mann and Whitney, the Kruskal-Wallis test (H-test), Jonckheere-Terpstra-test and the Wilcoxon-test.

The terms "treatment regimen", "dosing protocol" and dosing regimen are used interchangeably to refer to the dose and timing of administration of each therapeutic agent in a combination of the invention.

"Tumor" as it applies to a subject diagnosed with, or suspected of having, a cancer refers to a malignant or potentially malignant neoplasm or tissue mass of any size, and includes primary tumors and secondary neoplasms. A solid tumor is an abnormal growth or mass of tissue that usually does not contain cysts or liquid areas. Different types of solid tumors are named for the type of cells that form them. Examples of solid tumors are sarcomas, carcinomas, and lymphomas. Leukemias (cancers of the blood) generally do not form solid tumors (National Cancer Institute, Dictionary of Cancer Terms).

"Tumor burden" also referred to as "tumor load", refers to the total amount of tumor material distributed throughout the body. Tumor burden refers to the total number of cancer cells or the total size of tumor(s), throughout the body, including lymph nodes and bone narrow. Tumor burden can be determined by a variety of methods known in the art, such as, e.g. by measuring the dimensions of tumor(s) upon removal from the subject, e.g., using calipers, or while in the body using imaging techniques, e.g., ultrasound, bone scan, computed tomography (CT) or magnetic resonance imaging (MRI) scans.

The term "tumor size" refers to the total size of the tumor which can be measured as the length and width of a tumor. Tumor size may be determined by a variety of methods known in the art, such as, e.g. by measuring the dimensions of tumor(s) upon removal from the subject, e.g., using calipers, or while in the body using imaging techniques, e.g., bone scan, ultrasound, CT or MRI scans.

In some embodiment, this invention provides an immunogenic composition comprising a live attenuated bacteria strain, for example a *Listeria* vaccine strain comprises a nucleic acid molecule, wherein the nucleic acid molecule comprises a first open reading frame encoding fusion polypeptide, wherein said fusion polypeptide comprises a PEST sequence-containing polypeptide or a PEST sequence-containing peptide fused to a PSA antigen or fragment thereof. In one embodiment, an immunogenic composition comprises a live-attenuated bacterial strain that is used to stimulate APCs capable of driving a cellular immune response to PSA expressing cells. In another embodiment, an immunogenic composition comprises a live-attenuated *Listeria monocytogenes* strain bioengineered, by transforming it with an expression vector to express a PSA antigen fused to a tLLO. In yet another embodiment, an immunogenic composition comprises an LmddA-142 (10403S dal$^{(-)}$ dat$^{(-)}$ actA$^{(-)}$ pADV142) strain. In still another embodiment, an immunogenic composition comprises an LmddA-143 (10403S dal$^{(-)}$ dat$^{(-)}$ actA$^{(-)}$ with klk3 fused to the hly gene in the chromosome) strain. In some embodiments, the present invention provides methods of treating, protecting against, and inducing an immune response against a tumor or a cancer, for example treating a prostate cancer comprising the step of administering to a subject an immunogenic composition provided herein.

In some embodiments, the immunogenic compositions comprising a live attenuated bacteria strain, for example a *Listeria* vaccine strain comprises a nucleic acid molecule, wherein the nucleic acid molecule comprises a first open reading frame encoding fusion polypeptide, wherein said fusion polypeptide comprises a PEST sequence-containing polypeptide or a PEST sequence-containing peptide fused to a PSA antigen or fragment thereof may be used in a method of preventing or treating a tumor or cancer in a human subject, for example a prostate cancer, comprising the step of administering to the subject the immunogenic composition strain provided herein, the recombinant *Listeria* strain comprising a recombinant polypeptide comprising an N-terminal fragment of an LLO protein and tumor-associated antigen, whereby the recombinant *Listeria* strain induces an immune response against the tumor-associated antigen, thereby treating a tumor or cancer in a human subject. In another embodiment, the immune response is a T-cell response. In another embodiment, the T-cell response is a CD4+FoxP3−T cell response. In another embodiment, the T-cell response is a CD8+T cell response. In another embodiment, the T-cell response is a CD4+FoxP3− and CD8+T cell response.

In some embodiments, the live-attenuated *Listeria* strain comprises a nucleic acid molecule, the nucleic acid molecule comprising a first open reading frame encoding a fusion polypeptide, wherein said fusion polypeptide comprises a PEST sequence-containing polypeptide or a PEST sequence-containing peptide fused to a PSA antigen or fragment thereof. In some embodiments, the nucleic acid molecule is comprised in an episomal expression vector. In other embodiments, the nucleic acid molecule is integrated into the chromosomal DNA.

In one embodiment, the nucleic acid molecule comprising a first open reading frame encoding a fusion polypeptide is integrated into the *Listeria* genome. In another embodiment, the nucleic acid is in a plasmid in said attenuated *Listeria* vaccine strain. In another embodiment, the nucleic acid molecule is in a bacterial artificial chromosome in said attenuated *Listeria* vaccine strain.

It will be well appreciated an "immunogenic composition" may comprise the recombinant *Listeria* provided herein, and an adjuvant. In another embodiment, an immunogenic composition comprises a recombinant *Listeria* provided herein. In another embodiment, an immunogenic composition comprises an adjuvant known in the art or as provided herein. It is also to be understood that such compositions enhance an immune response, or increase a T effector cell to regulatory T cell ratio or elicit an anti-tumor immune response, as further provided herein. As used throughout, the term "immunogeneic composition" and "composition" may be used interchangeably having all the same meanings and qualities.

Following the administration of the immunogenic compositions provided herein, the methods provided herein induce the expansion of T effector cells in peripheral lymphoid organs, leading to an enhanced presence of T effector cells at the tumor site. In another embodiment, the methods provided herein induce the expansion of T effector cells in peripheral lymphoid organs, leading to an enhanced presence of T effector cells at the periphery. Such expansion of T effector cells leads to an increased ratio of T effector cells to regulatory T cells in the periphery and at the tumor site without affecting the number of Tregs. It will be appreciated by the skilled artisan that peripheral lymphoid organs include, but are not limited to, the spleen, peyer's patches, the lymph nodes, the adenoids, etc. In one embodiment, the increased ratio of T effector cells to regulatory T cells occurs in the periphery without affecting the number of Tregs. In another embodiment, the increased ratio of T effector cells to regulatory T cells occurs in the periphery, the lymphoid organs and at the tumor site without affecting the number of Tregs at these sites. In another embodiment, the increased ratio of T effector cells decrease the frequency of Tregs, but not the total number of Tregs at these sites. The term "attenuation" as used herein, is meant a diminution in the ability of the bacterium to cause disease in an animal. In other words, the pathogenic characteristics of the attenuated *Listeria* strain have been lessened compared with wild-type *Listeria*, although the attenuated *Listeria* is capable of growth and maintenance in culture. Using as an example the intravenous inoculation of Balb/c mice with an attenuated *Listeria*, the lethal dose at which 50% of inoculated animals survive ($LD_{50}$) is preferably increased above the $LD_{50}$ of wild-type *Listeria* by at least about 10-fold, more preferably by at least about 100-fold, more preferably at least about 1,000 fold, even more preferably at least about 10,000 fold, and most preferably at least about 100,000-fold. An attenuated strain of *Listeria* is thus one which does not kill an animal to which it is administered, or is one which kills the animal only when the number of bacteria administered is vastly greater than the number of wild type non-attenuated bacteria which would be required to kill the same animal. An attenuated bacterium should also be construed to mean one which is incapable of replication in the general environment because the nutrient required for its growth is not present therein. Thus, the bacterium is limited to replication in a controlled environment wherein the required nutrient is provided. The attenuated strains of the present invention are therefore environmentally safe in that they are incapable of uncontrolled replication.

In one embodiment, the attenuated *Listeria* strain provided herein lacks antibiotic resistance genes. In another embodiment, the attenuated *Listeria* strain provided herein comprises a plasmid comprising a nucleic acid encoding an antibiotic resistance gene. In another embodiment, an attenuated *Listeria* strain expressing a PSA polypeptide in which the nucleic acid encoding the polypeptide is operably integrated into the *Listeria* genome in an open reading frame with an LLO gene.

In one embodiment, the attenuated *Listeria* provided herein is capable of escaping the phagolysosome.

In one embodiment, the *Listeria* genome comprises a deletion of the endogenous ActA gene, which in one embodiment is a virulence factor. In one embodiment, such a deletion provides a more attenuated and thus safer *Listeria* strain for human use. According to this embodiment, the PSA antigen or fragment thereof is integrated in frame with LLO in the *Listeria* chromosome. In another embodiment, the integrated nucleic acid molecule is integrated into the ActA locus.

In one embodiment, an exression vector comprises at nucleic acid molecule comprising a recombinant polypeptide comprising a PSA antigen or fragment thereof. In another embodiment, the recombinant polypeptide further comprises a truncated LLO protein, a truncated ActA protein or a PEST sequence peptide fused to the PSA antigen. In another embodiment, the truncated LLO protein is a N-terminal LLO or fragment thereof. In another embodiment, the truncated ActA protein is a N-terminal ActA protein or fragment thereof.

In another embodiment the attenuated strain is LmddA. In another embodiment, the attenuated strain is LmΔactA. In another embodiment, the attenuated strain is LmΔPrfA. In another embodiment, the attenuated strain is LmΔPlcB. In another embodiment, the attenuated strain is LmΔPlcA. In another embodiment, the strain is the double mutant or triple mutant of any of the above-mentioned strains. In another embodiment, this strain exerts a strong adjuvant effect which is an inherent property of *Listeria*-based strains. In another embodiment, this strain is constructed from the EGD *Listeria* backbone. In another embodiment, the strain used in the invention is a *Listeria* strain that expresses a non-hemolytic LLO.

In another embodiment, the *Listeria* strain is an auxotrophic mutant. In another embodiment, the *Listeria* strain is deficient in a gene encoding a vitamin synthesis gene. In another embodiment, the *Listeria* strain is deficient in a gene encoding pantothenic acid synthase.

In one embodiment, the generation of AA strains of *Listeria* deficient in D-alanine, for example, may be accomplished in a number of ways that are well known to those of skill in the art, including deletion mutagenesis, insertion mutagenesis, and mutagenesis which results in the generation of frameshift mutations, mutations which cause premature termination of a protein, or mutation of regulatory sequences which affect gene expression. In another embodiment, mutagenesis can be accomplished using recombinant DNA techniques or using traditional mutagenesis technology using mutagenic chemicals or radiation and subsequent selection of mutants. In another embodiment, deletion mutants are preferred because of the accompanying low probability of reversion of the auxotrophic phenotype. In another embodiment, mutants of D-alanine which are generated according to the protocols presented herein may be tested for the ability to grow in the absence of D-alanine in a simple laboratory culture assay. In another embodiment, those mutants which are unable to grow in the absence of this compound are selected for further study.

In another embodiment, in addition to the aforementioned D-alanine associated genes, other genes involved in synthesis of a metabolic enzyme, as provided herein, may be used as targets for mutagenesis of *Listeria*.

In another embodiment, the metabolic enzyme complements an endogenous metabolic gene that is lacking in the remainder of the chromosome of the recombinant bacterial strain. In one embodiment, the endogenous metabolic gene is mutated in the chromosome. In another embodiment, the endogenous metabolic gene is deleted from the chromosome. In another embodiment, said metabolic enzyme is an amino acid metabolism enzyme. In another embodiment, said metabolic enzyme catalyzes a formation of an amino acid used for a cell wall synthesis in said recombinant *Listeria* strain. In another embodiment, said metabolic enzyme is an alanine racemase enzyme. In another embodiment, said metabolic enzyme is a D-amino acid transferase enzyme. Each possibility represents a separate embodiment of the methods and compositions as provided herein.

In one embodiment, said auxotrophic *Listeria* strain comprises an episomal expression vector comprising a metabolic enzyme that complements the auxotrophy of said auxotrophic *Listeria* strain. In another embodiment, the construct is contained in the *Listeria* strain in an episomal fashion. In another embodiment, the foreign antigen is expressed from a vector harbored by the recombinant *Listeria* strain. In another embodiment, said episomal expression vector lacks an antibiotic resistance marker. In one embodiment, an antigen of the methods and compositions as provided herein is fused to an polypeptide comprising a PEST sequence. In another embodiment, said polypeptide comprising a PEST sequence is a truncated LLO. In another embodiment, said polypeptide comprising a PEST sequence is ActA.

In another embodiment, the *Listeria* strain is deficient in an AA metabolism enzyme. In another embodiment, the *Listeria* strain is deficient in a D-glutamic acid synthase gene. In another embodiment, the *Listeria* strain is deficient in the dat gene. In another embodiment, the *Listeria* strain is deficient in the dal gene. In another embodiment, the *Listeria* strain is deficient in the dga gene. In another embodiment, the *Listeria* strain is deficient in a gene involved in the synthesis of diaminopimelic acid. CysK. In another embodiment, the gene is vitamin-B12 independent methionine synthase. In another embodiment, the gene is trpA. In another embodiment, the gene is trpB. In another embodiment, the gene is trpE. In another embodiment, the gene is asnB. In another embodiment, the gene is gltD. In another embodiment, the gene is gltB. In another embodiment, the gene is leuA. In another embodiment, the gene is argG. In another embodiment, the gene is thrC. In another embodiment, the *Listeria* strain is deficient in one or more of the genes described hereinabove.

In another embodiment, the *Listeria* strain is deficient in a synthase gene. In another embodiment, the gene is an AA synthesis gene. In another embodiment, the gene is folP. In another embodiment, the gene is dihydrouridine synthase family protein. In another embodiment, the gene is ispD. In another embodiment, the gene is ispF. In another embodiment, the gene is phosphoenolpyruvate synthase. In another embodiment, the gene is hisF. In another embodiment, the gene is hisH. In another embodiment, the gene is fliI. In another embodiment, the gene is ribosomal large subunit pseudouridine synthase. In another embodiment, the gene is ispD. In another embodiment, the gene is bifunctional GMP synthase/glutamine amidotransferase protein. In another embodiment, the gene is cobS. In another embodiment, the gene is cobB. In another embodiment, the gene is cbiD. In another embodiment, the gene is uroporphyrin-III C-methyltransferase/uroporphyrinogen-III synthase. In another embodiment, the gene is cobQ. In another embodiment, the gene is uppS. In another embodiment, the gene is truB. In another embodiment, the gene is dxs. In another embodiment, the gene is mvaS. In another embodiment, the gene is dapA. In another embodiment, the gene is ispG. In another embodiment, the gene is folC. In another embodiment, the gene is citrate synthase. In another embodiment, the gene is argJ. In another embodiment, the gene is 3-deoxy-7-phosphoheptulonate synthase. In another embodiment, the gene is indole-3-glycerol-phosphate synthase. In another embodiment, the gene is anthranilate synthase/glutamine amidotransferase component. In another embodiment, the gene is menB. In another embodiment, the gene is menaquinone-specific isochorismate synthase. In another embodiment, the gene is phosphoribosylformylglycinamidine synthase I or II. In another embodiment, the gene is phosphoribosylaminoimidazole-succinocarboxamide synthase. In another embodiment, the gene is carB. In another embodiment, the gene is carA. In another embodiment, the gene is thyA. In another embodiment, the gene is mgsA. In another embodiment, the gene is aroB. In another embodiment, the gene is hepB. In another embodiment, the gene is rluB. In another embodiment, the gene is ilvB. In another embodiment, the gene is ilvN. In another embodiment, the gene is alsS. In another embodiment, the gene is fabF. In another embodiment, the gene is fabH. In another embodiment, the gene is pseudouridine synthase. In another embodiment, the gene is pyrG. In another embodiment, the gene is truA. In another embodiment, the gene is pabB. In another embodiment, the gene is an atp synthase gene (e.g. atpC, atpD-2, aptG, atpA-2, etc).

In another embodiment, the gene is phoP. In another embodiment, the gene is aroA. In another embodiment, the gene is aroC. In another embodiment, the gene is aroD. In another embodiment, the gene is plcB.

In another embodiment, the *Listeria* strain is deficient in a peptide transporter. In another embodiment, the gene is ABC transporter/ATP-binding/permease protein. In another embodiment, the gene is oligopeptide ABC transporter/oligopeptide-binding protein. In another embodiment, the gene is oligopeptide ABC transporter/permease protein. In another embodiment, the gene is zinc ABC transporter/zinc-binding protein. In another embodiment, the gene is sugar ABC transporter. In another embodiment, the gene is phosphate transporter. In another embodiment, the gene is ZIP zinc transporter. In another embodiment, the gene is drug resistance transporter of the EmrB/QacA family. In another embodiment, the gene is sulfate transporter. In another embodiment, the gene is proton-dependent oligopeptide transporter. In another embodiment, the gene is magnesium transporter. In another embodiment, the gene is formate/nitrite transporter. In another embodiment, the gene is spermidine/putrescine ABC transporter. In another embodiment, the gene is Na/Pi-cotransporter. In another embodiment, the gene is sugar phosphate transporter. In another embodiment, the gene is glutamine ABC transporter. In another embodiment, the gene is major facilitator family transporter. In another embodiment, the gene is glycine betaine/L-proline ABC transporter. In another embodiment, the gene is molybdenum ABC transporter. In another embodiment, the gene is techoic acid ABC transporter. In another embodiment, the gene is cobalt ABC transporter. In another embodiment, the gene is ammonium transporter. In another embodiment, the gene is amino acid ABC transporter. In another embodiment, the gene is cell division ABC transporter. In another embodiment, the gene is manganese ABC transporter. In another embodiment, the gene is iron compound ABC transporter. In another embodiment, the gene is maltose/maltodextrin ABC transporter. In another embodiment, the gene is drug resistance transporter of the Bcr/CflA family. In another embodiment, the gene is a subunit of one of the above proteins.

In one embodiment, provided herein is a nucleic acid molecule that is used to transform the *Listeria* in order to arrive at a recombinant *Listeria*. In another embodiment, the nucleic acid provided herein used to transform *Listeria* lacks a virulence gene. In another embodiment, the nucleic acid molecule is integrated into the *Listeria* genome and carries a non-functional virulence gene. In another embodiment, the virulence gene is mutated in the recombinant *Listeria*. In yet another embodiment, the nucleic acid molecule is used to inactivate the endogenous gene present in the *Listeria* genome. In yet another embodiment, the virulence gene is an actA gene, an inlA gene, and inlB gene, an inlC gene, inlJ gene, a plbC gene, a bsh gene, or a prfA gene. It is to be understood by a skilled artisan, that the virulence gene can be any gene known in the art to be associated with virulence in the recombinant *Listeria*.

In yet another embodiment the *Listeria* strain is an inlA mutant, an inlB mutant, an inlC mutant, an inlJ mutant, prfA mutant, actA mutant, a dal/dat mutant, a prfA mutant, a plcB deletion mutant, or a double mutant lacking both plcA and plcB. In another embodiment, the *Listeria* comprise a deletion or mutation of these genes individually or in combination. In another embodiment, the *Listeria* provided herein lack each one of genes. In another embodiment, the *Listeria* provided herein lack at least one and up to ten of any gene provided herein, including the actA, prfA, and dal/dat genes. In another embodiment, the prfA mutant is a D133V prfA mutant.

In one embodiment, the live attenuated *Listeria* is a recombinant *Listeria*. In another embodiment, the recombinant *Listeria* comprises a mutation or a deletion of a genomic internalin C (inlC) gene. In another embodiment, the recombinant *Listeria* comprises a mutation or a deletion of a genomic actA gene and a genomic internalin C gene. In one embodiment, translocation of *Listeria* to adjacent cells is inhibited by the deletion of the actA gene and/or the inlC gene, which are involved in the process, thereby resulting in unexpectedly high levels of attenuation with increased immunogenicity and utility as a strain backbone. Each possibility represents a separate embodiment of the present invention.

In one embodiment, the metabolic gene, the virulence gene, etc. is lacking in a chromosome of the *Listeria* strain. In another embodiment, the metabolic gene, virulence gene, etc. is lacking in the chromosome and in any episomal genetic element of the *Listeria* strain. In another embodiment, the metabolic gene, virulence gene, etc. is lacking in the genome of the virulence strain. In one embodiment, the virulence gene is mutated in the chromosome. In another embodiment, the virulence gene is deleted from the chromosome. Each possibility represents a separate embodiment of the present invention In one embodiment, the recombinant *Listeria* strain provided herein is attenuated. In another embodiment, the recombinant *Listeria* lacks the actA virulence gene. In another embodiment, the recombinant *Listeria* lacks the prfA virulence gene. In another embodiment, the recombinant *Listeria* lacks the inlB gene. In another embodiment, the recombinant *Listeria* lacks both, the actA and inlB genes. In another embodiment, the recombinant *Listeria* strain provided herein comprise an inactivating mutation of the endogenous actA gene. In another embodiment, the recombinant *Listeria* strain provided herein comprise an inactivating mutation of the endogenous inlB gene. In another embodiment, the recombinant *Listeria* strain provided herein comprise an inactivating mutation of the endogenous inlC gene. In another embodiment, the recombinant *Listeria* strain provided herein comprise an inactivating mutation of the endogenous actA and inlB genes. In another embodiment, the recombinant *Listeria* strain provided herein comprise an inactivating mutation of the endogenous actA and inlC genes. In another embodiment, the recombinant *Listeria* strain provided herein comprise an inactivating mutation of the endogenous actA, inlB, and inlC genes. In another embodiment, the recombinant *Listeria* strain provided herein comprise an inactivating mutation of the endogenous actA, inlB, and inlC genes. In another embodiment, the recombinant *Listeria* strain provided herein comprise an inactivating mutation of the endogenous actA, inlB, and inlC genes. In another embodiment, the recombinant *Listeria* strain provided herein comprise an inactivating mutation in any single gene or combination of the following genes: actA, dal, dat, inlB, inlC, prfA, plcA, plcB.

It will be appreciated by the skilled artisan that the term "mutation" and grammatical equivalents thereof, include any type of mutation or modification to the sequence (nucleic acid or amino acid sequence), and includes a deletion mutation, a truncation, an inactivation, a disruption, or a translocation. These types of mutations are readily known in the art.

In one embodiment, in order to select for an auxotrophic bacteria comprising a plasmid encoding a metabolic enzyme or a complementing gene provided herein, transformed auxotrophic bacteria are grown on a media that will select for expression of the amino acid metabolism gene or the complementing gene. In another embodiment, a bacteria auxotrophic for D-glutamic acid synthesis is transformed with a plasmid comprising a gene for D-glutamic acid synthesis, and the auxotrophic bacteria will grow in the absence of D-glutamic acid, whereas auxotrophic bacteria that have not been transformed with the plasmid, or are not expressing the plasmid encoding a protein for D-glutamic acid synthesis, will not grow. In another embodiment, a bacterium auxotrophic for D-alanine synthesis will grow in the absence of D-alanine when transformed and expressing the plasmid of the present invention if the plasmid comprises an isolated nucleic acid encoding an amino acid metabolism enzyme for D-alanine synthesis. Such methods for making appropriate media comprising or lacking necessary growth factors, supplements, amino acids, vitamins, antibiotics, and the like are well known in the art, and are available commercially (Becton-Dickinson, Franklin Lakes, N.J.). Each method represents a separate embodiment of the present invention.

In another embodiment, once the auxotrophic bacteria comprising the plasmid of the present invention have been selected on appropriate media, the bacteria are propagated in the presence of a selective pressure. Such propagation comprises growing the bacteria in media without the auxotrophic factor. The presence of the plasmid expressing an amino acid metabolism enzyme in the auxotrophic bacteria ensures that the plasmid will replicate along with the bacteria, thus continually selecting for bacteria harboring the plasmid. The skilled artisan, when equipped with the present disclosure and methods herein will be readily able to scale-up the production of the *Listeria* strain vector by adjusting the volume of the media in which the auxotrophic bacteria comprising the plasmid are growing.

The skilled artisan will appreciate that, in another embodiment, other auxotroph strains and complementation systems are adopted for the use with this invention.

In one embodiment, the N-terminal LLO protein fragment and PSA antigen are fused directly to one another. In another embodiment, the genes encoding the N-terminal LLO protein fragment and PSA antigen are not fused directly to one another. In another embodiment, the N-terminal LLO protein fragment and PSA antigen are operably attached via a linker peptide. In another embodiment, the N-terminal LLO protein fragment and PSA antigen are attached via a heterologous peptide. In another embodiment, the N-terminal LLO protein fragment is N-terminal to the PSA antigen. In another embodiment, the N-terminal LLO protein fragment is the N-terminal-most portion of the fusion protein. In another embodiment, a truncated LLO is truncated at the C-terminal to arrive at an N-terminal LLO. Each possibility represents a separate embodiment of the present invention.

The term "linker", as used herein refers to an amino acid sequence that joins two heterologous polypeptides, or fragments or domains thereof. For example, linking a tLLO and a PSA polypeptide. In general, as used herein, a linker is an amino acid sequence that covalently links the polypeptides to form a fusion polypeptide. A linker typically includes the amino acids translated from the remaining recombination signal after removal of a reporter gene from a display vector to create a fusion protein comprising an amino acid sequence encoded by an open reading frame and the display protein. As appreciated by one of skill in the art, the linker can comprise additional amino acids, such as glycine and other small neutral amino acids.

The term "operably linked" as used herein means that the transcriptional and translational regulatory nucleic acid, is positioned relative to any coding sequences in such a manner that transcription is initiated. Generally, this will mean that the promoter and transcriptional initiation or start sequences are positioned 5' to the coding region.

The term "open reading frame" or "ORF" is a portion of an organism's genome which contains a sequence of bases that could potentially encode a protein. In another embodiment, the start and stop ends of the ORF are not equivalent to the ends of the mRNA, but they are usually contained within the mRNA. In one embodiment, ORFs are located between the start-code sequence (initiation codon) and the stop-codon sequence (termination codon) of a gene. Thus, in one embodiment, a nucleic acid molecule operably integrated into a genome as an open reading frame with an endogenous polypeptide is a nucleic acid molecule that has integrated into a genome in the same open reading frame as an endogenous polypeptide.

In one embodiment, the attenuated *Listeria* strain provided herein expresses a recombinant polypeptide. In another embodiment, the attenuated *Listeria* strain comprises a plasmid that encodes a recombinant polypeptide. In another embodiment, a recombinant nucleic acid provided herein is in a plasmid in the attenuated *Listeria* strain provided herein. In another embodiment, the plasmid is an episomal plasmid that does not integrate into said attenuated *Listeria* strain's chromosome. In another embodiment, the plasmid is an integrative plasmid that integrates into said *Listeria* strain's chromosome. In another embodiment, the plasmid is a multicopy plasmid.

In one embodiment, the attenuated *Listeria* strain of the compositions and methods as provided herein comprise a first or second nucleic acid molecule that encodes a Prostate Specific Antigen (PSA), which in one embodiment, is a marker for prostate cancer that is highly expressed by prostate tumors. In one embodiment, PSA is a kallikrein serine protease (KLK3) secreted by prostatic epithelial cells, which in one embodiment, is widely used as a marker for prostate cancer.

In one embodiment, the recombinant *Listeria* strain as provided herein comprises a nucleic acid molecule encoding KLK3 protein.

In another embodiment, the KLK3 protein has the sequence:

```
MWVPVVFLTLSVTWIGAAPLILSRIVGGWECEKHSQPWQVLVASRGRAVC

GGVLVHPQWVLTAAHCIRNKSVILLGRHSLFHPEDTGQVFQVSHSFPHPL

YDMSLLKNRFLRPGDDSSHDLMLLRLSEPAELTDAVKVMDLPTQEPALGT

TCYASGWGSIEPEEFLTPKKLQCVDLHVISNDVCAQVHPQKVTKFMLCAG

RWTGGKSTCSGDSGGPLVCNGVLQGITSWGSEPCALPERPSLYTKVVHYR

KWIKDTIVANP (SEQ ID No: 25; GenBank Accession No. CAA32915).
```

In another embodiment, the KLK3 protein is a homologue of SEQ ID No: 25. In another embodiment, the KLK3 protein is a variant of SEQ ID No: 25. In another embodiment, the KLK3 protein is an isomer of SEQ ID No: 25. In another embodiment, the KLK3 protein is a fragment of SEQ ID No: 25. Each possibility represents a separate embodiment of the methods and compositions as provided herein.

In another embodiment, the KLK3 protein has the sequence:

```
                                         (SEQ ID No: 26)
IVGGWECEKHSQPWQVLVASRGRAVCGGVLVHPQWVLTAAHCIRNKSVIL

LGRHSLFHPEDTGQVFQVSHSFPHPLYDMSLLKNRFLRPGDDSSHDLMLL

RLSEPAELTDAVKVMDLPTQEPALGTTCYASGWGSIEPEEFLTPKKLQCV

DLHVISNDVCAQVHPQKVTKFMLCAGRWTGGKSTCSGDSGGPLVCYGVLQ

GITSWGSEPCALPERPSLYTKVVHYRKWIKDTIVANP.
```

In another embodiment, the KLK3 protein is a homologue of SEQ ID No: 26. In another embodiment, the KLK3 protein is a variant of SEQ ID No: 26. In another embodiment, the KLK3 protein is an isomer of SEQ ID No: 26. In another embodiment, the KLK3 protein is a fragment of SEQ ID No: 26. Each possibility represents a separate embodiment of the methods and compositions as provided herein.

In another embodiment, the KLK3 protein has the sequence:

IVGGWECEKHSQPWQVLVASRGRAVCGGVLVHPQWVLTAAHCIRNKSVIL
LGRHSLFHPEDTGQVFQVSHSFPHPLYDMSLLKNRFLRPGDDSSHDLMLL
RLSEPAELTDAVKVMDLPTQEPALGTTCYASGWGSIEPEEFLTPKKLQCV
DLHVISNDVCAQVHPQKVTKFMLCAGRWTGGKSTCSGDSGGPLVCNGVLQ
GITSWGSEPCALPERPSLYTKVVHYRKWIKDTIVANP (SEQ ID No: 27; GenBank Accession No. AAA59995.1).

In another embodiment, the KLK3 protein is a homologue of SEQ ID No: 27. In another embodiment, the KLK3 protein is a variant of SEQ ID No: 27. In another embodiment, the KLK3 protein is an isomer of SEQ ID No: 27. In another embodiment, the KLK3 protein is a fragment of SEQ ID No: 27. Each possibility represents a separate embodiment of the methods and compositions as provided herein.

In another embodiment, the KLK3 protein is encoded by a nucleotide molecule having the sequence:

ggtgtcttaggcacactggtcttggagtgcaaaggatctaggcacgtga
ggctttgtatgaagaatcggggatcgtacccacccctgtttctgatca
tcctgggcatgtctcctctgcctagtcccctagatgaagtctccatgag
ctacaagggcctggtgcatccaggtgatctagtaattgcagaacagca
agtgctagctctccctccccttccacagctctgggtgtgggaggggtt
gtccagcctccagcagcatggggagggccttggtcagcctctgggtgcc
agcagggcagggcggagtcctgggaatgaaggtttataggggctcct
gggggaggctccccagcccaagcttaccacctgcacccggagagctgt
gtcaccatgtgggtcccggagtatcctcaccctgtccgtgacgtggatt
ggtgagaggggccatggttggggggatgcaggagagggagccagccctg
actgtcaagctgaggctctttcccccccaacccagcaccccagcccaga
cagggagctgggctatactgtctctcccagccccacttcaagcccatac
ccccagtcccctccatattgcaacagtcctcactcccacaccaggtccc
cgctccctcccacttacccacagaactacttcccatttgcccagccagct
ccctgctcccagctgattactaaaggggaagacctgggcatctccgtga
tctctagtggggctcaaaacctccaaggacctctctcaatgccattgga
ccaggaccgtatcactggtccatctcctgagcccctcaatcctatcaca
gtctactgacttacccattcagctgtgagtgtccaaccctatcccagag
accttgatgatggcctcccaatcagccctaggatacccagatgccaacc
agacacctcatattcctagccaggctatctggcctgagacaacaaatgg
gtccctcagtctggcaatgggactctgagaactcctcattccctgactc
ttagccccagactcttcattcagtggcccacattttccttaggaaaaac atgagcatccccagccacaactgccagctctctgagtccccaaatctgc
atccattcaaaacctaaaaacaaaaagaaaaacaaataaaacaaaacca
actcagaccagaactgattctcaacctgggacttcctaaactaccaaaa
ccacctcaccagcaactgaacctcgccataaggcacttatccctggacc
tagcaccccttatcccctcagaatccacaacttgtaccaagtacccact
cccagtccaagaccccaaatcaccacaaaggacccaatccccagactca
agatatggtctgggcgctgtcttgtgtctcctaccctgatccctgggtt
caactctgctcccagagcatgaagcctctccaccagcaccagccaccaa
cctgcaaacctagggaagattgacagaattcccagcctacccagctccc
cctgcccatgtcccaggactcccagccaggactctgcccccgtgtattt
caaacccacatcctaaatccatctcctatccgagtccccccagacccccct
gtcaacctgattcccctgatctagcaccccctctgcaggcgctgcgcc
cctcatcctgtctcggattgtggggaggctgggagtgcgagaagcattcc
caacccctggcaggtgcttgtggcctctcgtggcagggcagtctgcggcg
gtgttctggtgcaccccccagtgggtcctcacagctgcccactgcatcag
gaagtgagtaggggcctgggtctggggagcaggtgtctgtgtcccaga
ggaataacagctgggcattaccccaggataacctctaaggccagccagg
gactggggggagagagggaaagactggacaggtcacatggggaggcaggg
aggggctggaccaccctccccatggctgcctgggtctccatctgtgtcc
ctctatgtctctagtgtcgattcattatgtctcaggtaactggcttcgg
agtgtctctccgtgtgactattagactctctctccctctcactctgtct
tcagtctccatatctccccctctctctgtccactctggtccctctctag
ccagtgtgtctcacctgtatctctctgccaggctctgtctctcggtct
ctgtctcacctgtgccttctccctactgaacacacgcacgggatgggcc
tgggggaccctgagaaaaggaagggctaggctgggcgcggtggctcaca
cctgtaatcccagcactagggaggccaaggcaggtagatcacctgaggt
caggagttcgagaccagcctggccaactggtgaaacccatctctacta
aaaatacaaaaaattagccaggcgtggtggcgcatgcctgtagtcccag
ctactcaggagctgagggaggagaattgcattgaacctggaggagagga
gcagtgagccgagaccgtgccactgcactccagcctgggtgacagagtg
agactccgcctcaaaaaaaaaaaaaaaaaaaaaaaaaaaaaagaaaaga
aaagaaaagaaaggaagtgattatccctgatgtgtgtgggtatgaggg
tatgagagggcccctctcactccattccactccaggacatccctccact
cagggagacacagagaagggctggaccagctggagctgggaggggcaat
tgagggaggaggaaggagaaggggggaaggaaaacagggtatgggggaaa
ggaccctggggagcgaagtggaggatacaaccagggcctgcaggcaggc
tacctacccacttggaaacccacgccaaagccgcatctacagctgagcc
actctgaggcctcccctccccggcggtccccactcagctccaaagtctc
tctccatactctcccacactttatcatccccggattcctctctacttg
gactcattcttcattgacttcctgatccctactcattcatctgatctca -continued

```
ctactgcctggattgacttctctctctcatctctggcccatgtctgatc
tctatgtactgtcattctactcatcctgtgtattacggctcaccagtag
tcactgactcccctctgccattcattctctctgccatttaccctatcct
tacccaggactctcagactgtatctgcccacaccctctcacactgctga
tcccaactcgagtctgtattaggcctgaactgtgtatcccaaccctgtg
attctcactgatctattctataggagcctcctccttgctcctctgtcca
tctctattccttatcatcctcgctcctcattcctgcgtctgatcctccc
cagcaaaagcgtgatcttgctgggtcggcacagcctgatcatcctgaag
acacaggccaggtatttcaggtcagccacagatcccacaccgctctac
gatatgagcctcctgaagaatcgattcctcaggccaggtgatgactcca
gccacgacctcatgctgctccgcctgtcagagcctgccgagctcacgga
tgctgtgaaggtcatggacctgcccacccaggagccagcactgggggcc
acctgctacgcctcaggctggggcagcattgaaccagaggagtgtacgc
ctgggccagatggtgcagccgggagcccagatgcctgggtctgagggag
gaggggacaggactcctgggtctgagggaggagggccaaggaaccaggt
ggggtccagcccacaacagtgatttgcctggcccgtagtcttgacccca
aagaaacttcagtgtgtggacctccatgttataccaatgacgtgtgtgc
gcaagttcaccctcagaaggtgaccaagttcatgctgtgtgctggacgc
tggacaggggggcaaaagcacctgctcggtgagtcatccctactcccaag
atcttgagggaaaggtgagtgggaccttaattctgggctggggtctaga
agccaacaaggcgtctgcctcccctgctcccagctgtagccatgccac
ctcccgtgtctcatctcattcctccaccctatattgactccctcaag
gcaataggttattcttacagcacaactcatctgacctgcgttcagcaca
cggttactaggcacctgctatgcacccagcactgccctagagcctggga
catagcagtgaacagacagagagcagcccctccatctgtagcccccaag
ccagtgaggggcacaggcaggaacagggaccacaacacagaaagctgg
agggtgtcaggaggtgatcaggctctcggggagggagaagggtgggga
gtgtgactgggaggagacatcctgcagaaggtgggagtgagcaaacacc
tgcgcagggggagggagggcctgcggcacctgggggagcagagggaaca
gcatctggccaggcctgggaggagggcctagagggcgtcaggagcaga
gaggaggttgcctggctggagtgaaggatcggggcagggtgcgagaggg
aacaaaggaccccctcctgcagggcctcacctgggccacaggaggacact
gcttacctctgaggagtcaggaactgtggatggtgctggacagaagcag
gacagggcctggctcaggtgtccagaggctgcgctggcctcctatggga
tcagactgcagggagggagggcagcagggatgtggagggagtgatgatg
gggctgacctgggggtggctccaggcattgtcccacctgggcccttac
ccagcctccctcacaggctcctggccctcagtctctcccctccactcca
ttctccacctacccacagtgggtcattctgatcaccgaactgaccatgc
cagccctgccgatggtcctccatggctccctagtgccctggagaggagg
tgtctagtcagagagtagtcctggaaggtggcctctgtgaggagccacg
gggacagcatcctgcagatggtcctggcccttgtcccaccgacctgtct
```

```
acaaggactgtcctcgtggaccctcccctctgcacaggagctggaccct
gaagtcccacctaccggccaggactggagcccctacccctctgaggaat
ccctgcccaccacttctggaagtcggctctggagacatactctcttcac
caaagctgggaactgctatctgttatctgcctgtccaggtctgaaagat
aggattgcccaggcagaaactgggactgacctatctcactctctccctg
cattacccttagggtgattctgggggcccacttgtctgtaatggtgtgc
ttcaaggtatcacgtcatggggcagtgaaccatgtgcctgcccgaaag
gccttccctgtacaccaaggtggtgcattaccggaagtggatcaaggac
accatcgtggccaaccctgagcaccctatcaagtcctattgtagta
aacttggaaccaggaaatgaccaggccaagactcaagcctcccagact
actgaccatgtccttaggtgtgaggtccagggagctaggaaaagaaatc
agcagacacaggtgtagaccagagtgatcttaaatggtgtaattagtcc
tctctgtgtcctggggaatactggccatgcctggagacatatcactcaa
tactctgaggacacagttaggatggggtgtctgtgttatagtgggatac
agagatgaaagaggggtgggatcc
```

(SEQ ID No: 28; GenBank Accession No. X14810).

In another embodiment, the KLK3 protein is encoded by residues 401 . . . 446, 1688 . . . 1847, 3477 . . . 3763, 3907 . . . 4043, and 5413 . . . 5568 of SEQ ID No: 28. In another embodiment, the KLK3 protein is encoded by a homologue of SEQ ID No: 28. In another embodiment, the KLK3 protein is encoded by a variant of SEQ ID No: 28. In another embodiment, the KLK3 protein is encoded by an isomer of SEQ ID No: 28. In another embodiment, the KLK3 protein is encoded by a fragment of SEQ ID No: 28. Each possibility represents a separate embodiment of the methods and compositions as provided herein.

In another embodiment, the KLK3 protein has the sequence:

MWVPVVFLTLSVTWIGAAPLILSRIVGGWECEKHSQPWQVLVASRGRAV
CGGVLVHPQWVLTAAHCIRNKSVILLGRHSLFHPEDTGQVFQVSHSFPH
PLYDMSLLKNRFLRPGDDSSHDLMLLRLSEPAELTDAVKVMDLPTQEPA
LGTTCYASGWGSIEPEEFLTPKKLQCVDLHVISNDVCAQVHPQKVTKFM
LCAGRWTGGKSTCSWVILITELTMPALPMVLHGSLVPWRGGV (SEQ ID No: 29; GenBank Accession No. NP_001025218)

In another embodiment, the KLK3 protein is a homologue of SEQ ID No: 29. In another embodiment, the KLK3 protein is a variant of SEQ ID No: 29. In another embodiment, the KLK3 protein is an isomer of SEQ ID No: 29. In another embodiment, the KLK3 protein is a fragment of SEQ ID No: 29. Each possibility represents a separate embodiment as provided herein.

In another embodiment, the KLK3 protein is encoded by a nucleotide molecule having the sequence:

```
agccccaagcttaccacctgcaccggagagctgtgtcaccatgtgggt
cccggagtatcctcaccctgtccgtgacgtggattggtgctgcacccct
```

-continued
```
catcctgtctcggattgtgggaggctgggagtgcgagaagcattcccaa ccctggcaggtgcttgtggcctctcgtggcagggcagtctgcggcggtg actggtgcaccccagtgggtcctcacagctgcccactgcatcaggaac aaaagcgtgatcttgctgggtcggcacagcctgatcatcctgaagacac aggccaggtatttcaggtcagccacagatcccacaccgctctacgata tgagcctcctgaagaatcgattcctcaggccaggtgatgactccagcca cgacctcatgctgctccgcctgtcagagcctgccgagctcacggatgct gtgaaggtcatggacctgcccacccaggagccagcactgggaccacct gctacgcctcaggctggggcagcattgaaccagaggagacttgacccca aagaaacttcagtgtgtggacctccatgttataccaatgacgtgtgtgc gcaagttcaccctcagaaggtgaccaagttcatgctgtgtgctggacgc tggacaggggcaaaagcacctgctcgtgggtcattctgatcaccgaac tgaccatgccagccctgccgatggtcctccatggctcccctagtgcctg gagaggaggtgtctagtcagagagtagtcctggaaggtggcctctgtga ggagccacggggacagcatcctgcagatggtcctggcccttgtcccacc gacctgtctacaaggactgtcctcgtggaccctcccctctgcacaggag ctggaccctgaagtcccttccccaccggccaggactggagccctaccc ctctgttggaatccctgcccaccttcttctggaagtcggctctggagac atttctctcttcttccaaagctgggaactgctatctgttatctgcctgt ccaggtctgaaagataggattgcccaggcagaaactgggactgacctat ctcactctctccctgcttttacccttagggtgattctgggggcccactt gtctgtaatggtgtgcttcaaggtatcacgtcatggggcagtgaaccat gtgccctgcccgaaaggccttccctgtacaccaaggtggtgcattaccg gaagtggatcaaggacaccatcgtggccaaccctgagcacccctatca acccctattgtagtaaacttggaaccttggaaatgaccaggccaagac tcaagcctccccagttctactgacctttgtccttaggtgtgaggtccag ggttgctaggaaaagaaatcagcagacacaggtgtagaccagagtgttt cttaaatggtgtaattttgtcctctctgtgtcctggggaatactggcca tgcctggagacatatcactcaatttctctgaggacacagataggatggg gtgtctgtgttatttgtggggtacagagatgaaagagggtgggatcca cactgagagagtggagagtgacatgtgctggacactgtccatgaagcac tgagcagaagctggaggcacaacgcaccagacactcacagcaaggatgg agctgaaaacataacccactctgtcctggaggcactgggaagcctagag aaggctgtgagccaaggagggagggtcttcctttggcatgggatggga tgaagtaaggagagggactggacccctggaagctgattcactatgggg ggaggtgtattgaagtcctccagacaaccctcagatttgatgatttcct agtagaactcacagaaataaagagctgttatactgtg
```

(SEQ ID No: 30; GenBank Accession No. NM_001030047).

In another embodiment, the KLK3 protein is encoded by residues 42-758 of SEQ ID No: 30. In another embodiment, the KLK3 protein is encoded by a homologue of SEQ ID No: 30. In another embodiment, the KLK3 protein is encoded by a variant of SEQ ID No: 30. In another embodiment, the KLK3 protein is encoded by an isomer of SEQ ID No: 30. In another embodiment, the KLK3 protein is encoded by a fragment of SEQ ID No: 30. Each possibility represents a separate embodiment of the methods and compositions as provided herein.

In another embodiment, the KLK3 protein has the sequence:

MWVPVVFLTLSVTWIGAAPLILSRIVGGWECEKHSQPWQVLVASRGR
AVCGGVLVHPQWVLTAAHCIRK (SEQ ID No: 31; GenBank Accession No. NP_001025221).

In another embodiment, the KLK3 protein is a homologue of SEQ ID No: 31. In another embodiment, the KLK3 protein is a variant of SEQ ID No: 31. In another embodiment, the sequence of the KLK3 protein comprises SEQ ID No: 31. In another embodiment, the KLK3 protein is an isomer of SEQ ID No: 31. In another embodiment, the KLK3 protein is a fragment of SEQ ID No: 31. Each possibility represents a separate embodiment of the methods and compositions as provided herein.

In another embodiment, the KLK3 protein is encoded by a nucleotide molecule having the sequence:

(SEQ ID No: 32)
```
agccccaagcttaccacctgcacccggagagctgtgtcaccatgtgggt cccggagtcacctcacccaccgtgacgtggattggtgctgcacccctca tcctgtctcggattgtgggaggctgggagtgcgagaagcattcccaacc ctggcaggtgcttgtggcctctcgtggcagggcagtctgcggcggtgac tggtgcaccccagtgggtcctcacagctgcccactgcatcaggaagtg agtaggggcctggggtctggggagcaggtgtctgtgtcccagaggaata acagctgggcattttccccaggataacctctaaggccagccttgggact gggggagagagggaaagttctggttcaggtcacatggggaggcagggtt ggggctggaccaccctccccatggctgcctgggtctccatctgtgacct ctatgtctctagtgtcgattcattatgtctcaggtaactggcttcggag tgtctctccgtgtgactattagactctctctccctctcttctctgtctt cagt.
```

In another embodiment, the KLK3 protein is encoded by residues 42-758 of SEQ ID No: 32. In another embodiment, the KLK3 protein is encoded by a homologue of SEQ ID No: 32. In another embodiment, the KLK3 protein is encoded by a variant of SEQ ID No: 32. In another embodiment, the KLK3 protein is encoded by an isomer of SEQ ID No: 32. In another embodiment, the KLK3 protein is encoded by a fragment of SEQ ID No: 32. Each possibility represents a separate embodiment of the methods and compositions as provided herein.

In another embodiment, the KLK3 protein that is the source of the KLK3 peptide has the sequence:

(SEQ ID No: 33)
MWVPVVFLTLSVTWIGAAPLILSRIVGGWECEKHSQPWQVLVASRGRAV
CGGVLVHPQWVLTAAHCIRNKSVILLGRHSLFHPEDTGQVFQVSHSFPH

```
PLYDMSLLKNRFLRPGDDSSIEPEEFLTPKKLQCVDLHVISNDVCAQVH

PQKVTKFMLCAGRWTGGKSTCSGDSGGPLVCNGVLQGITSWGSEPCALP

ERPSLYTKVVHYRKWIKDTIVANP.
```

In another embodiment, the KLK3 protein is a homologue of SEQ ID No: 33. In another embodiment, the KLK3 protein is a variant of SEQ ID No: 33. In another embodiment, the KLK3 protein is an isomer of SEQ ID No: 33. In another embodiment, the KLK3 protein is a fragment of SEQ ID No: 33. Each possibility represents a separate embodiment of the methods and compositions as provided herein.

In another embodiment, the KLK3 protein is encoded by a nucleotide molecule having the sequence:

```
                                         (SEQ ID No: 34)
agccccaagcttaccacctgcacccggagagctgtgtcaccatgtgggt cccggagtcacctcaccctgtccgtgacgtggattggtgctgcacccct catcctgtctcggattgtgggaggctgggagtgcgagaagcattcccaa ccctggcaggtgcttgtggcctctcgtggcagggcagtctgcggcggtg actggtgcaccccagtgggtcctcacagctgcccactgcatcaggaac aaaagcgtgatcttgctgggtcggcacagcctgatcatcctgaagacac aggccaggtatttcaggtcagccacagcacccacacccgctctacgata tgagcctcctgaagaatcgattcctcaggccaggtgatgactccagcat tgaaccagaggagttcttgaccccaaagaaacttcagtgtgtggacctc catgttataccaatgacgtgtgtgcgcaagttcaccctcagaaggtgac caagttcatgctgtgtgctggacgctggacaggggggcaaaagcacctgc tcgggtgattctgggggcccacttgtctgtaatggtgtgcttcaaggta tcacgtcatgggcagtgaaccatgtgccctgcccgaaaggccaccctg tacaccaaggtggtgcattaccggaagtggatcaaggacaccatcgtgg ccaaccctgagcaccctatcaaccccctattgtagtaaacttggaac caggaaatgaccaggccaagactcaagcctccccagactactgacctag tccttaggtgtgaggtccagggagctaggaaaagaaatcagcagacaca ggtgtagaccagagtgatcttaaatggtgtaattagtcctctctgtgtc ctggggaatactggccatgcctggagacatatcactcaatactctgagg acacagataggatgggtgtctgtgttatagtggggtacagagatgaaa gaggggtgggatccacactgagagagtggagagtgacatgtgctggaca ctgtccatgaagcactgagcagaagctggaggcacaacgcaccagacac tcacagcaaggatggagctgaaaacataacccactctgtcctggaggca ctgggaagcctagagaaggctgtgagccaaggagggagggtatcctagg catgggatgggatgaagtaaggagagggactggaccccctggaagctg attcactatgggggaggtgtattgaagtcctccagacaaccctcagat ttgatgatacctagtagaactcacagaaataaagagctgaatactgtg.
```

In another embodiment, the KLK3 protein is encoded by residues 42-758 of SEQ ID No: 34. In another embodiment, the KLK3 protein is encoded by a homologue of SEQ ID No: 34. In another embodiment, the KLK3 protein is encoded by a variant of SEQ ID No: 34. In another embodiment, the KLK3 protein is encoded by an isomer of SEQ ID No: 34. In another embodiment, the KLK3 protein is encoded by a fragment of SEQ ID No: 34. Each possibility represents a separate embodiment of the methods and compositions as provided herein.

In another embodiment, the KLK3 protein has the sequence:

```
MWVPVVFLTLSVTWIGAAPLILSRIVGGWECEKHSQPWQVLVASRGRAVC

GGVLVHPQWVLTAAHCIRKPGDDSSHDLMLLRLSEPAELTDAVKVMDLPT

QEPALGTTCYASGWGSIEPEEFLTPKKLQCVDLHVISNDVCAQVHPQKVT

KFMLCAGRWTGGKSTCSGDSGGPLVCNGVLQGITSWGSEPCALPERPSLY

TKVVHYRKWIKDTIVANP          (SEQ ID No: 35; GenBank

Accession No. NP_001025219).
```

In another embodiment, the KLK3 protein is a homologue of SEQ ID No: 35. In another embodiment, the KLK3 protein is a variant of SEQ ID No: 35. In another embodiment, the KLK3 protein is an isomer of SEQ ID No: 35. In another embodiment, the KLK3 protein is a fragment of SEQ ID No: 35. Each possibility represents a separate embodiment of the methods and compositions as provided herein.

In another embodiment, the KLK3 protein is encoded by a nucleotide molecule having the sequence:

```
agccccaagcttaccacctgcacccggagagctgtgtcaccatgtgggt cccggagtatcctcaccctgtccgtgacgtggattggtgctgcacccct catcctgtctcggattgtgggaggctgggagtgcgagaagcattcccaa ccctggcaggtgcttgtggcctctcgtggcagggcagtctgcggcggtg actggtgcaccccagtgggtcctcacagctgcccactgcatcaggaag ccaggtgatgactccagccacgacctcatgctgctccgcctgtcagagc ctgccgagctcacggatgctgtgaaggtcatggacctgcccacccagga gccagcactggggacccacctgctacgcctcaggctggggcagcattgaa ccagaggagttcttgaccccaaagaaacttcagtgtgtggacctccatg ttataccaatgacgtgtgtgcgcaagttcaccctcagaaggtgaccaag ttcatgctgtgtgctggacgctggacaggggggcaaaagcacctgctcgg gtgattctgggggcccacttgtctgtaatggtgtgcttcaaggtatcac gtcatgggcagtgaaccatgtgccctgcccgaaaggccaccctgtaca ccaaggtggtgcattacccaaggacaccatcgtggccaacccctgagca cccctatcaaccccctaagtagtaaacttggaaccaggaaatgaccagg ccaagactcaagcctccccagactactgacctagtccttaggtgtgagg tccagggagctaggaaaagaaatcagcagacacaggtgtagaccagagt gatcttaaatggtgtaattagtcctctctgtgtcctggggaatactggc catgcctggagacatatcactcaatactctgaggacacagataggatgg ggtgtctgtgttatagtggggtacagagatgaaagagggtgggatcca cactgagagagtggagagtgacatgtgctggacactgtccatgaagcac tgagcagaagctggaggcacaacgcaccagacactcacagcaaggatgg agctgaaaacataacccactctgtcctggaggcactgggaagcctagag
``` aaggctgtgagccaaggagggagggtcttcctttggcatgggatgggga tgaagtaaggagagggactggaccccctggaagctgattcactatgggg ggaggtgtattgaagtcctccagacaaccctcagatttgatgataccta gtagaactcacagaaataaagagctgttatactgtg (SEQ ID No: 36; GenBank Accession No. NM_001030048).

In another embodiment, the KLK3 protein is encoded by residues 42-758 of SEQ ID No: 36. In another embodiment, the KLK3 protein is encoded by a homologue of SEQ ID No: 36. In another embodiment, the KLK3 protein is encoded by a variant of SEQ ID No: 36. In another embodiment, the KLK3 protein is encoded by an isomer of SEQ ID No: 36. In another embodiment, the KLK3 protein is encoded by a fragment of SEQ ID No: 36. Each possibility represents a separate embodiment of the methods and compositions as provided herein In another embodiment, the KLK3 protein has the sequence:

MWVPVVFLTLSVTWIGAAPLILSRIVGGWECEKHSQPWQVLVASRGRAV

CGGVLVHPQWVLTAAHCIRNKSVILLGRHSLFHPEDTGQVFQVSHSFPH

PLYDMSLLKNRFLRPGDDSSHDLMLLRLSEPAELTDAVKVMDLPTQEPA

LGTTCYASGWGSIEPEEFLTPKKLQCVDLHVISNDVCAQVHPQKVTKFM

LCAGRWTGGKSTCSGDSGGPLVCNGVLQGITSWGSEPCALPERPSLYTK

VVHYRKWIKDTIVANP (SEQ ID No: 37; GenBank Accession

No. NP_001639).

In another embodiment, the KLK3 protein is a homologue of SEQ ID No: 37. In another embodiment, the KLK3 protein is a variant of SEQ ID No: 37. In another embodiment, the KLK3 protein is an isomer of SEQ ID No: 37. In another embodiment, the KLK3 protein is a fragment of SEQ ID No: 37. Each possibility represents a separate embodiment of the methods and compositions as provided herein.

In another embodiment, the KLK3 protein is encoded by a nucleotide molecule having the sequence:

agccccaagcttaccacctgcacccggagagctgtgtcaccatgtgggt cccggagtcacctcaccctgtccgtgacgtggattggtgctgcacccct catcctgtctcggattgtggaggctgggagtgcgagaagcattcccaa ccctggcaggtgcttgtggcctctcgtggcagggcagtctgcggcgtg actggtgcaccccagtgggtcctcacagctgcccactgcatcaggaac aaaagcgtgatcttgctgggtcggcacagcctgatcatcctgaagacac aggccaggtatttcaggtcagccacagcacccacacccgctctacgata tgagcctcctgaagaatcgattcctcaggccaggtgatgactccagcca cgacctcatgctgctccgcctgtcagagcctgccgagctcacggatgct gtgaaggtcatggacctgcccacccaggagccagcactggggaccacct gctacgcctcaggctggggcagcattgaaccagaggagacttgacccca aagaaacttcagtgtgtggacctccatgttataccaatgacgtgtgtgc gcaagttcacctcagaaggtgaccaagttcatgctgtgtgctggacgc tggacaggggcaaaagcacctgctcgggtgattctggggcccacttg tctgtaatggtgtgcttcaaggtatcacgtcatgggcagtgaaccatg tgccctgcccgaaaggccaccctgtacaccaaggtggtgcattaccgga agtggatcaaggacaccatcgtggccaaccctgagcaccctatcaac cccctattgtagtaaacttggaaccaggaaatgaccaggccaagactca agcctccccagttctactgacctttgtccttaggtgtgaggtccagggt tgctaggaaaagaaatcagcagacacaggtgtagaccagagtgtttctt aaatggtgtaattngtcctctctgtgtcctggggaatactggccatgcc tggagacatatcactcaatttctctgaggacacagataggatggggtgt ctgtgttatttgtggggtacagagatgaaagaggggtgggatccacact gagagagtggagagtgacatgtgctggacactgtccatgaagcactgag cagaagctggaggcacaacgcaccagacactcacagcaaggatggagct gaaaacataacccactctgtcctggaggcactgggaagcctagagaagg ctgtgagccaaggagggagggtcttcctttggcatgggatggggatgaa gtaaggagagggactggaccccctggaagctgattcactatgggggag gtgtattgaagtcctccagacaaccctcagatttgatgatttcctagta gaactcacagaaataaagagctgttatactgtg (SEQ ID No: 38;

GenBank Accession No. NM_001648).

In another embodiment, the KLK3 protein is encoded by residues 42-827 of SEQ ID No: 38. In another embodiment, the KLK3 protein is encoded by a homologue of SEQ ID No: 38. In another embodiment, the KLK3 protein is encoded by a variant of SEQ ID No: 38. In another embodiment, the KLK3 protein is encoded by an isomer of SEQ ID No: 38. In another embodiment, the KLK3 protein is encoded by a fragment of SEQ ID No: 38. Each possibility represents a separate embodiment of the methods and compositions as provided herein.

In another embodiment, the KLK3 protein has the sequence:

MWVPVVFLTLSVTWIGAAPLILSRIVGGWECEKHSQPWQVLVASRGRAV

CGGVLVHPQWVLTAAHCIRNKSVILLGRHSLFHPEDTGQVFQVSHSFPH

PLYDMSLLKNRFLRPGDDSSHDLMLLRLSEPAELTDAVKVMDLPTQEPA

LGTTCYASGWGSIEPEEFLTPKKLQCVDLHVISNDVCAQVHPQKVTKFM

LCAGRWTGGKSTCSGDSGGPLVCNGVLQGITSWGSEPCALPERPSLYTK

VVHYRKWIKDTIVANP (SEQ ID No: 39 GenBank Accession

No. AAX29407.1).

In another embodiment, the KLK3 protein is a homologue of SEQ ID No: 39. In another embodiment, the KLK3 protein is a variant of SEQ ID No: 39. In another embodiment, the KLK3 protein is an isomer of SEQ ID No: 39. In another embodiment, the sequence of the KLK3 protein comprises SEQ ID No: 39. In another embodiment, the KLK3 protein is a fragment of SEQ ID No: 39. Each possibility represents a separate embodiment of the methods and compositions as provided herein.

In another embodiment, the KLK3 protein is encoded by a nucleotide molecule having the sequence:

```
gggggagccccaagcttaccacctgcacccggagagctgtgtcaccatg
tgggtcccggttgtcttcctcaccctgtccgtgacgtggattggtgctg
caccccctcatcctgtctcggattgtgggaggctgggagtgcgagaagca
ttcccaaccctggcaggtgcttgtggcctctcgtggcagggcagtctgc
ggcggtgttctggtgcaccccagtgggtcctcacagctgcccactgca
tcaggaacaaaagcgtgatcttgctgggtcggcacagcctgatcatcct
gaagacacaggccaggtatttcaggtcagccacagcacccacacccgct
ctacgatatgagcctcctgaagaatcgattcctcaggccaggtgatgac
tccagccacgacctcatgctgctccgcctgtcagagcctgccgagctca
cggatgctgtgaaggtcatggacctgcccacccaggagccagcactggg
gaccacctgctacgcctcaggctggggcagcattgaaccagaggagact
tgacccaaagaaacttcagtgtgtggacctccatgttataccaatgac
gtgtgtgcgcaagttcacccctcagaaggtgaccaagttcatgctgtgtg
ctggacgctggacagggggcaaaagcacctgctcgggtgattctggggg
cccacttgtctgtaatggtgtgcttcaaggtatcacgtcatggggcagt
gaaccatgtgccctgcccgaaaggccttccctgtacaccaaggtggtgc
attaccggaagtggatcaaggacaccatcgtggccaaccccctgagcacc
cctatcaactccctattgtagtaaacttggaaccaggaaatgaccaggc
caagactcaggcctccccagactactgacctagtccttaggtgtgaggt
ccagggagctaggaaaagaaatcagcagacacaggtgtagaccagagtg
atcttaaatggtgtaattagtcctctctgtgtcctggggaatactggcc
atgcctggagacatatcactcaatactctgaggacacagataggatggg
gtgtctgtgttatttgtggggtacagagatgaaagaggggtgggatcca
cactgagagagtggagagtgacatgtgctggacactgtccatgaagcac
tgagcagaagctggaggcacaacgcaccagacactcacagcaaggatgg
agctgaaaacataaccactctgtcctggaggcactgggaagcctagag
aaggctgtgagccaaggagggagggtcttcctttggcatgggatgggga
tgaagtagggagagggactggaccccctggaagctgattcactatgggg
ggaggtgtattgaagtcctccagacaaccctcagatttgatgatacctc
gtagaactcacagaaataaagagctgttatactgcgaaaaaaaaaaaa
aaaaaaaaaaaa (SEQ ID No: 40;
GenBank Accession No. BC056665).
```

In another embodiment, the KLK3 protein is encoded by residues 47-832 of SEQ ID No: 40. In another embodiment, the KLK3 protein is encoded by a homologue of SEQ ID No: 40. In another embodiment, the KLK3 protein is encoded by a variant of SEQ ID No: 40. In another embodiment, the KLK3 protein is encoded by an isomer of SEQ ID No: 40. In another embodiment, the KLK3 protein is encoded by a fragment of SEQ ID No: 40. Each possibility represents a separate embodiment of the methods and compositions as provided herein.

In another embodiment, the KLK3 protein has the sequence:

MWVPVVFLTLSVTWIGAAPLILSRIVGGWECEKHSQPWQVLVASRGRA

VCGGVLVHPQWVLTAAHCIRNKSVILLGRHSLFHPEDTGQVFQVSHSF

PHPLYDMSLLKNRFLRPGDDSSIEPEEFLTPKKLQCVDLHVISNDVCA

QVHPQKVTKFMLCAGRWTGGKSTCSGDSGGPLVCNGVLQGITSWGSEP

CALPERPSLYTKVVHYRKWIKDTIVA.

(SEQ ID No: 41; GenBank Accession No. AJ459782)

In another embodiment, the KLK3 protein is a homologue of SEQ ID No: 41. In another embodiment, the KLK3 protein is a variant of SEQ ID No: 41. In another embodiment, the KLK3 protein is an isomer of SEQ ID No: 41. In another embodiment, the KLK3 protein is a fragment of SEQ ID No: 41. Each possibility represents a separate embodiment of the methods and compositions as provided herein.

In another embodiment, the KLK3 protein has the sequence:

MWVPVVFLTLSVTWIGAAPLILSRIVGGWECEKHSQPWQVLVASRGRAV

CGGVLVHPQWVLTAAHCIRNKSVILLGRHSLFHPEDTGQVFQVSHSFPH

PLYDMSLLKNRFLRPGDDSSHDLMLLRLSEPAELTDAVKVMDLPTQEPA

LGTTCYASGWGSIEPEEFLTPKKLQCVDLHVISNDVCAQVHPQKVTKFM

LCAGRWTGGKSTCSVSHPYSQDLEGKGEWGP.

(SEQ ID No: 42, GenBank Accession No. AJ512346)

In another embodiment, the KLK3 protein is a homologue of SEQ ID No: 42. In another embodiment, the KLK3 protein is a variant of SEQ ID No: 42. In another embodiment, the KLK3 protein is an isomer of SEQ ID No: 42. In another embodiment, the sequence of the KLK3 protein comprises SEQ ID No: 42. In another embodiment, the KLK3 protein is a fragment of SEQ ID No: 42. Each possibility represents a separate embodiment of the methods and compositions as provided herein.

In another embodiment, the KLK3 protein has the sequence:

MWVPVVFLTLSVTWIGERGHGWGDAGEGASPDCQAEALSPPTQHPSPDRE

LGSFLSLPAPLQAHTPSPSILQQSSLPHQVPAPSHLPQNFLPIAQPAPCS

QLLY.

(SEQ ID No: 43 GenBank Accession No. AJ459784)

In another embodiment, the KLK3 protein is a homologue of SEQ ID No 43. In another embodiment, the KLK3 protein is a variant of SEQ ID No: 43. In another embodiment, the sequence of the KLK3 protein comprises SEQ ID No: 43. In another embodiment, the KLK3 protein is an isomer of SEQ ID No: 43. In another embodiment, the KLK3 protein is a fragment of SEQ ID No: 43. Each possibility represents a separate embodiment of the methods and compositions as provided herein.

In another embodiment, the KLK3 protein has the sequence:

MWVPVVFLTLSVTWIGAAPLILSRIVGGWECEKHSQPWQVLVASRGRAVC
GGVLVHPQWVLTAAHCIRNKSVILLGRHSLFHPEDTGQVFQVSHSFPHPL
YDMSLLKNRFLRPGDDSSHDLMLLRLSEPAELTDAVKVMDLPTQEPALGT
TCYASGWGSIEPEEFLTPKKLQCVDLHVISNDVCAQVHPQKVTKFMLCAG
RWTGGKSTCSGDSGGPLVCNGVLQGITSWGSEPCALPERPSLYTKVVHYR
KWIKDTIVANP.

(SEQ ID NO: 44 GenBank Accession No. AJ459783)

In another embodiment, the KLK3 protein is a homologue of SEQ ID No: 44. In another embodiment, the KLK3 protein is a variant of SEQ ID No: 44. In another embodiment, the KLK3 protein is an isomer of SEQ ID No: 44. In another embodiment, the KLK3 protein is a fragment of SEQ ID No: 44. Each possibility represents a separate embodiment of the methods and compositions as provided herein.

In another embodiment, the KLK3 protein is encoded by a nucleotide molecule having the sequence:

aagtacccactcccagtccaagaccccaaatcaccacaaaggacccaa
tccccagactcaagatatggtctgggcgctgtcagtgtctcctaccct
gatccctgggttcaactctgctcccagagcatgaagcctctccaccag
caccagccaccaacctgcaaacctaggagaagattgacagaattcccag
cctttcccagctcccctgccatgtcccaggactcccagccttggtt
ctctgccccgtgtctttcaaacccacatcctaaatccatctcctat
ccgagtcccagacctcctgtcaaccctgattccctgatctagcac
ccctctgcaggtgctgcaccctcatcctgtctcggattgtgggagg
ctgggagtgcgagaagcattcccaaccctggcaggtgcttgtagcctc
tcgtggcagggcagtctgcggcggtgactggtgcaccccagtgggtc
ctcacagctacccactgcatcaggaacaaaagcgtgatcttgctgggt
cggcacagcctgatcatcctgaagacacaggccaggtatttcaggtca
gccacagcacccacacccgctctacgatatgagcctcctgaagaatcg
attcctcaggccaggtgatgactccagccacgacctcatgctgctccg
cctgtcagagcctgccgagctcacggatgctatgaaggtcatggacct
gcccacccaggagccagcactggggaccacctgctacgcctcaggctg
gggcagcattgaaccagaggagacttgaccccaaagaaacttcagtgt
gtggacctccatgttatttccaatgacgtgtgtgcgcaagttcaccct
cagaaggtgaccaagttcatgctgtgtgctggacgctggacagggggc
aaaagcacctgctcgggtgattctgggggcccacttgtctgtaatggt
gtgcttcaaggtatcacgtcatggggcagtgaaccatgtgccctgccc
gaaaggccttccctgtacaccaaggtggtgcattaccggaagtggatc
aaggacaccatcgtggccaacccctgagcaccctatcaactccctat
tgtagtaaacttggaaccaggaaatgaccaggccaagactcaggcctc
cccagactactgacctagtccttaggtgtgaggtccagggagctagga aaagaaatcagcagacacaggtgtagaccagagtgatcttaaatggtg
taattagtcctctctgtgtcctggggaatactggccatgcctggagac
atatcactcaatactctgaggacacagataggatggggtgtctgtgtt
atttgtggggtacagagatgaaagaggggtgggatccacactgagaga
gtggagagtgacatgtgctggacactgtccatgaagcactgagcagaa
gctggaggcacaacgcaccagacactcacagcaaggatggagctgaaa
acataacccactctgtcctggaggcactgggaagcctagagaaggctg
tgaaccaaggagggagggtatcctaggcatgggatggggatgaagtaa
ggagagggactgaccccctggaagctgattcactatgggggaggtgt
attgaagtcctccagacaacccctcagatttgatgatacctagtagaac
tcacagaaataaagagctgttatactgtgaa.

(SEQ ID NO: 45; GenBank Accession No. X07730)

In another embodiment, the KLK3 protein is encoded by residues 67-1088 of SEQ ID No: 45. In another embodiment, the KLK3 protein is encoded by a homologue of SEQ ID No: 45. In another embodiment, the KLK3 protein is encoded by a variant of SEQ ID No: 45. In another embodiment, the KLK3 protein is encoded by an isomer of SEQ ID No: 45. In another embodiment, the KLK3 protein is encoded by a fragment of SEQ ID No: 45. Each possibility represents a separate embodiment of the methods and compositions as provided herein.

In another embodiment, the KLK3 protein has the sequence:

MWVPVVFLTLSVTWIGAAPLILSRIVGGWECEKHSQPWQVLVASRGRAVC
GGVLVHPQWVLTAAHCIRK.

(SEQ ID NO: 63; GenBank Accession No. NM_001030050)

In another embodiment, the KLK3 protein is a homologue of SEQ ID No: 63. In another embodiment, the KLK3 protein is a variant of SEQ ID No: 63. In another embodiment, the sequence of the KLK3 protein comprises SEQ ID No: 63. In another embodiment, the KLK3 protein is an isomer of SEQ ID No: 63. In another embodiment, the KLK3 protein is a fragment of SEQ ID No: 63. Each possibility represents a separate embodiment of the present invention.

In another embodiment, the KLK3 protein that is the source of the KLK3 peptide has the sequence:

MWVPVVFLTLSVTWIGAAPLILSRIVGGWECEKHSQPWQVLVASRGRAVC
GGVLVHPQWVLTAAHCIRNKSVILLGRHSLFHPEDTGQVFQVSHSFPHPL
YDMSLLKNRFLRPGDDSSIEPEEFLTPKKLQCVDLHVISNDVCAQVHPQK
VTKFMLCAGRWTGGKSTCSGDSGGPLVCNGVLQGITSWGSEPCALPERPS
LYTKVVHYRKWIKDTIVANP.

(SEQ ID NO: 64; GenBank Accession No. NM_001064049)

In another embodiment, the KLK3 protein is a homologue of SEQ ID No: 64. In another embodiment, the KLK3 protein is a variant of SEQ ID No: 64. In another embodiment, the KLK3 protein is an isomer of SEQ ID No: 64. In another embodiment, the KLK3 protein is a fragment of SEQ ID No: 64. Each possibility represents a separate embodiment of the present invention.

In another embodiment, the KLK3 protein has the sequence:

MWVPVVFLTLSVTWIGAAPLILSRIVGGWECEKHSQPWQVLVASRGRAVC
GGVLVHPQWVLTAAHCIRKPGDDSSHDLMLLRLSEPAELTDAVKVMDLPT
QEPALGTTCYASGWGSIEPEEFLTPKKLQCVDLHVISNDVCAQVHPQKVT
KFMLCAGRWTGGKSTCSGDSGGPLVCNGVLQGITSWGSEPCALPERPSLY
TKVVHYRKWIKDTIVANP.

(SEQ ID No: 65; GenBank Accession No. NM_001030048)

In another embodiment, the KLK3 protein is a homologue of SEQ ID No: 65. In another embodiment, the KLK3 protein is a variant of SEQ ID No: 65. In another embodiment, the KLK3 protein is an isomer of SEQ ID No: 65. In another embodiment, the KLK3 protein is a fragment of SEQ ID No: 65. Each possibility represents a separate embodiment of the present invention.

In another embodiment, the KLK3 protein has the sequence:

MWVPVVFLTLSVTWIGAAPLILSRIVGGWECEKHSQPWQVLVASRGRAVC
GGVLVHPQWVLTAAHCIRNKSVILLGRHSLFHPEDTGQVFQVSHSFPHPL
YDMSLLKNRFLRPGDDSSIEPEEFLTPKKLQCVDLHVISNDVCAQVHPQK
VTKFMLCAGRWTGGKSTCSGDSGGPLVCNGVLQGITSWGSEPCALPERPS
LYTKVVHYRKWIKDTIVA.

(SEQ ID No: 66; GenBank Accession No. AJ459782)

In another embodiment, the KLK3 protein is a homologue of SEQ ID No: 66. In another embodiment, the KLK3 protein is a variant of SEQ ID No: 66. In another embodiment, the KLK3 protein is an isomer of SEQ ID No: 66. In another embodiment, the KLK3 protein is a fragment of SEQ ID No: 66. Each possibility represents a separate embodiment of the present invention.

In another embodiment, the KLK3 protein has the sequence:

MWVPVVFLTLSVTWIGAAPLILSRIVGGWECEKHSQPWQVLVASRGRAVC
GGVLVHPQWVLTAAHCIRNKSVILLGRHSLFHPEDTGQVFQVSHSFPHPL
YDMSLLKNRFLRPGDDSSHDLMLLRLSEPAELTDAVKVMDLPTQEPALGT
TCYASGWGSIEPEEFLTPKKLQCVDLHVISNDVCAQVHPQKVTKFMLCAG
RWTGGKSTCSVSHPYSQDLEGKGEWGP.

(SEQ ID NO: 50 GenBank Accession No. AJ512346)

In another embodiment, the KLK3 protein is a homologue of SEQ ID NO: 50. In another embodiment, the KLK3 protein is a variant of SEQ ID NO: 50. In another embodiment, the KLK3 protein is an isomer of SEQ ID NO: 50. In another embodiment, the sequence of the KLK3 protein comprises SEQ ID NO: 50. In another embodiment, the KLK3 protein is a fragment of SEQ ID NO: 50. Each possibility represents a separate embodiment of the present invention.

In another embodiment, the KLK3 protein has the sequence:

MWVPVVFLTLSVTWIGERGHGWGDAGEGASPDCQAEALSPPTQHPSPDRE
LGSFLSLPAPLQAHTPSPSILQQSSLPHQVPAPSHLPQNFLPIAQPAPCS
QLLY.

(SEQ ID NO: 51 GenBank Accession No. AJ459784)

In another embodiment, the KLK3 protein is a homologue of SEQ ID NO: 51. In another embodiment, the KLK3 protein is a variant of SEQ ID NO: 51. In another embodiment, the sequence of the KLK3 protein comprises SEQ ID NO: 51. In another embodiment, the KLK3 protein is an isomer of SEQ ID NO: 51. In another embodiment, the KLK3 protein is a fragment of SEQ ID NO: 51.

In another embodiment, the KLK3 protein is encoded by a sequence set forth in one of the following GenBank Accession Numbers: BC005307, AJ310938, AJ310937, AF335478, AF335477, M27274, and M26663. In another embodiment, the KLK3 protein is encoded by a sequence set forth in one of the above GenBank Accession Numbers. Each possibility represents a separate embodiment of the methods and compositions as provided herein.

In another embodiment, the KLK3 protein is encoded by a sequence set forth in one of the following GenBank Accession Numbers: NM_001030050, NM_001030049, NM_001030048, NM_001030047, NM_001648, AJ459782, AJ512346, or AJ459784. Each possibility represents a separate embodiment of the methods and compositions as provided herein.

In one embodiment, the KLK3 protein is encoded by a variation of any of the sequences described herein wherein the sequence lacks

```
                                          (SEQ ID NO: 52)
MWVPVVFLTLSVTWIGAAPLILSR.
```

In another embodiment, the KLK3 protein has the sequence that comprises a sequence set forth in one of the following GenBank Accession Numbers: X13943, X13942, X13940, X13941, and X13944. Each possibility represents a separate embodiment of the methods and compositions as provided herein.

In another embodiment, the KLK3 protein is any other KLK3 protein known in the art. Each KLK3 protein represents a separate embodiment of the methods and compositions as provided herein.

In another embodiment, the KLK3 peptide is any other KLK3 peptide known in the art. In another embodiment, the KLK3 peptide is a fragment of any other KLK3 peptide known in the art. Each type of KLK3 peptide represents a separate embodiment of the methods and compositions as provided herein.

"KLK3 peptide" refers, in another embodiment, to a full-length KLK3 protein. In another embodiment, the term refers to a fragment of a KLK3 protein. In another embodiment, the term refers to a fragment of a KLK3 protein that is lacking the KLK3 signal peptide. In another embodiment, the term refers to a KLK3 protein that contains the entire KLK3 sequence except the KLK3 signal peptide. "KLK3 signal sequence" refers, in another embodiment, to any signal sequence found in nature on a KLK3 protein. In another embodiment, a KLK3 protein of methods and compositions as provided herein does not contain any signal sequence. Each possibility represents a separate embodiment of the methods and compositions as provided herein.

In another embodiment, the kallikrein-related peptidase 3 (KLK3 protein) that is the source of a KLK3 peptide for use in the methods and compositions as provided herein is a PSA protein. In another embodiment, the KLK3 protein is a P-30 antigen protein. In another embodiment, the KLK3 protein is a gamma-seminoprotein protein. In another embodiment, the KLK3 protein is a kallikrein 3 protein. In another embodiment, the KLK3 protein is a semenogelase protein. In another embodiment, the KLK3 protein is a seminin protein. In another embodiment, the KLK3 protein is any other type of KLK3 protein that is known in the art. Each possibility represents a separate embodiment of the methods and compositions as provided herein.

In another embodiment, the KLK3 protein is a splice variant 1 KLK3 protein. In another embodiment, the KLK3 protein is a splice variant 2 KLK3 protein. In another embodiment, the KLK3 protein is a splice variant 3 KLK3 protein. In another embodiment, the KLK3 protein is a transcript variant 1 KLK3 protein. In another embodiment, the KLK3 protein is a transcript variant 2 KLK3 protein. In another embodiment, the KLK3 protein is a transcript variant 3 KLK3 protein. In another embodiment, the KLK3 protein is a transcript variant 4 KLK3 protein. In another embodiment, the KLK3 protein is a transcript variant 5 KLK3 protein. In another embodiment, the KLK3 protein is a transcript variant 6 KLK3 protein. In another embodiment, the KLK3 protein is a splice variant RP5 KLK3 protein. In another embodiment, the KLK3 protein is any other splice variant KLK3 protein known in the art. In another embodiment, the KLK3 protein is any other transcript variant KLK3 protein known in the art. Each possibility represents a separate embodiment of the methods and compositions as provided herein.

In another embodiment, the KLK3 protein is a mature KLK3 protein. In another embodiment, the KLK3 protein is a pro-KLK3 protein. In another embodiment, the leader sequence has been removed from a mature KLK3 protein of methods and compositions as provided herein. Each possibility represents a separate embodiment of the methods and compositions as provided herein.

In another embodiment, the KLK3 protein that is the source of a KLK3 peptide of methods and compositions as provided herein is a human KLK3 protein. In another embodiment, the KLK3 protein is a primate KLK3 protein. In another embodiment, the KLK3 protein is a KLK3 protein of any other species known in the art. In another embodiment, one of the above KLK3 proteins is referred to in the art as a "KLK3 protein." Each possibility represents a separate embodiment of the methods and compositions as provided herein.

The term "isoform" refers to a version of a molecule, for example, a protein, with only slight differences compared to another isoform, or version, of the same protein. In one embodiment, isoforms may be produced from different but related genes, or in another embodiment, may arise from the same gene by alternative splicing. In another embodiment, isoforms are caused by single nucleotide polymorphisms.

The term, "fragment" refers to a protein or polypeptide that is shorter or comprises fewer amino acids than the full length protein or polypeptide. In another embodiment, fragment refers to a nucleic acid that is shorter or comprises fewer nucleotides than the full length nucleic acid. In another embodiment, the fragment is an N-terminal fragment. In another embodiment, the fragment is a C-terminal fragment. In one embodiment, the fragment is an intrasequential section of the protein, peptide, or nucleic acid. In one embodiment, the fragment is a functional fragment. In another embodiment, the fragment is an immunogenic fragment. In one embodiment, a fragment has 10-20 nucleic or amino acids, while in another embodiment, a fragment has more than 5 nucleic or amino acids, while in another embodiment, a fragment has 100-200 nucleic or amino acids, while in another embodiment, a fragment has 100-500 nucleic or amino acids, while in another embodiment, a fragment has 50-200 nucleic or amino acids, while in another embodiment, a fragment has 10-250 nucleic or amino acids.

The term, "immunogenicity" or "immunogenic" is used herein to refer to the innate ability of a protein, peptide, nucleic acid, antigen or organism to elicit an immune response in an animal when the protein, peptide, nucleic acid, antigen or organism is administered to the animal. Thus, "enhancing the immunogenicity" in one embodiment, refers to increasing the ability of a protein, peptide, nucleic acid, antigen or organism to elicit an immune response in an animal when the protein, peptide, nucleic acid, antigen or organism is administered to an animal. The increased ability of a protein, peptide, nucleic acid, antigen or organism to elicit an immune response can be measured by, in one embodiment, a greater number of antibodies to a protein, peptide, nucleic acid, antigen or organism, a greater diversity of antibodies to an antigen or organism, a greater number of T-cells specific for a protein, peptide, nucleic acid, antigen or organism, a greater cytotoxic or helper T-cell response to a protein, peptide, nucleic acid, antigen or organism, and the like.

In one embodiment, a PSA antigen comprises a truncated PSA open reading frame (GenBank Accession Number NM_001648), lacking its secretory signal sequence the first 24 AA. The truncated PSA may be amplified using the primers: Adv60-PSA(XhoI-no ATG)F: gtgCTCGAGattgtgggaggctgggagtg (SEQ ID No: 46) and Adv61-PSA(SpeI-Stop)R: gatACTAGTttaggggttggccacgatgg (SEQ ID No: 47) and may be subcloned in-frame with the first 441 amino acids of LLO to create a tLLO-PSA fusion polypeptide of this invention. The AA sequence of LLO-PSA is as follows:

MKKIMLVFITLILVSLPIAQQTEAKDASAFNKENSISSMAPPASPPASP

KTPIEKKHADEIDKYIQGLDYNKNNVLVYHGDAVTNVPPRKGYKDGNEY

IVVEKKKKSINQNNADIQVVNAISSLTYPGALVKANSELVENQPDVLPV

KRDSLTLSIDLPGMTNQDNKIVVKNATKSNVNNAVNTLVERWNEKYAQA

YPNVSAKIDYDDEMAYSESQLIAKFGTAFKAVNNSLNVNFGAISEGKMQ

EEVISFKQIYYNVNVNEPTRPSRFFGKAVTKEQLQALGVNAENPPAYIS

SVAYGRQVYLKLSTNSHSTKVKAAFDAAVSGKSVSGDVELTNIIKNSSF

KAVIYGGSAKDEVQIIDGNLGDLRDILKKGATFNRETPGVPIAYTTNFL

KDNELAVIKNNSEYIETTSKAYTDGKINIDHSGGYVAQFNISWDEVNYD

LE<u>IVGGWECEKHSQPWQVLVASRGRAVCGGVLVHPQWVLTAAHCIRNKS</u>

<u>VILLGRHSLFHPEDTGQVFQVSHSFPHPLYDMSLLKNRFLRPGDDSSHD</u>

<u>LMLLRLSEPAELTDAVKVMDLPTQEPALGTTCYASGWGSIEPEEFLTPK</u>

<u>KLQCVDLHVISNDVCAQVHPQKVTKFMLCAGRWTGGKSTCSGDSGGPLV</u>

<u>CYGVLQGITSWGSEPCALPERPSLYTKVVHYRKWIKDTIVANP</u>

(SEQ ID No: 48; PSA sequence is underlined).

In some embodiments, a live-attenuated *Listeria monocytogenes* comprises a tLLO-PSA fusion polypeptide comprising the sequence SEQ ID NO: 48. In some embodiments, a live-attenuated *Listeria monocytogenes* comprises a tLLO-PSA fusion polypeptide consisting essentially of the sequence SEQ ID NO: 48. In some embodiments, a live-attenuated *Listeria monocytogenes* comprises a tLLO-PSA fusion polypeptide consisting of the sequence SEQ ID NO: 48.

There is one AA difference between this PSA and the sequence in NM_001648, at position N 221 Y).

In one embodiment, a recombinant fusion polypeptide of methods and compositions of the present invention is an LLO-KLK3 fusion polypeptide. In another embodiment, the fusion polypeptide has the sequence set forth in SEQ ID No: 48. In another embodiment, the fusion polypeptide is homologous to the sequence set forth in SEQ ID No: 48. In another embodiment, the fusion polypeptide is a variant of the sequence set forth in SEQ ID No: 48. In another embodiment, "homology" refers to identity to one of SEQ ID No: 48 of greater than 72%. In another embodiment, the homology is greater than 75%. In another embodiment, "homology" refers to identity to a sequence of greater than 78%. In another embodiment, the homology is greater than 80%. In another embodiment, the homology is greater than 82%. In another embodiment, "homology" refers to identity to a sequence of greater than 83%. In another embodiment, the homology is greater than 85%. In another embodiment, the homology is greater than 87%. In another embodiment, "homology" refers to identity to a sequence of greater than 88%. In another embodiment, the homology is greater than 90%. In another embodiment, the homology is greater than 92%. In another embodiment, "homology" refers to identity to a sequence of greater than 93%. In another embodiment, the homology is greater than 95%. In another embodiment, "homology" refers to identity to a sequence of greater than 96%. In another embodiment, the homology is greater than 97%. In another embodiment, the homology is greater than 98%. In another embodiment, the homology is greater than 99%. Each possibility represents a separate embodiment of the present invention.

In one embodiment, the truncated LLO comprises a PEST amino acid (AA) sequence. In another embodiment, the PEST amino acid sequence is KENSISSMAPPASPPASPK-TPIEKKHADEIDK (SEQ ID NO: 49). In another embodiment, fusion of an antigen to other LM PEST AA sequences from *Listeria* will also enhance immunogenicity of the antigen.

The N-terminal LLO protein fragment of methods and compositions of the present invention comprises, in another embodiment, SEQ ID No: 54. In another embodiment, the fragment comprises an LLO signal peptide. In another embodiment, the fragment comprises SEQ ID No: 55. In another embodiment, the fragment consists approximately of SEQ ID No: 55. In another embodiment, the fragment consists essentially of SEQ ID No: 54. In another embodiment, the fragment corresponds to SEQ ID No: 55. In another embodiment, the fragment is homologous to SEQ ID No: 55. In another embodiment, the fragment is homologous to a fragment of SEQ ID No: 55. In some embodiments, the ALLO fused to a PSA antigen is 416 AA long (exclusive of the signal sequence), as 88 residues from the amino terminus which is inclusive of the activation domain containing cysteine 484 were truncated. It will be clear to those skilled in the art that any ALLO without the activation domain, and in particular without cysteine 484, are suitable for methods and compositions of the present invention. In another embodiment, fusion of a heterologous antigen to any ALLO, including the PEST AA sequence, SEQ ID NO: 49, enhances cell mediated and anti-tumor immunity of the antigen. Each possibility represents a separate embodiment of the present invention.

The LLO protein utilized to construct strains of the present invention has, in another embodiment, the sequence:

MKKIMLVFITLILVSLPIAQQTEAKDASAFNKENSISSMAPPASPPASP

KTPIEKKHADEIDKYIQGLDYNKNNVLVYHGDAVTNVPPRKGYKDGNEY

IVVEKKKKSINQNNADIQVVNAISSLTYPGALVKANSELVENQPDVLPV

KRDSLTLSIDLPGMTNQDNKIVVKNATKSNVNNAVNTLVERWNEKYAQA

YPNVSAKIDYDDEMAYSESQLIAKFUTAFKAVNNSLNVNFGAISEGKMQ

EEVISFKQIYYNVNVNEPTRPSRFFGKAVTKEQLQALGVNAENPPAYIS

SVAYGRQVYLKLSTNSHSTKVKAAFDAAVSGKSVSGDVELTNIIKNSSF

KAVIYGGSAKDEVQIIDGNLGDLRDILKKGATFNRETPGVPIAYTTNFL

KDNELAVIKNNSEYIETTSKAYTDGKINIDHSGGYVAQFNISWDEVNYD

PEGNEIVQHKNWSENNKSKLAHETSSIYLPGNARNINVYAKECTGLAWE

WWRTVIDDRNLPLVKNRNISIWGTTLYPKYSNKVDNPIE (GenBank Accession No. P13128; SEQ ID NO: 53;

nucleic acid sequence is set forth in GenBank

Accession No. X15127).

The first 25 AA of the proprotein corresponding to this sequence are the signal sequence and are cleaved from LLO when it is secreted by the bacterium. Thus, in this embodiment, the full length active LLO protein is 504 residues long. In another embodiment, the above LLO fragment is used as the source of the LLO fragment incorporated in a strain of the present invention. Each possibility represents a separate embodiment of the present invention.

In another embodiment, the N-terminal fragment of an LLO protein utilized in compositions and methods of the present invention has the sequence:

(SEQ ID NO: 54)
MKKIMLVFITLILVSLPIAQQTEAKDASAFNKENSISSVAPPASPPASPK

TPIEKKHADEIDKYIQGLDYNKNNVLVYHGDAVTNVPPRKGYKDGNEYIV

VEKKKKSINQNNADIQVVNAISSLTYPGALVKANSELVENQPDVLPVKRD

SLTLSIDLPGMTNQDNKIVVKNATKSNVNNAVNTLVERWNEKYAQAYSNV

SAKIDYDDEMAYSESQLIAKFGTAFKAVNNSLNVNFGAISEGKMQEEVIS

FKQIYYNVNVNEPTRPSRFFGKAVTKEQLQALGVNAENPPAYISSVAYGR

QVYLKLSTNSHSTKVKAAFDAAVSGKSVSGDVELTNIIKNSSFKAVIYGG

SAKDEVQIIDGNLGDLRDILKKGATFNRETPGVPIAYTTNFLKDNELAVI

KNNSEYIETTSKAYTDGKINIDHSGGYVAQFNISWDEVNYD.

In another embodiment, the LLO fragment corresponds to about AA 20-442 of an LLO protein utilized herein.

In another embodiment, the LLO fragment has the sequence:

(SEQ ID NO: 55)
MKKIMLVFITLILVSLPIAQQTEAKDASAFNKENSISSVAPPASPPASPK

TPIEKKHADEIDKYIQGLDYNKNNVLVYHGDAVTNVPPRKGYKDGNEYIV

VEKKKKSINQNNADIQVVNAISSLTYPGALVKANSELVENQPDVLPVKRD

SLTLSIDLPGMTNQDNKIVVKNATKSNVNNAVNTLVERWNEKYAQAYSNV

SAKIDYDDEMAYSESQLIAKFGTAFKAVNNSLNVNFGAISEGKMQEEVIS

FKQIYYNVNVNEPTRPSRFFGKAVTKEQLQALGVNAENPPAYISSVAYGR

QVYLKLSTNSHSTKVKAAFDAAVSGKSVSGDVELTNIIKNSSFKAVIYGG

SAKDEVQIIDGNLGDLRDILKKGATFNRETPGVPIAYTTNFLKDNELAVI

KNNSEYIETTSKAYTD.

In another embodiment, "truncated LLO" or "ΔLLO" refers to a fragment of LLO that comprises the PEST-like domain. In another embodiment, the terms refer to an LLO fragment that comprises a PEST amino acid sequence.

In another embodiment, the terms refer to an LLO fragment that does not contain the activation domain at the amino terminus and does not include cysteine 484. In another embodiment, the terms refer to an LLO fragment that is not hemolytic. In another embodiment, the LLO fragment is rendered non-hemolytic by deletion or mutation of the activation domain. In another embodiment, the LLO fragment is rendered non-hemolytic by deletion or mutation of cysteine 484. In another embodiment, the LLO fragment is rendered non-hemolytic by deletion or mutation at another location. In another embodiment, the LLO is rendered non-hemolytic by a deletion or mutation of the cholesterol binding domain (CBD) as detailed in U.S. Pat. No. 8,771,702, which is incorporated by reference herein. In another embodiment, there is a mutation in a cholesterol-binding domain (CBD) of the LLO or a fragment thereof, wherein said mutation comprises a substitution of a 1-50 amino acid peptide comprising a CBD. In one embodiment, there is a mutation in a CBD of the LLO or a fragment thereof, wherein said mutation comprises a substitution of residue C484, W491, W492 of SEQ ID NO: 53, alone or in combination, wherein said recombinant protein exhibits a greater than 100-fold reduction in hemolytic activity relative to wild-type LLO. Each possibility represents a separate embodiment of the present invention.

In another embodiment, the LLO fragment consists of about the first 441 AA of the LLO protein. In another embodiment, the LLO fragment consists of about the first 420 AA of LLO. In another embodiment, the LLO fragment is a non-hemolytic form of the LLO protein.

In another embodiment, the LLO fragment consists of about residues 1-25. In another embodiment, the LLO fragment consists of about residues 1-50. In another embodiment, the LLO fragment consists of about residues 1-75. In another embodiment, the LLO fragment consists of about residues 1-100. In another embodiment, the LLO fragment consists of about residues 1-125. In another embodiment, the LLO fragment consists of about residues 1-150. In another embodiment, the LLO fragment consists of about residues 1175. In another embodiment, the LLO fragment consists of about residues 1-200. In another embodiment, the LLO fragment consists of about residues 1-225. In another embodiment, the LLO fragment consists of about residues 1-250. In another embodiment, the LLO fragment consists of about residues 1-275. In another embodiment, the LLO fragment consists of about residues 1-300. In another embodiment, the LLO fragment consists of about residues 1-325. In another embodiment, the LLO fragment consists of about residues 1-350. In another embodiment, the LLO fragment consists of about residues 1-375. In another embodiment, the LLO fragment consists of about residues 1-400. In another embodiment, the LLO fragment consists of about residues 1-425. Each possibility represents a separate embodiment of the present invention.

In another embodiment, the LLO fragment contains residues of a homologous LLO protein that correspond to one of the above AA ranges. The residue numbers need not, in another embodiment, correspond exactly with the residue numbers enumerated above; e.g. if the homologous LLO protein has an insertion or deletion, relative to an LLO protein utilized herein, then the residue numbers can be adjusted accordingly. In another embodiment, the LLO fragment is any other LLO fragment known in the art.

In another embodiment, a homologous LLO refers to identity to an LLO sequence (e.g. to one of SEQ ID No: 53-55) of greater than 70%. In another embodiment, a homologous LLO refers to identity to one of SEQ ID No: 53-55 of greater than 72%. In another embodiment, a homologous refers to identity to one of SEQ ID No: 53-55 of greater than 75%. In another embodiment, a homologous refers to identity to one of SEQ ID No: 53-55 of greater than 78%. In another embodiment, a homologous refers to identity to one of SEQ ID No: 53-55 of greater than 80%. In another embodiment, a homologous refers to identity to one of SEQ ID No: 53-55 of greater than 82%. In another embodiment, a homologous refers to identity to one of SEQ ID No: 53-55 of greater than 83%. In another embodiment, a homologous refers to identity to one of SEQ ID No: 53-55 of greater than 85%. In another embodiment, a homologous refers to identity to one of SEQ ID No: 53-55 of greater than 87%. In another embodiment, a homologous refers to identity to one of SEQ ID No: 53-55 of greater than 88%. In another embodiment, a homologous refers to identity to one of SEQ ID No: 53-55 of greater than 90%. In another embodiment, a homologous refers to identity to one of SEQ ID No: 53-55 of greater than 92%. In another embodiment, a homologous refers to identity to one of SEQ ID No: 53-55 of greater than 93%. In another embodiment, a homologous refers to identity to one of SEQ ID No: 53-55 of greater than 95%. In another embodiment, a homologous refers to identity to one of SEQ ID No: 53-55 of greater than 96%. In another embodiment, a homologous refers to identity to one of SEQ ID No: 53-55 of greater than 97%. In another embodiment, a homologous refers to identity to one of SEQ ID No: 53-55 of greater than 98%. In another embodiment, a homologous refers to identity to one of SEQ ID No: 53-55 of greater than 99%. In another embodiment, a homologous refers to identity to one of SEQ ID No: 53-55 of 100%. Each possibility represents a separate embodiment of the present invention.

The amino acid and nucleotide sequences from United States Publication Nos. US-2007-0253976-A1 and US-2011-0129499-A1 are incorporated herein in their entirety.

The term "homologue" refers to a nucleic acid or amino acid sequence which shares a certain percentage of sequence identity with a particular nucleic acid or amino acid sequence. In one embodiment, a sequence useful in the composition and methods as provided herein may be a homologue of a particular LLO sequence or N-terminal fragment thereof. In another embodiment, a sequence useful in the composition and methods as provided herein may be a homologue of an antigenic polypeptide, which in one embodiment, is KLK3 or a functional fragment thereof. In one embodiment, a homolog of a polypeptide and, in one embodiment, the nucleic acid encoding such a homolog, of the present invention maintains the functional characteristics of the parent polypeptide. For example, in one embodiment, a homolog of an antigenic polypeptide of the present invention maintains the antigenic characteristic of the parent polypeptide. In another embodiment, a sequence useful in the composition and methods as provided herein may be a homologue of any sequence described herein. In one embodiment, a homologue shares at least 70% identity with a particular sequence. In another embodiment, a homologue shares at least 72% identity with a particular sequence. In another embodiment, a homologue shares at least 75% identity with a particular sequence. In another embodiment, a homologue shares at least 78% identity with a particular sequence. In another embodiment, a homologue shares at least 80% identity with a particular sequence. In another embodiment, a homologue shares at least 82% identity with a particular sequence. In another embodiment, a homologue shares at least 83% identity with a particular sequence. In another embodiment, a homologue shares at least 85% identity with a particular sequence. In another embodiment, a homologue shares at least 87% identity with a particular sequence. In another embodiment, a homologue shares at least 88% identity with a particular sequence. In another embodiment, a homologue shares at least 90% identity with a particular sequence. In another embodiment, a homologue shares at least 92% identity with a particular sequence. In another embodiment, a homologue shares at least 93% identity with a particular sequence. In another embodiment, a homologue shares at least 95% identity with a particular sequence. In another embodiment, a homologue shares at least 96% identity with a particular sequence. In another embodiment, a homologue shares at least 97% identity with a particular sequence. In another embodiment, a homologue shares at least 98% identity with a particular sequence. In another embodiment, a homologue shares at least 99% identity with a particular sequence. In another embodiment, a homologue shares 100% identity with a particular sequence. Each possibility represents a separate embodiment as provided herein.

Homology is, in one embodiment, determined by computer algorithm for sequence alignment, by methods well described in the art. For example, computer algorithm analysis of nucleic acid sequence homology may include the utilization of any number of software packages available, such as, for example, the BLAST, DOMAIN, BEAUTY (BLAST Enhanced Alignment Utility), GENPEPT and TREMBL packages.

In another embodiment, homology is determined via determination of candidate sequence hybridization, methods of which are well described in the art (See, for example, "Nucleic Acid Hybridization" Hames, B. D., and Higgins S. J., Eds. (1985); Sambrook et al., 2001, Molecular Cloning, A Laboratory Manual, Cold Spring Harbor Press, N.Y.; and Ausubel et al., 1989, Current Protocols in Molecular Biology, Green Publishing Associates and Wiley Interscience, N.Y). For example methods of hybridization may be carried out under moderate to stringent conditions, to the complement of a DNA encoding a native caspase peptide. Hybridization conditions being, for example, overnight incubation at 42° C. in a solution comprising: 10-20% formamide, 5×SSC (150 mM NaCl, 15 mM trisodium citrate), 50 mM sodium phosphate (pH 7.6), 5×Denhardt's solution, 10% dextran sulfate, and 20 µg/ml denatured, sheared salmon sperm DNA.

In one embodiment, it is to be understood that a homolog of any of the sequences as provided herein and/or as described herein is considered to be a part of the invention.

In another embodiment, a recombinant *Listeria* strain of the methods and compositions as provided herein comprise a nucleic acid molecule encoding a PSA fussion polypeptide operably integrated into the *Listeria* genome as an open reading frame with an endogenous ActA sequence. In another embodiment, a recombinant *Listeria* strain of the methods and compositions as provided herein comprise an episomal expression vector comprising a nucleic acid molecule encoding PSA fusion protein comprising an antigen fused to an ActA or a truncated ActA. In one embodiment, the expression and secretion of the antigen is under the control of an actA promoter and ActA signal sequence and it is expressed as fusion to 1-233 amino acids of ActA (truncated ActA or tActA). In another embodiment, the truncated ActA consists of the first 390 amino acids of the wild type ActA protein as described in U.S. Pat. No. 7,655,238, which is incorporated by reference herein in its entirety. In another embodiment, the truncated ActA is an ActA-N100 or a modified version thereof (referred to as ActA-N100*) in which a PEST motif has been deleted and containing the nonconservative QDNKR substitution as described in US Patent Publication Serial No. 2014/0186387.

The term "functional" within the meaning of the invention, is used herein to refer to the innate ability of a protein, peptide, nucleic acid, fragment or a variant thereof to exhibit a biological activity or function. In one embodiment, such a biological function is its binding property to an interaction partner, e.g., a membrane-associated receptor, and in another embodiment, its trimerization property. In the case of functional fragments and the functional variants of the invention, these biological functions may in fact be changed, e.g., with respect to their specificity or selectivity, but with retention of the basic biological function.

In another embodiment, a "functional fragment" is an immunogenic fragment and elicits an immune response when administered to a subject alone or in a strain composition provided herein. In another embodiment, a functional fragment has biological activity as will be understood by a skilled artisan and as further provided herein.

The term "nucleic acids" or "nucleotide" refers to a string of at least two base-sugar-phosphate combinations. The term includes, in one embodiment, DNA and RNA. "Nucleotides" refers, in one embodiment, to the monomeric units of nucleic acid polymers. RNA may be, in one embodiment, in the form of a tRNA (transfer RNA), snRNA (small nuclear RNA), rRNA (ribosomal RNA), mRNA (messenger RNA), anti-sense RNA, small inhibitory RNA (siRNA), micro RNA (miRNA) and ribozymes. The use of siRNA and miRNA has been described (Caudy A A et al, Genes & Devel 16: 2491-96 and references cited therein). DNA may be in form of plasmid DNA, viral DNA, linear DNA, or chromosomal DNA or derivatives of these groups. In addition, these forms of DNA and RNA may be single, double, triple, or quadruple stranded. The term also includes, in another embodiment, artificial nucleic acids that may contain other types of backbones but the same bases. In one embodiment, the artificial nucleic acid is a PNA (peptide nucleic acid). PNA contain peptide backbones and nucleotide bases and are able to bind, in one embodiment, to both DNA and RNA molecules. In another embodiment, the nucleotide is oxetane modified. In another embodiment, the nucleotide is modified by replacement of one or more phosphodiester bonds with a phosphorothioate bond. In another embodiment, the artificial nucleic acid contains any other variant of the phosphate backbone of native nucleic acids known in the art. The use of phosphothiorate nucleic acids and PNA are known to those skilled in the art, and are described in, for example, Neilsen P E, Curr Opin Struct Biol 9:353-57; and Raz N K et al Biochem Biophys Res Commun 297:1075-84. The production and use of nucleic acids is known to those skilled in art and is described, for example, in Molecular Cloning, (2001), Sambrook and Russell, eds. and Methods in Enzymology: Methods for molecular cloning in eukaryotic cells (2003) Purchio and G. C. Fareed. Each nucleic acid derivative represents a separate embodiment as provided herein.

The terms "polypeptide," "peptide" and "recombinant peptide" refer, in another embodiment, to a peptide or polypeptide of any length. In another embodiment, a peptide or recombinant peptide as provided herein has one of the lengths enumerated above for an HMW-MAA fragment. Each possibility represents a separate embodiment of the methods and compositions as provided herein. In one embodiment, the term "peptide" refers to native peptides (either degradation products, synthetically synthesized peptides or recombinant peptides) and/or peptidomimetics (typically, synthetically synthesized peptides), such as peptoids and semipeptoids which are peptide analogs, which may have, for example, modifications rendering the peptides more stable while in a body or more capable of penetrating into cells. Such modifications include, but are not limited to N terminus modification, C terminus modification, peptide bond modification, including, but not limited to, CH2-NH, CH2-S, CH2-S=O, O=C—NH, CH2-O, CH2-CH2, S=C—NH, CH=CH or CF=CH, backbone modifications, and residue modification. Methods for preparing peptidomimetic compounds are well known in the art and are specified, for example, in Quantitative Drug Design, C. A. Ramsden Gd., Chapter 17.2, F. Choplin Pergamon Press (1992), which is incorporated by reference as if fully set forth herein. Further details in this respect are provided hereinunder.

The term "antigenic polypeptide" is used herein to refer to a polypeptide, peptide or recombinant peptide as described hereinabove that is foreign to a host and leads to the mounting of an immune response when present in, or, in another embodiment, detected by, the host.

In one embodiment, "antigenic polypeptide" is used herein to refer to a polypeptide, peptide recombinant polypeptide or recombinant peptide as described herein that is processed and presented on MHC class I and/or class II molecules present in a subject's cells leading to the mounting of an immune response when present in, or, in another embodiment, detected by, the host. In one embodiment, the antigen may be foreign to the host. In another embodiment, the antigen might be present in the host but the host does not elicit an immune response against it because of immunologic tolerance.

In one embodiment, the antigen is a tumor-associated antigen. In one embodiment, the tumor-associated antigen is PSA. In one embodiment, the recombinant attenuated Listeria strain of the compositions and methods as provided herein express a PSA polypeptide that is expressed by a tumor cell. In one embodiment, the recombinant Listeria strain of the compositions and methods as provided herein comprise a first or second nucleic acid molecule that encodes a PSA, which in one embodiment, is a marker for prostate cancer that is highly expressed by prostate tumors. In one embodiment, PSA is a kallikrein serine protease (KLK3) secreted by prostatic epithelial cells, which in one embodiment, is widely used as a marker for prostate cancer.

Peptide bonds (—CO—NH—) within the peptide may be substituted, for example, by N-methylated bonds (—N (CH3)-CO—), ester bonds (—C(R)H—C—O—O—C(R)—N—), ketomethylen bonds (—CO—CH2-), *-aza bonds (—NH—N(R)—CO—), wherein R is any alkyl, e.g., methyl, carba bonds (—CH2-NH—), hydroxyethylene bonds (—CH(OH)—CH2-), thioamide bonds (—CS—NH—), olefinic double bonds (—CH=CH—), retro amide bonds (—NH—CO—), peptide derivatives (—N(R)—CH2-CO—), wherein R is the "normal" side chain, naturally presented on the carbon atom.

These modifications can occur at any of the bonds along the peptide chain and even at several (2-3) at the same time. Natural aromatic amino acids, Trp, Tyr and Phe, may be substituted for synthetic non-natural acid such as TIC, naphthylelanine (Nol), ring-methylated derivatives of Phe, halogenated derivatives of Phe or o-methyl-Tyr.

In addition to the above, the peptides as provided herein may also include one or more modified amino acids or one or more non-amino acid monomers (e.g. fatty acids, complex carbohydrates etc).

The term "oligonucleotide" is interchangeable with the term "nucleic acid", and may refer to a molecule, which may include, but is not limited to, prokaryotic sequences, eukaryotic mRNA, cDNA from eukaryotic mRNA, genomic DNA sequences from eukaryotic (e.g., mammalian) DNA, and even synthetic DNA sequences. The term also refers to sequences that include any of the known base analogs of DNA and RNA.

It will be appreciated by the skilled artisan that the term "PEST sequence-containing polypeptide" or "PEST sequence-containing protein" may encompass a truncated LLO protein, which in one embodiment is a N-terminal LLO, and a truncated ActA protein which in one embodiment is an N-terminal LLO, or fragments thereof. It will also be appreciated by the skilled artisan that the term "PEST-sequence containing peptide" may encompass a PEST sequence peptide or peptide fragments of an LLO protein or an ActA protein thereof. PEST sequence peptides are known in the art and are described in U.S. Pat. No. 7,635,479, and in US Patent Publication Serial No. 2014/0186387, both of which are hereby incorporated in their entirety herein.

In another embodiment, a PEST sequence of prokaryotic organisms can be identified routinely in accordance with methods such as described by Rechsteiner and Roberts (TBS 21:267-271, 1996) for *L. monocytogenes*. Alternatively, PEST amino acid sequences from other prokaryotic organisms can also be identified based by this method. Other prokaryotic organisms wherein PEST amino acid sequences would be expected to include, but are not limited to, other *Listeria* species. For example, the *L. monocytogenes* protein ActA contains four such sequences. These are KTEEQP-SEVNTGPR (SEQ ID NO: 56), KASVTDT-SEGDLDSSMQSADESTPQPLK (SEQ ID NO: 57), KNEEVNASDFPPPPTDEELR (SEQ ID NO: 58), and RGGIPTSEEFSSLNSGDFTDDENSETTEEEIDR (SEQ ID NO: 59). Also Streptolysin O from *Streptococcus* sp. contain a PEST sequence. For example, *Streptococcus pyogenes* Streptolysin O comprises the PEST sequence KQN-TASTETTTTNEQPK (SEQ ID NO: 60) at amino acids 35-51 and *Streptococcus equisimilis* Streptolysin O comprises the PEST-like sequence KQNTANTETTTTNEQPK (SEQ ID NO: 61) at amino acids 38-54. Further, it is believed that the PEST sequence can be embedded within the antigenic protein. Thus, for purposes of the present invention, by "fusion" when in relation to PEST sequence fusions, it is meant that the antigenic protein comprises both the antigen, for example PSA, and the PEST amino acid sequence either linked at one end of the antigen or embedded within the antigen.

In another embodiment, the construct or nucleic acid molecule is expressed from an episomal or plasmid vector, with a nucleic acid sequence encoding a PEST sequence-containing polypeptide or a PEST-sequence peptide. In another embodiment, the plasmid is stably maintained in the recombinant *Listeria* strain strain in the absence of antibiotic selection. In another embodiment, the plasmid does not confer antibiotic resistance upon the recombinant *Listeria*. In another embodiment, the fragment is a functional fragment. In another embodiment, the fragment is an immunogenic fragment.

The term "Stably maintained" refers, in another embodiment, to maintenance of a nucleic acid molecule or plasmid in the absence of selection (e.g. antibiotic selection) for 10 generations, without detectable loss. In another embodiment, the period is 15 generations. In another embodiment, the period is 20 generations. In another embodiment, the period is 25 generations. In another embodiment, the period is 30 generations. In another embodiment, the period is 40 generations. In another embodiment, the period is 50 generations. In another embodiment, the period is 60 generations. In another embodiment, the period is 80 generations. In another embodiment, the period is 100 generations. In another embodiment, the period is 150 generations. In another embodiment, the period is 200 generations. In another embodiment, the period is 300 generations. In another embodiment, the period is 500 generations. In another embodiment, the period is more than 500 generations. In another embodiment, the nucleic acid molecule or plasmid is maintained stably in vitro (e.g. in culture). In another embodiment, the nucleic acid molecule or plasmid is maintained stably in vivo. In another embodiment, the nucleic acid molecule or plasmid is maintained stably both in vitro and in vitro. Each possibility represents a separate embodiment of the methods and compositions as provided herein.

The term "amino acid" or "amino acids" is understood to include the 20 naturally occurring amino acids; those amino acids often modified post-translationally in vivo, including, for example, hydroxyproline, phosphoserine and phosphothreonine; and other unusual amino acids including, but not limited to, 2-aminoadipic acid, hydroxylysine, isodesmosine, nor-valine, nor-leucine and ornithine. Furthermore, the term "amino acid" may include both D- and L-amino acids.

The term "nucleic acid" or "nucleic acid sequence" refers to a deoxyribonucleotide or ribonucleotide oligonucleotide in either single- or double-stranded form. The term encompasses nucleic acids, i.e., oligonucleotides, containing known analogues of natural nucleotides which have similar or improved binding properties, for the purposes desired, as the reference nucleic acid. The term also includes nucleic acids which are metabolized in a manner similar to naturally occurring nucleotides or at rates that are improved thereover for the purposes desired. The term also encompasses nucleic-acid-like structures with synthetic backbones. DNA backbone analogues provided by the invention include phosphodiester, phosphorothioate, phosphorodithioate, methylphosphonate, phosphoramidate, alkyl phosphotriester, sulfamate, 3'-thioacetal, methylene(methylimino), 3'-N-carbamate, morpholino carbamate, and peptide nucleic acids (PNAs); see, e.g., Oligonucleotides and Analogues, a Practical Approach, edited by F. Eckstein, IRL Press at Oxford University Press (1991); Antisense Strategies, Annals of the New York Academy of Sciences, Volume 600, Eds. Baserga and Denhardt (NYAS 1992); Mulligan (1993) J. Med. Chem. 36:1923-1937; Antisense Research and Applications (1993, CRC Press). PNAs contain non-ionic backbones, such as N-(2-aminoethyl) glycine units. Phosphorothioate linkages are described, e.g., in WO 97/03211; WO 96/39154; Mata (1997) Toxicol. Appl. Pharmacol. 144:189-197. Other synthetic backbones encompasses by the term include methyl-phosphonate linkages or alternating methyl-phosphonate and phosphodiester linkages (Strauss-Soukup (1997) Biochemistry 36:8692-8698), and benzylphosphonate linkages (Samstag (1996) Antisense Nucleic Acid Drug Dev. 6:153-156). The term nucleic acid is used interchangeably with gene, cDNA, mRNA, oligonucleotide primer, probe and amplification product.

In another embodiment, the construct or nucleic acid molecule provided herein is integrated into the Listerial chromosome using homologous recombination. Techniques for homologous recombination are well known in the art, and are described, for example, in Baloglu S, Boyle S M, et al (Immune responses of mice to vaccinia virus recombinants expressing either *Listeria monocytogenes* partial listeriolysin or *Brucella abortus* ribosomal L7/L12 protein. Vet Microbiol 2005, 109(1-2): 11-7); and Jiang L L, Song H H, et al., (Characterization of a mutant *Listeria monocytogenes* strain expressing green fluorescent protein. Acta Biochim Biophys Sin (Shanghai) 2005, 37(1): 19-24). In another embodiment, homologous recombination is performed as described in U.S. Pat. No. 6,855,320. In another embodiment, a temperature sensitive plasmid is used to select the recombinants. Each technique represents a separate embodiment of the present invention.

In another embodiment, the construct or nucleic acid molecule is integrated into the Listerial chromosome using transposon insertion. Techniques for transposon insertion are well known in the art, and are described, inter alia, by Sun et al. (Infection and Immunity 1990, 58: 3770-3778) in the construction of DP-L967. Transposon mutagenesis has the advantage, in another embodiment, that a stable genomic insertion mutant can be formed but the disadvantage that the position in the genome where the foreign gene has been inserted is unknown.

In another embodiment, the construct or nucleic acid molecule is integrated into the Listerial chromosome using phage integration sites (Lauer P, Chow M Y et al, Construction, characterization, and use of two *Listeria monocytogenes* site-specific phage integration vectors. J Bacteriol 2002; 184(15): 4177-86). In certain embodiments of this method, an integrase gene and attachment site of a bacteriophage (e.g. U153 or PSA listeriophage) is used to insert the heterologous gene into the corresponding attachment site, which may be any appropriate site in the genome (e.g. comK or the 3' end of the arg tRNA gene). In another embodiment, endogenous prophages are cured from the attachment site utilized prior to integration of the construct or heterologous gene. In another embodiment, this method results in single-copy integrants. In another embodiment, the present invention further comprises a phage based chromosomal integration system for clinical applications, where a host strain that is auxotrophic for essential enzymes, including, but not limited to, d-alanine racemase can be used, for example Lmdal(–)dat(–). In another embodiment, in order to avoid a "phage curing step," a phage integration system based on PSA is used. This requires, in another embodiment, continuous selection by antibiotics to maintain the integrated gene. Thus, in another embodiment, the current invention enables the establishment of a phage based chromosomal integration system that does not require selection with antibiotics. Instead, an auxotrophic host strain can be complemented. Each possibility represents a separate embodiment of the present invention.

The term "recombination site" or "site-specific recombination site" refers to a sequence of bases in a nucleic acid molecule that is recognized by a recombinase (along with associated proteins, in some cases) that mediates exchange or excision of the nucleic acid segments flanking the recombination sites. The recombinases and associated proteins are collectively referred to as "recombination proteins" see, e.g., Landy, A., (Current Opinion in Genetics & Development) 3:699-707; 1993).

The term "phage expression vector" or "phagemid" refers to any phage-based recombinant expression system for the purpose of expressing a nucleic acid sequence of the methods and compositions as provided herein in vitro or in vivo, constitutively or inducibly, in any cell, including prokaryotic, yeast, fungal, plant, insect or mammalian cell. A phage expression vector typically can both reproduce in a bacterial cell and, under proper conditions, produce phage particles. The term includes linear or circular expression systems and encompasses both phage-based expression vectors that remain episomal or integrate into the host cell genome.

The term "episomal expression vector" as described herein refers to a nucleic acid vector which may be linear or circular, and which is usually double-stranded in form. In one embodiment, an episomal expression vector comprises a gene of interest. In another embodiment, the inserted gene of interest is not interrupted or subjected to regulatory constraints which often occur from integration into cellular DNA. In another embodiment, the presence of the inserted heterologous gene does not lead to rearrangement or interruption of the cell's own important regions. In another embodiment, episomal vectors persist in multiple copies in the bacterial cytoplasm, resulting in amplification of the gene of interest, and, in another embodiment, viral trans-acting factors are supplied when necessary. In another embodiment, in stable transfection procedures, the use of episomal vectors often results in higher transfection efficiency than the use of chromosome-integrating plasmids (Belt, P. B. G. M., et al (1991) Efficient cDNA cloning by direct phenotypic correction of a mutant human cell line (HPRT2) using an Epstein-Barr virus-derived cDNA expression vector. Nucleic Acids Res. 19, 4861-4866; Mazda, O., et al. (1997) Extremely efficient gene transfection into lympho-hematopoietic cell lines by Epstein-Barr virus-based vectors. J. Immunol. Methods 204, 143-151). In one embodiment, the episomal expression vectors of the methods and compositions as provided herein may be delivered to cells in vivo, ex vivo, or in vitro by any of a variety of the methods employed to deliver DNA molecules to cells. The vectors may also be delivered alone or in the form of a pharmaceutical composition that enhances delivery to cells of a subject.

The term "fused" refers to linkage by covalent bonding.

The term "Transforming," refers to engineering a bacterial cell to take up a plasmid or other heterologous DNA molecule. In another embodiment, "transforming" refers to engineering a bacterial cell to express a gene of a plasmid or other heterologous DNA molecule. Each possibility represents a separate embodiment of the methods and compositions as provided herein.

In another embodiment, conjugation is used to introduce genetic material and/or plasmids into bacteria. Methods for conjugation are well known in the art, and are described, for example, in Nikodinovic J et al (A second generation snp-derived *Escherichia coli-Streptomyces* shuttle expression vector that is generally transferable by conjugation. Plasmid. 2006 November; 56(3):223-7) and Auchtung J M et al (Regulation of a *Bacillus subtilis* mobile genetic element by intercellular signaling and the global DNA damage response. Proc Natl Acad Sci USA. 2005 Aug. 30; 102(35):12554-9). Each method represents a separate embodiment of the methods and compositions as provided herein.

In one embodiment, the expression vector comprising a nucleic acid molecule provided herein further comprises a second open reading frame encoding a metabolic enzyme. In another embodiment, the metabolic enzyme complements an endogenous gene that is lacking in the chromosome of the recombinant *Listeria* strain. In another embodiment, the metabolic enzyme encoded by the open reading frame is an alanine racemase enzyme (dal). In another embodiment, the metabolic enzyme encoded by the open reading frame is a D-amino acid transferase enzyme (dat). In another embodiment, the *Listeria* strains provided herein comprise a mutation in the endogenous dal/dat genes. In another embodiment, the *Listeria* lacks the dal/dat genes. In another embodiment, the *Listeria* lacks the dal/dat/and actA genes.

In another embodiment, a nucleic acid molecule of the methods and compositions of the present invention is operably linked to a promoter/regulatory sequence. In another embodiment, the nucleic acid sequence encoding PSA of methods and compositions of the present invention is operably linked to a promoter/regulatory sequence. In another embodiment, the second open reading frame of methods and compositions of the present invention is operably linked to a promoter/regulatory sequence. In another embodiment, each of the open reading frames are operably linked to a promoter/regulatory sequence. Each possibility represents a separate embodiment of the present invention.

The term "Metabolic enzyme" refers, in one embodiment, to an enzyme involved in synthesis of a nutrient required by the host bacteria. In another embodiment, the term refers to an enzyme required for synthesis of a nutrient required by the host bacteria. In another embodiment, the term refers to an enzyme involved in synthesis of a nutrient utilized by the host bacteria. In another embodiment, the term refers to an enzyme involved in synthesis of a nutrient required for sustained growth of the host bacteria. In another embodiment, the enzyme is required for synthesis of the nutrient. Each possibility represents a separate embodiment of the methods and compositions as provided herein.

In one embodiment, the PSA antigen used in the invention is associated with prostate cancer.

In one embodiment, strains as provided herein generate effector T cells that are able to infiltrate the tumor, destroy tumor cells and eradicate the disease. In one embodiment, naturally occurring tumor infiltrating lymphocytes (TILs) are associated with better prognosis in several tumors. Moreover, the infiltration of the tumor by T cells has been associated with success of immunotherapeutic approaches in both pre-clinical and human trials. In one embodiment, the infiltration of lymphocytes into the tumor site is dependent on the up-regulation of adhesion molecules in the endothelial cells of the tumor vasculature, generally by proinflammatory cytokines, such as IFN-γ, TNF-α and IL-1. Several adhesion molecules have been implicated in the process of lymphocyte infiltration into tumors, including intercellular adhesion molecule 1 (ICAM-1), vascular endothelial cell adhesion molecule 1 (V-CAM-1), vascular adhesion protein 1 (VAP-1) and E-selectin. However, these cell-adhesion molecules are commonly down-regulated in the tumor vasculature. Thus, in one embodiment, strains as provided herein increase TILs, up-regulate adhesion molecules (in one embodiment, ICAM-1, V-CAM-1, VAP-1, E-selectin, or a combination thereof), up-regulate pro-inflammatory cytokines (in one embodiment, IFN-γ, TNF-α, IL-1, or a combination thereof), or a combination thereof.

The attenuated *Listeria* strain of methods and compositions of the present invention is, in another embodiment, a attenuated *Listeria monocytogenes* strain. In another embodiment, the *Listeria* strain is a attenuated *Listeria seeligeri* strain. In another embodiment, the *Listeria* strain is a attenuated *Listeria grayi* strain. In another embodiment, the *Listeria* strain is a attenuated *Listeria ivanovii* strain. In another embodiment, the *Listeria* strain is a attenuated *Listeria murrayi* strain. In another embodiment, the *Listeria* strain is a attenuated *Listeria welshimeri* strain. In another embodiment, the *Listeria* strain is a attenuated strain of any other *Listeria* species known in the art. Each possibility represents a separate embodiment of the present invention.

In another embodiment, a recombinant *Listeria* strain of the present invention has been passaged through an animal host. In another embodiment, the passaging maximizes efficacy of the strain as a strain vector. In another embodiment, the passaging stabilizes the immunogenicity of the *Listeria* strain. In another embodiment, the passaging stabilizes the virulence of the *Listeria* strain. In another embodiment, the passaging increases the immunogenicity of the *Listeria* strain. In another embodiment, the passaging increases the virulence of the *Listeria* strain. In another embodiment, the passaging removes unstable sub-strains of the *Listeria* strain. In another embodiment, the passaging reduces the prevalence of unstable sub-strains of the *Listeria* strain. In another embodiment, the *Listeria* strain contains a genomic insertion of the gene encoding the antigen-containing recombinant peptide. In another embodiment, the *Listeria* strain carries a plasmid comprising the gene encoding the antigen-containing recombinant peptide. In another embodiment, the passaging is performed as described herein. In another embodiment, the passaging is performed by any other method known in the art. Each possibility represents a separate embodiment of the present invention.

It is understood that wherever embodiments are described herein with the language "comprising", otherwise analogous embodiments described in terms of "consisting of" and/or "consisting essentially of" are also provided.

Where aspects or embodiments of the invention are described in terms of a Markush group or other grouping of alternatives, the present invention encompasses not only the entire group listed as a whole, but each member of the group individually and all possible subgroups of the main group, but also the main group absent one or more of the group members. The present invention also envisages the explicit exclusion of one or more of any of the group members in the claimed invention.

Unless otherwise defined, all technical and scientific terms used herein have the same meaning as commonly understood by one of ordinary skill in the art to which this invention belongs. In case of conflict, the present specification, including definitions, will control. Throughout this specification and claims, the word "comprise," or variations such as "comprises" or "comprising" will be understood to imply the inclusion of a stated integer or group of integers but not the exclusion of any other integer or group of integers. Unless otherwise required by context, singular terms shall include pluralities and plural terms shall include the singular. Any example(s) following the term "e.g." or "for example" is not meant to be exhaustive or limiting.

Exemplary methods and materials are described herein, although methods and materials similar or equivalent to those described herein can also be used in the practice or testing of the present invention. The materials, methods, and examples are illustrative only and not intended to be limiting.

II. Methods, Uses And Medicaments

In one aspect of the invention, the invention provides a method for treating a cancer in an individual comprising administering to the individual a combination therapy which comprises a PD-1 antagonist and a live-attenuated bacterial strain that is used to stimulate APCs capable of driving a cellular immune response to PSA expressing cells. In another aspect of the invention, the invention provides a method for treating a cancer in an individual comprising administering to the individual a combination therapy which comprises a PD-1 antagonist and a live-attenuated *Listeria monocytogenes* strain bioengineered, by transforming it with an expression vector to express a PSA antigen fused to a tLLO. In yet another aspect of the invention, the invention provides a method for treating a cancer in an individual comprising administering to the individual a combination therapy which comprises a PD-1 antagonist and an LmddA-142 (10403S dal$^{(-)}$ dat$^{(-)}$ actA$^{(-)}$ pADV142) strain. In still another aspect of the invention, the invention provides a method for treating a cancer in an individual comprising administering to the individual a combination therapy which comprises a PD-1 antagonist and an LmddA-143 (10403S dal$^{(-)}$ dat$^{(-)}$ actA$^{(-)}$ with klk3 fused to the hly gene in the chromosome) strain.

The combination therapy may also comprise one or more additional therapeutic agents. The additional therapeutic agent may be, e.g., a chemotherapeutic, a biotherapeutic agent (including but not limited to antibodies to VEGF, VEGFR, EGFR, Her2/neu, other growth factor receptors, CD20, CD40, CD-40L, CTLA-4, OX-40, 4-1BB, and ICOS), an immunogenic agent (for example, attenuated cancerous cells, tumor antigens, antigen presenting cells such as dendritic cells pulsed with tumor derived antigen or nucleic acids, immune stimulating cytokines (for example, IL-2, IFNα2, GM-CSF), and cells transfected with genes encoding immune stimulating cytokines such as but not limited to GM-C SF).

Examples of chemotherapeutic agents include alkylating agents such as thiotepa and cyclophosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphoramide and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CBI-TMI); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as the enediyne antibiotics (e.g. calicheamicin, especially calicheamicin gamma1I and calicheamicin phiI1, see, e.g., Agnew, Chem. Intl. Ed. Engl., 33:183-186 (1994); dynemicin, including dynemicin A; bisphosphonates, such as clodronate; an esperamicin; as well as neocarzinostatin chromophore and related chromoprotein enediyne antibiotic chromomophores), aclacinomysins, actinomycin, authramycin, azaserine, bleomycins, cactinomycin, carabicin, caminomycin, carzinophilin, chromomycins, dactinomycin, daunorubicin, detorubicin, 6-diazo-5-oxo-L-norleucine, doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidamine; maytansinoids such as maytansine and ansamitocins; mitoguazone; mitoxantrone; mopidamol; nitracrine; pentostatin; phenamet; pirarubicin; losoxantrone; podophyllinic acid; 2-ethylhydrazide; procarbazine; razoxane; rhizoxin; sizofuran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g. paclitaxel and doxetaxel; chlorambucil; gemcitabine; 6-thioguanine; mercaptopurine; methotrexate; platinum analogs such as cisplatin and carboplatin; vinblastine; platinum; etoposide (VP-16); ifosfamide; mitoxantrone; vincristine; vinorelbine; novantrone; teniposide; edatrexate; daunomycin; aminopterin; xeloda; ibandronate; CPT-11; topoisomerase inhibitor RFS 2000; difluoromethylornithine (DMFO); retinoids such as retinoic acid; capecitabine; and pharmaceutically acceptable salts, acids or derivatives of any of the above. Also included are anti-hormonal agents that act to regulate or inhibit hormone action on tumors such as anti-estrogens and selective estrogen receptor modulators (SERMs), including, for example, tamoxifen, raloxifene, droloxifene, 4-hydroxytamoxifen, trioxifene, keoxifene, LY117018, onapristone, and toremifene (Fareston); aromatase inhibitors that inhibit the enzyme aromatase, which regulates estrogen production in the adrenal glands, such as, for example, 4(5)-imidazoles, aminoglutethimide, megestrol acetate, exemestane, formestane, fadrozole, vorozole, letrozole, and anastrozole; and anti-androgens such as flutamide, nilutamide, bicalutamide, leuprolide, and goserelin; and pharmaceutically acceptable salts, acids or derivatives of any of the above.

Each therapeutic agent in a combination therapy of the invention may be administered either alone or in a medicament (also referred to herein as a pharmaceutical composition) which comprises the therapeutic agent and one or more pharmaceutically acceptable carriers, excipients and diluents, according to standard pharmaceutical practice.

Each therapeutic agent in a combination therapy of the invention may be administered simultaneously (i.e., in the same medicament), concurrently (i.e., in separate medicaments administered one right after the other in any order) or sequentially in any order. Sequential administration is particularly useful when the therapeutic agents in the combination therapy are in different dosage forms (one agent is a tablet or capsule and another agent is a sterile liquid) and/or are administered on different dosing schedules, e.g., a chemotherapeutic that is administered at least daily and a biotherapeutic that is administered less frequently, such as once weekly, once every two weeks, or once every three weeks.

In another embodiment, administration of a combination therapy comprising Pembrolizumab (MK-3475) and a live-attenuated bacterial strain that is used to stimulate APCs capable of driving a cellular immune response to PSA expressing cells provides synergistic antitumor activity. In another embodiment, administration of a combination therapy comprising Pembrolizumab (MK-3475) and a live-attenuated Listeria monocytogenes strain bioengineered, by transforming it with an expression vector to express a PSA antigen fused to a tLLO provides synergistic antitumor activity. In another embodiment, administration of a combination therapy comprising Pembrolizumab (MK-3475) and an LmddA-142 (10403S dal$^{(-)}$ dat$^{(-)}$ actA$^{(-)}$ pADV142) strain provides synergistic antitumor activity. In another embodiment, administration of a combination therapy comprising Pembrolizumab (MK-3475) and an LmddA-143 (10403S dal$^{(-)}$ dat$^{(-)}$ actA$^{(-)}$ with klk3 fused to the hly gene in the chromosome) strain provides synergistic antitumor activity.

Dosage units for a PD-1 antagonist (e.g., MK-3475) may be expressed as a flat dose, i.e., 100 mg, 200 mg, 300 mg, or as a patient-specific dose, i.e., mg/kg (mg therapeutic agent/kg of body weight) or mg/m$^2$ (quantity in milligrams per square meter of body surface area).

In one embodiment, the dose of the attenuated Listeria strain comprised by the immunogenic composition provided herein is administered to a subject at a dose of $1 \times 10^7$-$3.31 \times 10^{10}$ CFU. In another embodiment, the dose is $1 \times 10^8$-$3.31 \times 10^{10}$ CFU. In another embodiment, the dose is $1 \times 10^9$-$3.31 \times 10^{10}$ CFU. In another embodiment, the dose is $5$-$500 \times 10^8$ CFU. In another embodiment, the dose is $7$-$500 \times 10^8$ CFU. In another embodiment, the dose is $10$-$500 \times 10^8$ CFU. In another embodiment, the dose is $20$-$500 \times 10^8$ CFU. In another embodiment, the dose is $30$-$500 \times 10^8$ CFU. In another embodiment, the dose is $50$-$500 \times 10^8$ CFU. In another embodiment, the dose is $70$-$500 \times 10^8$ CFU. In another embodiment, the dose is $100$-$500 \times 10^8$ CFU. In another embodiment, the dose is $150$-$500 \times 10^8$ CFU. In another embodiment, the dose is $5$-$300 \times 10^8$ CFU. In another embodiment, the dose is $5$-$200 \times 10^8$ CFU. In another embodiment, the dose is $5$-$150 \times 10^8$ CFU. In another embodiment, the dose is $5$-$100 \times 10^8$ CFU. In another embodiment, the dose is $5$-$70 \times 10^8$ CFU. In another embodiment, the dose is $5$-$50 \times 10^8$ CFU. In another embodiment, the dose is $5$-$30 \times 10^8$ CFU. In another embodiment, the dose is $5$-$20 \times 10^8$ CFU. In another embodiment, the dose is $1$-$30 \times 10^9$ CFU. In another embodiment, the dose is $1$-$20 \times 10^9$ CFU. In another embodiment, the dose is $2$-$30 \times 10^9$ CFU. In another embodiment, the dose is $1$-$10 \times 10^9$ CFU. In another embodiment, the dose is $2$-$10 \times 10^9$ CFU. In another embodiment, the dose is $3$-$10 \times 10^9$ CFU. In another embodiment, the dose is $2$-$7 \times 10^9$ CFU. In another embodiment, the dose is 2-5×10⁹ CFU. In another embodiment, the dose is 3-5×10⁹ CFU. In another embodiment, the dose is 0.5×10⁹ CFU. In another embodiment, the dose is 1×10⁹ CFU. In another embodiment, the dose is 5×10⁹ CFU. In another embodiment, the dose is 1×10¹⁰ CFU.

In another embodiment, the dose is 1×10⁷ organisms. In another embodiment, the dose is 1×10⁸ organisms. In another embodiment, the dose is 1×10⁹ organisms. In another embodiment, the dose is 1.5×10⁹ organisms. In another embodiment, the dose is 2×10⁹ organisms. In another embodiment, the dose is 3×10⁹ organisms. In another embodiment, the dose is 4×10⁹ organisms. In another embodiment, the dose is 5×10⁹ organisms. In another embodiment, the dose is 6×10⁹ organisms. In another embodiment, the dose is 7×10⁹ organisms. In another embodiment, the dose is 8×10⁹ organisms. In another embodiment, the dose is 10×10⁹ organisms. In another embodiment, the dose is 1.5×10¹⁰ organisms. In another embodiment, the dose is 2×10¹⁰ organisms. In another embodiment, the dose is 2.5×10¹⁰ organisms. In another embodiment, the dose is 3×10¹⁰ organisms. In another embodiment, the dose is 3.3×10¹⁰ organisms. In another embodiment, the dose is 4×10¹⁰ organisms. In another embodiment, the dose is 5×10¹⁰ organisms. Each dose and range of doses represents a separate embodiment of the present invention.

It will be appreciated by the skilled artisan that the term "Boosting" may encompass administering an additional strain or immunogenic composition or recombinant *Listeria* strain dose or immune checkpoint inhibitor alone or in combination to a subject. In another embodiment of methods of the present invention, 2 boosts (or a total of 3 inoculations) are administered. In another embodiment, 3 boosts are administered. In another embodiment, 4 boosts are administered. In another embodiment, 5 boosts are administered. In another embodiment, 6 boosts are administered. In another embodiment, more than 6 boosts are administered. Each possibility represents a separate embodiment of the present invention.

In another embodiment, a method of present invention further comprises the step of boosting the subject with a recombinant *Listeria* strain or immune checkpoint inhibitor as provided herein. In another embodiment, the recombinant *Listeria* strain used in the booster inoculation is the same as the strain used in the initial "priming" inoculation. In another embodiment, the booster strain is different from the priming strain. In another embodiment, the recombinant immune checkpoint inhibitor used in the booster inoculation is the same as the inhibitor used in the initial "priming" inoculation. In another embodiment, the booster inhibitor is different from the priming inhibitor. In another embodiment, the same doses are used in the priming and boosting inoculations. In another embodiment, a larger dose is used in the booster. In another embodiment, a smaller dose is used in the booster. In another embodiment, the methods of the present invention further comprise the step of administering to the subject a booster vaccination. In one embodiment, the booster vaccination follows a single priming vaccination. In another embodiment, a single booster vaccination is administered after the priming vaccinations. In another embodiment, two booster vaccinations are administered after the priming vaccinations. In another embodiment, three booster vaccinations are administered after the priming vaccinations. In one embodiment, the period between a prime and a boost strain is experimentally determined by the skilled artisan. In another embodiment, the period between a prime and a boost strain is 1 week, in another embodiment it is 2 weeks, in another embodiment, it is 3 weeks, in another embodiment, it is 4 weeks, in another embodiment, it is 5 weeks, in another embodiment it is 6-8 weeks, in yet another embodiment, the boost strain is administered 8-10 weeks after the prime strain.

In another embodiment, a method of the present invention further comprises boosting the subject with a immunogenic composition comprising an attenuated *Listeria* strain provided herein. In another embodiment, a method of the present invention comprises the step of administering a booster dose of the immunogenic composition comprising the attenuated *Listeria* strain provided herein. In another embodiment, the booster dose is an alternate form of said immunogenic composition. In another embodiment, the methods of the present invention further comprise the step of administering to the subject a booster immunogenic composition. In one embodiment, the booster dose follows a single priming dose of said immunogenic composition. In another embodiment, a single booster dose is administered after the priming dose. In another embodiment, two booster doses are administered after the priming dose. In another embodiment, three booster doses are administered after the priming dose. In one embodiment, the period between a prime and a boost dose of an immunogenic composition comprising the attenuated *Listeria* provided herein is experimentally determined by the skilled artisan. In another embodiment, the dose is experimentally determined by a skilled artisan. In another embodiment, the period between a prime and a boost dose is 1 week, in another embodiment it is 2 weeks, in another embodiment, it is 3 weeks, in another embodiment, it is 4 weeks, in another embodiment, it is 5 weeks, in another embodiment it is 6-8 weeks, in yet another embodiment, the boost dose is administered 8-10 weeks after the prime dose of the immunogenic composition.

Heterologous "prime boost" strategies have been effective for enhancing immune responses and protection against numerous pathogens. Schneider et al., Immunol. Rev. 170: 29-38 (1999); Robinson, H. L., Nat. Rev. Immunol. 2:239-50 (2002); Gonzalo, R. M. et al., Strain 20:1226-31 (2002); Tanghe, A., Infect. Immun 69:3041-7 (2001). Providing antigen in different forms in the prime and the boost injections appears to maximize the immune response to the antigen. DNA strain priming followed by boosting with protein in adjuvant or by viral vector delivery of DNA encoding antigen appears to be the most effective way of improving antigen specific antibody and CD4+T-cell responses or CD8+T-cell responses respectively. Shiver J. W. et al., Nature 415: 331-5 (2002); Gilbert, S. C. et al., Strain 20:1039-45 (2002); Billaut-Mulot, O. et al., Strain 19:95-102 (2000); Sin, J. I. et al., DNA Cell Biol. 18:771-9 (1999). Recent data from monkey vaccination studies suggests that adding CRL1005 poloxamer (12 kDa, 5% POE), to DNA encoding the HIV gag antigen enhances T-cell responses when monkeys are vaccinated with an HIV gag DNA prime followed by a boost with an adenoviral vector expressing HIV gag (Ad5-gag). The cellular immune responses for a DNA/poloxamer prime followed by an Ad5-gag boost were greater than the responses induced with a DNA (without poloxamer) prime followed by Ad5-gag boost or for Ad5-gag only. Shiver, J. W. et al. Nature 415:331-5 (2002). U.S. Patent Appl. Publication No. US 2002/0165172 A1 describes simultaneous administration of a vector construct encoding an immunogenic portion of an antigen and a protein comprising the immunogenic portion of an antigen such that an immune response is generated. The document is limited to hepatitis B antigens and HIV antigens. Moreover, U.S. Pat. No. 6,500,432 is directed to methods of enhancing an immune response of nucleic acid vaccination by simultaneous administration of a polynucleotide and polypeptide of interest. According to the patent, simultaneous administration means administration of the polynucleotide and the polypeptide during the same immune response, preferably within 0-10 or 3-7 days of each other. The antigens contemplated by the patent include, among others, those of Hepatitis (all forms), HSV, HIV, CMV, EBV, RSV, VZV, HPV, polio, influenza, parasites (e.g., from the genus *Plasmodium*), and pathogenic bacteria (including but not limited to *M. tuberculosis, M. leprae, Chlamydia, Shigella, B. burgdorferi*, enterotoxigenic *E. coli, S. typhosa, H. pylori, V. cholerae, B. pertussis*, etc.). All of the above references are herein incorporated by reference in their entireties.

In another embodiment, the recombinant polypeptide of methods of the present invention is expressed by the recombinant *Listeria* strain. In another embodiment, the expression is mediated by a nucleotide molecule carried by the recombinant *Listeria* strain. Each possibility represents a separate embodiment of the present invention.

As used herein, the term "recombinant *Listeria*" in some embodiments refers to an attenuated *Listeria* having all the same meanings and qualities described throughout.

In another embodiment, a composition comprising a strain of the present invention further comprises an adjuvant. In yet another embodiment, a strain of the present invention may be administered with an adjuvant. The adjuvant utilized in methods and compositions of the present invention is, in another embodiment, a granulocyte/macrophage colony-stimulating factor (GM-CSF) protein. In another embodiment, the adjuvant comprises a GM-CSF protein. In another embodiment, the adjuvant is a nucleotide molecule encoding GM-CSF. In another embodiment, the adjuvant comprises a nucleotide molecule encoding GM-CSF. In another embodiment, the adjuvant is saponin QS21. In another embodiment, the adjuvant comprises saponin QS21. In another embodiment, the adjuvant is monophosphoryl lipid A. In another embodiment, the adjuvant comprises monophosphoryl lipid A. In another embodiment, the adjuvant is SBAS2. In another embodiment, the adjuvant comprises SBAS2. In another embodiment, the adjuvant is an unmethylated CpG-containing oligonucleotide. In another embodiment, the adjuvant comprises an unmethylated CpG-containing oligonucleotide. In another embodiment, the adjuvant is an immune-stimulating cytokine. In another embodiment, the adjuvant comprises an immune-stimulating cytokine. In another embodiment, the adjuvant is a nucleotide molecule encoding an immune-stimulating cytokine. In another embodiment, the adjuvant comprises a nucleotide molecule encoding an immune-stimulating cytokine. In another embodiment, the adjuvant is or comprises a quill glycoside. In another embodiment, the adjuvant is or comprises a bacterial mitogen. In another embodiment, the adjuvant is or comprises a bacterial toxin. In another embodiment, the adjuvant is or comprises any other adjuvant known in the art. Each possibility represents a separate embodiment of the present invention.

In one embodiment, the method provided herein further comprises the step of co-administering with, prior to or following the administration of said recombinant *Listeria* strain an an immune checkpoint protein inhibitor. In one embodiment, an adjuvant is selected from the group comprising Montanide ISA 51, GM-CSF, KLH, a cytokine, a growth factor, a cell population, QS21, Freund's incomplete adjuvant, aluminum phosphate, aluminum hydroxide, BCG, alum, an interleukin, an unmethylated CpG oligonucleotide, quill glycosides, monophosphoryl lipid A, a liposome, a bacterial mitogen, a bacterial toxin, or a chemokine, or any combination thereof.

In some instances, the PD-1 antagonist and the live-attenuated bacterial strain that is used to stimulate APCs capable of driving a cellular immune response to PSA expressing cells are combined in a single dosage form. In some instances, the PD-1 antagonist and the live-attenuated *Listeria monocytogenes* strain bioengineered, by transforming it with an expression vector to express a PSA antigen fused to a tLLO are combined in a single dosage form. In some instances, the PD-1 antagonist and the an LmddA-142 (10403S dal$^{(-)}$ dat$^{(-)}$ actA$^{(-)}$ pADV142) strain are combined in a single dosage form. In some instances, the PD-1 antagonist and the LmddA-143 (10403S dal$^{(-)}$ dat$^{(-)}$ actA$^{(-)}$ with klk3 fused to the hly gene in the chromosome) strain are combined in a single dosage form.

Although the simultaneous administration of the PD-1 antagonist and the live-attenuated bacterial strain that is used to stimulate APCs capable of driving a cellular immune response to PSA expressing cells may be maintained throughout a period of treatment or prevention, anti-cancer activity may also be achieved by subsequent administration of one compound in isolation (for example, PD-1 antagonist without the live-attenuated bacterial strain that is used to stimulate APCs capable of driving a cellular immune response to PSA expressing cells, following combination treatment, or alternatively the live-attenuated bacterial strain that is used to stimulate APCs capable of driving a cellular immune response to PSA expressing cells, without PD-1 antagonist, following combination treatment). In addition, although the simultaneous administration of the PD-1 antagonist and the live-attenuated *Listeria monocytogenes* strain bioengineered, by transforming it with an expression vector to express a PSA antigen fused to a tLLO may be maintained throughout a period of treatment or prevention, anti-cancer activity may also be achieved by subsequent administration of one compound in isolation (for example, PD-1 antagonist without the live-attenuated *Listeria monocytogenes* strain bioengineered, by transforming it with an expression vector to express a PSA antigen fused to a tLLO, following combination treatment, or alternatively the live-attenuated *Listeria monocytogenes* strain bioengineered, by transforming it with an expression vector to express a PSA antigen fused to a tLLO, without PD-1 antagonist, following combination treatment). Further, although the simultaneous administration of the PD-1 antagonist and the LmddA-142 (10403S dal$^{(-)}$ dat$^{(-)}$ actA$^{(-)}$ pADV142) strain may be maintained throughout a period of treatment or prevention, anti-cancer activity may also be achieved by subsequent administration of one compound in isolation (for example, PD-1 antagonist without the LmddA-142 (10403S dal$^{(-)}$ dat$^{(-)}$ actA$^{(-)}$ pADV142) strain, following combination treatment, or alternatively the LmddA-142 (10403S dal$^{(-)}$ dat$^{(-)}$ actA$^{(-)}$ pADV142) strain, without PD-1 antagonist, following combination treatment). In addition, although the simultaneous administration of the PD-1 antagonist and the LmddA-143 (10403S dal$^{(-)}$ dat$^{(-)}$ actA$^{(-)}$ with klk3 fused to the hly gene in the chromosome) strain may be maintained throughout a period of treatment or prevention, anti-cancer activity may also be achieved by subsequent administration of one compound in isolation (for example, PD-1 antagonist without the LmddA-143 (10403S dal$^{(-)}$ dat$^{(-)}$ actA$^{(-)}$ with klk3 fused to the hly gene in the chromosome) strain, following combination treatment, or alternatively the LmddA-143 (10403S dal$^{(-)}$ dat$^{(-)}$ actA$^{(-)}$ with klk3 fused to the hly gene in the chromosome) strain, without PD-1 antagonist, following combination treatment).

In some embodiments, the live-attenuated bacterial strain that is used to stimulate APCs capable of driving a cellular immune response to PSA expressing cells or the live-attenuated *Listeria monocytogenes* strain bioengineered, by transforming it with an expression vector to express a PSA antigen fused to a tLLO or the LmddA-142 (10403S dal$^{(-)}$ dat$^{(-)}$ actA$^{(-)}$ pADV142) strain or the LmddA-143 (10403S dal$^{(-)}$ dat$^{(-)}$ actA$^{(-)}$ with klk3 fused to the hly gene in the chromosome) strain is administered before administration of the PD-1 antagonist, while in other embodiments, the live-attenuated bacterial strain that is used to stimulate APCs capable of driving a cellular immune response to PSA expressing cells or the live-attenuated *Listeria monocytogenes* strain bioengineered, by transforming it with an expression vector to express a PSA antigen fused to a tLLO or the LmddA-142 (10403S dal$^{(-)}$ dat$^{(-)}$ actA$^{(-)}$ pADV142) strain or the LmddA-143 (10403S dal$^{(-)}$ dat$^{(-)}$ actA$^{(-)}$ with klk3 fused to the hly gene in the chromosome) strain is administered after administration of the PD-1 antagonist. Each possibility represents a separate embodiment of the methods and compositions as provided herein.

In some embodiments, at least one of the therapeutic agents in the combination therapy is administered using the same dosage regimen (dose, frequency and duration of treatment) that is typically employed when the agent is used as monotherapy for treating the same cancer. In other embodiments, the patient receives a lower total amount of at least one of the therapeutic agents in the combination therapy than when the agent is used as monotherapy, e.g., smaller doses, less frequent doses, and/or shorter treatment duration.

A combination therapy of the invention may be used prior to or following surgery to remove a tumor and may be used prior to, during or after radiation therapy.

In some embodiments, a combination therapy of the invention is administered to a patient who has not been previously treated with a biotherapeutic or chemotherapeutic agent, i.e., is treatment-naïve. In other embodiments, the combination therapy is administered to a patient who failed to achieve a sustained response after prior therapy with a biotherapeutic or chemotherapeutic agent, i.e., is treatment-experienced. In certain embodiments, a combination therapy of the invention is administered to a patient with previously treated metastatic Castration-Resistant Prostate Cancer (mCRPC).

A combination therapy of the invention is typically used to treat a tumor that is large enough to be found by palpation or by imaging techniques well known in the art, such as MRI, ultrasound, or CAT scan. In some embodiments, a combination therapy of the invention is used to treat an advanced stage tumor having dimensions of at least about 200 mm$^3$, 300 mm$^3$, 400 mm$^3$, 500 mm$^3$, 750 mm$^3$, or up to 1000 mm$^3$.

A combination therapy of the invention is preferably administered to a patient diagnosed with a prostate cancer that tests positive for PD-L1 expression. In some embodiments, PD-L1 expression is detected using a diagnostic anti-human PD-L1 antibody, or antigen binding fragment thereof, in an IHC assay on an FFPE or frozen tissue section of a tumor sample removed from the patient. Typically, the patient's physician would order a diagnostic test to determine PD-L1 expression in a tumor tissue sample removed from the patient prior to initiation of treatment with the PD-1 antagonist and the live-attenuated bacterial strain that is used to stimulate APCs capable of driving a cellular immune response to PSA expressing cells or the live-attenuated *Listeria monocytogenes* strain bioengineered, by transforming it with an expression vector to express a PSA antigen fused to a tLLO or the LmddA-142 (10403S dal$^{(-)}$ dat$^{(-)}$ actA$^{(-)}$ pADV142) strain or the LmddmddA-143 (10403S dal$^{(-)}$ dat$^{(-)}$ actA$^{(-)}$ with klk3 fused to the hly gene in the chromosome) strain, but it is envisioned that the physician could order the first or subsequent diagnostic tests at any time after initiation of treatment, such as for example after completion of a treatment cycle. Each possibility represents a separate embodiment of the methods and compositions as provided herein.

In one embodiment, the dosage regimen is tailored to the particular patient's conditions, response and associate treatments, in a manner which is conventional for any therapy, and may need to be adjusted in response to changes in conditions and/or in light of other clinical conditions.

In some embodiments, selecting a dosage regimen (also referred to herein as an administration regimen) for a combination therapy of the invention depends on several factors, including the serum or tissue turnover rate of the entity, the level of symptoms, the immunogenicity of the entity, and the accessibility of the target cells, tissue or organ in the individual being treated. Preferably, a dosage regimen maximizes the amount of each therapeutic agent delivered to the patient consistent with an acceptable level of side effects. Accordingly, the dose amount and dosing frequency of each biotherapeutic and chemotherapeutic agent in the combination depends in part on the particular therapeutic agent, the severity of the cancer being treated, and patient characteristics. Guidance in selecting appropriate doses of antibodies, cytokines, and small molecules are available. See, e.g., Wawrzynczak (1996) *Antibody Therapy*, Bios Scientific Pub. Ltd, Oxfordshire, UK; Kresina (ed.) (1991) *Monoclonal Antibodies, Cytokines and Arthritis*, Marcel Dekker, New York, N.Y.; Bach (ed.) (1993) *Monoclonal Antibodies and Peptide Therapy in Autoimmune Diseases*, Marcel Dekker, New York, N.Y.; Baert et al. (2003) *New Engl. J. Med.* 348:601-608; Milgrom et al. (1999) *New Engl. J. Med.* 341:1966-1973; Slamon et al. (2001) *New Engl. J. Med.* 344:783-792; Beniaminovitz et al. (2000) *New Engl. J. Med.* 342:613-619; Ghosh et al. (2003) *New Engl. J. Med.* 348: 24-32; Lipsky et al. (2000) *New Engl. J. Med.* 343:1594-1602; Physicians' Desk Reference 2003 (Physicians' Desk Reference, 57th Ed); Medical Economics Company; ISBN: 1563634457; 57th edition (November 2002). Determination of the appropriate dosage regimen may be made by the clinician, e.g., using parameters or factors known or suspected in the art to affect treatment or predicted to affect treatment, and will depend, for example, the patient's clinical history (e.g., previous therapy), the type and stage of the cancer to be treated and biomarkers of response to one or more of the therapeutic agents in the combination therapy.

Biotherapeutic agents in a combination therapy of the invention may be administered by continuous infusion, or by doses at intervals of, e.g., daily, every other day, three times per week, or one time each week, two weeks, three weeks, monthly, bimonthly, etc. A total weekly dose is generally at least 0.05 µg/kg, 0.2 µg/kg, 0.5 µg/kg, 1 µg/kg, 10 µg/kg, 100 µg/kg, 0.2 mg/kg, 1.0 mg/kg, 2.0 mg/kg, 10 mg/kg, 25 mg/kg, 50 mg/kg body weight or more. See, e.g., Yang et al. (2003) *New Engl. J. Med.* 349:427-434; Herold et al. (2002) *New Engl. J. Med.* 346:1692-1698; Liu et al. (1999) *J. Neurol. Neurosurg. Psych.* 67:451-456; Portielji et al. (20003) *Cancer Immunol. Immunother.* 52:133-144.

In some embodiments that employ an anti-human PD-1 mAb as the PD-1 antagonist in the combination therapy, the dosing regimen will comprise administering the anti-human PD-1 mAb at a flat dose of 100 to 500 mg or a weight-based dose of 1 to 10 mg/kg at intervals of about 14 days (±2 days) or about 21 days (±2 days) or about 30 days (±2 days) throughout the course of treatment.

In other embodiments that employ an anti-human PD-1 mAb as the PD-1 antagonist in the combination therapy, the dosing regimen will comprise administering the anti-human PD-1 mAb at a dose of from about 0.005 mg/kg to about 10 mg/kg, with intra-patient dose escalation. In other escalating dose embodiments, the interval between doses will be progressively shortened, e.g., about 30 days (±2 days) between the first and second dose, about 14 days (±2 days) between the second and third doses. In certain embodiments, the dosing interval will be about 14 days (±2 days), for doses subsequent to the second dose.

In certain embodiments, a subject will be administered an intravenous (IV) infusion of a medicament comprising any of the PD-1 antagonists described herein.

In one embodiment of the invention, the PD-1 antagonist in the combination therapy is nivolumab, which is administered intravenously at a dose selected from the group consisting of: 1 mg/kg Q2W, 2 mg/kg Q2W, 3 mg/kg Q2W, 5 mg/kg Q2W, 10 mg Q2W, 1 mg/kg Q3W, 2 mg/kg Q3W, 3 mg/kg Q3W, 5 mg/kg Q3W, and 10 mg Q3W.

In another embodiment of the invention, the PD-1 antagonist in the combination therapy is MK-3475, which is administered in a liquid medicament at a dose selected from the group consisting of 200 mg Q3W, 1 mg/kg Q2W, 2 mg/kg Q2W, 3 mg/kg Q2W, 5 mg/kg Q2W, 10 mg Q2W, 1 mg/kg Q3W, 2 mg/kg Q3W, 3 mg/kg Q3W, 5 mg/kg Q3W, and 10 mg Q3W or equivalents of any of these doses (e.g., a PK model of MK-3475 estimates that the fixed dose of 200 mg Q3W provides exposures that are consistent with those obtained with 2 mg/kg Q3W). In some embodiments, MK-3475 is administered as a liquid medicament which comprises 25 mg/ml MK-3475, 7% (w/v) sucrose, 0.02% (w/v) polysorbate 80 in 10 mM histidine buffer pH 5.5, and the selected dose of the medicament is administered by IV infusion over a time period of 30 minutes+/−10 min.

In another embodiment of the invention, the attenuated bacterial or attenuated *Listeria* in the combination therapy is a live-attenuated bacterial strain that is used to stimulate APCs capable of driving a cellular immune response to PSA expressing cells or a live-attenuated *Listeria monocytogenes* strain bioengineered, by transforming it with an expression vector to express a PSA antigen fused to a tLLO or an LmddA-142 (10403S dal$^{(-)}$ dat$^{(-)}$ actA$^{(-)}$ pADV142) strain or an LmddA-143 (10403S dal$^{(-)}$ dat$^{(-)}$ actA$^{(-)}$ with klk3 fused to the hly gene in the chromosome) strain, which is administered in a liquid medicament at a dose selected from the group consisting of 0.5×10$^9$, 1×10$^9$, 5×10$^9$ and 1×10$^{10}$ cfu. In some embodiments, a dose is selected from the group consisting of 1×10$^9$-3.31×10$^{10}$ CFU, 5-500×10$^8$ CFU, 7-500×10$^8$ CFU, 10-500×10$^8$ CFU, 20-500×10$^8$ CFU, 30-500×10$^8$ CFU, 50-500×10$^8$ CFU, 70-500×10$^8$ CFU, 100-500×10$^8$ CFU, 150-500×10$^8$ CFU, 5-300×10$^8$ CFU, 5-200×10$^8$ CFU, 5-150×10$^8$ CFU, 5-100×10$^8$ CFU, 5-70×10$^8$ CFU, 5-50×10$^8$ CFU, 5-30×10$^8$ CFU, 5-20×10$^8$ CFU, 1-30×10$^9$ CFU, 1-20×10$^9$CFU, 2-30×10$^9$ CFU, 1-10×10$^9$ CFU, 2-10×10$^9$ CFU, 3-10×10$^9$ CFU, 2-7×10$^9$ CFU, 2-5×10$^9$ CFU, or 3-5×10$^9$ CFU. In another embodiment, the dose is 0.5×10$^9$ CFU. In another embodiment, the dose is 1×10$^9$ CFU. In another embodiment, the dose is 5×10$^9$ CFU. In another embodiment, the dose is 1×10$^{10}$ CFU.

In other embodiments, a dose is selected from the group consisting of 1×10$^9$ organisms, 1.5×10$^9$ organisms, 2×10$^9$ organisms, 3×10$^9$ organisms, 4×10$^9$ organisms, 5×10$^9$ organisms, 6×10$^9$ organisms, 7×10$^9$ organisms, 8×10$^9$ organisms, 10×10$^9$ organisms, 1.5×10$^{10}$ organisms, x 10$^{10}$ organisms, 2.5×10$^{10}$ organisms, 3×10$^{10}$ organisms, 0.3×10$^{10}$ organisms, 4×10$^{10}$ organisms or 5×10$^{10}$ organisms.

Each dose and range of doses represents a separate embodiment of the present invention.

In some embodiments, pharmaceutical compositions containing strains and compositions of the present invention area dministered to a subject by any method known to a person skilled in the art, such as parenterally, paracancerally, transmucosally, transdermally, intramuscularly, intravenously, intra-dermally, subcutaneously, intra-peritonealy, intra-ventricularly, intra-cranially, intra-vaginally or intra-tumorally.

In another embodiment of the methods and compositions provided herein, the strains or compositions are administered orally, and are thus formulated in a form suitable for oral administration, i.e. as a solid or a liquid preparation. Suitable solid oral formulations include tablets, capsules, pills, granules, pellets and the like. Suitable liquid oral formulations include solutions, suspensions, dispersions, emulsions, oils and the like. In another embodiment of the present invention, the active ingredient is formulated in a capsule. In accordance with this embodiment, the compositions of the present invention comprise, in addition to the active compound and the inert carrier or diluent, a hard gelating capsule.

In another embodiment, the strains or compositions are administered by intravenous, intra-arterial, or intra-muscular injection of a liquid preparation. Suitable liquid formulations include solutions, suspensions, dispersions, emulsions, oils and the like. In one embodiment, the pharmaceutical compositions are administered intravenously and are thus formulated in a form suitable for intravenous administration. In another embodiment, the pharmaceutical compositions are administered intra-arterially and are thus formulated in a form suitable for intra-arterial administration. In another embodiment, the pharmaceutical compositions are administered intra-muscularly and are thus formulated in a form suitable for intra-muscular administration.

In another embodiment, the vaccines or compositions are administered by intravenous, intra-arterial, or intra-muscular injection of a liquid preparation. Suitable liquid formulations include solutions, suspensions, dispersions, emulsions, oils and the like. In one embodiment, the pharmaceutical compositions are administered intravenously and are thus formulated in a form suitable for intravenous administration. In another embodiment, the pharmaceutical compositions are administered intra-arterially and are thus formulated in a form suitable for intra-arterial administration. In another embodiment, the pharmaceutical compositions are administered intra-muscularly and are thus formulated in a form suitable for intra-muscular administration.

In one embodiment, the vaccines of the methods and compositions as provided herein may be administered to a host vertebrate animal, preferably a mammal, and more preferably a human, either alone or in combination with a pharmaceutically acceptable carrier. In another embodiment, the vaccine is administered in an amount effective to induce an immune response to the *Listeria* strain itself or to a heterologous antigen which the *Listeria* species has been modified to express. In another embodiment, the amount of vaccine or immunogenic composition to be administered may be routinely determined by one of skill in the art when in possession of the present disclosure. In another embodiment, a pharmaceutically acceptable carrier may include, but is not limited to, sterile distilled water, saline, phosphate buffered solutions or bicarbonate buffered solutions. In another embodiment, the pharmaceutically acceptable carrier selected and the amount of carrier to be used will depend upon several factors including the mode of administration, the strain of *Listeria* and the age and disease state of the vaccinee. In another embodiment, administration of the vaccine may be by an oral route, or it may be parenteral, intranasal, intramuscular, intravascular, intrarectal, intraperitoneal, or any one of a variety of well-known routes of administration. In another embodiment, the route of administration may be selected in accordance with the type of infectious agent or tumor to be treated.

In another embodiment, the present invention provides a method of treating, suppressing, or inhibiting at least one tumor in a subject comprising administering the immunogenic composition provided herein.

In some embodiments an attenuated bacteria, or attenuated *Listeria*, or LmddA-142 or LmddA-143 is administered as a liquid medicament, and the selected dose of the medicament is administered by IV infusion over a time period of 30 minutes+/−10 min.

The optimal dose for MK-3475 in combination with a live-attenuated bacterial strain that is used to stimulate APCs capable of driving a cellular immune response to PSA expressing cells or a live-attenuated *Listeria monocytogenes* strain bioengineered, by transforming it with an expression vector to express a PSA antigen fused to a tLLO or an LmddA-142 (10403S dal$^{(-)}$ dat$^{(-)}$ actA$^{(-)}$ pADV142) strain or an LmddA-143 (10403S dal$^{(-)}$ dat$^{(-)}$ actA$^{(-)}$ with klk3 fused to the hly gene in the chromosome) strain may be identified by dose escalation of one or both of these agents.

In one embodiment, the patient is treated with the combination therapy on day 1 of weeks 1, 4 and 7 in a 12 week cycle, with MK-3475 administered at a starting dose of 200 mg and a live-attenuated bacterial strain that is used to stimulate APCs capable of driving a cellular immune response to PSA expressing cells or a live-attenuated *Listeria monocytogenes* strain bioengineered, by transforming it with an expression vector to express a PSA antigen fused to a tLLO or an LmddA-142 (10403S dal$^{(-)}$ dat$^{(-)}$ actA$^{(-)}$ pADV142) strain or an LmddA-143 (10403S dal$^{(-)}$ dat$^{(-)}$ actA$^{(-)}$ with klk3 fused to the hly gene in the chromosome) strain administered at a starting dose of $1 \times 10^9$ cfu. In another embodiment, the live-attenuated bacterial strain that is used to stimulate APCs capable of driving a cellular immune response to PSA expressing cells or a live-attenuated *Listeria monocytogenes* strain bioengineered, by transforming it with an expression vector to express a PSA antigen fused to a tLLO or an LmddA-142 (10403S dal$^{(-)}$ dat$^{(-)}$ actA$^{(-)}$ pADV142) strain or an LmddA-143 (10403S dal$^{(-)}$ dat$^{(-)}$ actA$^{(-)}$ with klk3 fused to the hly gene in the chromosome) strain is administered at a starting dose of $0.5 \times 10^9$ CFU. In another embodiment, the live-attenuated bacterial strain that is used to stimulate APCs capable of driving a cellular immune response to PSA expressing cells or a live-attenuated *Listeria monocytogenes* strain bioengineered, by transforming it with an expression vector to express a PSA antigen fused to a tLLO or an LmddA-142 (10403S dal$^{(-)}$ dat$^{(-)}$ actA$^{(-)}$ pADV142) strain or an LmddA-143 (10403S dal$^{(-)}$ dat$^{(-)}$ actA$^{(-)}$ with klk3 fused to the hly gene in the chromosome) strain administered at a starting dose of $5 \times 10^9$ CFU. In another embodiment, the live-attenuated bacterial strain that is used to stimulate APCs capable of driving a cellular immune response to PSA expressing cells or a live-attenuated *Listeria monocytogenes* strain bioengineered, by transforming it with an expression vector to express a PSA antigen fused to a tLLO or an LmddA-142 (10403S dal$^{(-)}$ dat$^{(-)}$ actA$^{(-)}$ pADV142) strain or an LmddA-143 (10403S dal$^{(-)}$ dat$^{(-)}$ actA$^{(-)}$ with klk3 fused to the hly gene in the chromosome) strain is administered at a starting dose of $1 \times 10^{10}$ CFU.

In one embodiment, the patient is treated with the combination therapy, wherein MK-3475 is administered on Day 1 Q3W of a 12-week cycle at a starting dose of 200 mg, and a live-attenuated bacterial strain that is used to stimulate APCs capable of driving a cellular immune response to PSA expressing cells or a live-attenuated *Listeria monocytogenes* strain bioengineered, by transforming it with an expression vector to express a PSA antigen fused to a tLLO or an LmddA-142 (10403S dal$^{(-)}$ dat$^{(-)}$ actA$^{(-)}$ pADV142) strain or an LmddA-143 (10403S dal$^{(-)}$ dat$^{(-)}$ actA$^{(-)}$ with klk3 fused to the hly gene in the chromosome) strain is administered on Day 1 of Weeks 1, 4, and 7 of the 12-week cycle at a starting dose of $1 \times 10^9$ cfu. In another embodiment, the live-attenuated bacterial strain that is used to stimulate APCs capable of driving a cellular immune response to PSA expressing cells or a live-attenuated *Listeria monocytogenes* strain bioengineered, by transforming it with an expression vector to express a PSA antigen fused to a tLLO or an LmddA-142 (10403S dal$^{(-)}$ dat$^{(-)}$ actA$^{(-)}$ pADV142) strain or an LmddA-143 (10403S dal$^{(-)}$ dat$^{(-)}$ actA$^{(-)}$ with klk3 fused to the hly gene in the chromosome) strain is administered at a starting dose of $0.5 \times 10^9$ CFU. In another embodiment, the live-attenuated bacterial strain that is used to stimulate APCs capable of driving a cellular immune response to PSA expressing cells or a live-attenuated *Listeria monocytogenes* strain bioengineered, by transforming it with an expression vector to express a PSA antigen fused to a tLLO or an LmddA-142 (10403S dal$^{(-)}$ dat$^{(-)}$ actA$^{(-)}$ pADV142) strain or an LmddA-143 (10403S dal$^{(-)}$ dat$^{(-)}$ actA$^{(-)}$ with klk3 fused to the hly gene in the chromosome) strain administered at a starting dose of $5 \times 10^9$ CFU. In another embodiment, the live-attenuated bacterial strain that is used to stimulate APCs capable of driving a cellular immune response to PSA expressing cells or a live-attenuated *Listeria monocytogenes* strain bioengineered, by transforming it with an expression vector to express a PSA antigen fused to a tLLO or an LmddA-142 (10403S dal$^{(-)}$ dat$^{(-)}$ actA$^{(-)}$ pADV142) strain or an LmddA-143 (10403S dal$^{(-)}$ dat$^{(-)}$ actA$^{(-)}$ with klk3 fused to the hly gene in the chromosome) strain is administered at a starting dose of $1 \times 10^{10}$ CFU. In another embodiment, administration is administered up to 3 days before or 3 days after the scheduled Day 1 of each cycle.

In one embodiment, the patient is treated with the combination therapy, wherein MK-3475 is administered on Day 1 of week 1, 4, 7 and 10 of a 12-week cycle at a starting dose of 200 mg, and a live-attenuated bacterial strain that is used to stimulate APCs capable of driving a cellular immune response to PSA expressing cells or a live-attenuated *Listeria monocytogenes* strain bioengineered, by transforming it with an expression vector to express a PSA antigen fused to a tLLO or an LmddA-142 (10403S dal$^{(-)}$ dat$^{(-)}$ actA$^{(-)}$ pADV142) strain or an LmddA-143 (10403S dal$^{(-)}$ dat$^{(-)}$ actA$^{(-)}$ with klk3 fused to the hly gene in the chromosome) strain is administered on Day 1 of Weeks 1, 4, and 7 of the 12-week cycle at a starting dose of $1 \times 10^9$ cfu. In another embodiment, the live-attenuated bacterial strain that is used to stimulate APCs capable of driving a cellular immune response to PSA expressing cells or a live-attenuated *Listeria monocytogenes* strain bioengineered, by transforming it with an expression vector to express a PSA antigen fused to a tLLO or an LmddA-142 (10403S dal$^{(-)}$ dat$^{(-)}$ actA$^{(-)}$ pADV142) strain or an LmddA-143 (10403S dal$^{(-)}$ dat$^{(-)}$ actA$^{(-)}$ with klk3 fused to the hly gene in the chromosome) strain is administered at a starting dose of 0.5×10$^9$ CFU. In another embodiment, the live-attenuated bacterial strain that is used to stimulate APCs capable of driving a cellular immune response to PSA expressing cells or a live-attenuated *Listeria monocytogenes* strain bioengineered, by transforming it with an expression vector to express a PSA antigen fused to a tLLO or an LmddA-142 (10403S dal$^{(-)}$ dat$^{(-)}$ actA$^{(-)}$ pADV142) strain or an LmddA-143 (10403S dal$^{(-)}$ dat$^{(-)}$ actA$^{(-)}$ with klk3 fused to the hly gene in the chromosome) strain administered at a starting dose of 5×10$^9$ CFU. In another embodiment, the live-attenuated bacterial strain that is used to stimulate APCs capable of driving a cellular immune response to PSA expressing cells or a live-attenuated *Listeria monocytogenes* strain bioengineered, by transforming it with an expression vector to express a PSA antigen fused to a tLLO or an LmddA-142 (10403S dal$^{(-)}$ dat$^{(-)}$ actA$^{(-)}$ pADV142) strain or an LmddA-143 (10403S dal$^{(-)}$ dat$^{(-)}$ actA$^{(-)}$ with klk3 fused to the hly gene in the chromosome) strain is administered at a starting dose of 1×10$^{10}$ CFU. In another embodiment, administration is administered up to 3 days before or 3 days after the scheduled Day 1 of each cycle.

In an embodiment, the MK-3475 infusion is administered first, followed by a NSAIDS, e.g., naproxen or ibuprofen, and oral antiemetic medication within 30 minutes prior to the live-attenuated bacterial strain that is used to stimulate APCs capable of driving a cellular immune response to PSA expressing cells or the live-attenuated *Listeria monocytogenes* strain bioengineered, by transforming it with an expression vector to express a PSA antigen fused to a tLLO or the LmddA-142 (10403S dal$^{(-)}$ dat$^{(-)}$ actA$^{(-)}$ pADV142) strain or the LmddA-143 (10403S dal$^{(-)}$ dat$^{(-)}$ actA$^{(-)}$ with klk3 fused to the hly gene in the chromosome) strain infusion.

In another embodiment, MK-3475 is administered at a starting dose of 200 mg Q3W and a live-attenuated bacterial strain that is used to stimulate APCs capable of driving a cellular immune response to PSA expressing cells or a live-attenuated *Listeria monocytogenes* strain bioengineered, by transforming it with an expression vector to express a PSA antigen fused to a tLLO or an LmddA-142 (10403S dal$^{(-)}$ dat$^{(-)}$ actA$^{(-)}$ pADV142) strain or an LmddA-143 (10403S dal$^{(-)}$ dat$^{(-)}$ actA$^{(-)}$ with klk3 fused to the hly gene in the chromosome) strain is administered Q3W at a starting dose of between 1×10$^9$ and 1×10$^{10}$ cfu. In another embodiment, MK-3475 is administered at a starting dose of 200 mg Q3W and a live-attenuated bacterial strain that is used to stimulate APCs capable of driving a cellular immune response to PSA expressing cells or a live-attenuated *Listeria monocytogenes* strain bioengineered, by transforming it with an expression vector to express a PSA antigen fused to a tLLO or an LmddA-142 (10403S dal$^{(-)}$ dat$^{(-)}$ actA$^{(-)}$ pADV142) strain or an LmddA-143 (10403S dal$^{(-)}$ dat$^{(-)}$ actA$^{(-)}$ with klk3 fused to the hly gene in the chromosome) strain is administered Q3W at a starting dose of between 0.5×10$^9$ and 1×10$^{10}$ cfu.

In yet another embodiment, a live-attenuated bacterial strain that is used to stimulate APCs capable of driving a cellular immune response to PSA expressing cells or a live-attenuated *Listeria monocytogenes* strain bioengineered, by transforming it with an expression vector to express a PSA antigen fused to a tLLO or an LmddA-142 (10403S dal$^{(-)}$ dat$^{(-)}$ actA$^{(-)}$ pADV142) strain or an LmddA-143 (10403S dal$^{(-)}$ dat$^{(-)}$ actA$^{(-)}$ with klk3 fused to the hly gene in the chromosome) strain is administered at a starting dose of 5×10$^9$ Q3W and MK-3475 is administered at a starting dose of 200 mg Q3W, and if the starting dose of the combination is not tolerated by the patient, then the dose of a live-attenuated bacterial strain that is used to stimulate APCs capable of driving a cellular immune response to PSA expressing cells or a live-attenuated *Listeria monocytogenes* strain bioengineered, by transforming it with an expression vector to express a PSA antigen fused to a tLLO or an LmddA-142 (10403S dal$^{(-)}$ dat$^{(-)}$ actA$^{(-)}$ pADV142) strain or an LmddA-143 (10403S dal$^{(-)}$ dat$^{(-)}$ actA$^{(-)}$ with klk3 fused to the hly gene in the chromosome) strain is reduced to 1×10$^9$ cfu Q3W.

In some embodiments, dosage levels below the lower limit of the aforesaid range may be more than adequate, while in other cases still larger doses may be employed, as determined by those skilled in the art.

In some embodiments, a treatment cycle begins with the first day of combination treatment and lasts for at least 12 weeks, 24 weeks or 48 weeks. On any day of a treatment cycle that the drugs are co-administered, the timing between the separate IV infusions of MK-3475 and a live-attenuated bacterial strain that is used to stimulate APCs capable of driving a cellular immune response to PSA expressing cells or a live-attenuated *Listeria monocytogenes* strain bioengineered, by transforming it with an expression vector to express a PSA antigen fused to a tLLO or an LmddA-142 (10403S dal$^{(-)}$ dat$^{(-)}$ actA$^{(-)}$ pADV142) strain or an LmddA-143 (10403S dal$^{(-)}$ dat$^{(-)}$ actA$^{(-)}$ with klk3 fused to the hly gene in the chromosome) strain is between about 15 minutes to about 45 minutes. The invention contemplates that MK-3475 and a live-attenuated bacterial strain that is used to stimulate APCs capable of driving a cellular immune response to PSA expressing cells or a live-attenuated *Listeria monocytogenes* strain bioengineered, by transforming it with an expression vector to express a PSA antigen fused to a tLLO or an LmddA-142 (10403S dal$^{(-)}$ dat$^{(-)}$ actA$^{(-)}$ pADV142) strain or an LmddA-143 (10403S dal$^{(-)}$ dat$^{(-)}$ actA$^{(-)}$ with klk3 fused to the hly gene in the chromosome) strain may be administered in either order or by simultaneous IV infusion.

In some embodiments, the combination therapy is administered for at least 2 to 4 weeks after the patient achieves a CR.

In some embodiments, the patient selected for treatment with the combination therapy of the invention has been diagnosed with a metastatic prostate cancer and the patient has progressed or become resistant to no more than 3 prior systemic treatment regimens.

In an embodiment, the patient selected for treatment with the combination therapy of the invention had a serum PSA level ≥5 ng/mL within 1 week prior to starting the combination therapy.

In another embodiment, the patient selected for treatment with the combination therapy of the invention had a rising PSA level within the 4 weeks prior to starting the combination therapy.

The present invention also provides a medicament which comprises a PD-1 antagonist as described above and a pharmaceutically acceptable excipient. When the PD-1 antagonist is a biotherapeutic agent, e.g., a mAb, the antagonist may be produced in CHO cells using conventional cell culture and recovery/purification technologies.

In some embodiments, a medicament comprising an anti-PD-1 antibody as the PD-1 antagonist may be provided as a liquid formulation or prepared by reconstituting a lyophilized powder with sterile water for injection prior to use. WO 2012/135408 describes the preparation of liquid and lyophilized medicaments comprising MK-3475 that are suitable for use in the present invention. In some embodiments, a medicament comprising MK-3475 is provided in a glass vial which contains about 50 mg of MK-3475.

The present invention also provides a medicament which comprises a live-attenuated bacterial strain that is used to stimulate APCs capable of driving a cellular immune response to PSA expressing cells or a live-attenuated *Listeria monocytogenes* strain bioengineered, by transforming it with an expression vector to express a PSA antigen fused to a tLLO or an LmddA-142 (10403S dal$^{(-)}$ dat$^{(-)}$ actA$^{(-)}$ pADV142) strain or an LmddA-143 (10403S dal$^{(-)}$ dat$^{(-)}$ actA$^{(-)}$ with klk3 fused to the hly gene in the chromosome) strain and a pharmaceutically acceptable excipient. A live-attenuated bacterial strain that is used to stimulate APCs capable of driving a cellular immune response to PSA expressing cells or a live-attenuated *Listeria monocytogenes* strain bioengineered, by transforming it with an expression vector to express a PSA antigen fused to a tLLO or an LmddA-142 (10403S dal$^{(-)}$ dat$^{(-)}$ actA$^{(-)}$ pADV142) strain or an LmddA-143 (10403S dal$^{(-)}$ dat$^{(-)}$ actA$^{(-)}$ with klk3 fused to the hly gene in the chromosome) strain may be prepared as described in Wallecha et al. CLINICAL AND-STRAINIMMUNOLOGY, January 2009, p. 96-103.

The PD-1 antagonist medicament and the a live-attenuated bacterial strain that is used to stimulate APCs capable of driving a cellular immune response to PSA expressing cells or a live-attenuated *Listeria monocytogenes* strain bioengineered, by transforming it with an expression vector to express a PSA antigen fused to a tLLO or an LmddA-142 (10403S dal$^{(-)}$ dat$^{(-)}$ actA$^{(-)}$ pADV142) strain or an LmddA-143 (10403S dal$^{(-)}$ dat$^{(-)}$ actA$^{(-)}$ with klk3 fused to the hly gene in the chromosome) strain medicament may be provided as a kit which comprises a first container and a second containiner and a package insert. The first container contains at least one dose of a medicament comprising an anti-PD-1 antibody, the second container contains at least one dose of a medicament comprising a live-attenuated bacterial strain that is used to stimulate APCs capable of driving a cellular immune response to PSA expressing cells or a live-attenuated *Listeria monocytogenes* strain bioengineered, by transforming it with an expression vector to express a PSA antigen fused to a tLLO or an LmddA-142 (10403S dal$^{(-)}$ dat$^{(-)}$ actA$^{(-)}$ pADV142) strain or an LmddA-143 (10403S dal$^{(-)}$ dat$^{(-)}$ actA$^{(-)}$ with klk3 fused to the hly gene in the chromosome) strain, and the package insert, or label, which comprises instructions for treating a patient for a prostate cancer using the medicaments. The first and second containers may be comprised of the same or different shape (e.g., vials, syringes and bottles) and/or material (e.g., plastic or glass). The kit may further comprise other materials that may be useful in administering the medicaments, such as diluents, filters, IV bags and lines, needles and syringes. In some embodiments of the kit, the anti-PD-1 antagonist is an anti-PD-1 antibody and the instructions state that the medicaments are intended for use in treating a patient having a prostate cancer that tests positive for PD-L1 expression by an IHC assay.

These and other aspects of the invention, including the exemplary specific embodiments listed below, will be apparent from the teachings contained herein.

Exemplary Specific Embodiments of the Invention

1. A method for treating a prostate cancer in a patient comprising administering to the individual a combination therapy which comprises a PD-1 antagonist and a live-attenuated bacterial strain that is used to stimulate APCs capable of driving a cellular immune response to PSA expressing cells or a live-attenuated *Listeria monocytogenes* strain bioengineered, by transforming it with an expression vector to express a PSA antigen fused to a tLLO or an LmddA-142 (10403S dal$^{(-)}$ dat$^{(-)}$ actA$^{(-)}$ pADV142) strain or an LmddA-143 (10403S dal$^{(-)}$ dat$^{(-)}$ actA$^{(-)}$ with klk3 fused to the hly gene in the chromosome) strain. Each possibility represents a separate embodiment as provided herein.

2. A medicament comprising a PD-1 antagonist for use in combination with a live-attenuated bacterial strain that is used to stimulate APCs capable of driving a cellular immune response to PSA expressing cells or a live-attenuated *Listeria monocytogenes* strain bioengineered, by transforming it with an expression vector to express a PSA antigen fused to a tLLO or an LmddA-142 (10403S dal$^{(-)}$ dat$^{(-)}$ actA$^{(-)}$ pADV142) strain or an LmddA-143 (10403S dal$^{(-)}$ dat$^{(-)}$ actA$^{(-)}$ with klk3 fused to the hly gene in the chromosome) strain for treating a prostate cancer in a patient. Each possibility represents a separate embodiment as provided herein.

3. A medicament comprising a live-attenuated bacterial strain that is used to stimulate APCs capable of driving a cellular immune response to PSA expressing cells or a live-attenuated *Listeria monocytogenes* strain bioengineered, by transforming it with an expression vector to express a PSA antigen fused to a tLLO or an LmddA-142 (10403S dal$^{(-)}$ dat$^{(-)}$ actA$^{(-)}$ pADV142) strain or an LmddA-143 (10403S dal$^{(-)}$ dat$^{(-)}$ actA$^{(-)}$ with klk3 fused to the hly gene in the chromosome) strain for use in combination with a PD-1 antagonist for treating a prostate cancer in a patient. Each possibility represents a separate embodiment as provided herein.

4. The medicament of embodiment 3 or 4, which further comprises a pharmaceutically acceptable excipient or adjuvant, or a combination thereof.

5. Use of a PD-1 antagonist in the manufacture of medicament for treating a prostate cancer in a patient when administered in combination with a live-attenuated bacterial strain that is used to stimulate APCs capable of driving a cellular immune response to PSA expressing cells or a live-attenuated *Listeria monocytogenes* strain bioengineered, by transforming it with an expression vector to express a PSA antigen fused to a tLLO or an LmddA-142 (10403S dal$^{(-)}$ dat$^{(-)}$ actA$^{(-)}$ pADV142) strain or an LmddA-143 (10403S dal$^{(-)}$ dat$^{(-)}$ actA$^{(-)}$ with klk3 fused to the hly gene in the chromosome) strain. Each possibility represents a separate embodiment as provided herein.

6. Use of a live-attenuated bacterial strain that is used to stimulate APCs capable of driving a cellular immune response to PSA expressing cells or a live-attenuated *Listeria monocytogenes* strain bioengineered, by transforming it with an expression vector to express a PSA antigen fused to a tLLO or an LmddA-142 (10403S dal$^{(-)}$ dat$^{(-)}$ actA$^{(-)}$ pADV142) strain or an LmddA-143 (10403S dal$^{(-)}$ dat$^{(-)}$ actA$^{(-)}$ with klk3 fused to the hly gene in the chromosome) strain in the manufacture of a medicament for treating a prostate cancer in a patient when administered in combination with a PD-1 antagonist. Each possibility represents a separate embodiment as provided herein.

7. Use of a PD-1 antagonist and a live-attenuated bacterial strain that is used to stimulate APCs capable of driving a cellular immune response to PSA expressing cells or a live-attenuated *Listeria monocytogenes* strain bioengineered, by transforming it with an expression vector to express a PSA antigen fused to a tLLO or an LmddA-142 (10403S dal$^{(-)}$ dat$^{(-)}$ actA$^{(-)}$ pADV142) strain or an LmddA-143 (10403S dal$^{(-)}$ dat$^{(-)}$ actA$^{(-)}$ with klk3 fused to the hly gene in the chromosome) strain in the manufacture of medicaments for treating a cancer in a patient. Each possibility represents a separate embodiment as provided herein.

8. A kit which comprises a first container, a second container and a package insert, wherein the first container comprises at least one dose of a medicament comprising an anti-PD-1 antagonist, the second container comprises at least one dose of a medicament comprising a live-attenuated bacterial strain that is used to stimulate APCs capable of driving a cellular immune response to PSA expressing cells or a live-attenuated *Listeria monocytogenes* strain bioengineered, by transforming it with an expression vector to express a PSA antigen fused to a tLLO or an LmddA-142 (10403S dal$^{(-)}$ dat$^{(-)}$ actA$^{(-)}$ pADV142) strain or an LmddA-143 (10403S dal$^{(-)}$ dat$^{(-)}$ actA$^{(-)}$ with klk3 fused to the hly gene in the chromosome) strain, and the package insert comprises instructions for treating a patient for prostate cancer using the medicaments. Each possibility represents a separate embodiment as provided herein.

9. The kit of embodiment 8, wherein the instructions state that the medicaments are intended for use in treating a patient having a prostate cancer that tests positive for PD-L1 expression by an immunohistochemical (IHC) assay.

10. The method, medicament, use or kit of any of embodiments 1 to 9, wherein the PD-1 antagonist is a monoclonal antibody, or antigen binding fragment thereof.

11. The method, medicament, use or kit of embodiment 9, wherein the PD-1 antagonist is MPDL3280A, BMS-936559, MEDI4736, MSB0010718C or a monoclonal antibody which comprises the heavy chain and light chain variable regions of SEQ ID NO:24 and SEQ ID NO:21, respectively, of WO2013/019906.

12. The method, medicament, use or kit of embodiment 10, wherein the PD-1 antagonist is a monoclonal antibody, or antigen binding fragment thereof, and blocks binding of PD-L1 and PD-L2 to PD-1.

13. The method, medicament, use or kit of embodiment 12, wherein the monoclonal antibody, or antigen binding fragment thereof, comprises: (a) light chain CDRs of SEQ ID NOs: 1, 2 and 3 and heavy chain CDRs of SEQ ID NOs: 4, 5 and 6; or (b) light chain CDRs of SEQ ID NOs: 7, 8 and 9 and heavy chain CDRs of SEQ ID NOs: 10, 11 and 12.

14. The method, medicament, use or kit of embodiment 12, wherein the monoclonal antibody, or antigen binding fragment thereof, comprises light chain CDRs of SEQ ID NOs: 7, 8 and 9 and heavy chain CDRs of SEQ ID NOs: 10, 11 and 12.

15. The method, medicament, use or kit of embodiment 12, wherein the PD-1 antagonist is an anti-PD-1 monoclonal antibody which comprises a heavy chain and a light chain, and wherein the heavy chain comprises SEQ ID NO:21 and the light chain comprises SEQ ID NO:22.

16. The method, medicament, use or kit of embodiment 12, wherein the PD-1 antagonist is an anti-PD-1 monoclonal antibody which comprises a heavy chain and a light chain, and wherein the heavy chain comprises SEQ ID NO:23 and the light chain comprises SEQ ID NO:24.

17. The method, medicament, use or kit of any of embodiments 10-16, wherein the prostate cancer is metastatic.

18. The method, medicament, use or kit of embodiment 17, wherein the cancer is metastatic Castration-resistant Prostate Cancer (mCRPC).

19. The method, medicament, use or kit of any of embodiments 10-18, wherein the patient has not been previously treated for prostate cancer.

20. The method, medicament, use or kit of any of embodiments 10-18, wherein the patient has previously been treated for prostate cancer.

21. The method, medicament, use or kit of any of embodiments 10-20, wherein the prostate cancer tests positive for PD-L1.

22. The method, medicament, use or kit of embodiment 21, wherein the PD-L1 expression is elevated.

23. The method, medicament, use or kit of embodiment 12, wherein the PD-1 antagonist is MK-3475 or nivolumab.

24. The method, medicament, use or kit of embodiment 25, wherein MK-3475 is formulated as a liquid medicament which comprises 25 mg/ml MK-3475, 7% (w/v) sucrose, 0.02% (w/v) polysorbate 80 in 10 mM histidine buffer pH 5.5.

25. The method, medicament, use or kit of any of embodiments 1 to 24, wherein the attenuated *Listeria* is LmddA-142 or LmddA-143

26. The method, medicament, use of kit of any of embodiments 1 to 25, wherein the PD-1 antagonist is MK-3475, the attenuated *Listeria* is LmddA-142 or LmddA-143, the patient is diagnosed with a metastatic prostate cancer, and doses of the PD-1 antagonist and the attenuated *Listeria* are selected from the group consisting of one of the combinations in the table below:

| MK-3475 | LmddA-142 | LmddA-143 |
|---|---|---|
| 200 mg Q3W | $1 \times 10^9$ cfu | $1 \times 10^9$ cfu |
| 200 mg Q3W | $2 \times 10^9$ cfu | $2 \times 10^9$ cfu |
| 200 mg Q3W | $5 \times 10^9$ cfu | $5 \times 10^9$ cfu |
| 200 mg Q3W | $1 \times 10^{10}$ cfu | $1 \times 10^{10}$ cfu |

General Methods

Standard methods in molecular biology are described Sambrook, Fritsch and Maniatis (1982 & 1989 2$^{nd}$ Edition, 2001 3$^{rd}$ Edition) *Molecular Cloning, A Laboratory Manual*, Cold Spring Harbor Laboratory Press, Cold Spring Harbor, N.Y.; Sambrook and Russell (2001) *Molecular Cloning*, 3$^{rd}$ ed., Cold Spring Harbor Laboratory Press, Cold Spring Harbor, N.Y.; Wu (1993) *Recombinant DNA*, Vol. 217, Academic Press, San Diego, Calif.). Standard methods also appear in Ausbel, et al. (2001) *Current Protocols in Molecular Biology*, Vols. 1-4, John Wiley and Sons, Inc. New York, N.Y., which describes cloning in bacterial cells and DNA mutagenesis (Vol. 1), cloning in mammalian cells and yeast (Vol. 2), glycoconjugates and protein expression (Vol. 3), and bioinformatics (Vol. 4).

Methods for protein purification including immunoprecipitation, chromatography, electrophoresis, centrifugation, and crystallization are described (Coligan, et al. (2000) *Current Protocols in Protein Science*, Vol. 1, John Wiley and Sons, Inc., New York). Chemical analysis, chemical modification, post-translational modification, production of fusion proteins, glycosylation of proteins are described (see, e.g., Coligan, et al. (2000) *Current Protocols in Protein Science*, Vol. 2, John Wiley and Sons, Inc., New York; Ausubel, et al. (2001) *Current Protocols in Molecular Biology*, Vol. 3, John Wiley and Sons, Inc., NY, NY, pp. 16.0.5-16.22.17; Sigma-Aldrich, Co. (2001) *Products for*

*Life Science Research*, St. Louis, Mo.; pp. 45-89; Amersham Pharmacia Biotech (2001) *BioDirectory*, Piscataway, N.J., pp. 384-391). Production, purification, and fragmentation of polyclonal and monoclonal antibodies are described (Coligan, et al. (2001) *Current Protcols in Immunology, Vol.* 1, John Wiley and Sons, Inc., New York; Harlow and Lane (1999) *Using Antibodies*, Cold Spring Harbor Laboratory Press, Cold Spring Harbor, N.Y.; Harlow and Lane, supra). Standard techniques for characterizing ligand/receptor interactions are available (see, e.g., Coligan, et al. (2001) *Current Protocols in Immunology, Vol.* 4, John Wiley, Inc., New York).

Monoclonal, polyclonal, and humanized antibodies can be prepared (see, e.g., Sheperd and Dean (eds.) (2000) *Monoclonal Antibodies*, Oxford Univ. Press, New York, N.Y.; Kontermann and Dubel (eds.) (2001) *Antibody Engineering*, Springer-Verlag, New York; Harlow and Lane (1988) *Antibodies A Laboratory Manual*, Cold Spring Harbor Laboratory Press, Cold Spring Harbor, N.Y., pp. 139-243; Carpenter, et al. (2000) *J. Immunol.* 165:6205; He, et al. (1998) *J. Immunol.* 160:1029; Tang et al. (1999) *J. Biol. Chem.* 274:27371-27378; Baca et al. (1997) *J. Biol. Chem.* 272:10678-10684; Chothia et al. (1989) *Nature* 342:877-883; Foote and Winter (1992) *J. Mol. Biol.* 224:487-499; U.S. Pat. No. 6,329,511).

An alternative to humanization is to use human antibody libraries displayed on phage or human antibody libraries in transgenic mice (Vaughan et al. (1996) *Nature Biotechnol.* 14:309-314; Barbas (1995) *Nature Medicine* 1:837-839; Mendez et al. (1997) *Nature Genetics* 15:146-156; Hoogenboom and Chames (2000) *Immunol. Today* 21:371-377; Barbas et al. (2001) *Phage Display: A Laboratory Manual*, Cold Spring Harbor Laboratory Press, Cold Spring Harbor, New York; Kay et al. (1996) *Phage Display of Peptides and Proteins: A Laboratory Manual*, Academic Press, San Diego, Calif.; de Bruin et al. (1999) Nature Biotechnol. 17:397-399).

Purification of antigen is not necessary for the generation of antibodies. Animals can be immunized with cells bearing the antigen of interest. Splenocytes can then be isolated from the immunized animals, and the splenocytes can fused with a myeloma cell line to produce a hybridoma (see, e.g., Meyaard et al. (1997) *Immunity* 7:283-290; Wright et al. (2000) *Immunity* 13:233-242; Preston et al., supra; Kaithamana et al. (1999) *J. Immunol.* 163:5157-5164).

Antibodies can be conjugated, e.g., to small drug molecules, enzymes, liposomes, polyethylene glycol (PEG). Antibodies are useful for therapeutic, diagnostic, kit or other purposes, and include antibodies coupled, e.g., to dyes, radioisotopes, enzymes, or metals, e.g., colloidal gold (see, e.g., Le Doussal et al. (1991) *J. Immunol.* 146:169-175; Gibellini et al. (1998) *J. Immunol.* 160:3891-3898; Hsing and Bishop (1999) *J. Immunol.* 162:2804-2811; Everts et al. (2002) *J. Immunol.* 168:883-889).

Methods for flow cytometry, including fluorescence activated cell sorting (FACS), are available (see, e.g., Owens, et al. (1994) *Flow Cytometry Principles for Clinical Laboratory Practice*, John Wiley and Sons, Hoboken, N.J.; Givan (2001) *Flow Cytometry, 2$^{nd}$ ed.;* Wiley-Liss, Hoboken, N.J.; Shapiro (2003) *Practical Flow Cytometry*, John Wiley and Sons, Hoboken, N.J.). Fluorescent reagents suitable for modifying nucleic acids, including nucleic acid primers and probes, polypeptides, and antibodies, for use, e.g., as diagnostic reagents, are available (Molecular Probesy (2003) *Catalogue*, Molecular Probes, Inc., Eugene, Oreg.; Sigma-Aldrich (2003) *Catalogue*, St. Louis, Mo.).

Standard methods of histology of the immune system are described (see, e.g., Muller-Harmelink (ed.) (1986) *Human Thymus: Histopathology and Pathology*, Springer Verlag, New York, N.Y.; Hiatt, et al. (2000) *Color Atlas of Histology*, Lippincott, Williams, and Wilkins, Phila, Pa.; Louis, et al. (2002) *Basic Histology: Text and Atlas*, McGraw-Hill, New York, N.Y.).

Software packages and databases for determining, e.g., antigenic fragments, leader sequences, protein folding, functional domains, glycosylation sites, and sequence alignments, are available (see, e.g., GenBank, Vector NTI® Suite (Informax, Inc, Bethesda, Md.); GCG Wisconsin Package (Accelrys, Inc., San Diego, Calif.); DeCypher® (TimeLogic Corp., Crystal Bay, Nev.); Menne, et al. (2000) *Bioinformatics* 16: 741-742; Menne, et al. (2000) *Bioinformatics Applications Note* 16:741-742; Wren, et al. (2002) *Comput. Methods Programs Biomed.* 68:177-181; von Heijne (1983) *Eur. J. Biochem.* 133:17-21; von Heijne (1986) *Nucleic Acids Res.* 14:4683-4690).

TABLE 3 provides a brief description of the sequences in the sequence listing.

| SEQ ID NO: | Description |
| --- | --- |
| 1 | hPD-1.08A light chain CDR1 |
| 2 | hPD-1.08A light chain CDR2 |
| 3 | hPD-1-08A light chain CDR3 |
| 4 | hPD-1.08A heavy chain CDR1 |
| 5 | hPD-1.08A heavy chain CDR2 |
| 6 | hPD-1.08A heavy chain CDR3 |
| 7 | hPD-1.09A light chain CDR1 |
| 8 | hPD-1.09A light chain CDR2 |
| 9 | hPD-1.09A light chain CDR3 |
| 10 | hPD-1.09A heavy chain CDR1 |
| 11 | hPD-1.09A heavy chain CDR2 |
| 12 | hPD-1.09A heavy chain CDR3 |
| 13 | 109A-H heavy chain variable region |
| 14 | 409A-H heavy chain full length |
| 15 | K09A-L-11 light chain variable region |
| 16 | K09A-L-16 light chain variable region |
| 17 | K09A-L-17 light chain variable region |
| 18 | K09A-L-11 light chain full length |
| 19 | K09A-L-16 light chain full length |
| 20 | K09A-L-17 light chain full length |
| 21 | MK-3475 Heavy chain |
| 22 | MK-3475 Light chain |
| 23 | Nivolumab Heavy chain |
| 24 | Nivolumab light chain |
| 25 | KLK3 protein |
| 26 | KLK3 protein |
| 27 | KLK3 protein |
| 28 | Nucleotide encoding KLK3 protein |
| 29 | KLK3 protein |
| 30 | Nucleotide encoding KLK3 protein |
| 31 | KLK3 protein |
| 32 | Nucleotide encoding KLK3 protein |
| 33 | KLK3 protein |
| 34 | Nucleotide encoding KLK3 protein |
| 35 | KLK3 protein |
| 36 | Nucleotide encoding KLK3 protein |
| 37 | KLK3 protein |
| 38 | Nucleotide encoding KLK3 protein |
| 39 | KLK3 protein |
| 40 | Nucleotide encoding KLK3 protein |
| 41 | KLK3 protein |
| 42 | KLK3 protein |
| 43 | KLK3 protein |
| 44 | KLK3 protein |
| 45 | Nucleotide encoding KLK3 protein |
| 46 | Primer Adv60-PSA |
| 47 | Primer Adv61-PSA |
| 48 | tLLO-PSA fusion polypeptide |
| 49 | LLO PEST seqeunce |
| 50 | KLK3 protein |
| 51 | KLK3 protein |

TABLE 3-continued provides a brief description of the sequences in the sequence listing.

| SEQ ID NO: | Description |
|---|---|
| 52 | KLK3 protein |
| 53 | LLO polypeptide |
| 54 | LLO polypeptide |
| 55 | LLO polypeptide |
| 56 | ActA PEST sequence |
| 57 | ActA PEST sequence |
| 58 | ActA PEST sequence |
| 59 | ActA PEST sequence |
| 60 | *Streptococcus pyogenes* Streptolysin O PEST sequence |
| 61 | *Streptococcus equisimilis* Streptolysin O PEST-like sequence |
| 62 | pADV142 nucleic acid sequence |
| 63 | KLK3 protein |
| 64 | KLK3 protein |
| 65 | KLK3 protein |
| 66 | KLK3 protein |

A recombinant Lm of this invention secretes PSA fused to tLLO (Lm-LLO-PSA), which elicits a potent PSA-specific immune response associated with regression of tumors in a mouse model for prostate cancer. Details for the vectors used to create the LmddA-142 strain and the LmddA-143 strain are provided in Table 4 below. The pADV142 plasmid, which has no antibiotic resistance markers, was used to create the LmddA-142 strain. This new strain is 10 times more attenuated than Lm-LLO-PSA. In addition, LmddA-142 is slightly more immunogenic and significantly more efficacious in regressing PSA expressing tumors than the Lm-LLO-PSA.

TABLE 4

Figure 9A:
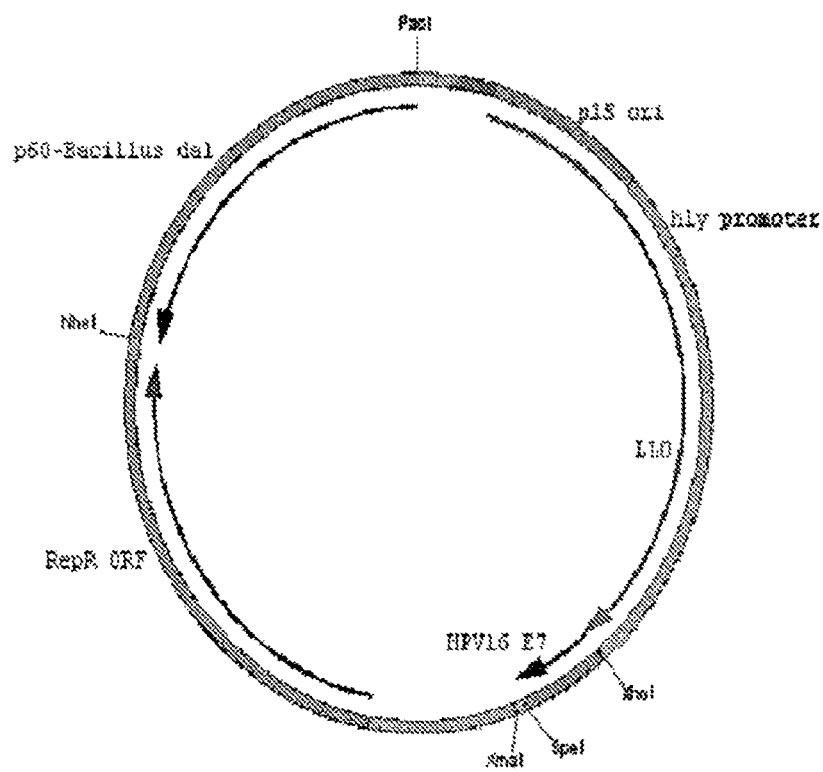
Figure 9B:
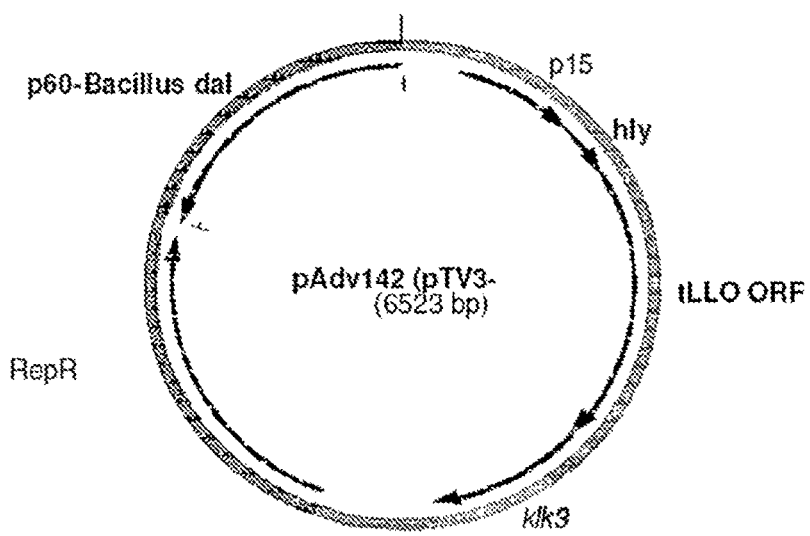

| Plasmids and strains | |
|---|---|
| Plasmids | Features |
| pADV119 | Derived from pTV3 by deleting the prfA gene |
| pADV134 | Derived from pADV119 by replacing the Lm dal gene by the *Bacillus* dal gene |
| pADV142 | Derived from pADV134 by replacing HPV16 e7 with klk3 (Map at FIG. 9B; sequence FIG. 9C) |
| Strains | Genotype |
| 10403S | Wild-type *Listeria monocytogenes*:: str |
| XFL-7 | 10403S prfA$^{(-)}$ |
| Lmdd | 10403S dal$^{(-)}$ dat$^{(-)}$ |
| LmddA | 10403S dal$^{(-)}$ dat$^{(-)}$ actA$^{(-)}$ |
| LmddA-142 | 10403S dal$^{(-)}$ dat$^{(-)}$ actA$^{(-)}$ pADV142 |
| Lmdd-143 | 10403S dal$^{(-)}$ dat$^{(-)}$ with klk3 fused to the hly gene in the chromosome |
| LmddA-143 | 10403S dal$^{(-)}$ dat$^{(-)}$ actA$^{(-)}$ with klk3 fused to the hly gene in the chromosome (FIG. 8 shows the chromosomal structure and FIG. 9A shows a map of the pADV143 plasmid) |

The sequence of the plasmid pAdv142 (6523 bp) was as follows:

(SEQ ID NO: 62)
cggagtgtatactggcttactatgaggcactgatgagggtgtcagtgaa gtgcttcatgtggcaggagaaaaaggctgcaccggtgcgtcagcagaa tatgtgatacaggatatattccgcacctcgctcactgactcgctacgct cggtcgttcgactgcggcgagcggaaatggcttacgaacggggcggaga tacctggaagatgccaggaagatacttaacagggaagtgagagggccgc ggcaaagccgtattccataggctccgccccctgacaagcatcacgaaa tctgacgctcaaatcagtggtggcgaaacccgacaggactataaagata ccaggcgtaccccctggcggctccctcgtgcgctctcctgacctgccat cggataccggtgtcattccgctgttatggccgcgtttgtctcattccac gcctgacactcagttccgggtaggcagttcgctccaagctggactgtat gcacgaaccccccgttcagtccgaccgctgcgccttatccggtaactat cgtcttgagtccaacccggaaagacatgcaaaagcaccactggcagcag ccactggtaattgatttagaggagttagtcttgaagtcatgcgccggtt aaggctaaactgaaaggacaagattggtgactgcgctcctccaagccag ttacctcggttcaaagagttggtagctcagagaaccttcgaaaaccgc cctgcaaggcggttttttcgttcagagcaagagattacgcgcagacc aaaacgatctcaagaagatcatcttattaatcagataaaatatactagc cctcattgattagtatattcctatcttaaagttactatatgtggaggca ttaacatagttaatgacgtcaaaaggatagcaagactagaataaagcta taaagcaagcatataatattgcgatcatattagaagcgaatttcgcca atattataattatcaaaagagaggggtggcaaacggtataggcattatt aggttaaaaaatgtagaaggagagtgaaacccatgaaaaaaataatgct agtattattacacttatattagttagtctaccaattgcgcaacaaactg aagcaaaggatgcatctgcattcaataaagaaaattcaatttcatccat ggcaccaccagcatctccgcctgcaagtcctaagacgccaatcgaaaag aaacacgcggatgaaatcgataagtatatacaaggattggattacaata aaaacaatgtattagtataccacggagatgcagtgacaaatgtgccgcc aagaaaaggttacaaagatggaaatgaatatattgagtggagaaaaaga agaaatccatcaatcaaaataatgcagacattcaagagtgaatgcaatt tcgagcctaacctatccaggtgctctcgtaaaagcgaattcggaattag tagaaaatcaaccagatgactccctgtaaaacgtgattcattaacactc agcattgatttgccaggtatgactaatcaagacaataaaatagttgtaa aaaatgccactaaatcaaacgttaacaacgcagtaaatacattagtgga aagatggaatgaaaaatatgctcaagcttatccaaatgtaagtgcaaaa attgattatgatgacgaaatggcttacagtgaatcacaattaattgcga aatttggtacagcatttaaagctgtaaataatagcttgaatgtaaactt cggcgcaatcagtgaagggaaaatgcaagaagaagtcattagttttaaa caaatttactataacgtgaatgttaatgaacctacaagaccttccagat ttttcggcaaagctgttactaaagagcagagcaagcgcttggagtgaat gcagaaaatcctcctgcatatatctcaagtgtggcgtatggccgtcaag tttatttgaaattatcaactaattcccatagtactaaagtaaaagctgc ttttgatgctgccgtaagcggaaatctgtctcaggtgatgtagaacta acaaatatcatcaaaaattcaccacaaagccgtaatttacggaggaccg caaaagatgaagttcaaatcatcgacggcaacctcggagacttacgcga tattttgaaaaaggcgctacttttaatcgagaaacaccaggagttccc -continued attgcttatacaacaaacttcctaaaagacaatgaattagctgttatta aaaacaactcagaatatattgaaacaacttcaaaagcttatacagatgg aaaaattaacatcgatcactctggaggatacgttgctcaattcaacatt tcagggatgaagtaaattatgatctcgag<u>attgtgggaggctgggagtg</u>

<u>cgagaagcattcccaaccctggcaggtgcttgtggcctctcgtggcagg</u>

<u>gcagtctgcggcggtgttctggtgcaccccagtgggtcctcacagctg</u>

<u>cccactgcatcaggaacaaaagcgtgatcttgctgggtcggcacagcct</u>

<u>gatcatcctgaagacacaggccaggtattcaggtcagccacagcaccc</u>

<u>acacccgctctacgatatgagcctcctgaagaatcgattcctcaggcca</u>

<u>ggtgatgactccagccacgacctcatgctgctccgcctgtcagagcctg</u>

<u>ccgagctcacggatgctgtgaaggtcatggacctgcccacccaggagcc</u>

<u>agcactggggaccacctgctacgcctcaggctggggcagcattgaacca</u>

<u>gaggagttcttgaccccaaagaaacttcagtgtgtggacctccatgtta</u>

<u>tttccaatgacgtgtgtgcgcaagttcaccctcagaaggtgaccaagtt</u>

<u>catgctgtgtgctggacgctggacagggggcaaaagcacctgctcgggt</u>

<u>gattctgggggcccacttgtctgttatggtgtgcttcaaggtatcacgt</u>

<u>catgggcagtgaaccatgtgccctgcccgaaaggccttccctgtacac</u>

<u>caaggtggtgcattaccggaagtggatcaaggacaccatcgtggccaac</u>

<u>cccTAA</u>cccgggccactaactcaacgctagtagtggatttaatcccaaa tgagccaacagaaccagaaccagaaacagaacaagtaacattggagtta gaaatggaagaagaaaaaagcaatgatttcgtgtgaataatgcacgaaa tcattgcttattatttaaaagcgatatactagatataacgaaacaacg aactgaataaagaatacaaaaaagagccacgaccagttaaagcctgag aaactttaactgcgagccttaattgattaccaccaatcaattaaagaag tcgagacccaaaataggtaaagtatttaattactttattaatcagatac ttaaatatctgtaaaccattatatcgggatttgaggggatttcaagtc ataagaagataccaggcaatcaattaagaaaaacttagttgattgccat tagagtgattcaactagatcgtagcttctaactaattaattacgtaaga aaggagaacagctgaatgaatatcccattgagtagaaactgtgcttcat gacggcagttaaagtacaaatttaaaaatagtaaaattcgctcaatcac taccaagccaggtaaaagtaaaggggctatattgcgtatcgctcaaaaa aaagcatgattggcggacgtggcgagactgacttccgaagaagcgattc acgaaaatcaagatacatttacgcattggacaccaaacgatatcgttat ggtacgtatgcagacgaaaaccgttcatacactaaaggacattctgaaa acaatttaagacaaatcaataccacttattgattagatattcacacgg aaaagaaactatttcagcaagcgatattttaacaacagctattgattt aggttttatgcctacgttaattatcaaatctgataaaaggttatcaagca tattttgttttagaaacgccagtctatgtgacttcaaaatcagaattta aatctgtcaaagcagccaaaataatctcgcaaaatatccgagaatatta ggaaagtattgccagttgatctaacgtgcaatcattagggattgctcgt -continued ataccaagaacggacaatgtagaattattgatcccaattaccgttattc tttcaaagaatggcaagattggtctttcaaacaaacagataataagggc tttactcgttcaagtctaacggttttaagcggtacagaaggcaaaaaac aagtagatgaaccctggataatctcttattgcacgaaacgaaattacag gagaaagggatagtagggcgcaatagcgttatgataccctctcatagc ctactttagttcaggctattcaatcgaaacgtgcgaatataatatgatg agataataatcgattagatcaacccttagaagaaaagaagtaatcaaa attgttagaagtgcctattcagaaaactatcaagggctaataggaat acattaccattattgcaaagcttgggtatcaagtgatttaaccagtaaa gatttatttgtccgtcaagggtggtttaaattcaagaaaaaagaagcg aacgtcaacgtgttcatttgtcagaatgaaagaagatttaatggctta tattagcgaaaaagcgatgtatacaagccttatttagcgacgaccaaa aaagagattagagaagtgctaggcattcctgaacggacattagataaat tgctgaaggtactgaaggcgaatcaggaaattactttaagattaaacca ggaagaaatggtggcattcaacttgctagtgttaaatcattgagctatc gatcattaaattaaaaaagaagaacgagaaagctatataaaggcgctg acagcttcgataatttagaacgtacatttattcaagaaactctaaacaa attggcagaacgccccaaaacggacccacaactcgatttgatagctacg atacaggctgaaaataaaacccgcactatgccattacatttatatctat gatacgtgatgatactagctggctagcttaattgcttatatttacctgc aataaaggatacttacttccattatactcccattaccaaaaacatacgg ggaacacgggaacttattgtacaggccacctcatagttaatggatcgag ccacctgcaatctcatccatggaaatatattcatcccctgccggccta ttaatgtgacttagtgcccggcggatattcctgatccagctccaccata aattggtccatgcaaattcggccggcaattacaggcgattcccttcaca aggatgtcggtccattcaattacggagccagccgtccgcatagcctaca ggcaccgtcccgatccatgtgtattaccgctgtgtactcggctccgtag ctgacgctctcgccattctgatcagatgacatgtgacagtgtcgaatgc agggtaaatgccggacgcagctgaaacggtatctcgtccgacatgtcag cagacgggcgaaggccatacatgccgatgccgaatctgactgcattaaa aaagccattacagccggagtccagcggcgctgacgcgcagtggaccatt agattattaacggcagcggagcaatcagctattaaagcgctcaaactgc attaagaaatagcctctactattcatccgctgtcgcaaaatgggtaaat acccattgcactttaaacgagggagcggtcaagaattgccatcacgact gaacttcacctctgatttacaccaagtctgacatccccgtatcgaccac agatgaaaatgaagagaaccattacgtgtggcgggctgcctcctgaagc cattcaacagaataacctgttaaggtcacgtcatactcagcagcgattg ccacatactccgggggaaccgcgccaagcaccaatataggcgcatcaat ccattagcgcagtgaaatcgcttcatccaaaatggccacggccaagcat gaagcacctgcgtcaagagcagccatgctgatctgcatcaccatgcccg taggcgatgattcacaactgccatcaagtggacatgacaccgatatgat

```
tacatattgctgacattaccatatcgcggacaagtcaataccgcccacg tatctctgtaaaaaggattgtgctcatggaaaactcctctcattacaga aaatcccagtacgtaattaagtatttgagaattaatatatattgattaa tactaagatacccagattcacctaaaaaacaaatgatgagataatagct ccaaaggctaaagaggactataccaactatttgttaattaa.
```

(FIG. 9C) This plasmid was sequenced at Genewiz facility from the E. coli strain on Feb.20, 2008. A map of the plasmid is presented as FIG. 9B.

REFERENCES

1. Sharpe, A. H, Wherry, E. J., Ahmed R., and Freeman G. J. The function of programmed cell death 1 and its ligands in regulating autoimmunity and infection. *Nature Immunology* (2007); 8:239-245.
2. Dong H et al. Tumor-associated B7-H1 promotes T-cell apoptosis: a potential mechanism of immune evasion. Nat Med. 2002 August; 8(8):793-800.
3. Yang et al. PD-1 interaction contributes to the functional suppression of T-cell responses to human uveal melanoma cells in vitro. *Invest Ophthalmol Vis Sci.* 2008 June; 49(6 (2008): 49: 2518-2525.
4. Ghebeh et al. The B7-H1 (PD-L1) T lymphocyte-inhibitory molecule is expressed in breast cancer patients with infiltrating ductal carcinoma: correlation with important high-risk propgnostic factors. *Neoplasia* (2006) 8: 190-198.
5. Hamanishi J et al. Programmed cell death 1 ligand 1 and tumor-infiltrating CD8+T lymphocytes are prognostic factors of human ovarian cancer. *Proceeding of the National Academy of Sciences* (2007): 104: 3360-3365.
6. Thompson R H et al. Significance of B7-H1 overexpression in kidney cancer. Clinical genitourin *Cancer* (2006): 5: 206-211.
7. Nomi, T. Sho, M., Akahori, T., et al. Clinical significance and therapeutic potential of the programmed death-1 ligand/programmed death-1 pathway in human pancreatic cancer. *Clinical Cancer Research* (2007); 13:2151-2157.
8. Ohigashi Y et al. Clinical significance of programmed death-1 ligand-1 and programmed death-1 ligand 2 expression in human esophageal cancer. *Clin. Cancer Research* (2005): 11: 2947-2953.
9. Inman et al. PD-L1 (B7-H1) expression by urothelial carcinoma of the bladder and BCG-induced granulomata: associations with localized stage progression. *Cancer* (2007): 109: 1499-1505.
10. Shimauchi T et al. Augmented expression of programmed death-1 in both neoplasmatic and nonneoplastic CD4+ T-cells in adult T-cell Leukemia/Lymphoma. *Int. J. Cancer* (2007): 121:2585-2590.
11. Gao et al. Overexpression of PD-L1 significantly associates with tumor aggressiveness and postoperative recurrence in human hepatocellular carcinoma. *Clinical Cancer Research* (2009) 15: 971-979.
12. Nakanishi J. Overexpression of B7-H1 (PD-L1) significantly associates with tumor grade and postoperative prognosis in human urothelial cancers. *Cancer Immunol Immunother.* (2007) 56: 1173-1182.
13. Hino et al. Tumor cell expression of programmed cell death-1 is a prognostic factor for malignant melanoma. *Cancer* (2010): 00: 1-9.
14. Ghebeh H. Foxp3+ tregs and B7-H1+/PD-1+T lymphocytes co-infiltrate the tumor tissues of high-risk breast cancer patients: implication for immunotherapy. *BMC Cancer.* 2008 Feb. 23; 8:57.
15. Ahmadzadeh M et al. Tumor antigen-specific CD8 T cells infiltrating the tumor express high levels of PD-1 and are functionally impaired. *Blood* (2009) 114: 1537-1544.
16. Thompson R H et al. PD-1 is expressed by tumor infiltrating cells and is associated with poor outcome for patients with renal carcinoma. *Clinical Cancer Research* (2007) 15: 1757-1761.

All references cited herein are incorporated by reference to the same extent as if each individual publication, database entry (e.g. Genbank sequences or GeneID entries), patent application, or patent, was specifically and individually indicated to be incorporated by reference. This statement of incorporation by reference is intended by Applicants, pursuant to 37 C.F.R. §1.57(b)(1), to relate to each and every individual publication, database entry (e.g. Genbank sequences or GeneID entries), patent application, or patent, each of which is clearly identified in compliance with 37 C.F.R. §1.57(b)(2), even if such citation is not immediately adjacent to a dedicated statement of incorporation by reference. The inclusion of dedicated statements of incorporation by reference, if any, within the specification does not in any way weaken this general statement of incorporation by reference. Citation of the references herein is not intended as an admission that the reference is pertinent prior art, nor does it constitute any admission as to the contents or date of these publications or documents.

In the following example, numerous specific details are set forth in order to provide a thorough understanding of the invention. However, it will be understood by those skilled in the art that the present invention may be practiced without these specific details. In other instances, well-known methods, procedures, and components have not been described in detail so as not to obscure the present invention.

EXAMPLE

A Phase 1-2 Dose-Escalation and Safety Study of ADXS31-142 Alone and in Combination with Pembrolizumab (MK-3475) in Patients with Previously Treated Metastatic Castration-Resistant Prostate Cancer (mCRPC)

Figure 10:
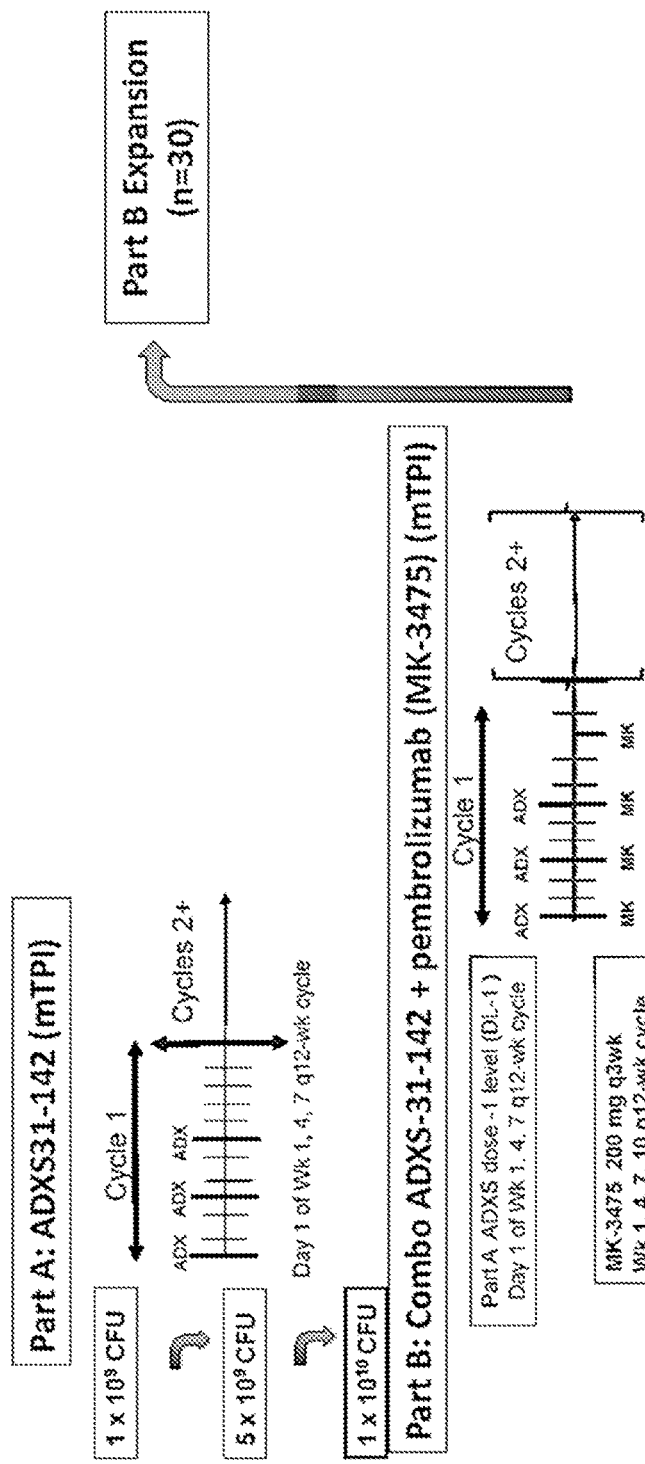
FIG. 10 shows a diagram of the two parts of the Phase 1-2 study designed to evaluate safety and tolerability of ADXS31-142 (*Listeria monocytogenes* (10403S dal$^{(-)}$ dat$^{(-)}$ actA$^{(-)}$ pADV142)) as monotherapy and in combination with pembrolizumab (MK-3475) in subjects with mCRPC.

This is a phase 1-2, open-label, multicenter, nonrandomized, 2-part study in patients with metastatic Castration-Resistant Prostate Cancer (mCRPC). Part A of the study will be an open-label, Phase 1, multicenter, non-randomized, dose-determining trial of ADX31-142 monotherapy in subjects with metastatic castration-resistant prostate cancer (mCRPC). Part B of the study will be an open-label, Phase 1-2, multicenter, non-randomized dose-determining trial of ADXS31-142 in combination with pembrolizumab (MK-3475) in subjects with mCRPC. FIG. 10 presents a diagram of the monotherapy and combination portions of this study. Objectives:

Part A: to evaluate safety and tolerability of ADXS31-142 monotherapy and select the recommended phase 2 dose (RP2D) in subjects with mCRPC Part B: to evaluate safety and tolerability of ADXS31-142 in combination with pembrolizumab (MK-3475) and to establish the RP2D for this combination in subjects with mCRPC In addition, objectives of the Study include evaluating anti-tumor activity and progression free survival (PFS)

signal of ADXS31-142 monotherapy and ADXS31-142+ pembrolizumab (MK-3475) combination therapy using RECIST 1.1, immune-related Response Evaluation Criteria in Solid Tumors (irRECIST) and Prostate Cancer Working Group 2 (PCWG2) criteria to inform design of a subsequent randomized Phase 2 trial. The effects on serum prostate specific antigen (PSA) and periphaeral immunologic measures of ADXS31-142 montherapy and ADXS31-142+pembrolizumab (MK-3475) combination therapy will be determined.

Product Description

Each of these products is described in detail above.

ADXS31-142 will be provided as a concentrated suspension for injection, at a concentration of $2.7 \times 10^9$ cfu/mL; 1.2 mL/vial.

Pembrolizumab (MK-3475) may be provided in two different forms: (1) as a lyophilized powder for injection (50 mg); and (2) as a solution for infusion at a concentration of 25 mg/mL.

Part A—ADXS31-124 Monotherapy

Materials and Methods

Subjects:

The study will be conducted in male subjects (≥18 years) with histologically confirmed mCRPC who have progressed or become resistant to no more than 3 prior systemic treatment regimens with chemotherapy, hormonal, or immunotherapy in the metastatic setting; and wuth an Eastern Cooperative Oncology Group (ECOG) performance status of 0-1 are eligble. However, subjects can not have had more than 1 prior chemotherapeutic regimen in the metastatic setting. Subjects with evidence of progressive bone or other metastases are acceptable. Subjects may remain on castration therapy (luteinizing-hormone-releasing 15 hormone [LHRH] agonist or antagonist) during the trial.

Dose:

The dose determining phase is intended to select a recommended Phase 2 dose (RP2D) for Part B. The starting dose level (DL) of ADSX31-142 monotherapy will be $1 \times 10^9$ colony forming units (cfu) (DL 1). The dose will be escalated ($5 \times 10^9$ cfu, $1 \times 10^{10}$ cfu), remain the same or be de-escalated according to pre-defined dose-limiting toxicity (DLT) criteria associated with a DLT rate ≤0.25 by applying the modified toxicity probability interval (mTPI) design. Table 5 summarizes ADXS31-142 Monotherapy Doses to be used.

Figure 11:
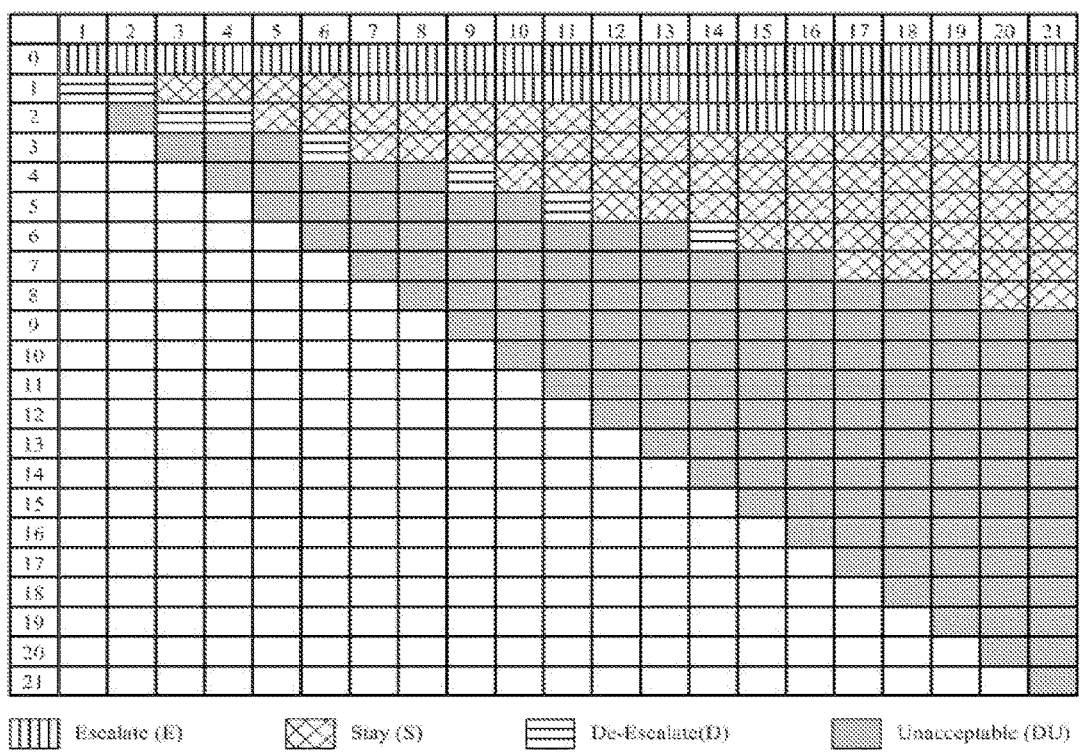
FIG. 11 is a table showing the dose decisions (e.g., escalate, stay, deescalate and unacceptable) for ADSX31-142 Monotherapy based on a sample size of 21 subjects.

FIG. 11 is based on a sample size of 21 subjects. Two parameters epsilon1 and epsilon2 are set at default values of 0.05. x-axis is number of subjects treated at current dose; yaxis is number of toxicities.

The Targeted dose limiting toxicity (DLT) Rate will increase to 30% for the combination regimen (Part B) in the event that a 25% DLT rate is observed at the recommended ADXS31-142 monotherapy dose.

The same DLT criteria will be utilized for study Part A and Part B. All 10 toxicities will be graded using CTCAE Version 4.0. The DLT window of observation will be 4 weeks (after 2 doses of each drug). The occurrence of any of the following toxicities will be considered a DLT, if judged by the investigator to be possibly, probably or definitely related to study treatment administration.

Endpoints

Efficacy Endpoints—The efficacy endpoints to be used in this study (PSA/PAP, other serum markers for prostate cancer, scans, and measureable and evaluable disease assessments) are those typically used to assess anti-tumor activity of mCRPC.

Safety Endpoint—The primary safety objective of this trial is to characterize the safety and tolerability of ADXS31-142 alone. The primary safety analysis will be based on subjects who experienced toxicities as defined by CTCAE criteria. Safety will be assessed by quantifying the toxicities and grades experienced by subjects who have received ADXS31-142 alone, including serious adverse events (SAEs) and events of clinical interest (ECIs).

Biomarkers

T-cells will be assessed for their specific response to PSA and other prostate cancer antigens which may include PSMA, PAP, and prostate stem cell antigen (PSCA). T-cell responses will be determined by enzyme-linked immunosorbent assay (ELISA) and/or ELISpot. PBMC immunologic gene expression analysis may also be conducted.

Serum cytokine and chemokine changes will be determined to assess immune stimulation as a result of treatment. Serum cytokine levels will include IL-2, IL-4, IL-6, IL-8, IL-10, IL-12, IL-15, IL-18, transforming growth factor beta (TGFβ), and tumor necrosis factor alpha (TNFα). Serum chemokines will include CXCL 9, 10, and 11.

Route of Administration

ADSX31-142 monotherapy will be administered by IV infusion by medically trained personnel.

TABLE 5

| Dose Level | Dose | Route of Administration | Regimen |
| --- | --- | --- | --- |
| 1 | $1 \times 10^9$ cfu | IV infusion | Day 1 of Weeks 1, 4 and 7 of 12-week cycle |
| 2 | $5 \times 10^9$ cfu | IV infusion | Day 1 of Weeks 1, 4 and 7 of 12-week cycle |
| 3 | $1 \times 10^{10}$ cfu | IV infusion | Day 1 of Weeks 1, 4 and 7 of 12-week cycle |
| −1 | $.5 \times 10^9$ cfu | IV infusion | Day 1 of Weeks 1, 4 and 7 of 12-week cycle |

Up to 21 subjects will be entered (with a minimum of 6 subjects treated at the recommended dose before proceeding to the next phase). A minimum of 3 subjects will be evaluated in each cohort before dose-escalation decisions are made.

FIG. 11 below presents Dose Decisions for ADSX31-142- Monotherapy.

Regimen

ADSX31-142 monotherapy will be administered on Day 1 of weeks 1, 4, and 7, of a once every 3 weeks in a 12-week treatment cycle. Trial treatment may be administered up to 3 days before or after the scheduled Day 1 of each cycle due to administrative reasons.

All trial treatments will be administered as a 30 minute IV infusion (treatment cycle intervals may be increased due to toxicity). In Part A, NSAIDs (naproxen or ibuprofen) and medication should be administered within 30 minutes prior to the ADXS31-142 infusion.

Tumor Imaging and Assessment of Disease

Computed tomography (CT), magnetic resonance imaging (MRI) or bone scan will be considered the best currently available and reproducible methods to measure target lesions selected for response assessment. Conventional CT and MRI of the abdomen/pelvis should be performed with contiguous cuts of 10 mm or less. Spiral CT scan should be performed using a 5 mm contiguous reconstruction algorithm (as a general rule, lesion diameter should be no less than double the slice thickness). Lesions on chest x-rays will be acceptable as measurable lesions when they are clearly defined and surrounded by aerated lung; however, CT is preferable. Ultrasound will not be an acceptable method to measure disease.

Measurable and Non-Measurable Lesions and Disease

Measurable lesions will be those that can be accurately measured in at least one dimension with the longest diameter ≥2.0 cm (for spiral CT scan or MRI scan, ≥1.0 cm). Measurable disease will be present if the subject has 1 or more measurable lesions.

Non-measurable lesions/disease will be all other lesions (or sites of disease), including small lesions (those with all measurements <2.0 cm with spiral CT or <1.0 cm with MRI), or any of the following: bone lesions, leptomeningeal disease, ascites, pleural or pericardial effusion, lymphangitis, cutis/pulmonis, abdominal masses that are not confirmed and followed by imaging techniques, cystic lesions, and lesions occurring within a previously irradiated area unless they are documented as new lesions since the completion of radiation therapy.

Target/Non-Target Lesions

All measurable lesions, up to a maximum of 2 per organ and 5 in total, should be identified as target lesions to be measured and recorded at baseline. The target lesions should be representative of all involved organs. Target lesions will be selected based on their size (the lesion with the longest diameter) and suitability for accurate repeated measurements. At baseline, a sum of the longest diameters for all target lesions will be calculated and recorded as the baseline tumor burden. The baseline sum will be used as the reference point to determine the objective tumor response of the target lesions.

Measurable lesions other than the target lesions and all sites of non-measurable disease will be identified as non-target lesions and will be recorded at baseline. Non-target lesions will be evaluated at the same timepoints as target lesions.

Response in Measureable Lesions (RECIST 1.1)

At baseline, the sum of the longest diameters (SumD) of all target lesions (up to 2 lesions per organ, up to total 5 lesions) is measured. At each subsequent tumor assessment (TA), the SumD of the target lesions and of new, measurable lesions are added together to provide the total measurable tumor burden (TMTB):

TMTB=SumD Target Lesions+SumD New, Measurable Lesions

Percentage changes in TMTB per assessment time point describe the size and growth kinetics of both old and new measurable lesions as they appear. At each TA, the response in target and new measurable lesions is defined based on the change in TMTB (after ruling out irPD) as follows:

Complete Response (CR): disappearance of all target lesions. Any pathological lymph nodes (whether target or non-target) must have reduction in short axis to ≤10 mm.

Partial Response (PR): At least a 30% decrease in sum of diameter of target lesions, taking as reference the baseline sum diameter.

Stable Disease (SD): Neither sufficient shrinkage to qualify for PR nor sufficient increase Progressive Disease (PD): At least a 20% increase in the sum of diameters of target lesions, taking as reference the smallest sum on study (this includes the baseline sum if that is the smallest on study). In addition to the relative increase of 20%, the sum must also demonstrate an absolute increase of at least 5 mm (Note: the appearance of one or more new lesions is also considered progression).

Response in non-measurable lesions will also be assessed.

Part B—ADSX31-142+Pembrolizumab (MK-3475) Combination Therapy

Materials and Methods

Subjects

Subjects have been described above in Part A of the study. The subjects for Part B will be included in the study based on the same population criteria. The plan is to treat a total of 30 subject at RP2D.

Dose

Part B will consist of a dose-determination phase followed by an expansion cohort phase. The dose-determining phase is intended to select a RP2D for the combination. Dose escalation/de-escalation will be explored by applying the mTPI design.

During the dose-determining stage, up to 21 subjects will be entered at escalating doses of ADXS31-142 (see Table 7) in combination with pembrolizumab (MK-3475) at 200 mg (with a minimum of 6 subjects treated at the RP2D before proceeding to expansion). Dose-determination will continue until identification of a preliminary maximum tolerated dose/maximum allowable dose (MTD/MAD), up to a maximum dose of $1 \times 10^{10}$ cfu of ADXS31-142. The MTD/MAD will be the RP2D for the dose expansion portion. If a MTD is not identified, then the highest planned dose level of ADXS31-142 in combination with pembrolizumab (MK-3475) will be considered the RP2D. The pembrolizumab (MK-3475) will remain constant at 200 mg.

TABLE 7

ADXS31-142 and Pembrolizumab (MK-3475) Combination Therapy
Doses to be used in Trial Part B

| Drug | Dose Level | Dose | Route of Administration | Regimen |
| --- | --- | --- | --- | --- |
| ADXS31-142 | 1 | One level below RP2D in Part A | IV infusion | Day 1 of Weeks 1, 4 and 7 of 12-week cycle |
|  | 2 | RP2D in Part A | IV infusion | Day 1 of Weeks 1, 4 and 7 of 12-week cycle |

TABLE 7-continued

ADXS31-142 and Pembrolizumab (MK-3475) Combination Therapy
Doses to be used in Trial Part B

| Drug | Dose Level | Dose | Route of Administration | Regimen |
|---|---|---|---|---|
| | −1 | Two dose levels below RP2D in Part A | IV infusion | Day 1 of Weeks 1, 4 and 7 of 12-week cycle |
| Pembrolizumab (MK-3475) | | 200 mg | IV infusion | Day 1 Q3W of 12-week cycle |

As for Part A of this study, the expected doses for ADXS31-142 will be $0.5\times10^9$, $1\times10^9$, $5\times10^9$, and $1\times10^{10}$.

The expansion cohort will be open for enrollment once the RP2D of ADXS31-142 in combination with pembrolizumab (MK-3475) is selected in the Part B dose determination phase. Further assessment of the RP2D will be explored in up to 30 patients 15 with mCRPC to evaluate the safety and clinical activity of ADXS31-142 in combination with pembrolizumab (MK-3475).

Figure 12:
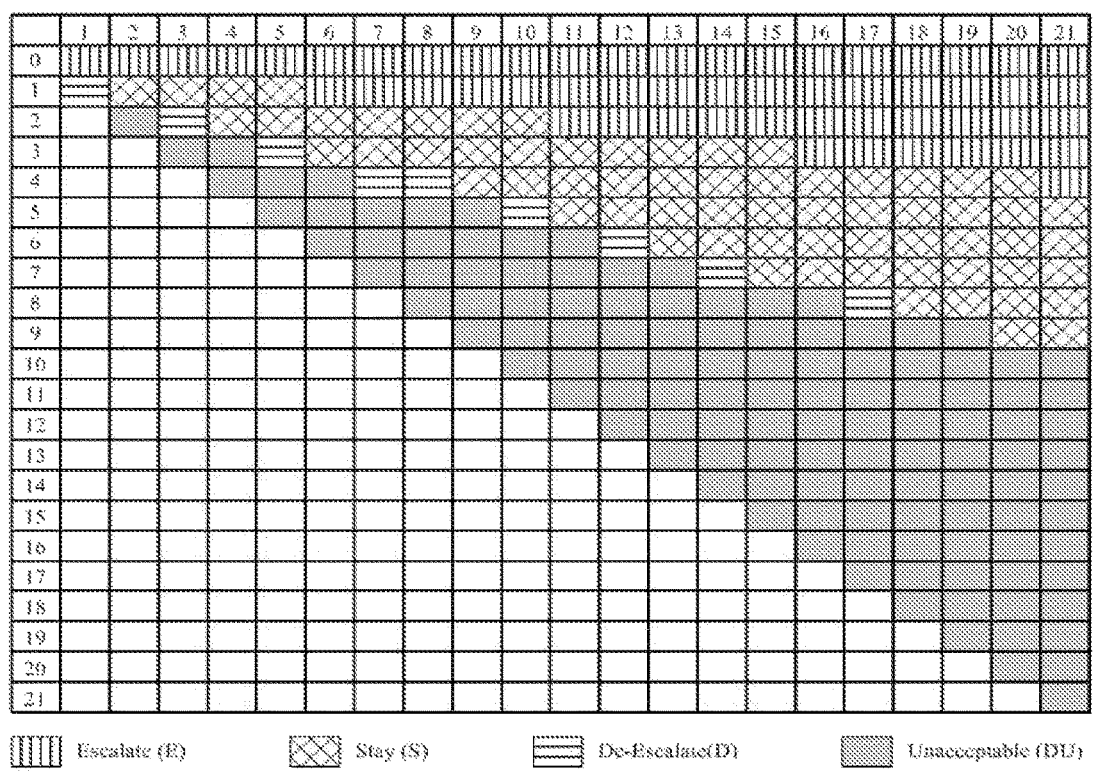
FIG. 12 is a table showing the dose decisions (e.g., escalate, stay deescalate and unacceptable) for a combination therapy of ADSX31-142 and pembrolizumab (MK-3475) based on a sample size of 21 subjects.

FIG. 12 below presents Dose Decisions for Combination Therapy

Adverse events will be monitored from the time informed consent is obtained and graded in severity according to the guidelines outlined in the National Cancer Institute (NCI) Common Terminology Criteria for Adverse Events (CT-CAE) Version 4.0.

Treatment with ADXS31-142 in combination with pembrolizumab (MK3475) will continue until documented disease progression, unacceptable adverse event(s), intercurrent illness that prevents further administration of treatment, investigator's decision to withdraw the subject, subject withdraws consent, subject experiences a complete response (irCR) and receives one additional cycle of treatment, non-compliance with trial treatment or procedure requirements, completion of 24 months of treatment with ADXS31142 and pembrolizumab (MK-3475), or administrative reasons. Subjects who attain an investigator confirmed irCR, after receiving at least 2 cycles of therapy, may consider stopping pembrolizumab (MK-3475) and continue treatment with ADX S31-142 only. After the end of treatment, each subject will be followed for 30 days after the last study drug administration for adverse event and 90 days for serious adverse events or events of clinical interest monitoring. Subjects who discontinue treatment for reasons other than disease progression will have post-treatment follow-up for disease status until disease progression, initiating a non-study cancer treatment, withdrawing consent, becoming lost to follow-up, or until the sponsor ends the study. The primary objectives of the trial are to establish a MTD or MAD and to determine safety and tolerability of ADXS31-142 in combination with pembrolizumab (MK-3475) in subjects with mCRPC.

Efficacy and Safety Endpoints will be as described for Part A of this Study.

Biomarker Research will be as described for Part A of this Study.

Route of Administration

ADSX31-142 and Pembrolizumab (MK-3475 will each be administered by IV infusion by medically trained personnel.

Regimen

Trial treatment should be administered on Day 1 of Week 1, 4 and 7 (for ADXS31-142) or Q3W (for pembrolizumab [MK-3475]) in each 12-week cycle after all procedures/assessments have been completed. Trial treatment may be administered up to 3 days before or after the scheduled Day 1 of each cycle due to administrative reasons.

All trial treatments will be administered as a 30 minute IV infusion (treatment cycle intervals may be increased due to toxicity. there should be approximately 60 minutes between the end of the first infusion and the start of the second infusion. Pembrolizumab (MK-3475) infusion will be administered first.

Assessment in target and non-target lesions is as described above for Part A.

The invention claimed is:

1. A method for treating prostate cancer in a patient comprising administering to the patient a combination therapy which comprises an antagonist of a Programmed Death 1 protein (PD-1) and a bioengineered live-attenuated *Listeria monocytogenes* strain transformed with an expression vector to express a PSA antigen fused to a truncated Listeriolysin O (tLLO), and wherein the live-attenuated *Listeria monocytogenes* strain stimulates Antigen Presenting Cells (APCs) capable of driving a cellular immune response to PSA expressing cells.

2. A method for treating prostate cancer in a patient comprising administering to the patient a combination therapy which comprises an anti-PD-1 monoclonal antibody, comprising a heavy chain and a light chain, wherein the heavy and light chains comprise SEQ ID NO:21 and SEQ ID NO:22, respectively, and a bioengineered live-attenuated *Listeria monocytogenes* strain transformed with an expression vector to express a PSA antigen fused to a truncated Listeriolysin O (tLLO), wherein the live-attenuated *Listeria monocytogenes* strain stimulates Antigen Presenting Cells (APCs) capable of driving a cellular immune response to PSA expressing cells.

3. The method of claim 1, wherein the PD-1 antagonist and the live-attenuated *Listeria monocytogenes* strain are administered simultaneously.

4. The method of claim 1 or 2, wherein said tLLO-PSA fusion polypeptide consists of the sequence of SEQ ID NO: 54 or a sequence at least 99% homologous thereto, wherein said tLLO enhances the immunogenicity of the fusion polypeptide.

5. The method of claim 1 or 2, wherein the live-attenuated *Listeria monocytogenes* strain comprises an LmddA-142 (10403S dal$^{(-)}$ dat$^{(-)}$ actA$^{(-)}$ pADV142) strain.

6. A method for treating prostate cancer in a patient comprising administering to the patient a combination therapy which comprises, an anti-PD-1 monoclonal antibody comprising a heavy chain and a light chain, wherein the heavy and light chains comprise SEQ ID NO:21 and SEQ ID NO:22, respectively, and a live-attenuated *Listeria monocytogenes* strain comprising a LmddA-143 (10403S dal$^{(-)}$ dat$^{(-)}$ actA$^{(-)}$ with klk3 fused to the hly gene in the chromosome) strain, wherein the live-attenuated *Listeria monocytogenes* strain stimulates Antigen Presenting Cells (APCs) capable of driving a cellular immune response to PSA expressing cells.

7. The method of claim 2 or 6, wherein the anti-PD-1 monoclonal antibody and the live-attenuated *Listeria monocytogenes* strain are administered simultaneously.

8. The method of claim 1, 2 or 6, wherein the prostate cancer is metastatic Castration-Resistant Prostate Cancer (mCRPC).

9. The method of claim 1, 2 or 6, wherein said live attenuated *Listeria monocytogenes* strain is administered with an adjuvant, wherein said adjuvant comprises Montanide ISA 51, GM-CSF, KLH, a cytokine, a growth factor, a cell population, QS21, Freund's incomplete adjuvant, aluminum phosphate, aluminum hydroxide, BCG, alum, an interleukin, an unmethylated CpG oligonucleotide, quill glycosides, monophosphoryl lipid A, a liposomes, a bacterial mitogen, a bacterial toxin, or a chemokine, or any combination thereof.

10. The method of claim 2 or 6, wherein the antibody is formulated as a liquid medicament which comprises 7% (w/v) sucrose, 0.02% (w/v) polysorbate 80 in 10 mM histidine buffer pH 5.5.

11. The method of claims 1, 2 or 6, wherein the prostate cancer tests positive for PD-L1 expression.

12. The method of claims 1, wherein the PD-1 antagonist is pembrolizumab.

13. The method of claim 2 or 6, wherein the anti-PD 1 monoclonal antibody is pembrolizumab.

14. The method of claim 1, wherein the PD-1 antagonist and the live-attenuated *Listeria monocytogenes* strain are administered sequentially.

15. The method of claim 2 or 6, wherein the anti-PD-1 monoclonal antibody and the live-attenuated *Listeria monocytogenes* strain are administered sequentially.

* * * * *